(12) United States Patent
Lu et al.

(10) Patent No.: US 11,840,691 B2
(45) Date of Patent: Dec. 12, 2023

(54) COMPOUND AND APPLICATION THEREOF

(71) Applicant: Kylonova (Xiamen) Biopharma Co., Ltd., Fujian (CN)

(72) Inventors: Xueqin Lu, Xiamen (CN); Zhuo Mu, Xiamen (CN); Shengjun Wang, Xiamen (CN); Yanchun Du, Xiamen (CN)

(73) Assignee: Kylonova (Xiamen) Biopharma Co., Ltd., Fujian (CN)

( * ) Notice: Subject to any disclaimer, the term of this patent is extended or adjusted under 35 U.S.C. 154(b) by 0 days.

(21) Appl. No.: 17/807,731

(22) Filed: Jun. 20, 2022

(65) Prior Publication Data

US 2023/0110095 A1   Apr. 13, 2023

Related U.S. Application Data

(63) Continuation of application No. 17/623,569, filed as application No. PCT/CN2020/097732 on Jun. 23, 2020.

(30) Foreign Application Priority Data

Jun. 28, 2019  (CN) .......................... 201910576037.1
Dec. 13, 2019  (CN) .......................... 201911281389.0

(51) Int. Cl.
| | | |
|---|---|---|
| *C12N 15/113* | (2010.01) | |
| *A61K 47/54* | (2017.01) | |
| *A61K 47/55* | (2017.01) | |
| *A61P 31/20* | (2006.01) | |

(52) U.S. Cl.
CPC ........ *C12N 15/1131* (2013.01); *A61K 47/545* (2017.08); *A61K 47/55* (2017.08); *A61P 31/20* (2018.01); *C12N 2310/11* (2013.01); *C12N 2310/14* (2013.01)

(58) Field of Classification Search
CPC ............ C12N 2310/11; C12N 2310/14; C12N 15/1131; C12N 2310/351; A61K 31/713
See application file for complete search history.

(56) References Cited

FOREIGN PATENT DOCUMENTS

| | | |
|---|---|---|
| CN | 102869774 A | 1/2013 |
| CN | 106434665 A | 2/2017 |
| CN | 108064294 A | 5/2018 |
| CN | 109331185 A | 2/2019 |
| CN | 110218728 A | 9/2019 |
| CN | 110846320 A | 2/2020 |
| EP | 3888685 A1 | 10/2021 |
| WO | 2011104169 A1 | 9/2011 |
| WO | 2013003520 A1 | 1/2013 |
| WO | 2015188194 A1 | 12/2015 |
| WO | 2016077321 A1 | 5/2016 |
| WO | 2017027350 A2 | 2/2017 |

*Primary Examiner* — J. E. Angell
(74) *Attorney, Agent, or Firm* — Lin Yu; Wanli Tang; Juniv LLP

(57) ABSTRACT

The present invention relates to a novel compound and application thereof in the inhibition of HBV gene expression. The structure of the compound comprises an interfering nucleic acid for inhibiting HBV gene expression, transition points, and delivery chains of the interfering nucleic acid. By means of the delivery chains, two or three N-acetylgalactosamines can be introduced to an antisense strand 3' end of such siRNA, and two or one N-acetylgalactosamine can be correspondingly introduced to a sense strand 5' end, the total number of the introduced N-acetylgalactosamines being four. In vitro and in vivo pharmacological experiments prove that such a novel compound can continuously and efficiently inhibit HBV gene expression.

20 Claims, 6 Drawing Sheets
Specification includes a Sequence Listing.

COMPOUND AND APPLICATION THEREOF

CROSS REFERENCE TO RELATED APPLICATIONS

This application is a continuation of U.S. application Ser. No. 17/623,569, which was the National Stage of International Application No. PCT/CN2020/097732, filed Jun. 23, 2020; which claims the benefit of Chinese Application No. 201910576037.1, filed Jun. 28, 2019, and Chinese Application No. 201911281389.0, filed Dec. 13, 2019; the disclosure of each of which is incorporated herein by reference in its entirety.

TECHNICAL FIELD

The present invention relates to a novel compound and its application in the inhibition of HBV gene expression. The structure of the compound comprises an interfering nucleic acid for inhibiting HBV gene expression, transition points and delivery chains of the interfering nucleic acid. By means of the delivery chains, such siRNA can be introduced with two to three N-acetylgalactosamines at the 3' end of the antisense strand, and correspondingly, two to one N-acetylgalactosamine at the 5' end of the sense strand, with the total number of the introduced N-acetylgalactosamines being four. Pharmacological experiments on HepG2 cells and transgenic mice demonstrate that, this novel compound can continuously inhibit the expression of HbsAg and HBeAg of HBV and HBV DNA.

REFERENCE TO A SEQUENCE LISTING

The present specification is being filed with a Sequence Listing in Computer Readable Form (CRF), which is entitled 413A001US02_SEQ_LIST_ST25.txt of 28,637 bytes in size and created Aug. 29, 2022; the content of which is incorporated herein by reference in its entirety.

BACKGROUND ART

RNAi

RNAi (RNA interference) was discovered in an antisense RNA inhibition experiment on *Caenorhabditis elegans* carried out by Andrew Z. Fire et al. in 1998, and this process was named as RNAi. This discovery was recognized by Science as one of the top ten scientific advances in 2001, and ranked the first on the list of the top ten scientific advances in 2002. Since then, siRNA with the mechanism of RNAi has attracted much attention as a potential genetic therapeutic drug. In 2006, Andrew Z. Fire and Craig C. Mello won the Nobel Prize for Physiology or Medicine for their contribution in the study of RNAi mechanism. RNAi can be triggered by double stranded RNA (dsRNA) in many organisms, including animals, plants and fungi. In the process of RNAi, a long-chain dsRNA is cleaved or "diced" into small fragments of 21 to 25 nucleotides in length by an endonuclease known as "Dicer". These small fragments are known as small interfering RNA (siRNA), in which the antisense strand (Guide strand) is loaded onto Argonaute protein (AGO2). AGO2 loading occurs in a RISC-loading complex, which is a ternary complex composed of an Argonaute protein, a Dicer and a dsRNA binding protein (briefly referred as TRBP). In the process of loading, the sense strands (Passenger strand) are cleaved by AGO2 and discharged. Then, AGO2 utilizes the antisense strands to bind to mRNAs containing complete complementary sequences, and catalyzes the cleavage of these mRNAs, such that mRNAs are cleaved to lose their function of translation template, which in turn prevents the synthesis of related proteins. After cleavage, the cleaved mRNAs are released, and the RISC-loading complex loaded with the antisense strand was recycled into another round of cleavage.

According to statistics, among disease-related proteins in human body, more than about 80% of proteins cannot be targeted by currently conventional small molecule drugs and biological macromolecules, so they belong to undruggable proteins. Gene therapy, aiming to treat diseases through gene expression, silencing and other functions, is regarded in the industry as the third generation of therapeutic drugs following small chemical molecule drugs and biological macromolecules. Such therapy realizes the treatment of diseases at the genetic level and is not restricted by undruggable proteins. As the most mainstream type in gene therapy, RNAi technology treats diseases at mRNA level, with much higher efficiency compared with the treatment by small chemical molecule drugs and biological macromolecules at protein level. By use of RNAi technology, sequences for sense strands and antisense strands of siRNA with high specificity and effective inhibition can be designed according to particular gene sequences, and these single-strand sequences may be synthesized in solid phase, and then the sense strands and the antisense strands are hybridized following the principle of base pairing in a particular annealing buffer into siRNA, which is finally delivered to corresponding target points in vivo through a carrier system to degrade the targeted mRNA and destroy the function of the targeted mRNA as translation template, thereby blocking the synthesis of corresponding proteins.

Delivery System of siRNA siRNA is labile in blood and tissues and prone to be degraded by nucleases. To improve the stability of siRNA, the skeleton of siRNA can be modified. However, these chemical modifications only provide limited protection from nuclease degradation and may eventually affect the activity of siRNA. Therefore, a delivery system is further needed to ensure that siRNA can cross cell membranes efficiently. Because siRNA has a large molecular mass with a large amount of negative charges and a high solubility in water, they cannot cross the cell membranes to get into the cells.

A liposome has a basic structure consisting of a hydrophilic nucleus and a phospholipid bilayer. Due to the similarity and high biocompatibility of phospholipid bilayer to a biological membrane, liposome was once the most popular and widely used siRNA carrier. In liposome-mediated siRNA delivery, siRNA is mainly encapsulated inside the liposome to protect the siRNA from nuclease degradation, thus improving the efficiency of siRNA passing the cell membrane barriers and promoting the uptake of cells. Liposome includes e.g., anionic liposomes, pH-sensitive liposomes, immunoliposomes, fusogenic liposomes and cationic liposomes and the like. Although some progresses have been made, liposomes themselves are prone to triggering an inflammatory response, so before administration of a liposome, various antihistamine and hormone drugs, such as Cetirizine and dexamethasone, must be used so as to reduce acute inflammatory responses that may occur. Therefore, liposomes are not suitable for all therapeutic areas in practical clinical applications, especially diseases with long treatment cycles such as chronic hepatitis B, and the cumulative toxicity that may be generated from long-term use is a potential safety hazard.

Asialoglycoprotein Receptor (ASGPR)

The asialoglycoprotein receptor (ASGPR) in liver is a receptor specifically expressed in liver cells, and a highly efficient endocytic receptor. Because the secondary end of various glycoproteins exposed by enzymatic or acid hydrolysis of sialic acid under physiological conditions in vivo is a galactose residue, the sugar specifically bound by ASGPR is galactosyl, and ASGPR is also known as a galactose-specific receptor. Monosaccharide and polysaccharide molecules, such as galactose, galactosamine, N-acetylgalactosamine and the like, have a high affinity to ASGPR. The main physiological function of ASGPR is to mediate the removal of asialoglycoprotein, lipoprotein and other substances from the blood, and it is closely related to the occurrence and development of viral hepatitis, liver cirrhosis, liver cancer and other liver diseases. The discovered property of ASGPR has an important effect on the diagnosis and treatment of liver-derived diseases (Ashwell G, Harford J, Carbohydrate specific Receptors of the Liver, Ann Rev Biochem 1982 51:531-554). Therapeutic drugs containing galactose or galactosamine or derivatives thereof in their structures for treating liver-derived diseases may have a specific affinity with ASGPR, so that they may have an active hepatic targeting property, without the need of other carrier systems for delivery.

SUMMARY OF THE INVENTION

The present invention relates to a novel compound and an application thereof in the inhibition of HBV gene expression. The structure of the compound comprises an interfering nucleic acid for inhibiting HBV gene expression, transition points and delivery chains of the interfering nucleic acid. The delivery chains are linked to the interfering nucleic acid through transition points. By means of the delivery chains, such siRNA can be introduced with two or three N-acetylgalactosamines at the 3' end of the antisense strand, and correspondingly, two or one N-acetylgalactosamine at 5' end of the sense strand, with a total number of N-acetylgalactosamines being four, which is a completely novel introduction manner. In vitro and in vivo pharmacological experiments demonstrate that, this novel compound can continuously and efficiently inhibit the expression of HBsAg, HBeAg of HBV and HBV DNA.

In one aspect, the present invention provides a compound comprising an interfering nucleic acid for inhibiting HBV gene expression, transition points and delivery chains of the interfering nucleic acid in its structure, wherein the delivery chains consist of a linking chain D, a linker B, a branched chain L and a liver targeting specific ligand X and are linked to the interfering nucleic acid through transition points $R_1/R_2$, wherein the compound has a structure of formula (I):

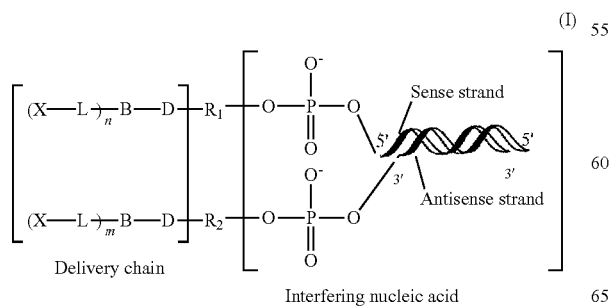

wherein:

when n is 1, m is 3; when n is 2, m is also 2;

$R_1$ is —NH(CH$_2$)$_x$CH$_2$—, wherein x may be an integer of 3-10;

$R_2$ is —NHCH$_2$CH(OH)CH$_2$—, or another nitrogen-containing structure with both primary and secondary alcohol moieties or only primary alcohol moieties, which may be a linear chain or a linear chain with one or more branched chains, and may also be a cyclic structure, preferably, $R_2$ may be a pyrrole or piperidine ring with primary and secondary alcohol moieties, and specifically, $R_2$ is selected from the following structures:

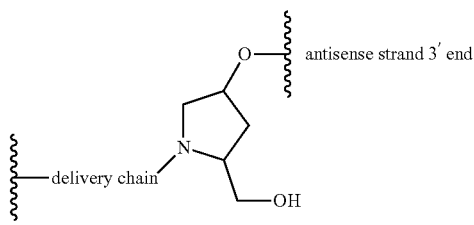

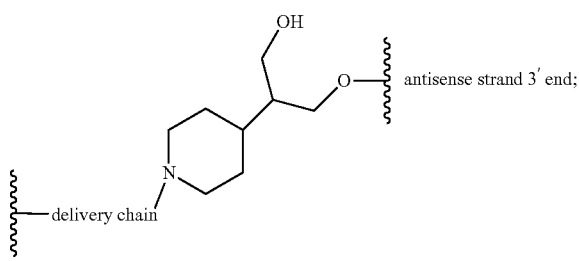

the liver targeting specific ligand X is selected from galactose, galactosamine and N-acetylgalactosamine;

the branched chain L is a C3-C18 linear chain containing carbonyl, amido, phosphoryl, oxygen atom or a combination of these groups;

the linker B is selected from the following structural formulae:

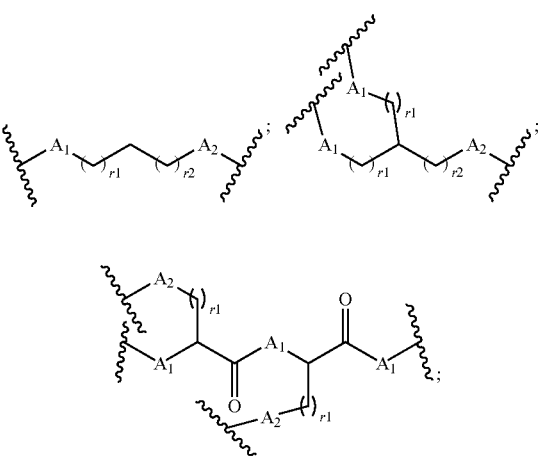

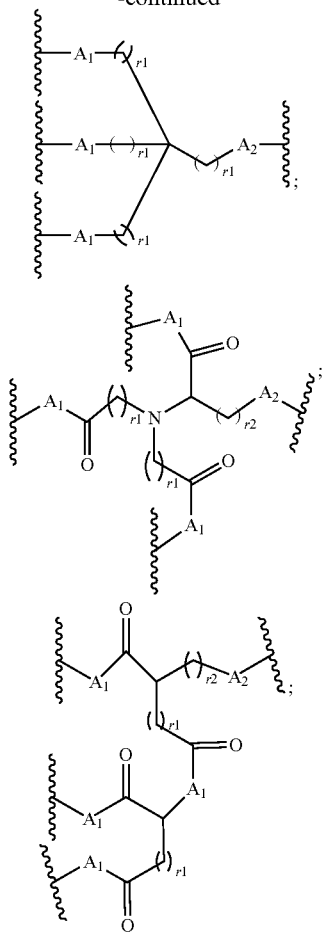

wherein, $A_1$ is C, O, S or NH; r1 is a positive integer of 1-15, r2 is an integer of 0-5; $A_2$ is C, O, S, amino, carbonyl, amido, phosphoryl or thiophosphoryl;

the linking chain D contains 5 to 20 carbon atoms, and contains amino, carbonyl, amido, oxygen atom, sulphur atom, thiophosphoryl, phosphoryl, cyclic structure or a combination of these groups.

In the above technical solution, the interfering nucleic acid includes, but not limited to, siRNA, miRNA and Agomir, preferably is a siRNA, further preferably is an anti-hepatitis B virus siRNA.

The sequence of the siRNA used for 19 mer of HBV RNAi is designed according to the target sequences of HBV cDNA (GenBankAccession #AF100309.1). These target sequences include 19 mer del core areas and corresponding extended or shifted DNA sequences dominated by these core areas. It intends to find optimal efficient sequences through basic target sites, and part or all of these sequences can be suitable for the target sites, and can be applied to treatment of chronic hepatitis B. The 19 mer nucleotide sequence at the target site comprises two strands, a sense strand (S) and an antisense strand (AS), wherein, the $19^{th}$ nucleotide (5'→3') on the sense strand can form a base pair with the first nucleotide (5'→3') on the antisense strand according to the Watson-Crick principle. Following this principle, the $1^{st}$ to $19^{th}$ bases of the sense strand (5'→3') and the $19^{th}$ to $1^{st}$ bases of the antisense strand (5'→3') can form a double strand by pairing with their corresponding bases. One to three unpaired bases can be allowed at the ends of the double strand. In the present invention, HBV siRNA basic sequences can be screened according to practical applications. Through 3' or 5' end displacement on the basis of the basic sequence, more efficient and specific sequences can be screened. According to the study results on the siRNA structure, the optimal choice for the single-strand protrusion at the 3' end of the sense strand or antisense strand is TT, UU, AU or UA, and thus varied sequences are obtained. Any one of the sense strands can be used to form a double strand with an antisense strand, in which the two strands must maintain at least 16, 17, 18, 19, 20, 21, 22 or 23 continuous base pairs. Some of the listed sequences may differ from the target site by 1, 2 or 3 bases, and the last base at the 3' end of the sense strand may be U, A or T. The last base at 3' end of the antisense strand may be U, A or T. Following the above principle, the following candidate sequences are screened in the present invention:

| Targeting position of first nucleotide | SEQ ID No. | Sense strand (5'→3') (without a protective base moiety such as TT, UU, UA) | SEQ ID No. | Antisense strand (5'→3') (without a protective base moiety such as TT, UU, UA) |
|---|---|---|---|---|
| 208 | SEQ ID NO: 1 | GGGUUUUCUUGUUGACAA | SEQ ID NO. 2 | UUGUCAACAAGAAAAACC |
| 209 | SEQ ID NO. 3 | GGUUUUCUUGUUGACAAA | SEQ ID NO. 4 | UUUGUCAACAAGAAAAAC |
| 210 | SEQ ID NO. 5 | GUUUUCUUGUUGACAAAA | SEQ ID NO. 6 | UUUUGUCAACAAGAAAAA C |
| 1575 | SEQ ID NOT | GACCGUGUGCACUUCGCUU | SEQ ID NO. 8 | AAGCGAAGUGCACACGGU C |
| 1576 | SEQ ID NO. 9 | ACCGUGUGCACUUCGCUUC | SEQ ID NO. 10 | GAAGCGAAGUGCACACGG U |
| 1577 | SEQ ID NO. 11 | CCGUGUGCACUUCGCUUCA | SEQ ID NO. 12 | UGAAGCGAAGUGCACACG G |
| 1578 | SEQ ID NO. 13 | CGUGUGCACUUCGCUUCAC | SEQ ID NO. 14 | GUGAAGCGAAGUGCACAC G |

-continued

| Targeting position of first nucleotide | SEQ ID No. | Sense strand (5'→3') (without a protective base moiety such as TT, UU, UA) | SEQ ID No. | Antisense strand (5'→3') (without a protective base moiety such as TT, UU, UA) |
|---|---|---|---|---|
| 1579 | SEQ ID NO. 15 | GUGUGCACUUCGCUUCACC | SEQ ID NO. 16 | GGUGAAGCGAAGUGCACAC |
| 1580 | SEQ ID NO. 17 | UGUGCACUUCGCUUCACCU | SEQ ID NO. 18 | AGGUGAAGCGAAGUGCACA |
| 1677 | SEQ ID NO. 19 | CAGCAAUGUCAACGACCGA | SEQ ID NO. 20 | GGUCGUUGACAUUGCUGA |
| 377 | SEQ ID NO. 21 | GGAUGUGUCUGCGGCGUUU | SEQ ID NO. 22 | AAACGCCGCAGACACAUC C |
| 376 | SEQ ID NO. 23 | UGGAUGUGUCUGCGGCGUU | SEQ ID NO. 24 | AACGCCGCAGACACAUCC A |
| 375 | SEQ ID NO. 25 | CUGGAUGUGUCUGCGGCGU | SEQ ID NO. 26 | ACGCCGCAGACACAUCCA G |
| 1522 | SEQ ID NO. 27 | CGGGGCGCACCUCUCUUUA | SEQ ID NO. 28 | UAAAGAGAGGUGCGCCCC G |
| 1523 | SEQ ID NO. 29 | GGGGCGCACCUCUCUUUAC | SEQ ID NO. 30 | GUAAAGAGAGGUGCGCCC C |
| 1525 | SEQ ID NO. 31 | GGCGCACCUCUCUUUACGC | SEQ ID NO. 32 | GCGUAAAGAGAGGUGCGC C |
| 1526 | SEQ ID NO. 33 | GCGCACCUCUCUUUACGCG | SEQ ID NO. 34 | CGCGUAAAGAGAGGUGCG C |
| 434 | SEQ ID NO. 35 | UCUUGUUGGUUCUUCUGGA | SEQ ID NO. 36 | UCCAGAAGAACCAACAAG A |
| 433 | SEQ ID NO. 37 | UUCUUGUUGGUUCUUCUGG | SEQ ID NO. 38 | CCAGAAGAACCAACAAGA A |
| 435 | SEQ ID NO. 39 | CUUGUUGGUUCUUCUGGAC | SEQ ID NO. 40 | GUCCAGAAGAACCAACAA G |
| 436 | SEQ ID NO. 41 | UUGUUGGUUCUUCUGGACU | SEQ ID NO. 42 | AGUCCAGAAGAACCAACA A |

For the stability of siRNA in tissues, each monomer of the siRNAs is modified under the conditions of no negative effects or even enhancing its activity. One, two or three incompletely paired bases are allowed in the sense strand and antisense strand. The nucleotides therein can carry different modifying groups and can be modified in the whole chain or in part. There may be one or more thio-bases in each strand, even all the bases are thio-bases.

In the compound of the present invention, the modified sense strand and antisense strand are selected from the following sequences:

| SEQ ID No. | Targeting position of first nucleotide | Sense strand (5'→3') | SEQ ID No. | Antisense strand (5'→3') |
|---|---|---|---|---|
| SEQ ID NO. 43 | 208 | mGsmGsmGmUmUmUfUmCfUfUmGmUmUmGmAmCmAmAsTsT | SEQ ID NO. 44 | mUsfUsmGmUmCfAmAfCfAfAmGmAmAfAfAfAmCmCmCsmUsmU |
| SEQ ID NO. 45 | 208 | mGsmGsmGmUmUmUfUmCfUfUmGmUmUmGmAmCmAmAsmUsmU | SEQ ID NO. 46 | mUsfUsmGmUfCmAfCfAmAmGmAfAfAfAmAmCmCmCsmAsmU |
| SEQ ID NO. 47 | 209 | mGsmGsmUmUmUmUfUmCfUfUfGmUmUmGmAmCmAmAsmAsmU | SEQ ID NO. 48 | mUsfUsmUmGmUfCfAfAmCmAmAfGfAfAfAmAmAmCmCsmUsmU |
| SEQ ID NO. 49 | 210 | mGsmUsmUmUmUmUfCmUfUfGfUmUmGmAmCmAmAmAsmUsmU | SEQ ID NO. 50 | mUsfUsmUmUmGfUmCfAfAfCmAmAmGfAfAfAmAmAmCsmUsmU |
| SEQ ID NO. 51 | 1575 | mGsfAsmCfCmGmUmGmUfGfCfAmCmUmUmCmGmCmUmUsmAsmU | SEQ ID NO. 52 | mAsfAsmGmCmGfAmAfGfUfGmCmAmCfAfCfGmGmUmUmCsTsT |

| SEQ ID No. | Targeting position of first nucleotide | Sense strand (5'→3') | SEQ ID No. | Antisense strand (5'→3') |
|---|---|---|---|---|
| SEQ ID NO. 53 | 1576 | mAsmCsmCmGmUfGmUfGfCfAmCmU mUmCmGmCmUmUmCsTsT | SEQ ID NO. 54 | mGsfAsmAmGmCfGmAfAfGfUmGmCm AfCfAfCmGmGmUsmUsmU |
| SEQ ID NO. 55 | 1576 | mAsfCsmCfGmUfGmUfGmCfAmCmUm UmCfGmCmUmUmCsmAsmU | SEQ ID NO. 56 | mGsfAsmAmGmCfGmAfAfGfUmGmCm AfCfAfCmGmGmUsTsT |
| SEQ ID NO. 57 | 1577 | mCsmCsmGmUmGmUfGmCfAfCfUmU mCmGmCmUmUmCmAsTsT | SEQ ID NO. 58 | mUsfGsmAmAmGfCmGfA fAfGmUmG mCfAfCfAmCmGmGsmUsmU |
| SEQ ID NO. 59 | 1578 | mCsmGmUmGmUmGfCmAfCfUfUmC mGmCmUmUmCmAmCsmUsmU | SEQ ID NO. 60 | mGsfUsmGmAmAfGmCfGfAfAmGmU mGfCfAfCmAmCmGsmUsmU |
| SEQ ID NO. 61 | 1579 | mGsmUsmUmGmUfGfCmAfCfUfUmCmG mCmUmUmCmAmCmCsmAsmU | SEQ ID NO. 62 | mGsfGsmUmGmAfAmGfCfGfAmAmG mUfGfCfAmCmAmCsmAsmU |
| SEQ ID NO. 63 | 1580 | mUsmGsmUmGmCmAfCmUfUfCfGfCm UmUmCmAmCmCmUsmAsmU | SEQ ID NO. 64 | mAsfGsmGmUmGfAmAfGfCfGmAmA mGfUfGfCmAmCmAsmAsmU |
| SEQ ID NO. 65 | 1677 | mCsmAsmCmCmAmAfUmGfUfCfAmA mCmGmAmCmCmGmAsmAsmU | SEQ ID NO. 66 | mGsfGsmUmCmGfUmUfGfAfCmAmUm UfGfCfUmGmAmAsmAsmU |
| SEQ ID NO. 67 | 377 | mGsmGsmAmUmGmUfGmUfCfUfGmC mGmCmCmGmUmUmUsmAsmU | SEQ ID NO. 68 | mAsfAsmAmCmGfCmCfGfCfAmGmAm CfAfCfAmUmCmCsTsT |
| SEQ ID NO. 69 | 376 | mUsmGsmAmAmUmGfUmGfUfCfUmG mCmGmCmCmGmUmUsmAsmU | SEQ ID NO. 70 | mAsfAsmCmGmCfCmGfCfAfGmAmCm AfCfAfUmCmCmAsTsT |
| SEQ ID NO. 71 | 375 | mCsmUsmGmAmAmUfGmUfGfUfCmU mGmCmGmCmCmGmUsmUsmA | SEQ ID NO. 72 | mAsfCsmGmCmCfGmCfAfGfAmCmAm CfAfUfCmCmAmGsTsT |
| SEQ ID NO. 73 | 1522 | mCsmGsmGmGmCmCfGmCfAfCfCmU mCmUmCmUmUmAsmUsmA | SEQ ID NO. 74 | mUsfAsmAmAmGfAmGfAfGfGmUmG mCfGfCfCmCmCmGsmUsmU |
| SEQ ID NO. 75 | 1522 | mCsfGsmGfGmGfCmGfCmAfCmCfUm CfUmCfUmUfUmAsmUsmU | SEQ ID NO. 76 | mUsfAsmAmAmGfAmGfAfGfGmUmG mCfGfCfCmCmCmGsTsT |
| SEQ ID NO. 77 | 1523 | mGsmGsmGmCmCmGfCmAfCfCfUmC mUmCmUmUmAmCsmUsmA | SEQ ID NO. 78 | mGsfUsmAmAfAmGfAfGmAfGmGmU mGfCfGfCmCmCmCsTsT |
| SEQ ID NO. 79 | 1525 | mGsmGsmCmGmCmAfCmCfUfCfUmC mUmUmAmCmGmCsmAsmU | SEQ ID NO. 80 | mGsfCsmGmUmAfAmGfAfGmGmG mGfUfGfCmGmCmCsTsT |
| SEQ ID NO. 81 | 1526 | mGsmCsmGmCmAmCfCmUfCfUfCmU mUmAmCmGmCmGsmUsmA | SEQ ID NO. 82 | mCsfGsmCmGmUfAmAfAfGfAmGmAm GfGfUfGmCmGmCsTsT |
| SEQ ID NO. 83 | 434 | mUsmCsmUmUmGmUfUmGfCfUfUmC mUmUmCmUmGmGmAsmAsmU | SEQ ID NO. 84 | mUsfCsmCmAmGfAmAfGfAfAmCmCm AfAfCfAmAmGmAsmUsmA |
| SEQ ID NO. 85 | 434 | mUsmCsfUmUmGmUfUmGfGfUfUmCm UmUmCmUmGmGmAsmUsmA | SEQ ID NO. 86 | mUsfCsmCmAmGfAmAfGfAfAmCmCm AfAfCfAmAmGmAsmAsmU |
| SEQ ID NO. 87 | 433 | mUsmUsmCmUmUfGmUfUfGfGmUmU mCmUmUmCmUmGmGsmAsmU | SEQ ID NO. 88 | mCsfCsmAmGmAfAmGfAfAfCmCmAm AfCfAfAmGmAmAsmAsmU |
| SEQ ID NO. 89 | 435 | mCsmUsmUmGmUmUfGmGfUfUfCmU mUmCmUmGmGmAmCsmUsmU | SEQ ID NO. 90 | mGsfUsmCmCmAfGmAfAfGfAmAmCm CfAfAfCmAmAmGsmUsmA |
| SEQ ID NO. 91 | 436 | mUsmUsmGmUmUfGmGfUfUfCmUmU mCmUmGmGmAmCmUsmAsmU | SEQ ID NO. 92 | mAsfGsmUmCmCfAmGfAmAfGmAmAm CfCfAfAmCmAmAsmAsmU | wherein:

mG, mA, mC and mU are 2'-methoxy (2'-OMe) modified nucleotides; fG, fA, fC and fU are 2'-fluoro modified nucleotides; s is an inter-nucleoside phosphorothioate bond, the rest of nucleotide monomers are linked through phosphodiester bonds. In particular:

G=guanosine, A=adenosine, U=uridylic acid, C=cytidylic acid, dT or T=2'-deoxythymidine nucleotide;

Gs=3'-thioguanosine, As=3'-thioadenosine, Us=3'-thiouridylic acid, Cs=3'-thiocytidylic acid, dTs or Ts=2'-deoxy-3'-thiothymidine nucleotide;

mG=2'-O-methylguanosine, mA=2'-O-methyladenosine, mU=2'-O-methyluridylic acid, mC=2'-O-methylcytidylic acid;

mGs=2'-O-methyl-3'-thioguanosine, mAs=2'-O-methyl-3'-thioadenosine, mUs=2'-O-methyl-3'-thiouridylic acid, mCs=2'-O-methyl-3'-thiocytidylic acid;

fG=2'-fluoroguanosine, fA=2'-fluoroadenosine, fU=2'-fluorouridylic acid, fC=2'-fluorocytidylic acid;

fGs=2'-fluoro-3'-thioguanosine, fAs=2'-fluoro-3'-thioadenosine, fUs=2'-fluoro-3'-thiouridylic acid, fCs=2'-fluoro-3'-thiocytidylic acid.

Further preferably, in some preferable embodiments, in the compound, the modified sense strand and antisense strand are selected from the following sequences:

| SEQ ID NO. | Targeting position of first nucleotide | Sense strand 5'→3' | SEQ ID NO. | Antisense strand 5'→3' |
|---|---|---|---|---|
| 43 | 208 | mGsmGsmGmUmUmUfUmUfCfUfUmGm UmUmGmAmCmAmAsTsT | 44 | mUsfUsmGmUmCfAmAfCfAfAmGmAmAfAfA fAmCmCmCsmUsmU |
| 49 | 210 | mGsmUsmUmUmUmUfCmUfUfGfUmUm GmAmCmAmAmAmAsmUsmU | 50 | mUsfUsmUmUmGfUmCfAfAfCmAmAmGfAfA fAmAmAmCsmUsmU |
| 51 | 1575 | mGsfAsmCfCmGmUmGmUfGfCfAmCmU mUmCmGmCmUmUsmAsmU | 52 | mAsfAsmCmGfAmAfGfUfGmCmAmCfAfC fGmGmUmCsTsT |
| 53 | 1576 | mAsmCsmCmGmUfGmUfGfCfAmCmUmU mCmGmCmUmUmCsTsT | 54 | mGsfAsmAmGmCfGmAfAfGfUmGmCmAfCfA fCmGmGmUsmUsmU |
| 59 | 1578 | mCsmGsmUmGmUmGfCmAfCfUfUmCmG mCmUmUmCmAmCsmUsmU | 60 | mGsfUsmGmAmAfGmCfGfAfAmGmUmGfCfA fCmAmCmGsmUsmU |
| 63 | 1580 | mUsmGsmUmGmCmAfCmUfUfCfGfCmU mUmCmAmCmUmsmAsmU | 64 | mAsfGsmGmUmGfAmAfGfCfGmAmAmGfUf GfCmAmCmAsmAsmU |
| 75 | 1522 | mCsfGsmGfGmGfCmGfCmAfCmCfUmCfU mCfUmUfUmAsmUsmU | 76 | mUsfAsmAmAmGfAmGfAfGfGmUmGmCfGfC fCmCmCmGsTsT |
| 79 | 1525 | mGsmGsmCmGmCmAfCmCfUfCfUmCmU mUmUmAmCmGmCsmAsmU | 80 | mGsfCsmGmUmAfAmAfGfAfGmAmGmGfUf GfCmGmCmCsTsT |

The delivery chains consist of a linking chain D, a linker B, a branched chain L containing a structure for stabilizing steric hindrance and a liver targeting specific ligand X, and the delivery chains are represented by formula (II) as below:

$$[(X-L)_{n\ or\ m}B-D]-.$$

When n=1, the formula (II) is:

$$[X-L-B-D]-.$$

When n or m=2, the formula (II) is:

$$\begin{bmatrix} X-L \\ X-L \end{bmatrix} B-D \Big]-.$$

When m=3, the formula (II) is:

$$\begin{bmatrix} X-L \\ X-L \\ X-L \end{bmatrix} B-D \Big]-.$$

The liver targeting specific ligand X may be one or more polysaccharides, polysaccharide derivatives or monosaccharides and monosaccharide derivatives.

Preferably, the liver targeting specific ligand X is represented by formula (III) as below:

(III)

[Structure of formula (III): sugar with OR$_1$, R$_2$O, R$_3$O, HN-acetyl groups]

wherein, R$_1$, R$_2$ and R$_3$ are hydrogen or a hydroxy protective group, respectively.

Further preferably, the liver targeting specific ligand X is one or more structures selected from the group consisting of galactose, galactosamine, N-acetylgalactosamine and the following structures:

[Four sugar structures with OH, HO, and R$_1$ substituents]

-continued

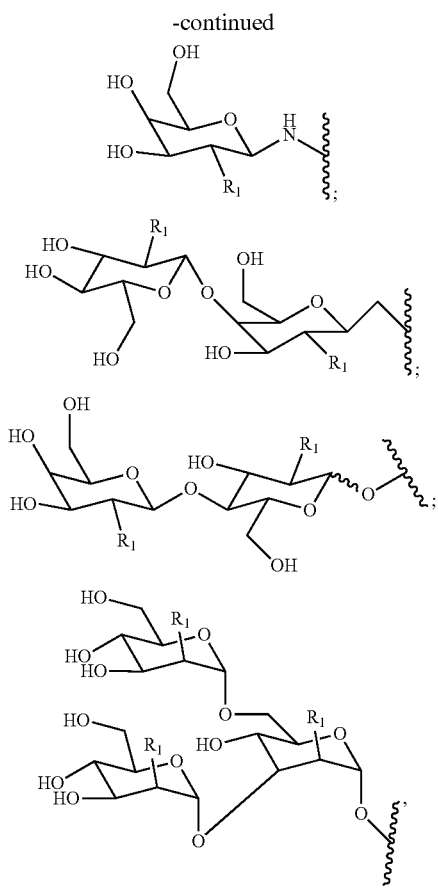

wherein, R₁s are one or two groups selected from the group consisting of OH, NHCOH and NHCOCH₃.

The branched chain L containing a structure for stabilizing steric hindrance is a C3-C18 linear chain containing one or more carbonyl, amido, phosphoryl, oxygen atom or a combination of these groups, and may be one or more structures selected from the following structures:

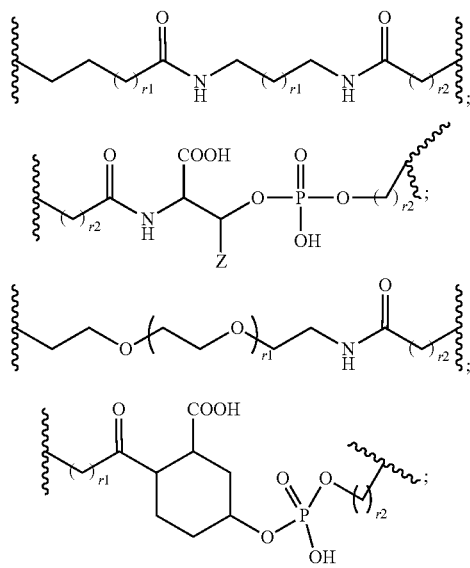

-continued

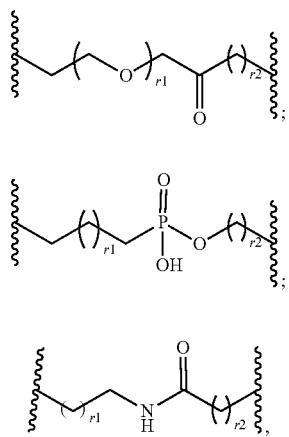

wherein, r1 is a positive integer of 1-12, r2 is an integer of 0-20, Z is H or CH₃.

The linker B is selected from the following formulae:

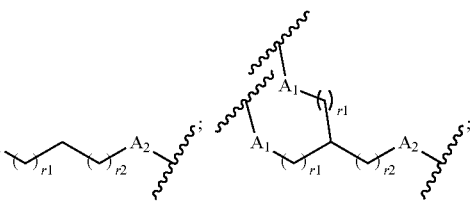

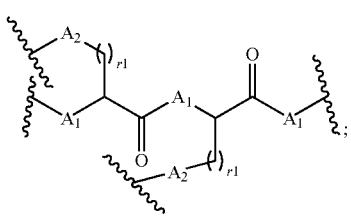

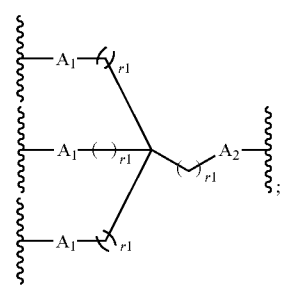

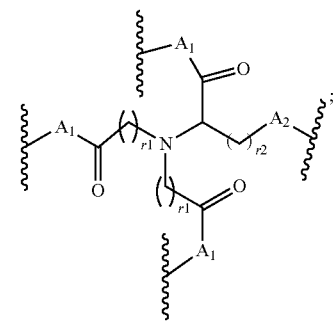

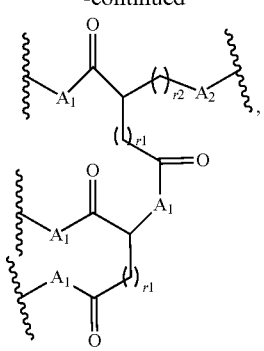
wherein, $A_1$ is C, O, S or NH; r1 is a positive integer of 1-15, r2 is an integer of 0-5; $A_2$ is C, O, S, NH, carbonyl, amido, phosphoryl or thiophosphoryl.
Preferably, the linker B is selected from the following formulae:
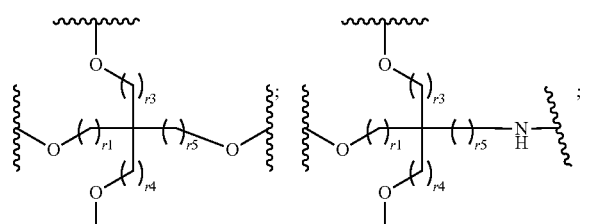
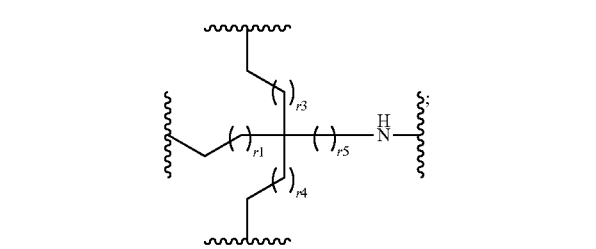
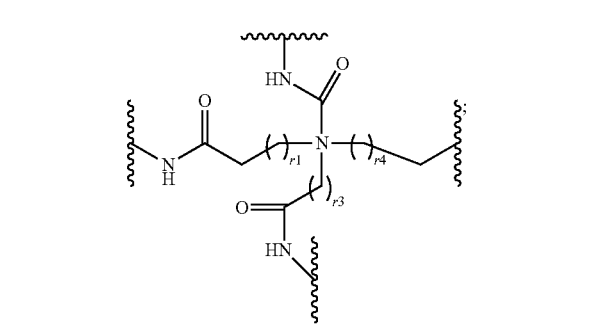
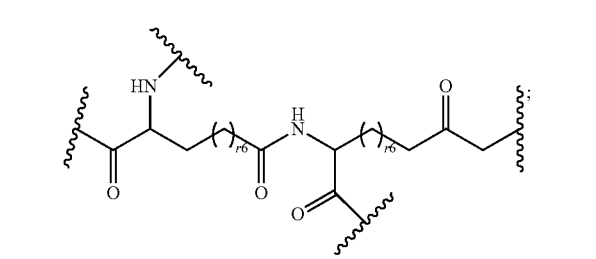
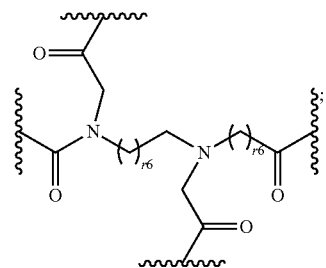
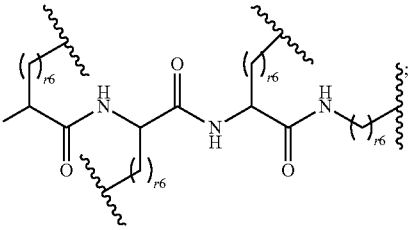
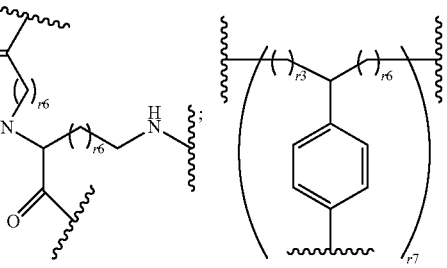
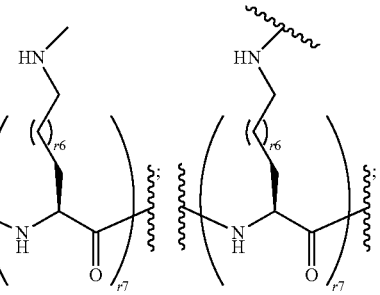

-continued
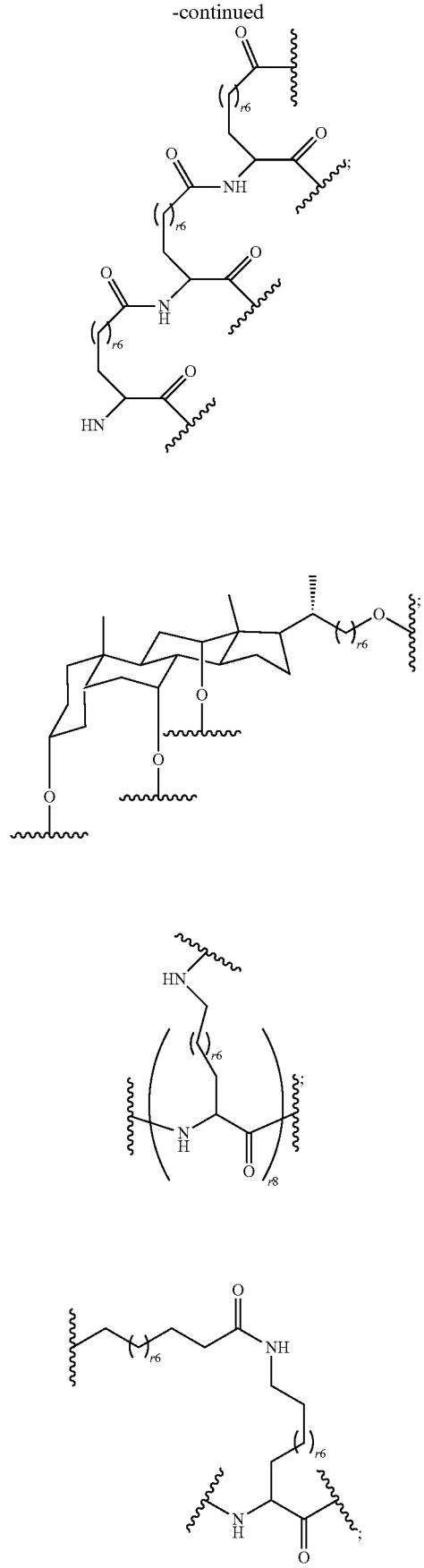
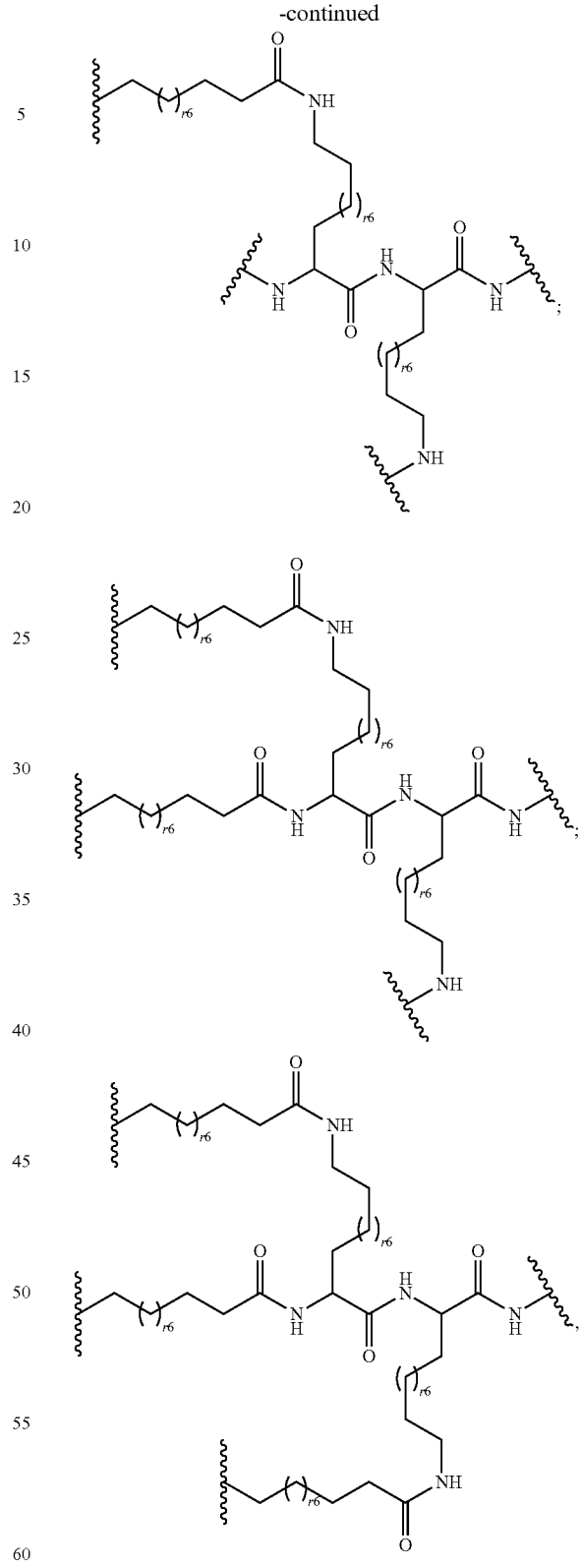
wherein, r1, r3, r4 and r5 are a positive integer of 1-15, respectively; r6 is a positive integer of 1-20, r7 is a positive integer of 2-6, r8 is a positive integer of 1-3.
Further preferably, the linker B is selected from the following structures:

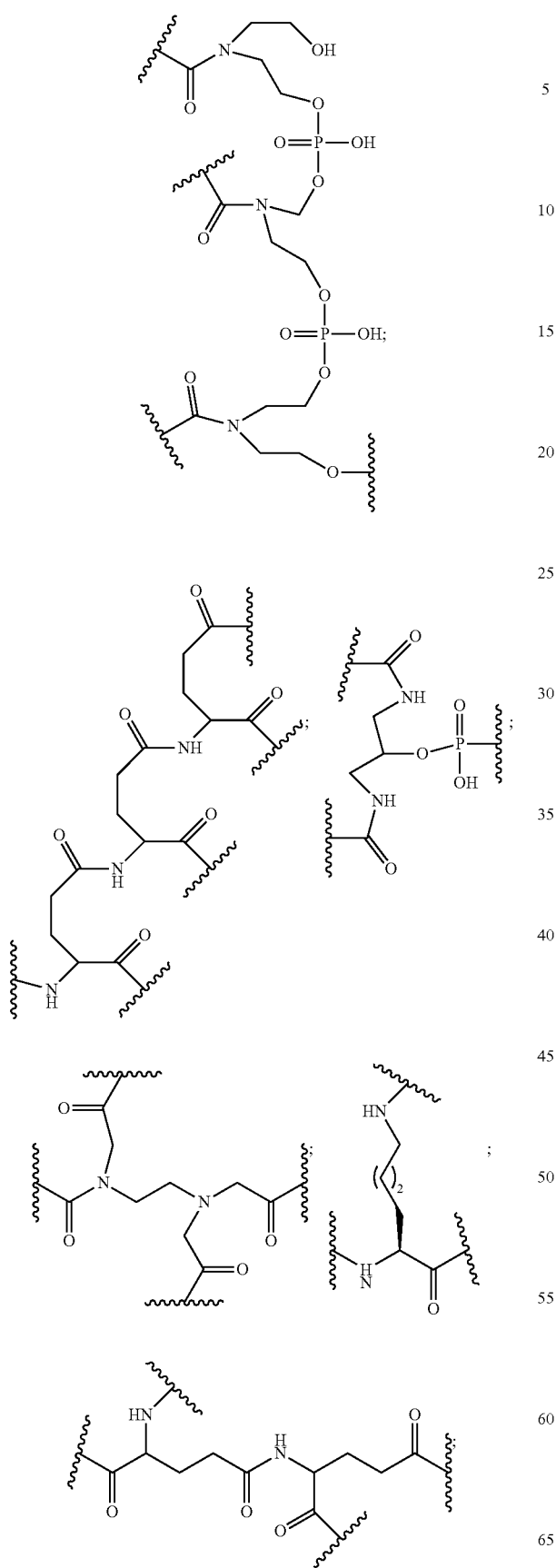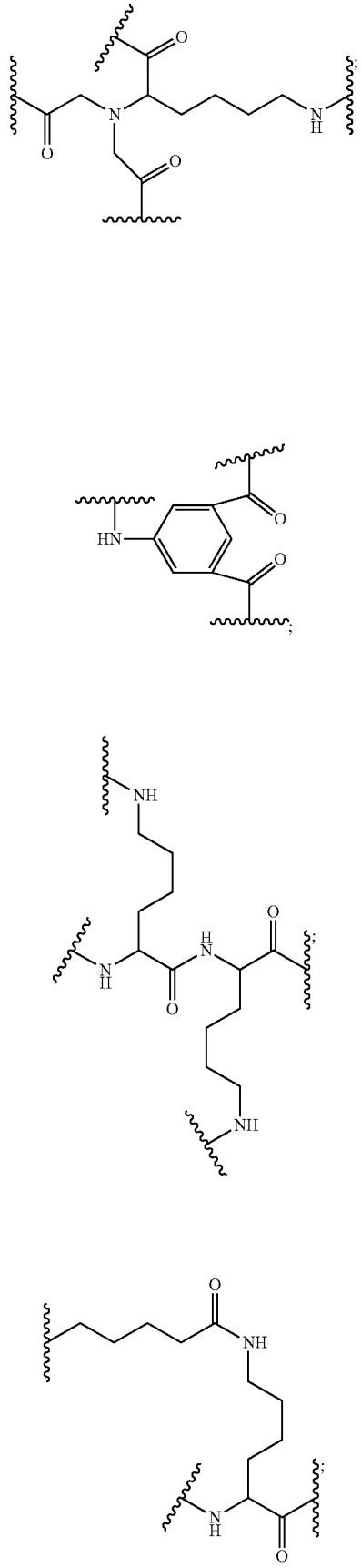

-continued
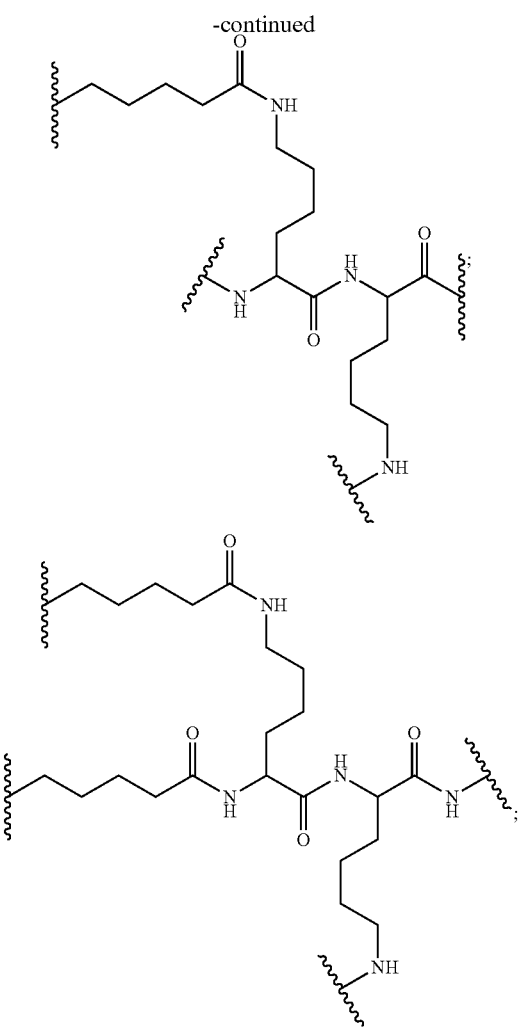
-continued
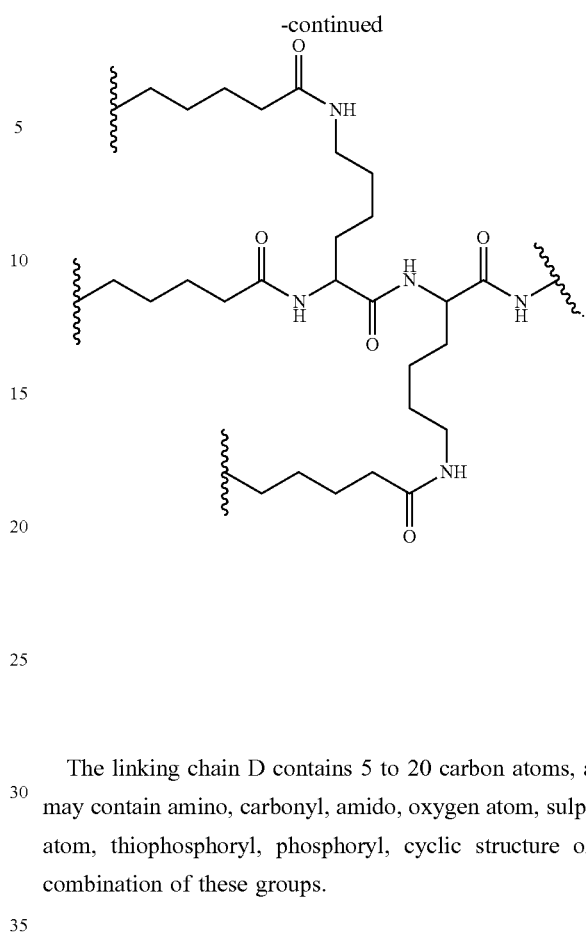
The linking chain D contains 5 to 20 carbon atoms, and may contain amino, carbonyl, amido, oxygen atom, sulphur atom, thiophosphoryl, phosphoryl, cyclic structure or a combination of these groups.
Preferably, the linking chain D is one selected from the following structures:
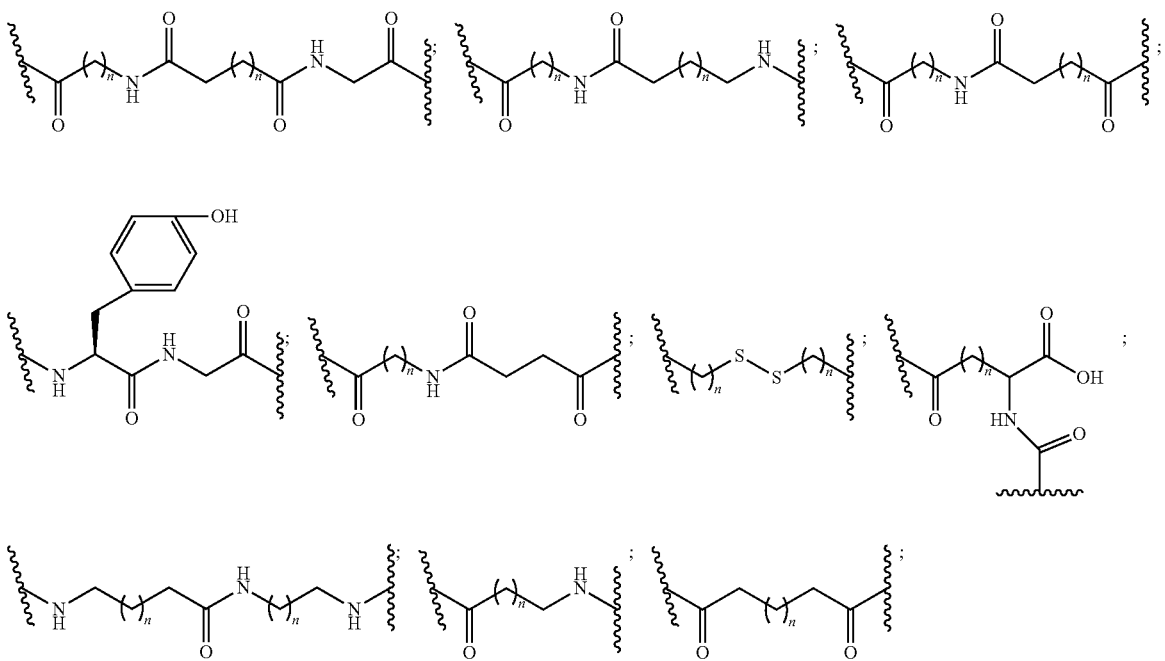

-continued
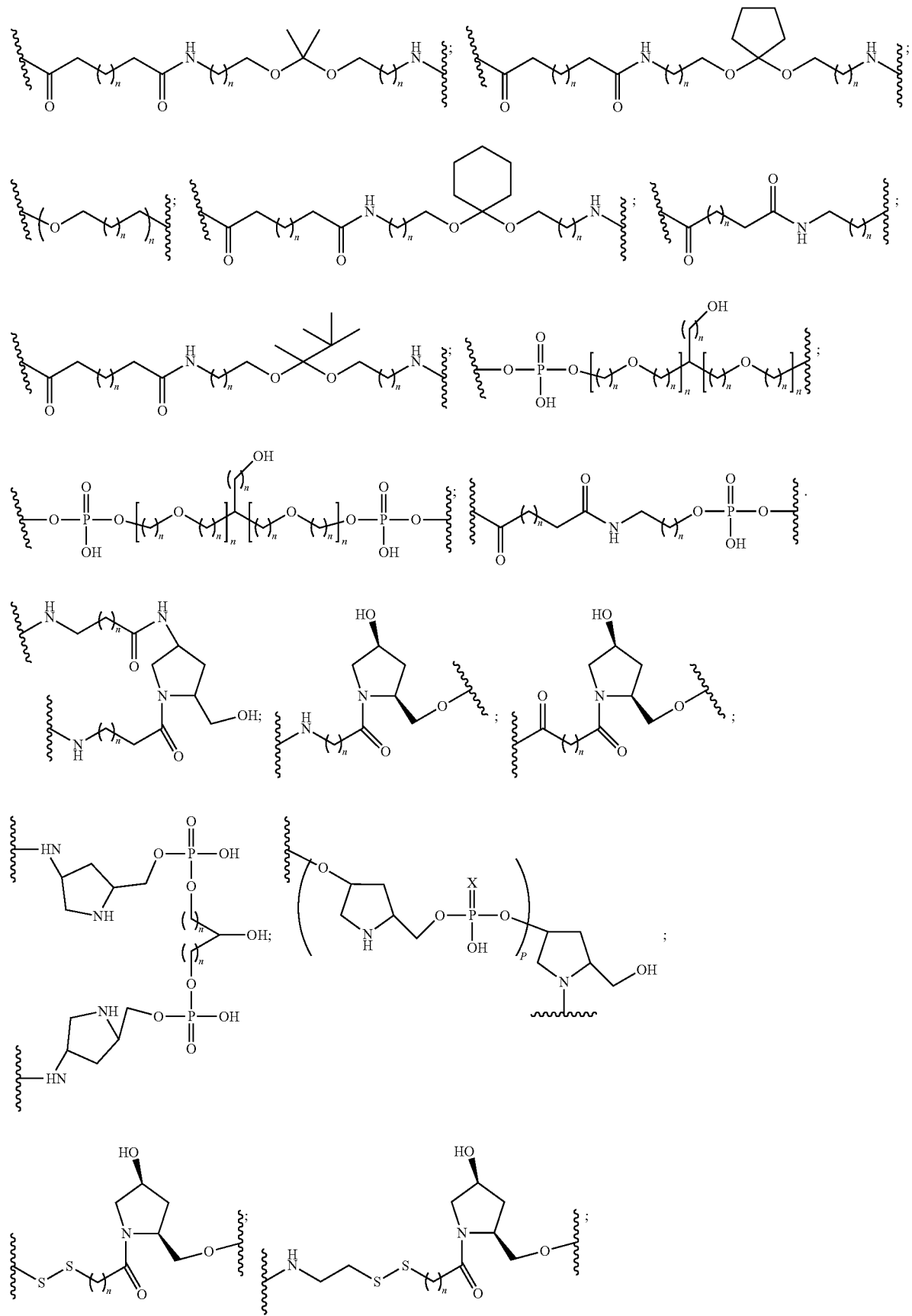

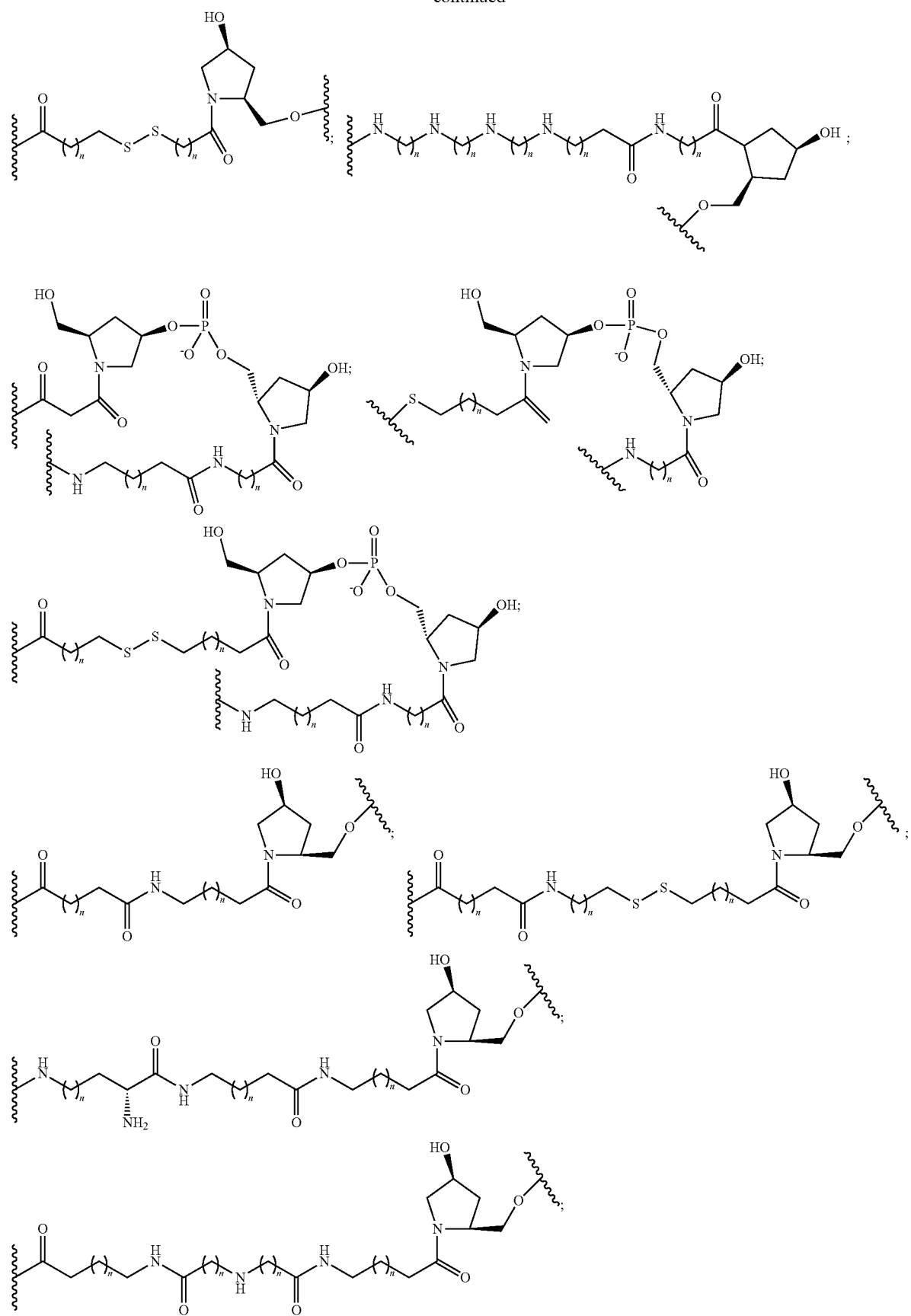

-continued wherein, each n is a positive integer of 1-20, and each n is the same or different positive integer, p is a positive integer of 1-6; s is a positive integer of 2-13; $R_1$ and $R_2$ are the same or different substituents represented by a formula selected from the following structures: —H, —$CH_3$, —CH—$(CH_3)_2$, —$CH_2$—CH$(CH_3)_2$, —CH$(CH_3)$—$CH_2$—$CH_3$, —$CH_2$—$C_6H_5$, —$C_8NH_6$, —$CH_2$—$C_6H_4$—OH, —$CH_2$—COOH, —$CH_2$—$CONH_2$, —$(CH_2)_2$—COOH, —$(CH_2)_4$—$NH_2$, —$(CH_2)_2$—$CONH_2$, —$(CH_2)$—S—$CH_3$, —$CH_2$—OH, —CH$(CH_3)$—OH, —$CH_2$—SH, —$CH_2$—$C_3H_3N_2$, —$(CH_2)_3$NHC(NH)$NH_2$.

Further preferably, the linking chain D is one selected from the following structures:

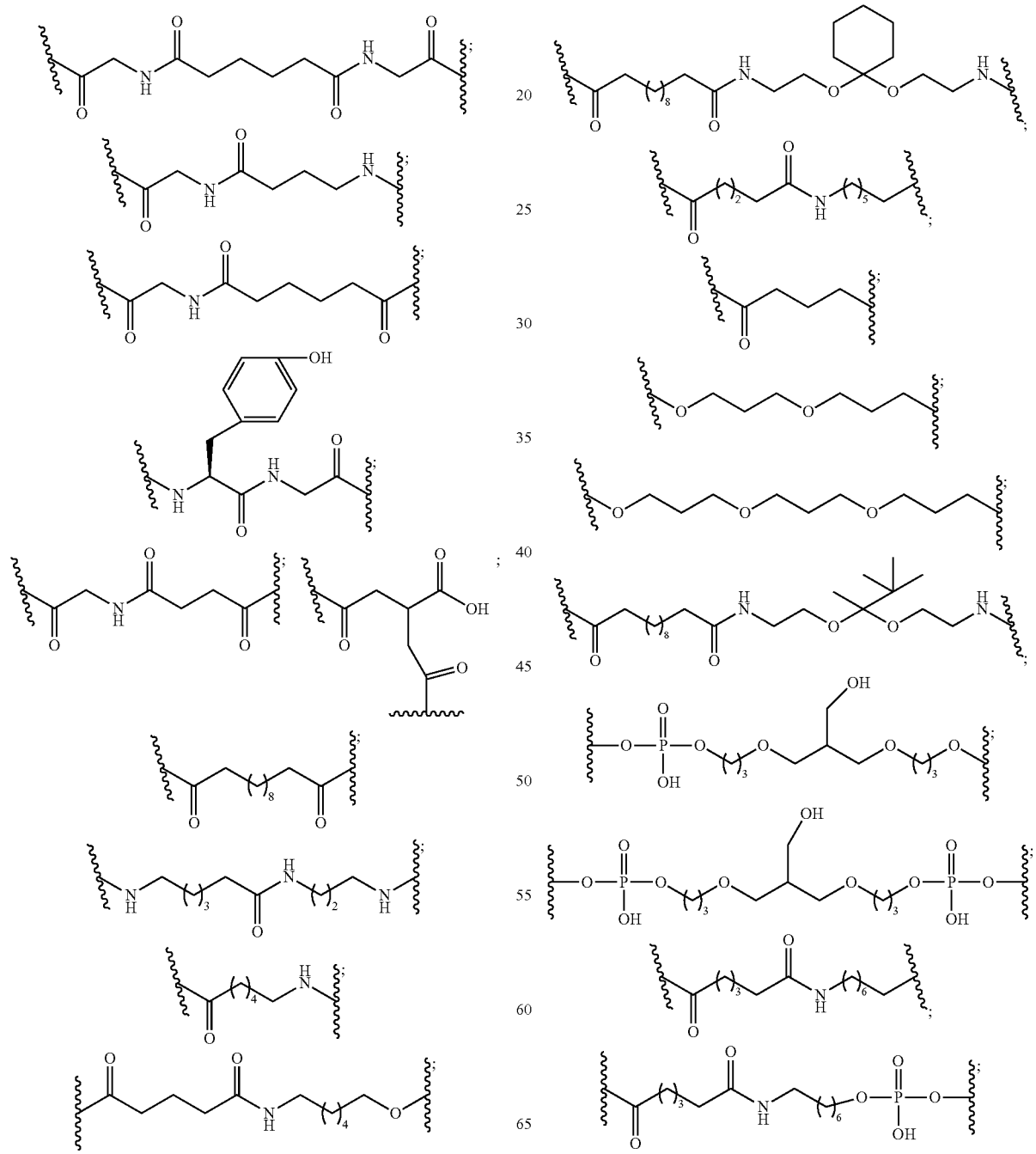

31
-continued
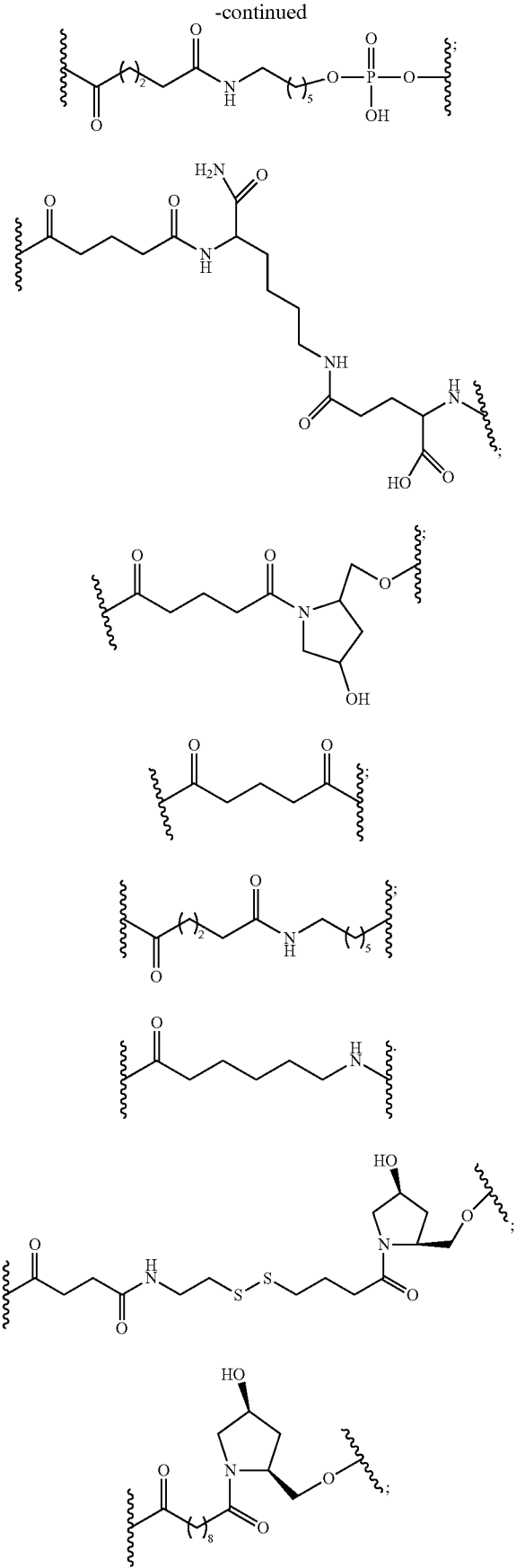
32
-continued
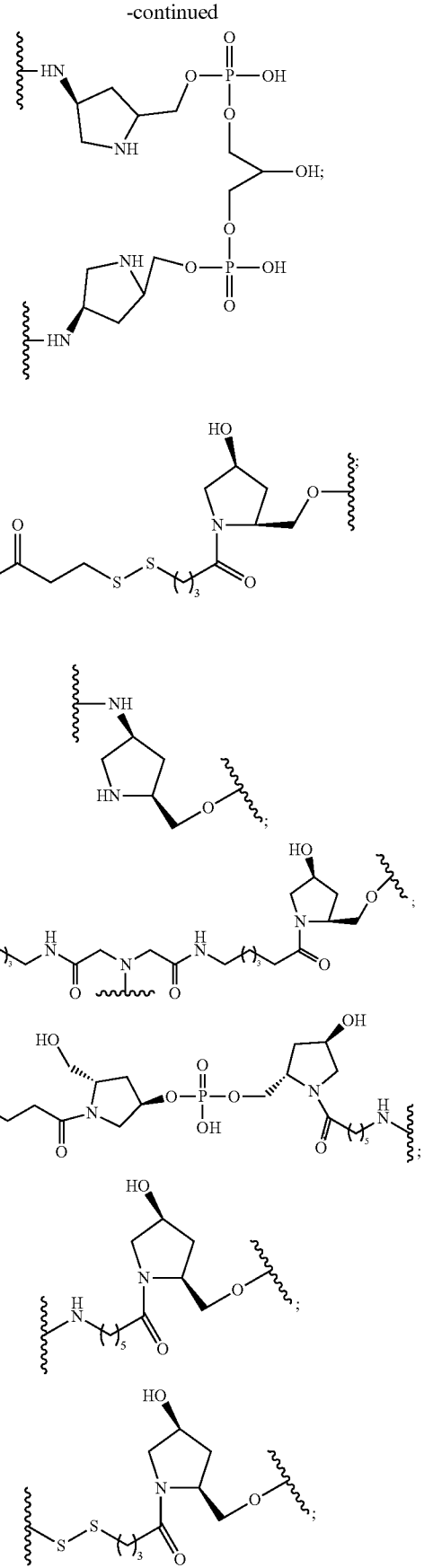

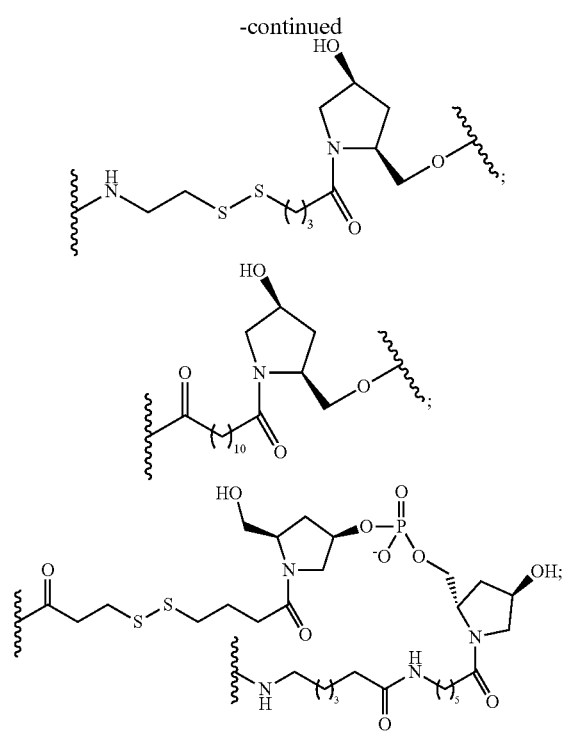
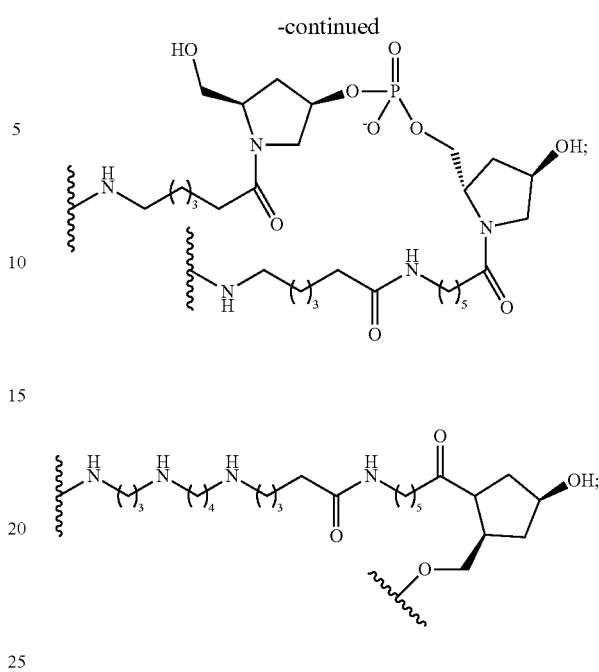
The delivery chain at the 5' end of the sense strand of the compound carries one or two N-acetylgalactosamines, and is one selected from the following structures:
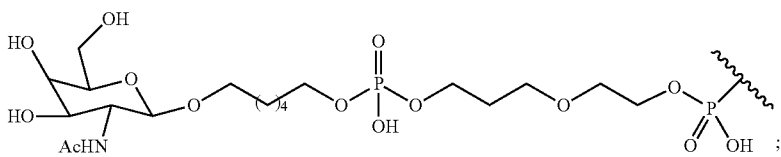
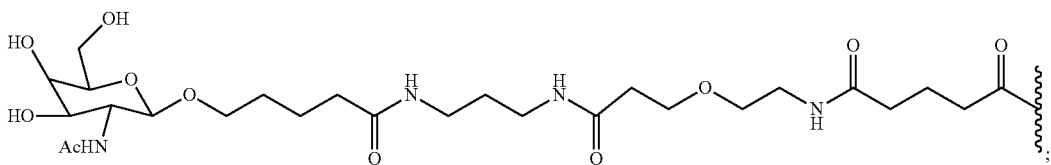
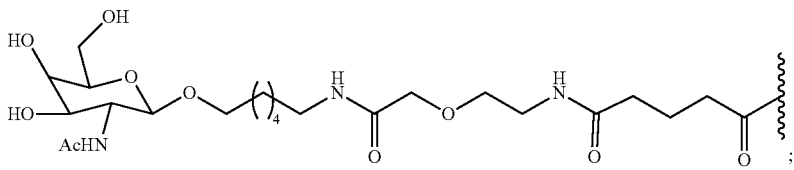
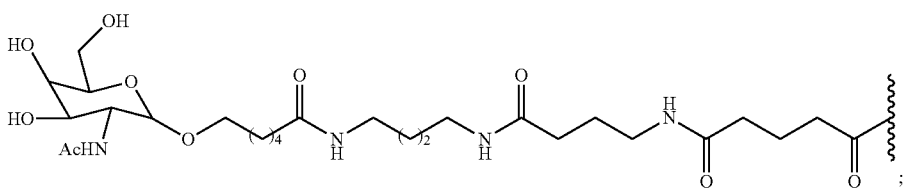
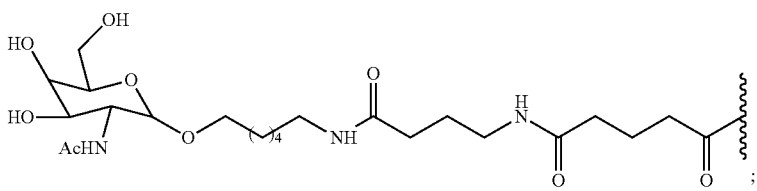

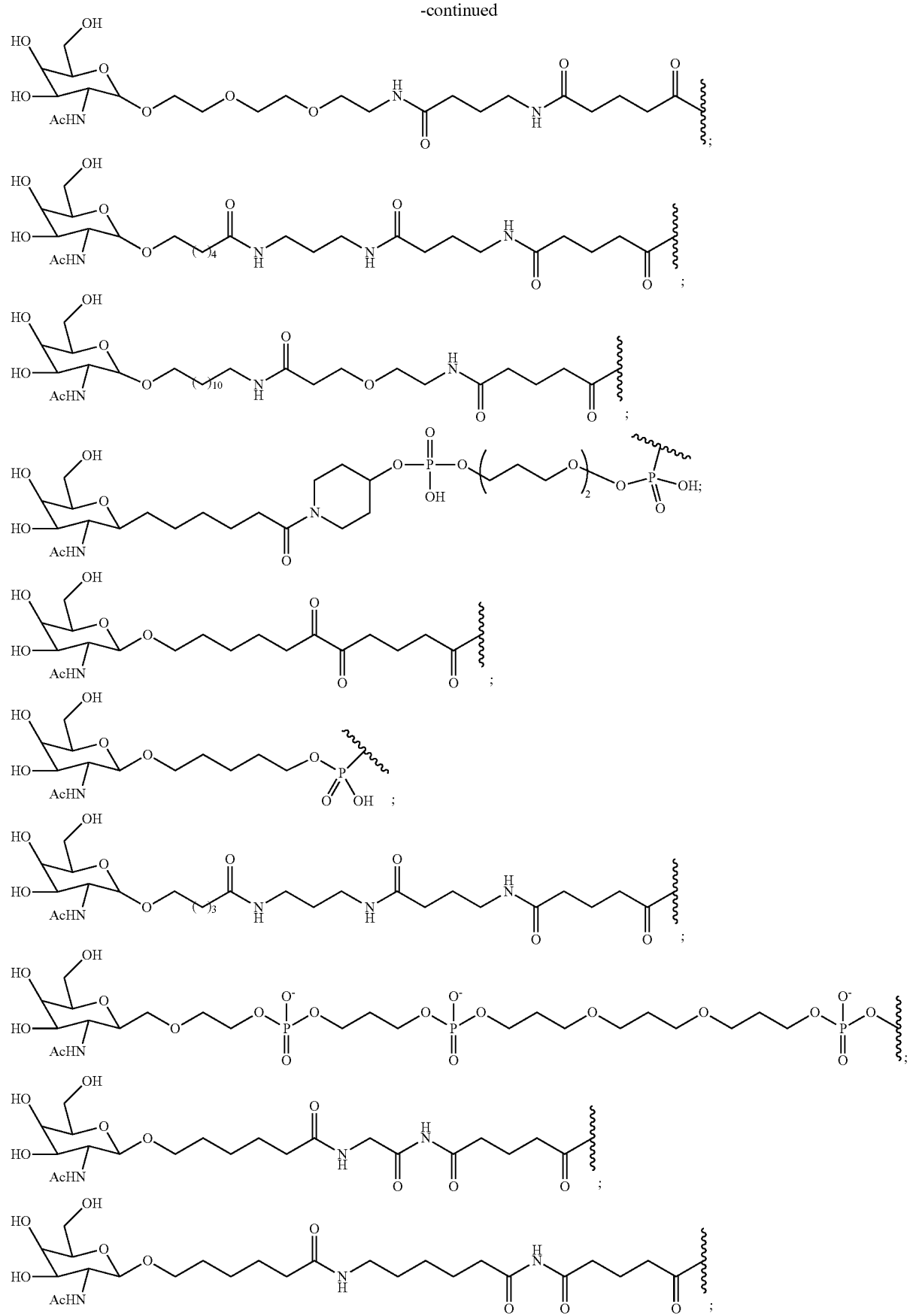

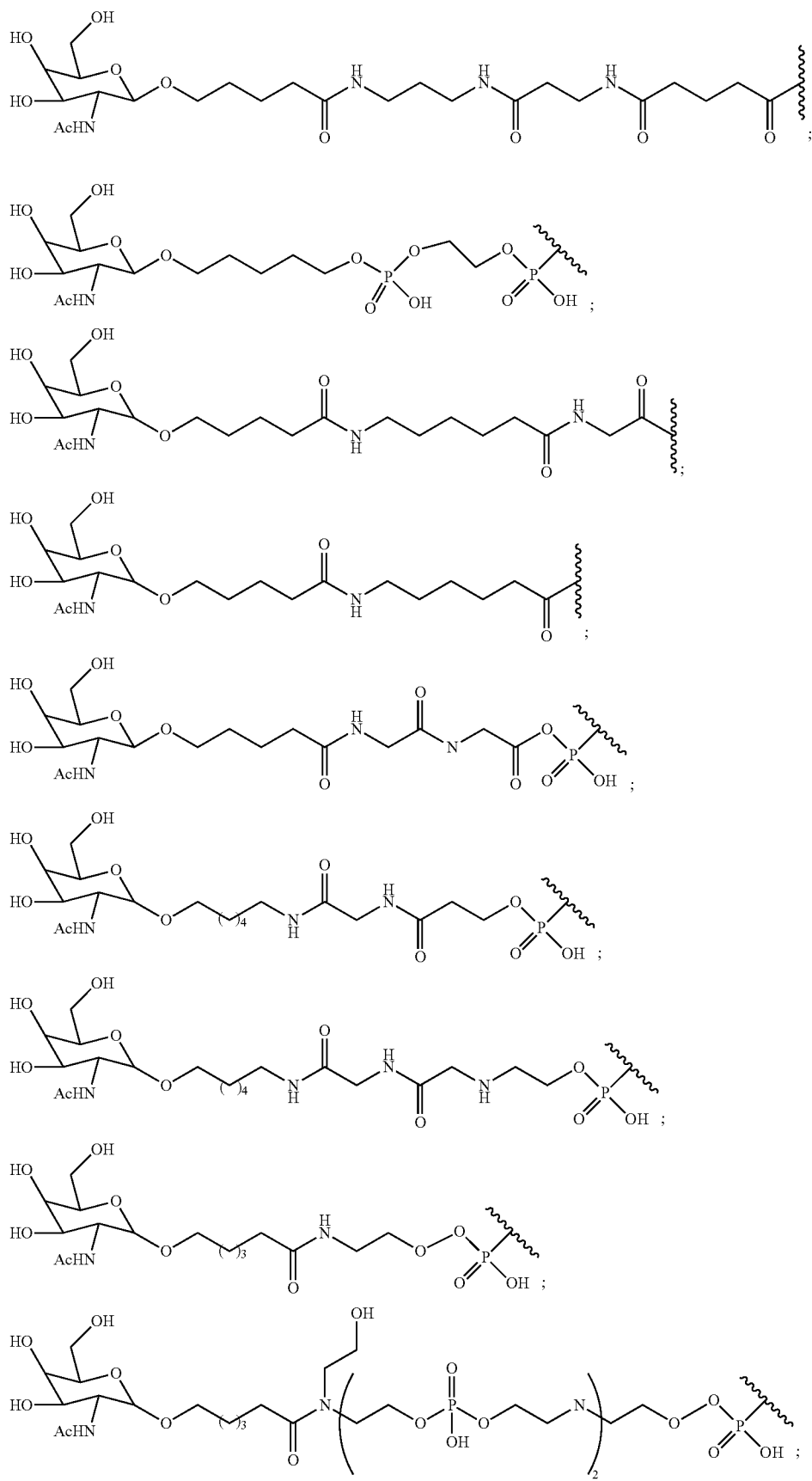

-continued
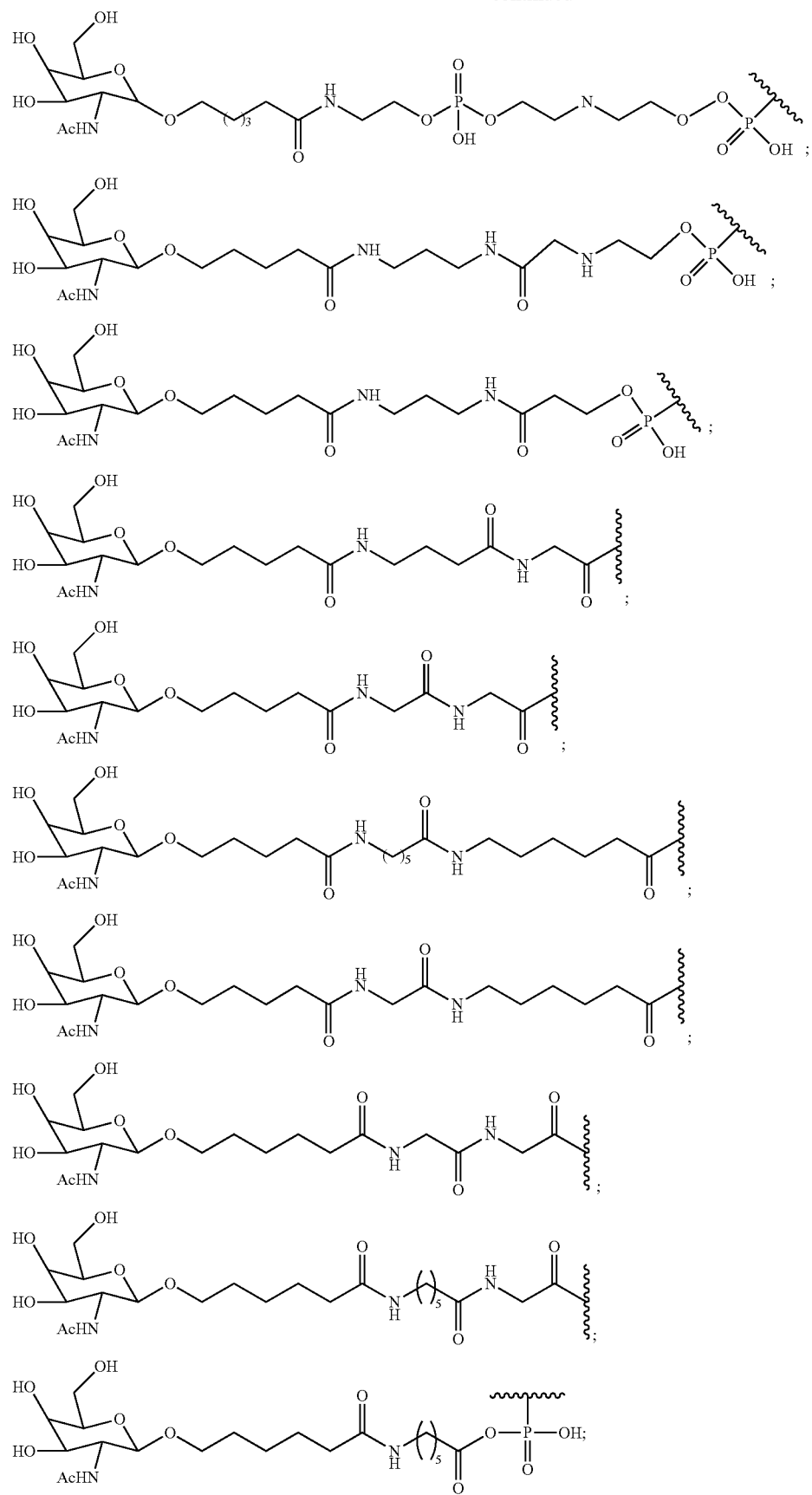

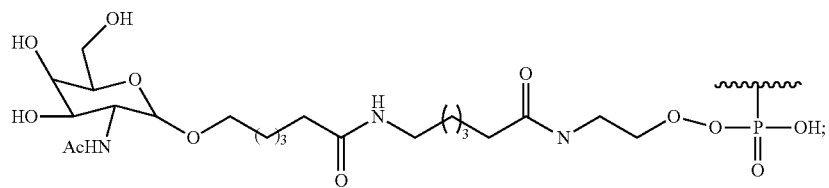
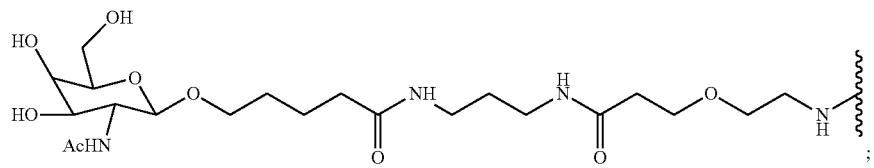
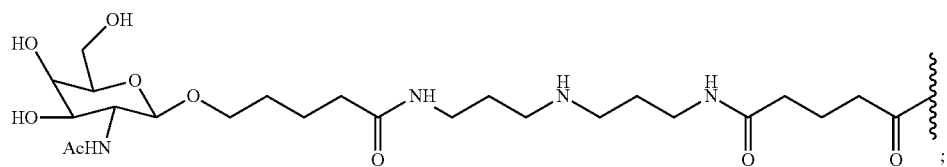
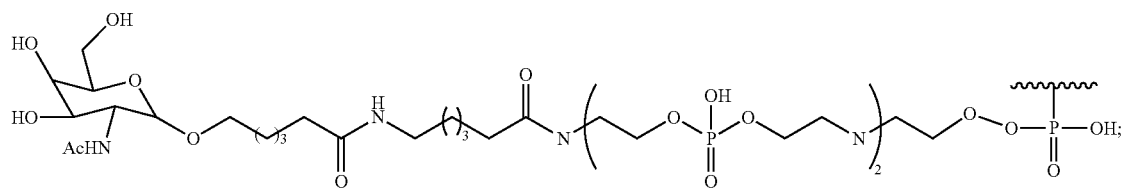
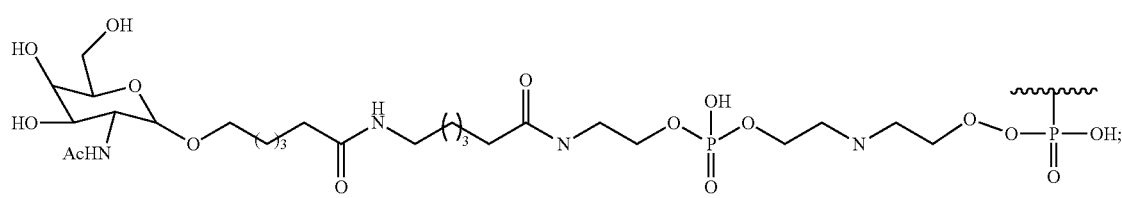
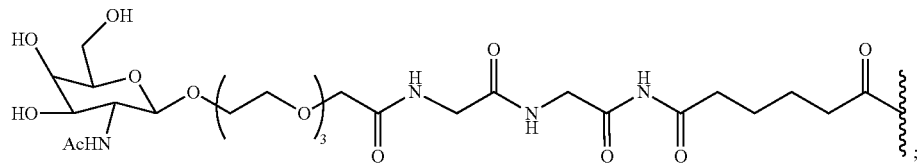
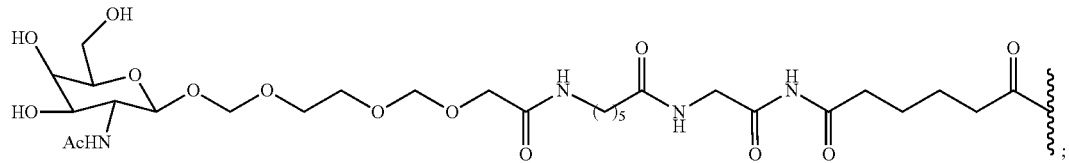
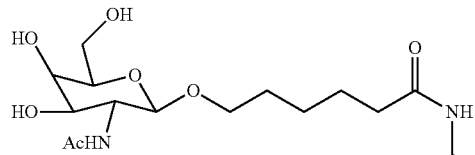
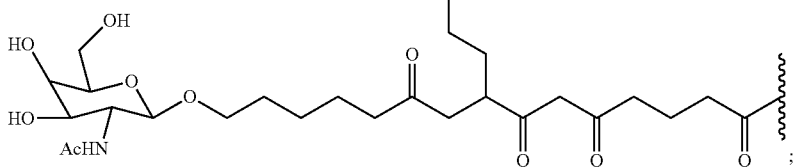

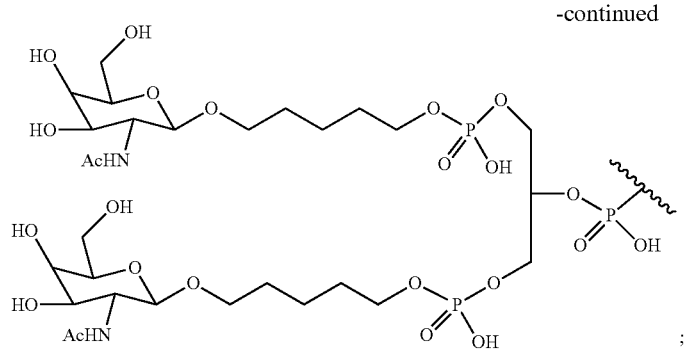
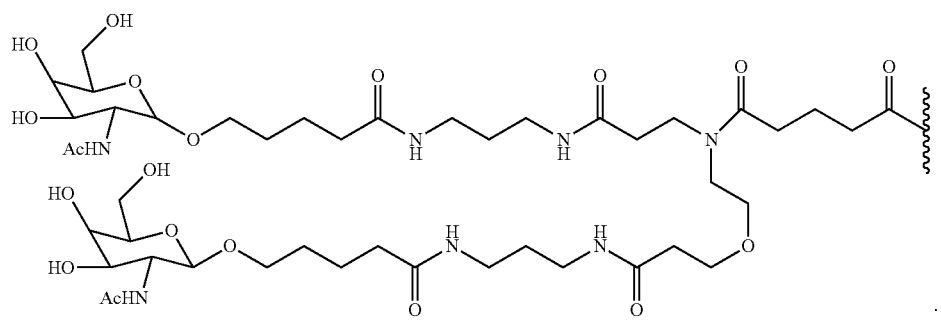
In some preferable examples, the delivery chain at the 5' end of the sense strand of the compound is selected from the formulae listed in the table below:
| Code of the delivery chain at the 5' end of the sense strand | Structure |
| --- | --- |
| 5'YICd-01 | 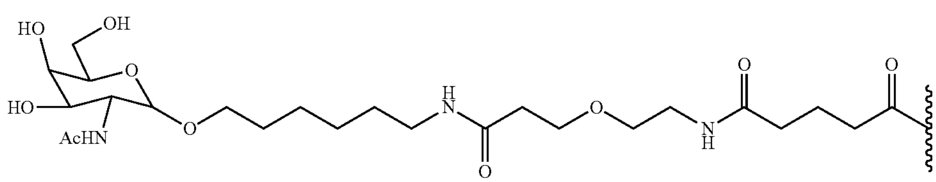 [SMILES: *C(=O)CCCC(=O)NCCOCCC(=O)NCCCCCCOC1OC(CO)C(O)C(O)C1NC(C)=O] |
| 5'YICc-01 | 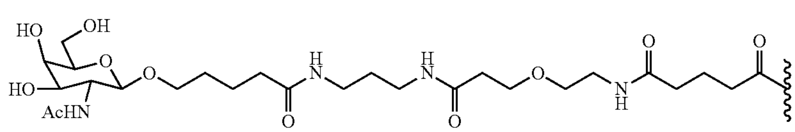 [SMILES: *C(=O)CCCC(=O)NCCOCCC(=O)NCCCNC(=O)CCCCOC1OC(CO)C(O)C(O)C1NC(C)=O] |
| 5'ERCd-01 | 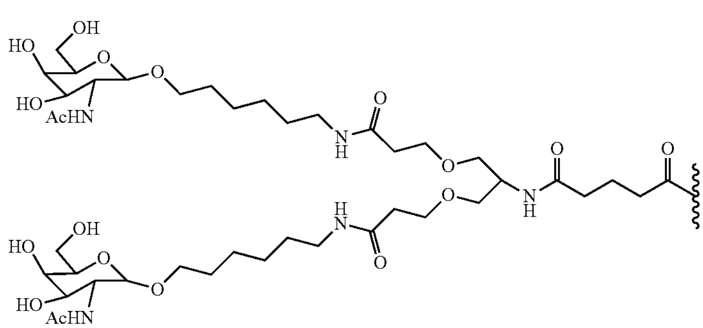 [SMILES: *C(=O)CCCC(=O)NC(COCCC(=O)NCCCCCCOC1OC(CO)C(O)C(O)C1NC(C)=O)COCCC(=O)NCCCCCCOC1OC(CO)C(O)C(O)C1NC(C)=O] |

-continued
| Code of the delivery chain at the 5' end of the sense strand | Structure |
|---|---|
| 5'ERCc-01 | 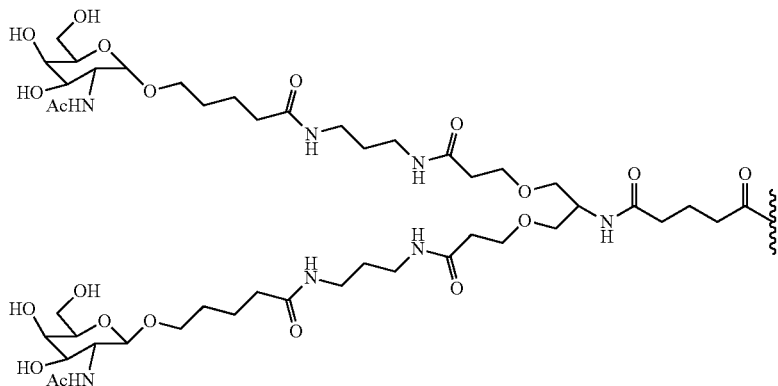 [SMILES: *C(=O)CCCC(=O)NC(COCCC(=O)NCCCNC(=O)CCCCOC1OC(CO)C(O)C(O)C1NC(C)=O)COCCC(=O)NCCCNC(=O)CCCCOC1OC(CO)C(O)C(O)C1NC(C)=O] |
| 5'YICa-01 | 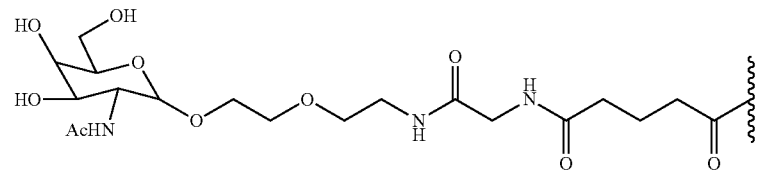 [SMILES: *C(=O)CCCC(=O)NCC(=O)NCCOCCOC1OC(CO)C(O)C(O)C1NC(C)=O] |
| 5'YICa-02 | 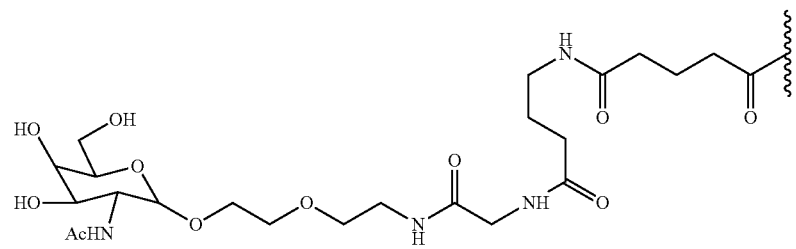 [SMILES: *C(=O)CCCC(=O)NCCCC(=O)NCC(=O)NCCOCCOC1OC(CO)C(O)C(O)C1NC(C)=O] |
| 5'YICa-03 | 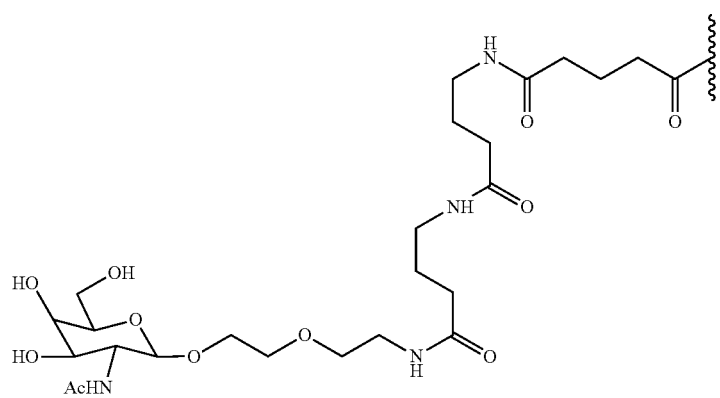 [SMILES: *C(=O)CCCC(=O)NCCCC(=O)NCCCC(=O)NCCOCCOC1OC(CO)C(O)C(O)C1NC(C)=O] |
| 5'YICa-04 | 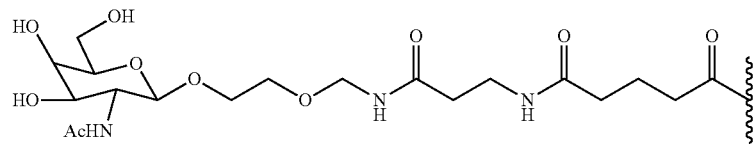 [SMILES: *C(=O)CCCC(=O)NCCC(=O)NCOCCOC1OC(CO)C(O)C(O)C1NC(C)=O] |
| 5'YICa-05 | 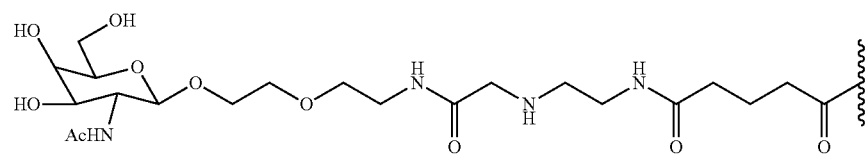 [SMILES: *C(=O)CCCC(=O)NCCNCC(=O)NCCOCCOC1OC(CO)C(O)C(O)C1NC(C)=O] |

-continued
| Code of the delivery chain at the 5' end of the sense strand | Structure |
|---|---|
| 5'ERCa-01 | 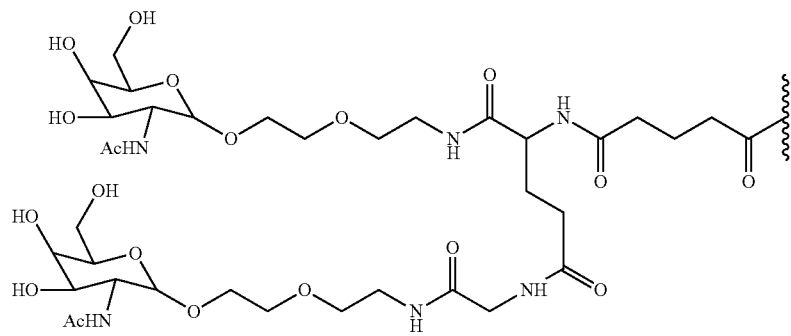 [SMILES: *C(=O)CCCC(=O)NC(CCC(=O)NCC(=O)NCCOCCOC1OC(CO)C(O)C(O)C1NC(C)=O)C(=O)NCCOCCOC1OC(CO)C(O)C(O)C1NC(C)=O] |
| 5'ERCa-02 | 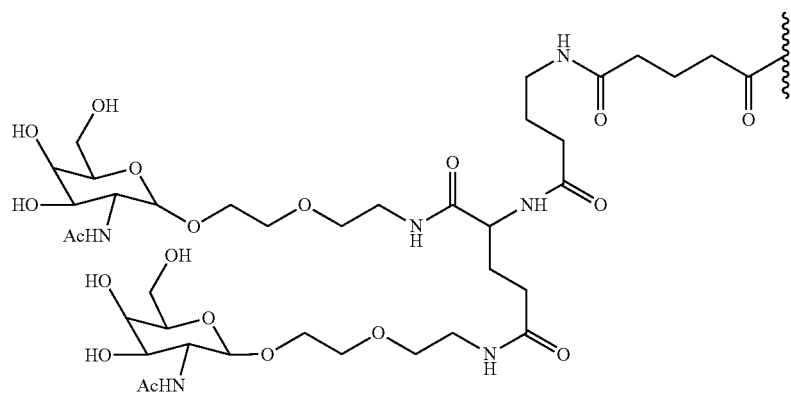 [SMILES: *C(=O)CCCC(=O)NCCCC(=O)NC(CCC(=O)NCCOCCOC1OC(CO)C(O)C(O)C1NC(C)=O)C(=O)NCCOCCOC1OC(CO)C(O)C(O)C1NC(C)=O] |
| 5'ERCa-03 | 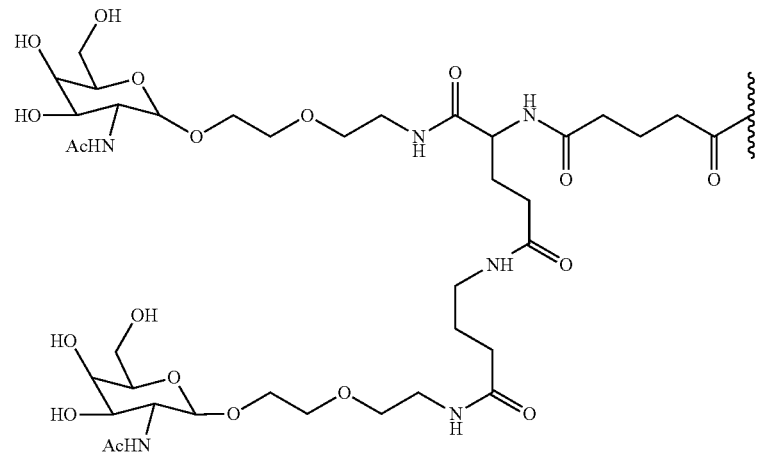 [SMILES: *C(=O)CCCC(=O)NC(CCC(=O)NCCCC(=O)NCCOCCOC1OC(CO)C(O)C(O)C1NC(C)=O)C(=O)NCCOCCOC1OC(CO)C(O)C(O)C1NC(C)=O] |
| 5'ERCa-04 | 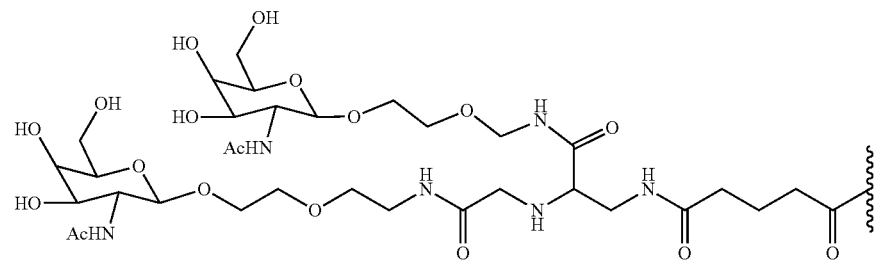 [SMILES: *C(=O)CCCC(=O)NCC(NCC(=O)NCCOCCOC1OC(CO)C(O)C(O)C1NC(C)=O)C(=O)NCOCCOC1OC(CO)C(O)C(O)C1NC(C)=O] |

| Code of the delivery chain at the 5' end of the sense strand | Structure |
|---|---|
| 5 5'ERCa-05 | 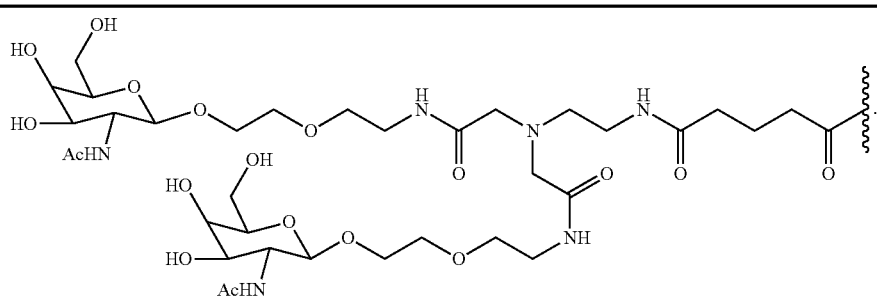 |
The delivery chain at the 3' end of the antisense strand of the compound carries two or three N-acetylgalactosamines, and the
$$(X-L)_n-B-$$
in the delivery chain is one selected from the following structures:
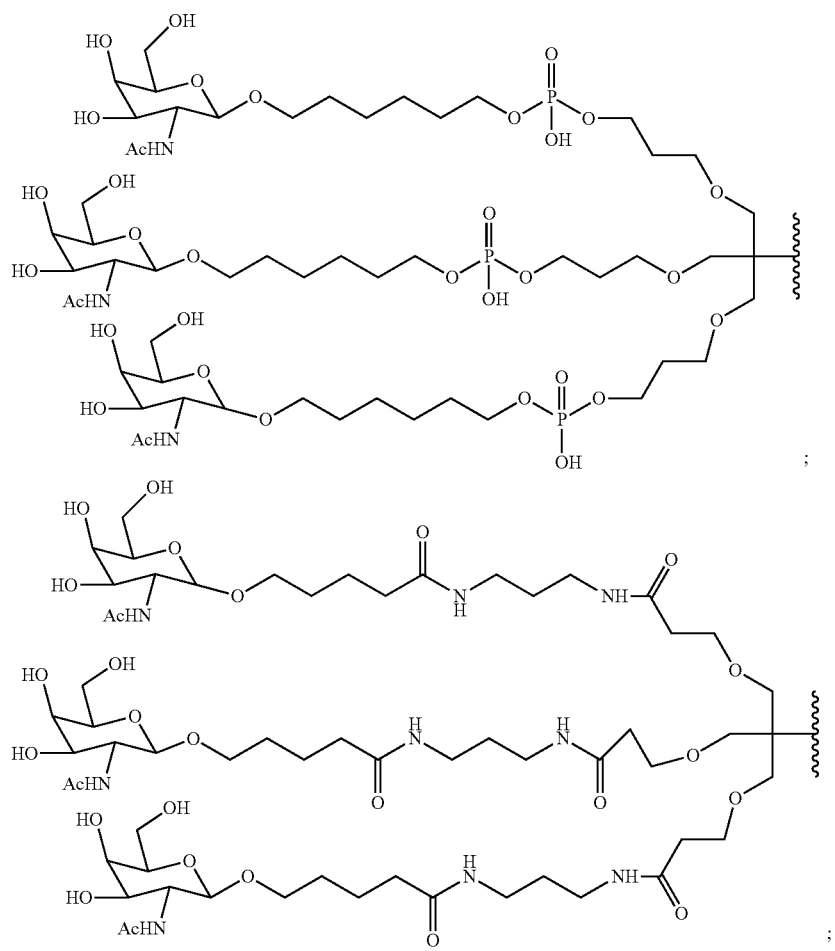

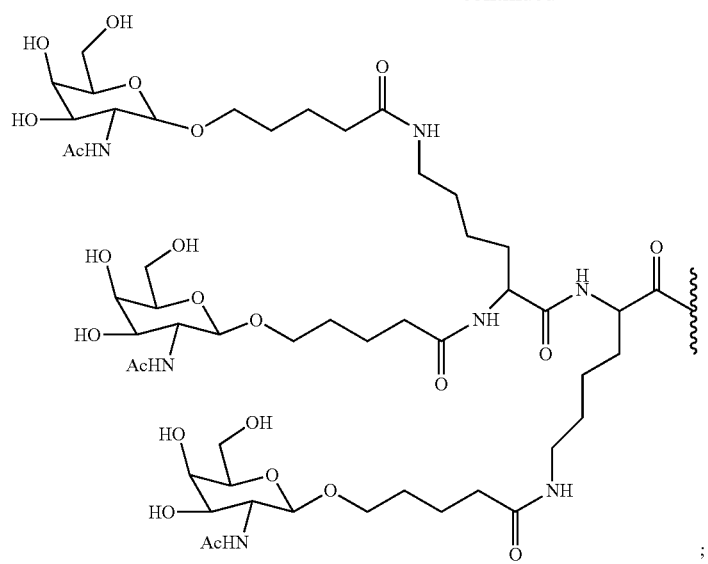
;
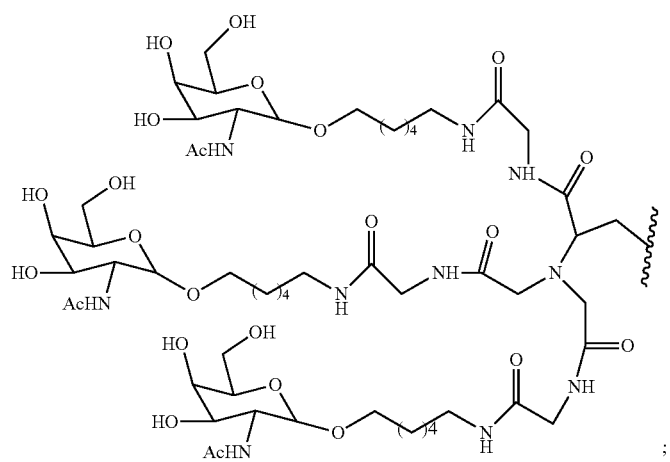
;
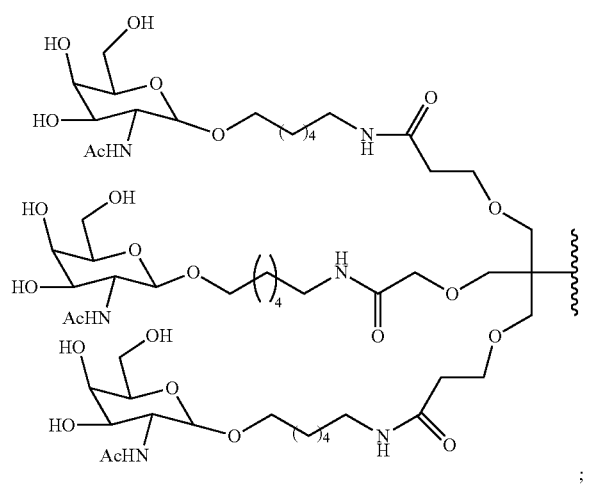
;

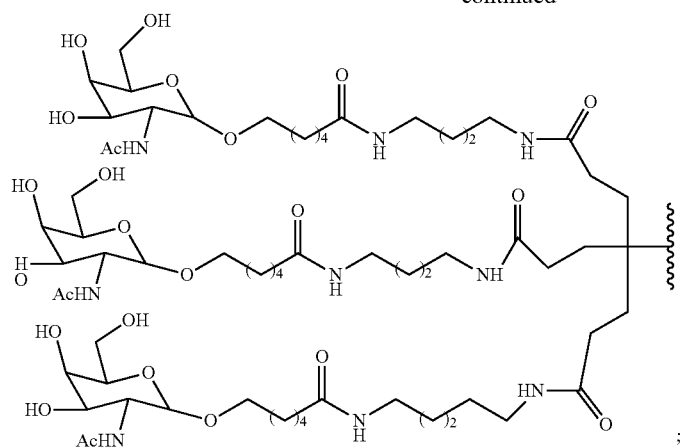
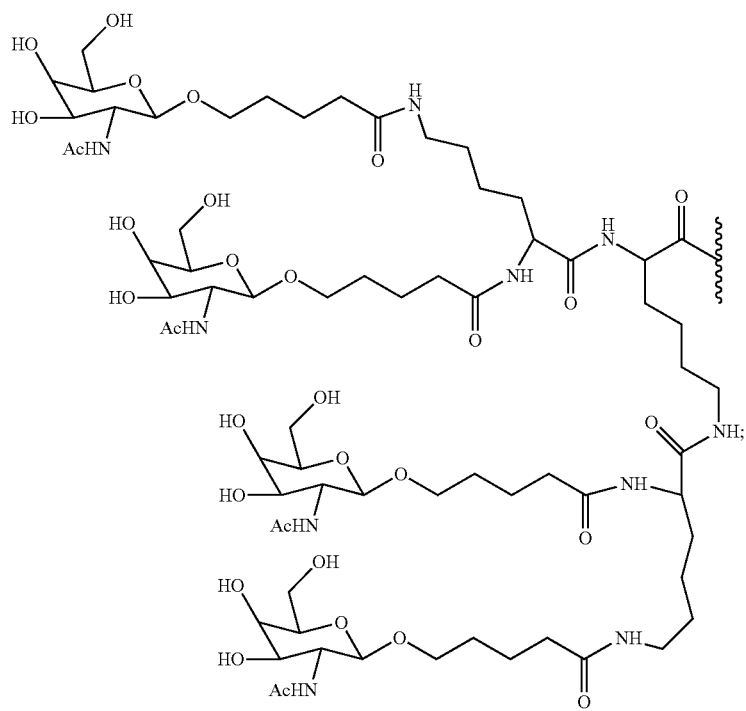
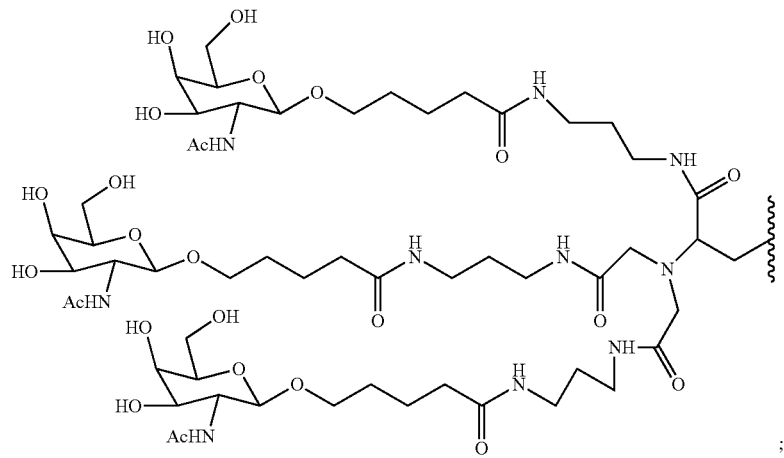

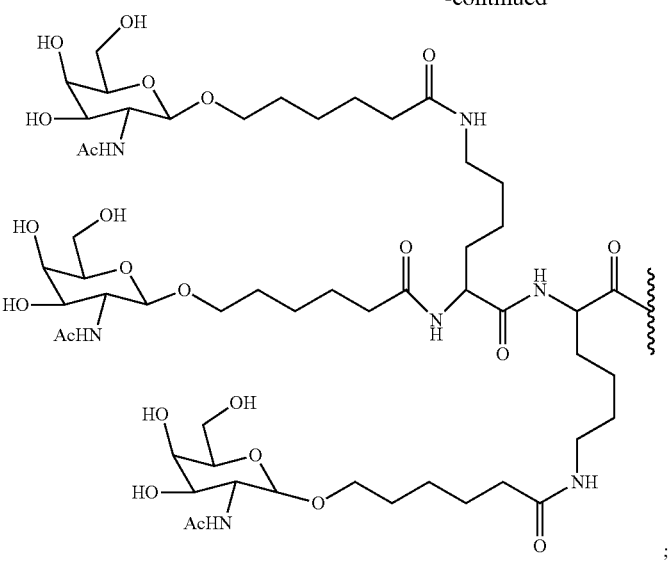
;
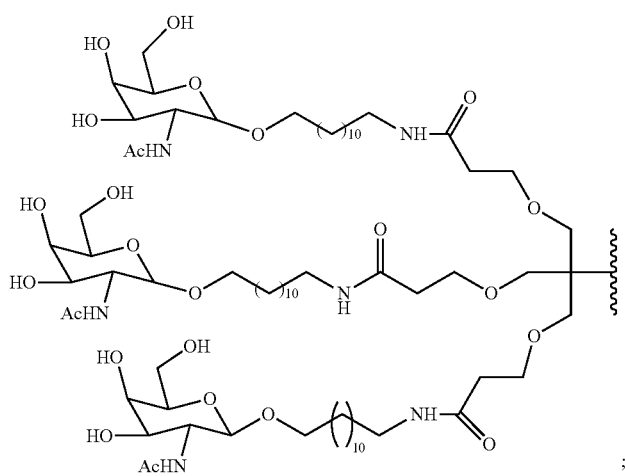
;
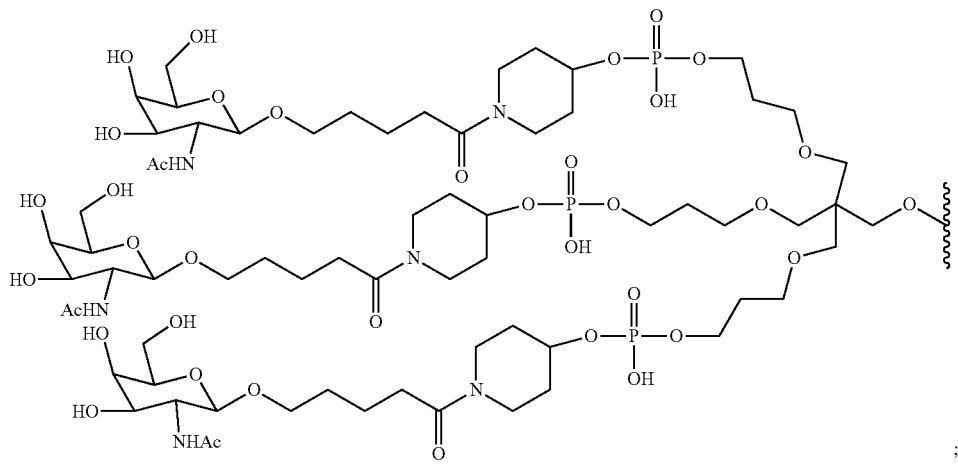
;

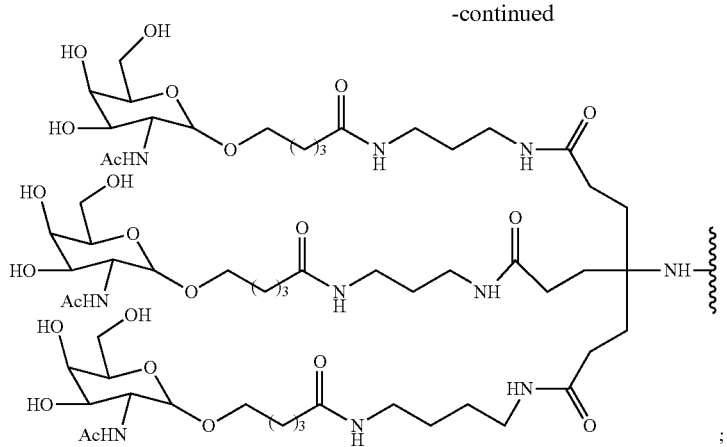
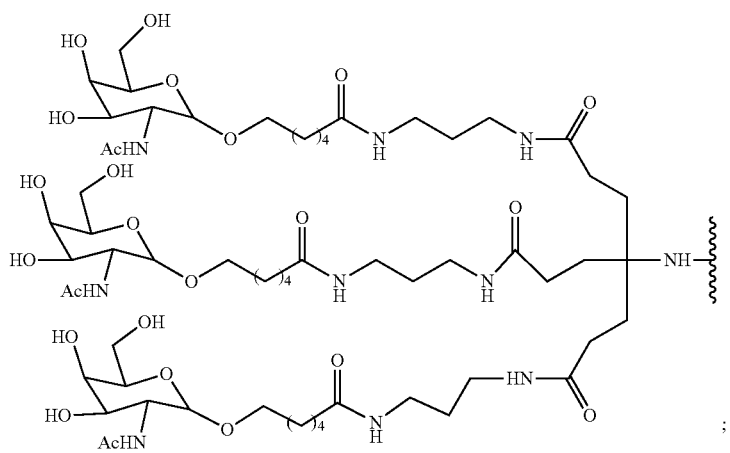
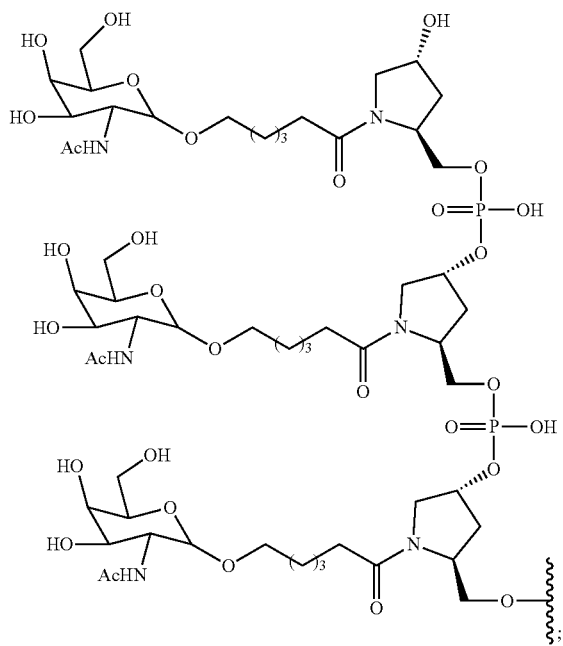

-continued
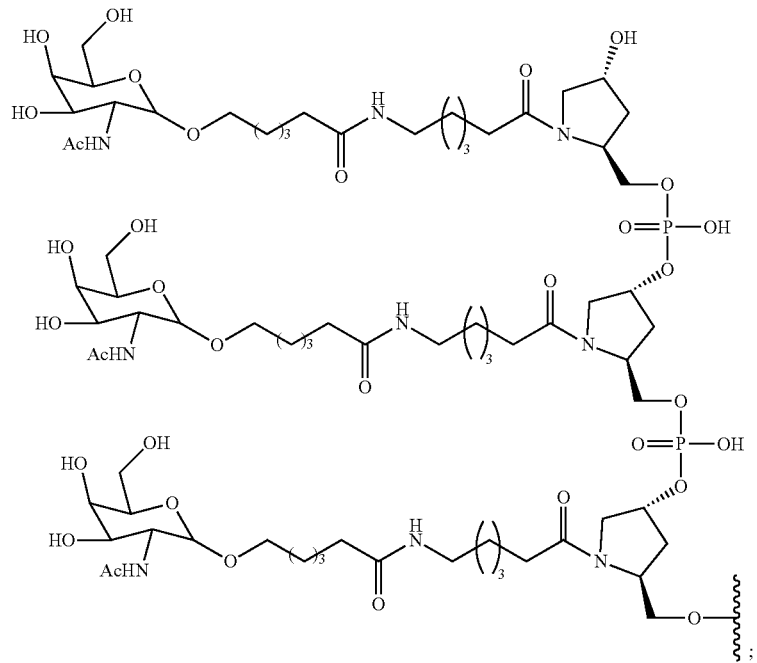
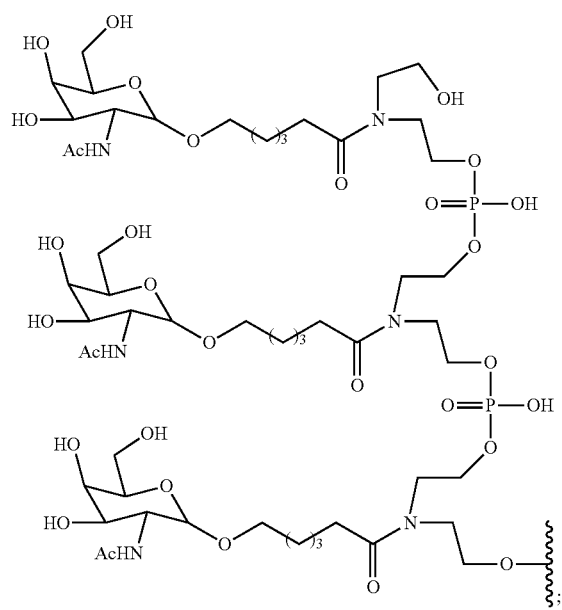

-continued
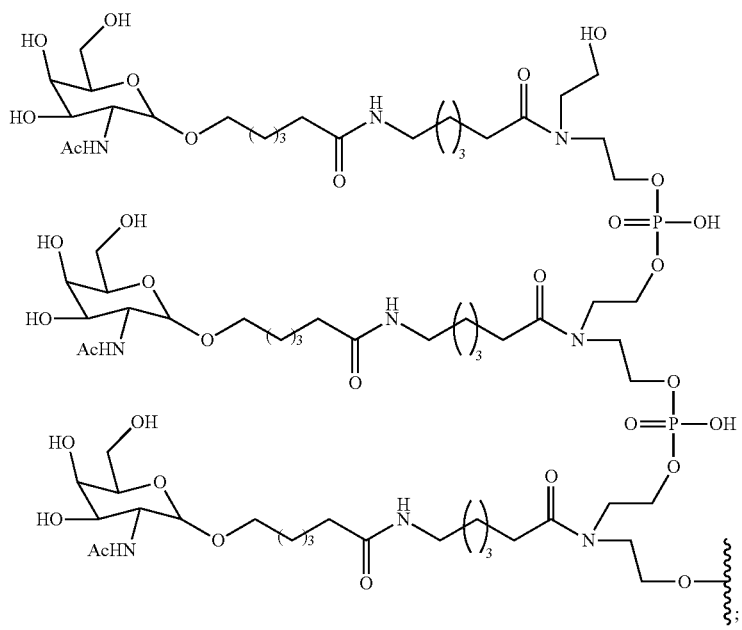
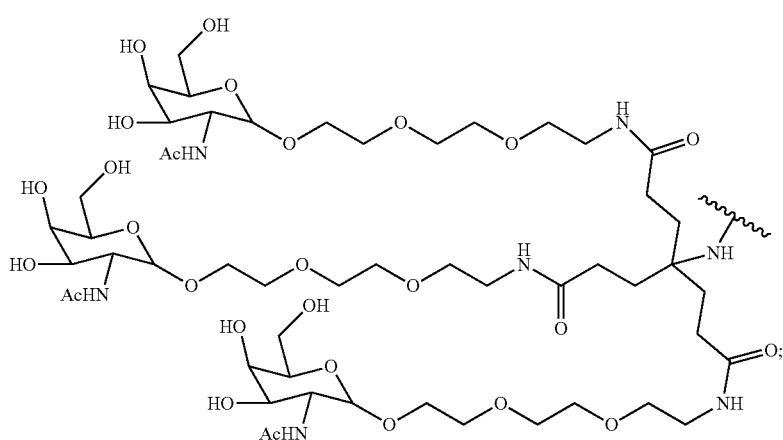
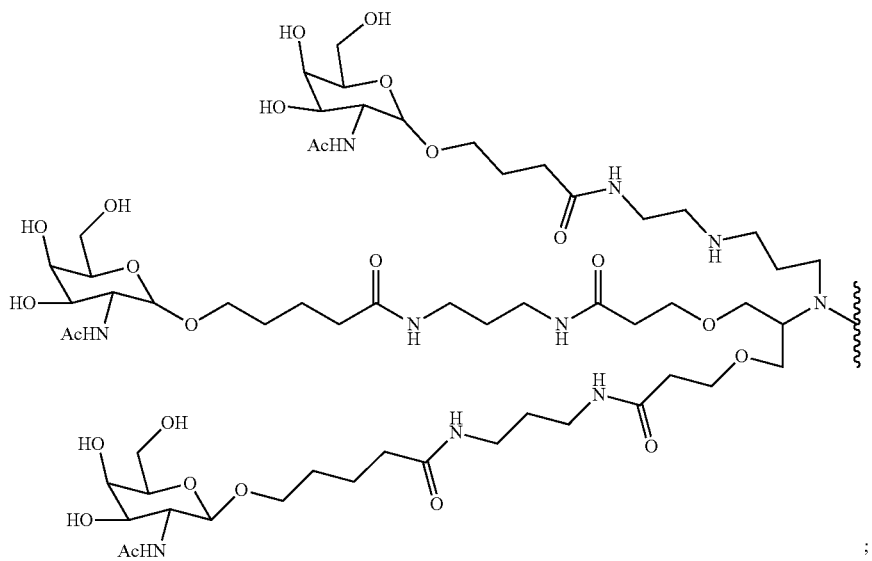

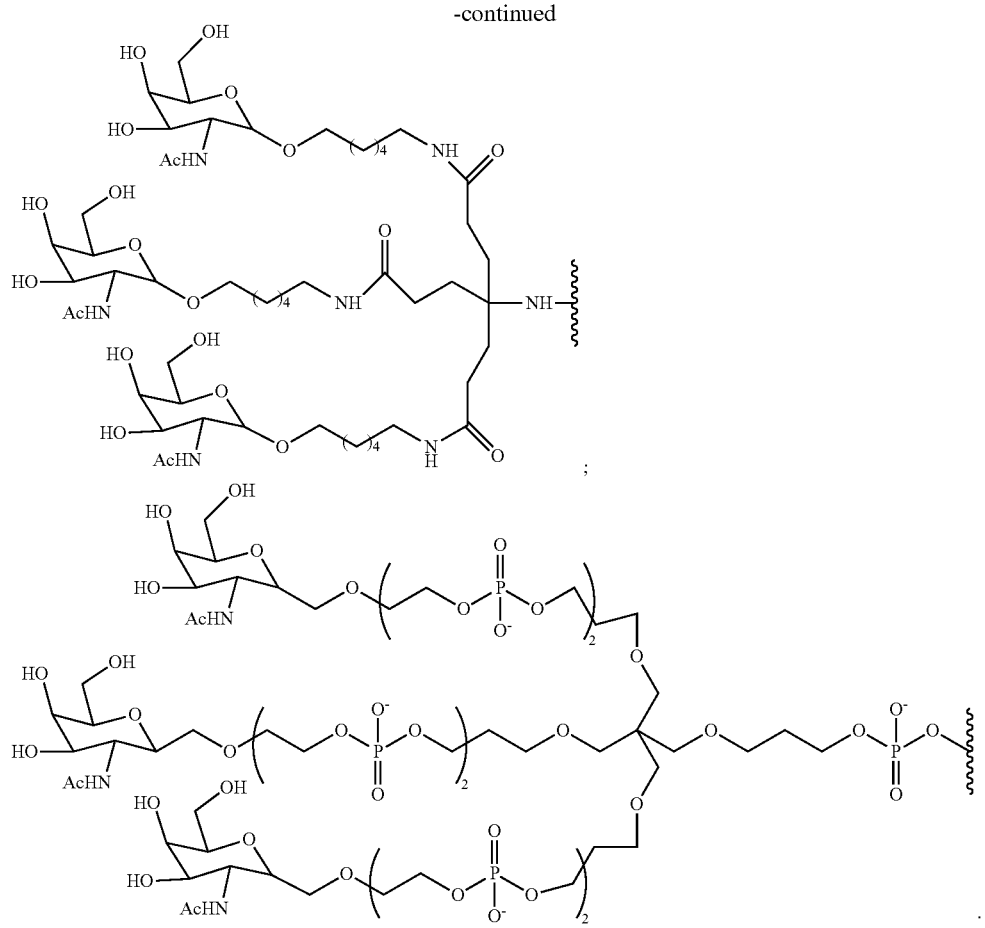
In some preferable examples, the delivery chain at the 3' end of the antisense strand of the compound is preferably selected from the formulae listed in the table below:
| Code of the delivery chain at the 3' end of the antisense strand | Structure |
|---|---|
| 3'SANCd-01 | 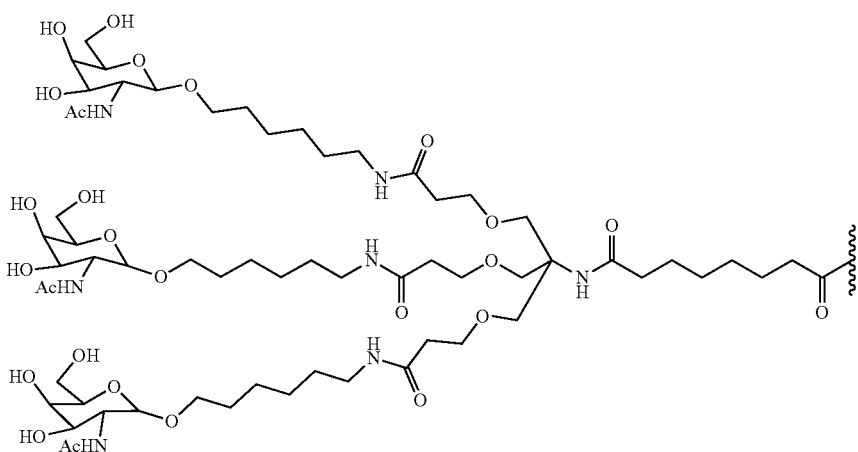 [SMILES: *C(=O)CCCCCCC(=O)NC(COCCC(=O)NCCCCCCOC1OC(CO)C(O)C(O)C1NC(C)=O)(COCCC(=O)NCCCCCCOC1OC(CO)C(O)C(O)C1NC(C)=O)COCCC(=O)NCCCCCCOC1OC(CO)C(O)C(O)C1NC(C)=O] |

| Code of the delivery chain at the 3' end of the antisense strand | Structure |
| --- | --- |
| 3'SANCc-01 | 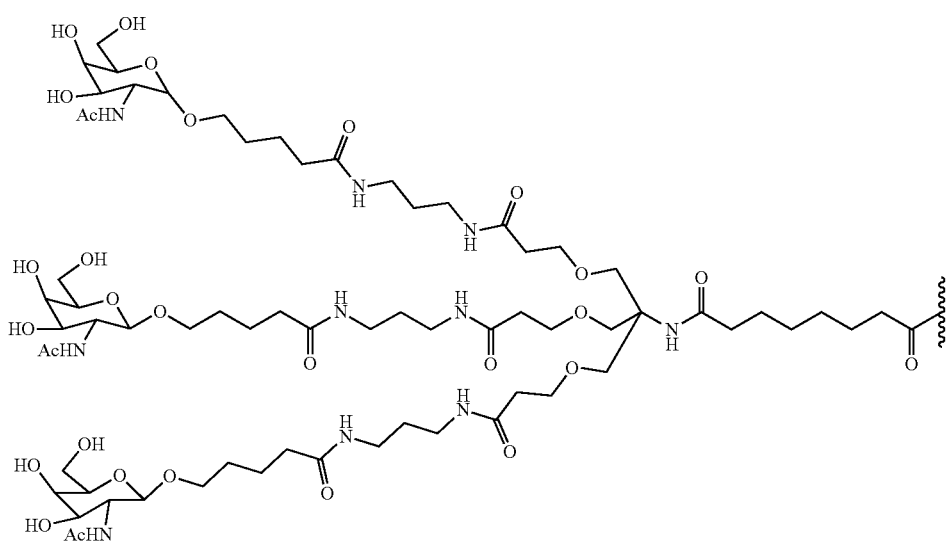 [SMILES: *C(=O)CCCCCCC(=O)NC(COCCC(=O)NCCCNC(=O)CCCCOC1OC(CO)C(O)C(O)C1NC(C)=O)(COCCC(=O)NCCCNC(=O)CCCCOC1OC(CO)C(O)C(O)C1NC(C)=O)COCCC(=O)NCCCNC(=O)CCCCOC1OC(CO)C(O)C(O)C1NC(C)=O] |
| 3'SANCa-01 | 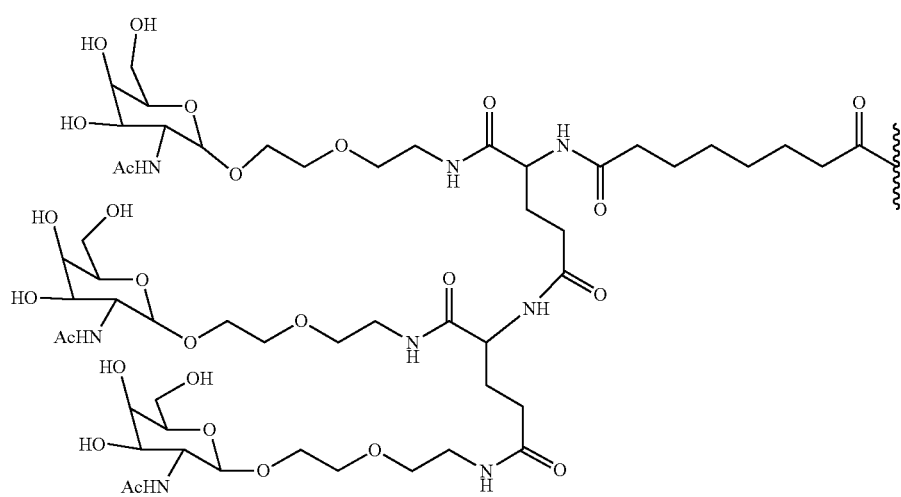 [SMILES: *C(=O)CCCCCCC(=O)NC(CCC(=O)NC(CCC(=O)NCCOCCOC1OC(CO)C(O)C(O)C1NC(C)=O)C(=O)NCCOCCOC1OC(CO)C(O)C(O)C1NC(C)=O)C(=O)NCCOCCOC1OC(CO)C(O)C(O)C1NC(C)=O] |
| 3'SANCa-02 | 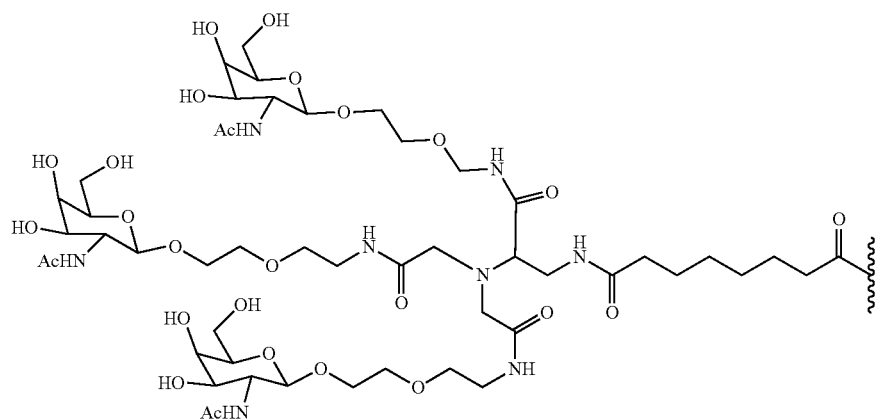 [SMILES: *C(=O)CCCCCCC(=O)NCC(C(=O)NCOCCOC1OC(CO)C(O)C(O)C1NC(C)=O)N(CC(=O)NCCOCCOC1OC(CO)C(O)C(O)C1NC(C)=O)CC(=O)NCCOCCOC1OC(CO)C(O)C(O)C1NC(C)=O] |

| Code of the delivery chain at the 3' end of the antisense strand | Structure |
|---|---|
| 3'ERCd-01 | 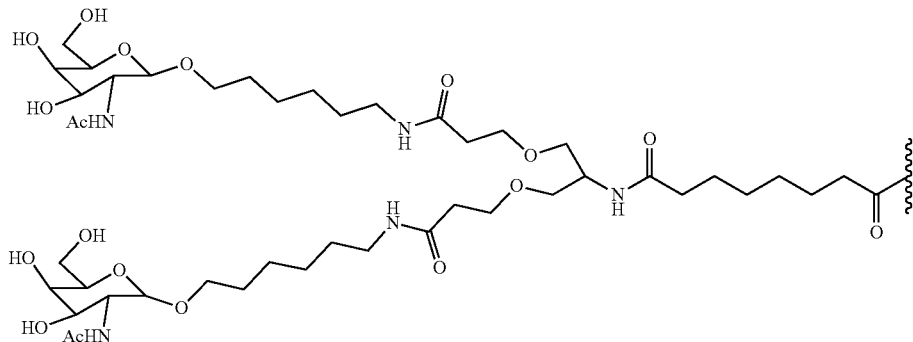 [SMILES: *C(=O)CCCCCCC(=O)NC(COCCC(=O)NCCCCCCOC1OC(CO)C(O)C(O)C1NC(C)=O)COCCC(=O)NCCCCCCOC1OC(CO)C(O)C(O)C1NC(C)=O] |
| 3'ERCc-01 | 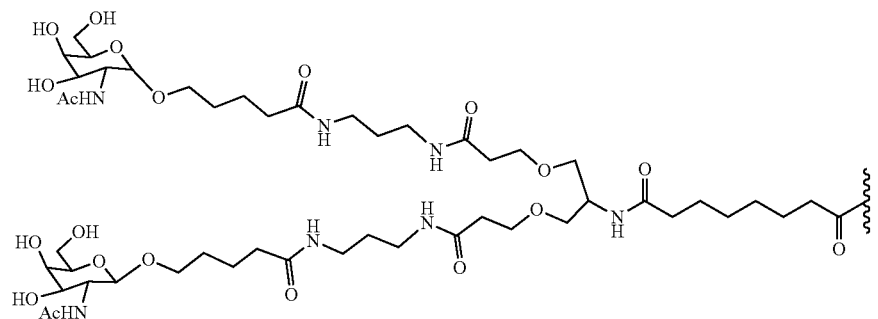 |
| 3'ERCa-01 | 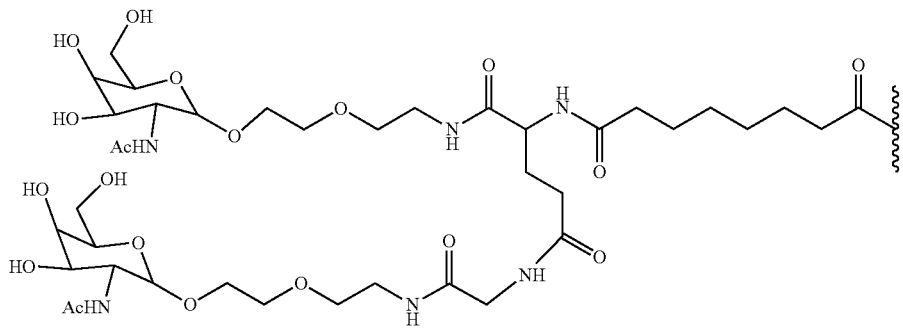 [SMILES: *C(=O)CCCCCCC(=O)NC(CCC(=O)NCC(=O)NCCOCCOC1OC(CO)C(O)C(O)C1NC(C)=O)C(=O)NCCOCCOC1OC(CO)C(O)C(O)C1NC(C)=O] |
| 3'ERCa-02 | 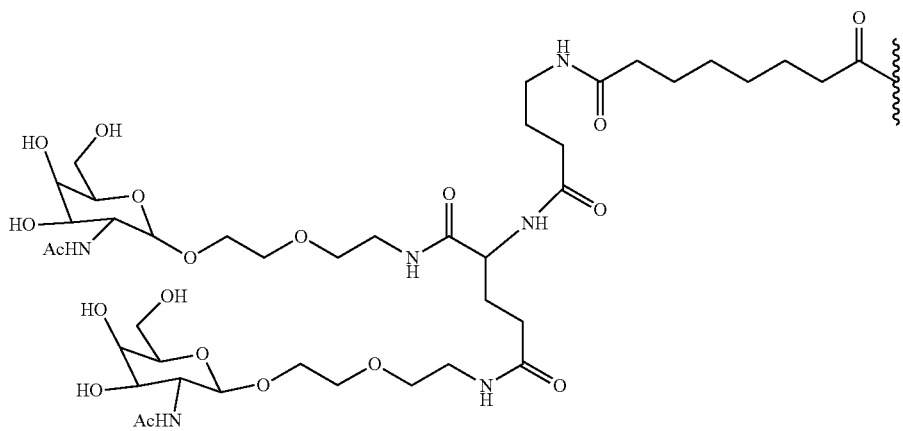 [SMILES: *C(=O)CCCCCCC(=O)NCCCC(=O)NC(CCC(=O)NCCOCCOC1OC(CO)C(O)C(O)C1NC(C)=O)C(=O)NCCOCCOC1OC(CO)C(O)C(O)C1NC(C)=O] |

| Code of the delivery chain at the 3' end of the antisense strand | Structure |
|---|---|
| 3'ERCa-03 | 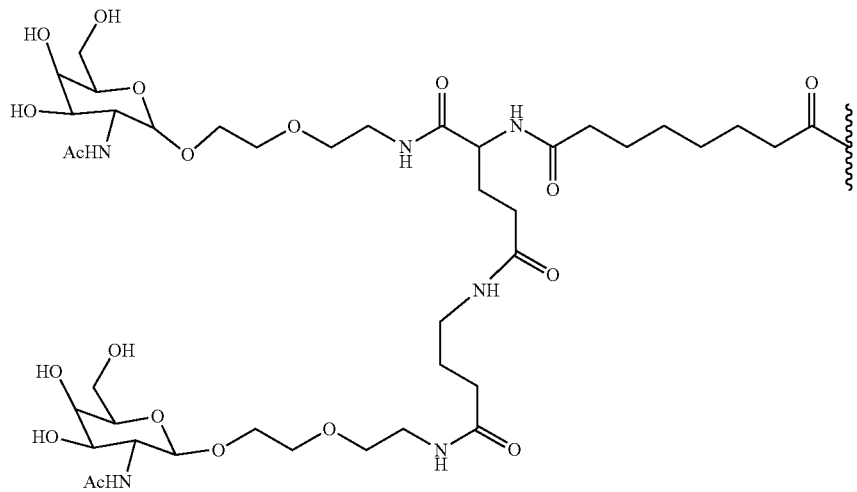 [SMILES: *C(=O)CCCCCCC(=O)NC(CCC(=O)NCCCC(=O)NCCOCCOC1OC(CO)C(O)C(O)C1NC(C)=O)C(=O)NCCOCCOC1OC(CO)C(O)C(O)C1NC(C)=O] |
| 3'ERCa-04 | 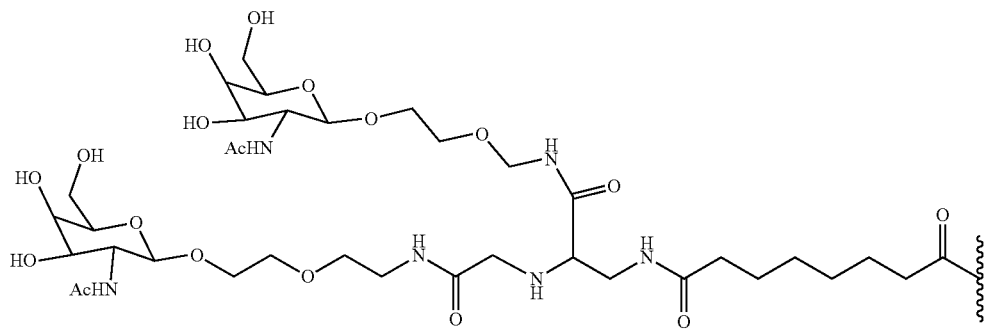 [SMILES: *C(=O)CCCCCCC(=O)NCC(NCC(=O)NCCOCCOC1OC(CO)C(O)C(O)C1NC(C)=O)C(=O)NCOCCOC1OC(CO)C(O)C(O)C1NC(C)=O] |
| 3'ERCa-05 | 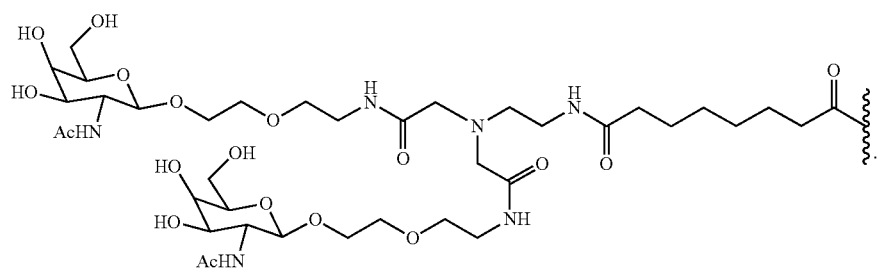 [SMILES: *C(=O)CCCCCCC(=O)NCCN(CC(=O)NCCOCCOC1OC(CO)C(O)C(O)C1NC(C)=O)CC(=O)NCCOCCOC1OC(CO)C(O)C(O)C1NC(C)=O] |

In some preferable examples, the combination of the delivery chain at the 5' end of the sense strand and the delivery chain at the 3' end of the antisense strand of the compound is preferably one of the structures as shown in the table below:

| No. | Code of the combination of delivery chains | Delivery chain at the 5' end of the sense strand |
|---|---|---|
| 1 | GBL-01 | 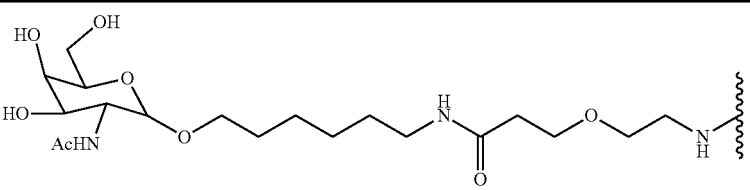<br>5'YICd-01 |
| 2 | GBL-02 | 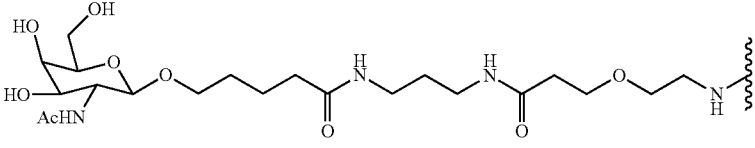<br>5'YICc-01 |
| 3 | GBL-03 | 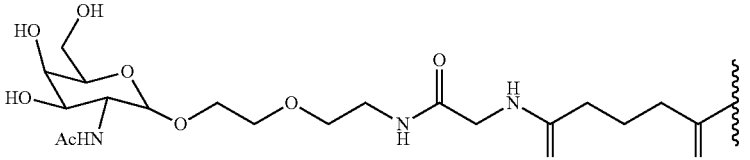<br>5'YICa-01 |
| 4 | GBL-04 | <br>5'YICa-02 |
| 5 | GBL-05 | <br>5'YICa-03 |

| | | |
|---|---|---|
| 6 | GBL-06 | 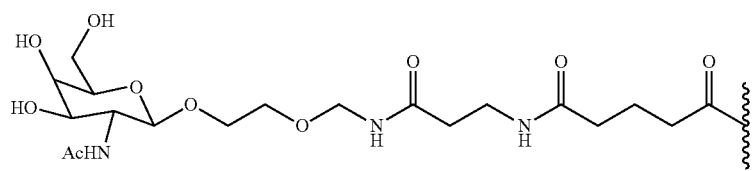
5'YICa-04 |
| 7 | GBL-07 | 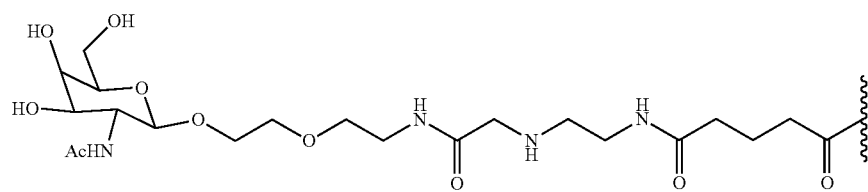
5'YICa-05 |
| 8 | GBL-08 | 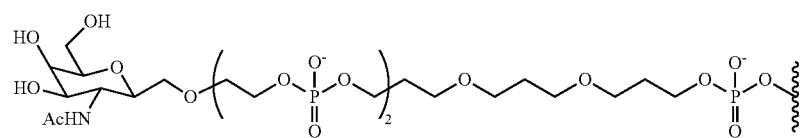
5'YICr-06 |
| 9 | GBL-09 | 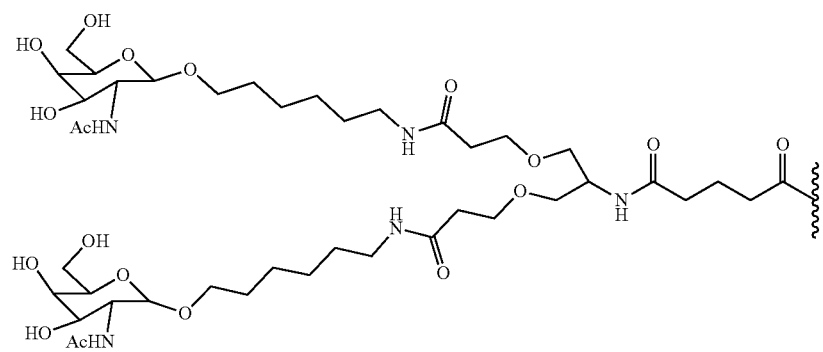
5'ERCd-01 |
| 10 | GBL-10 | 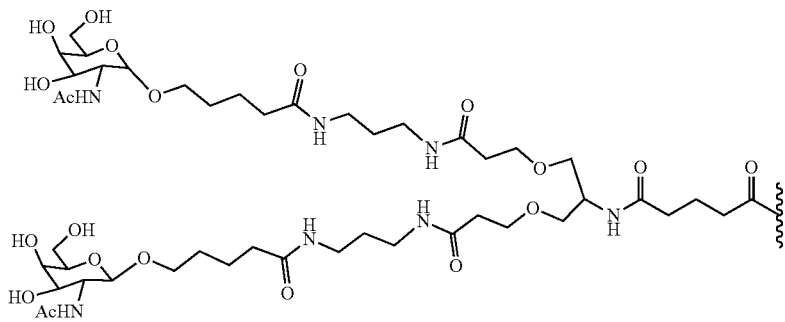
5'ERCc-01 |

| 11 | GBL-11 | 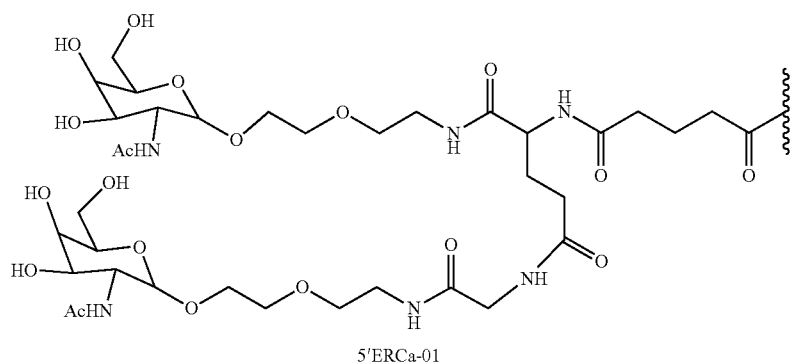 [SMILES: *C(=O)CCCC(=O)NC(CCC(=O)NCC(=O)NCCOCCOC1OC(CO)C(O)C(O)C1NC(C)=O)C(=O)NCCOCCOC1OC(CO)C(O)C(O)C1NC(C)=O] |
| | | 5'ERCa-01 |
| 12 | GBL-12 | 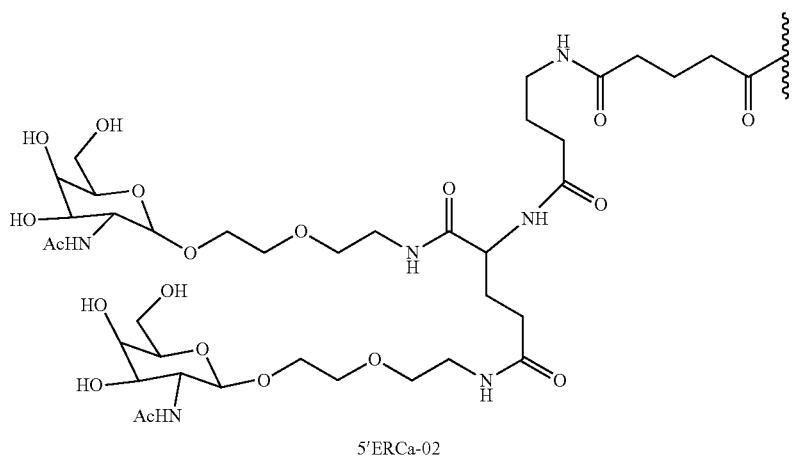 [SMILES: *C(=O)CCCC(=O)NCCCC(=O)NC(CCC(=O)NCCOCCOC1OC(CO)C(O)C(O)C1NC(C)=O)C(=O)NCCOCCOC1OC(CO)C(O)C(O)C1NC(C)=O] |
| | | 5'ERCa-02 |
| 13 | GBL-13 | 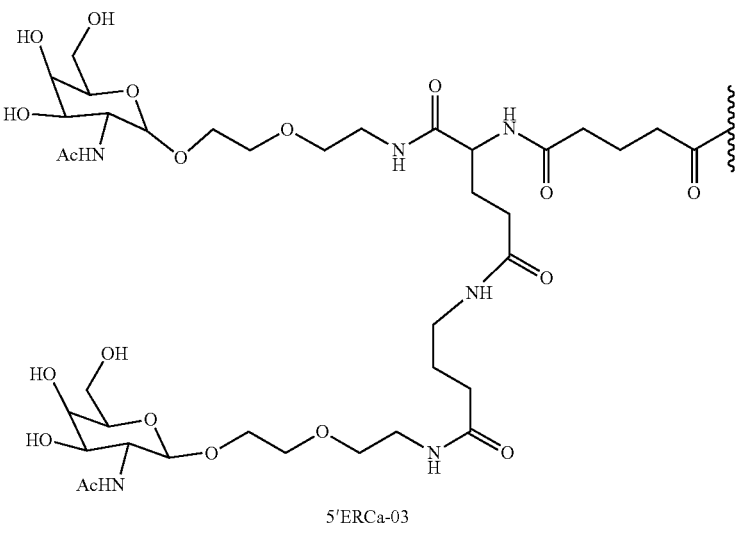 [SMILES: *C(=O)CCCC(=O)NC(CCC(=O)NCCCC(=O)NCCOCCOC1OC(CO)C(O)C(O)C1NC(C)=O)C(=O)NCCOCCOC1OC(CO)C(O)C(O)C1NC(C)=O] |
| | | 5'ERCa-03 |

| 14 | GBL-14 | 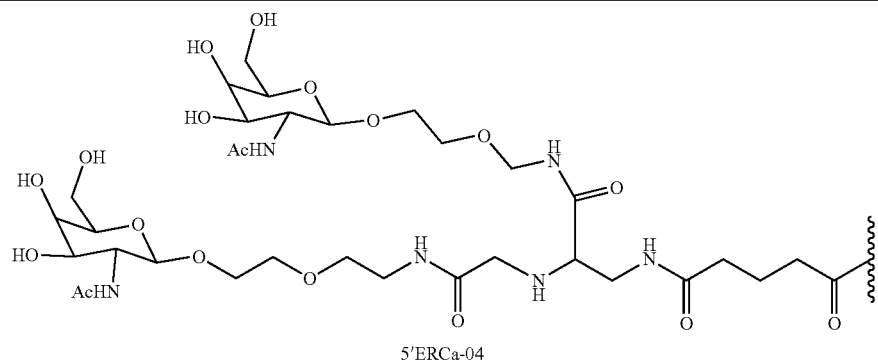 |
| | | 5′ERCa-04 |
| 15 | GBL-15 | 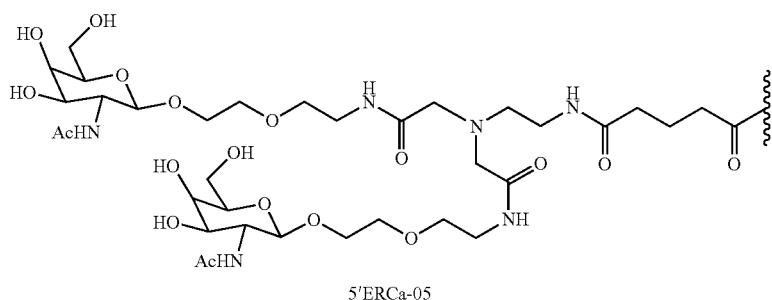 [SMILES: *C(=O)CCCC(=O)NCCN(CC(=O)NCCOCCOC1OC(CO)C(O)C(O)C1NC(C)=O)CC(=O)NCCOCCOC1OC(CO)C(O)C(O)C1NC(C)=O] |
| | | 5′ERCa-05 |
| 16 | GBL-16 | 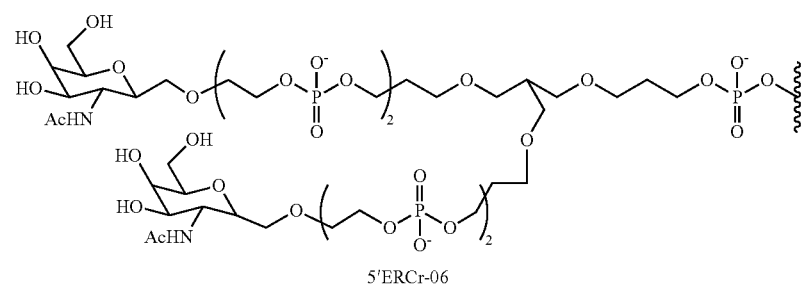 |
| | | 5′ERCr-06 |
| No. | Delivery chain at the 3′ end of the antisense strand |
|---|---|
| 1 | 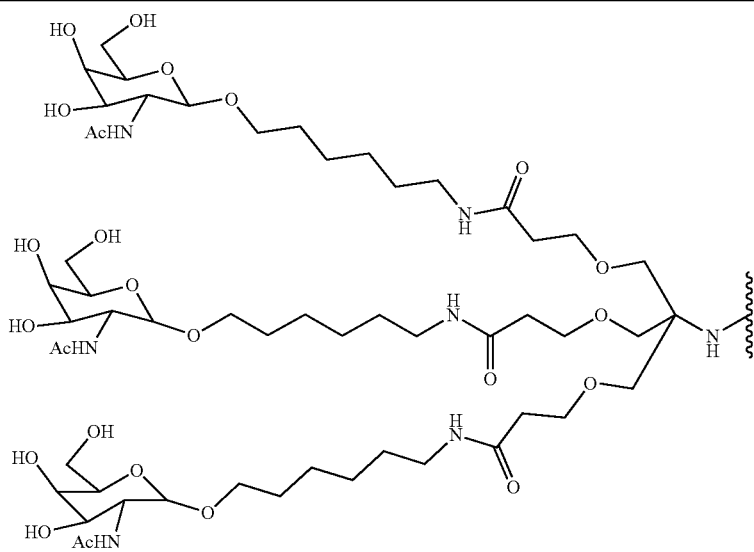 |
| | 3′SANCd-01 |

2  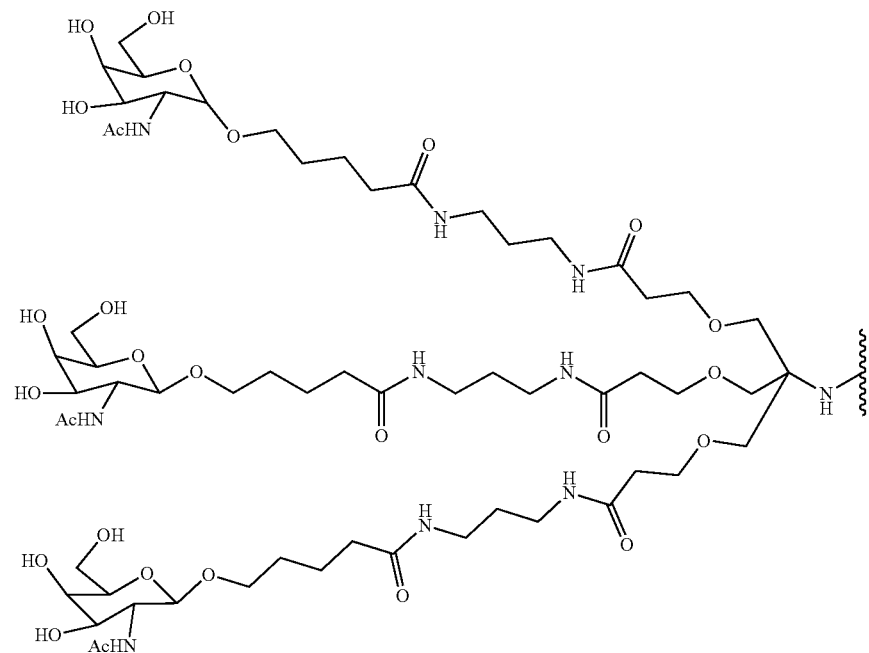
3'SANCc-01
3  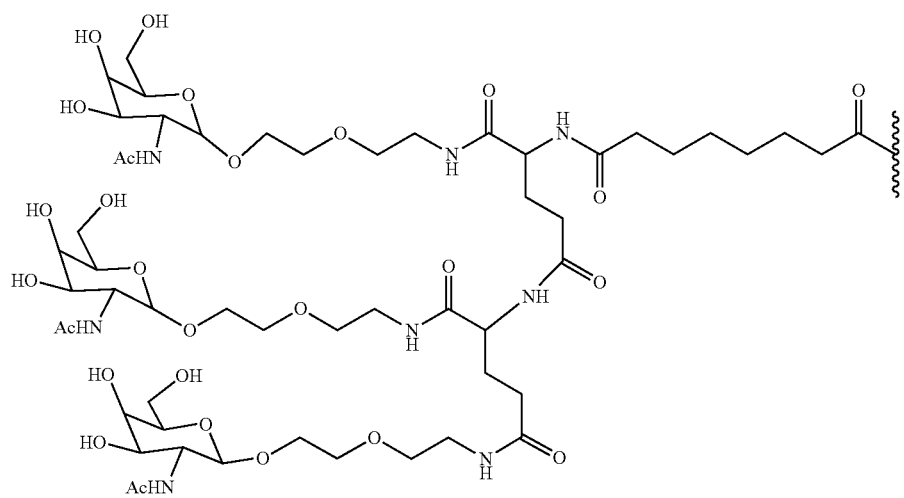
3'SANCa-01

4
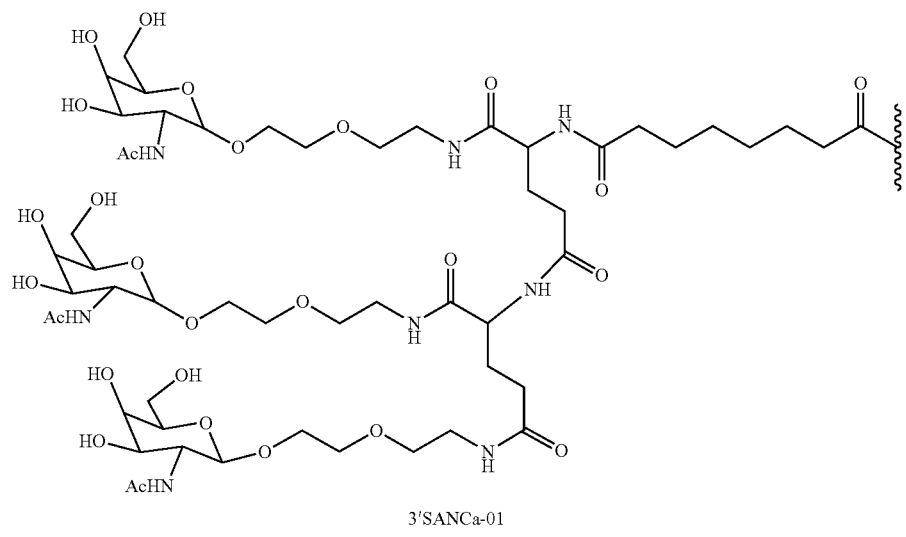 [SMILES: *C(=O)CCCCCCC(=O)NC(CCC(=O)NC(CCC(=O)NCCOCCOC1OC(CO)C(O)C(O)C1NC(C)=O)C(=O)NCCOCCOC1OC(CO)C(O)C(O)C1NC(C)=O)C(=O)NCCOCCOC1OC(CO)C(O)C(O)C1NC(C)=O]
3'SANCa-01
5
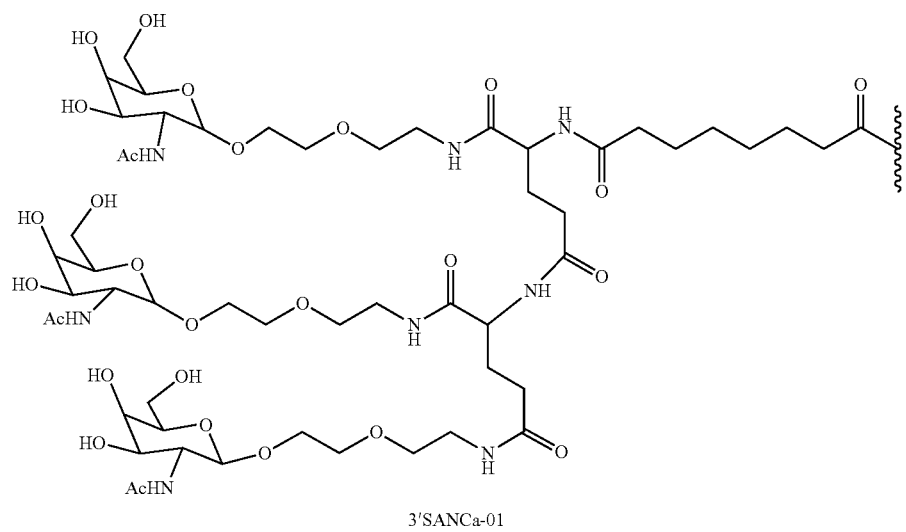 [SMILES: *C(=O)CCCCCCC(=O)NC(CCC(=O)NC(CCC(=O)NCCOCCOC1OC(CO)C(O)C(O)C1NC(C)=O)C(=O)NCCOCCOC1OC(CO)C(O)C(O)C1NC(C)=O)C(=O)NCCOCCOC1OC(CO)C(O)C(O)C1NC(C)=O]
3'SANCa-01
6
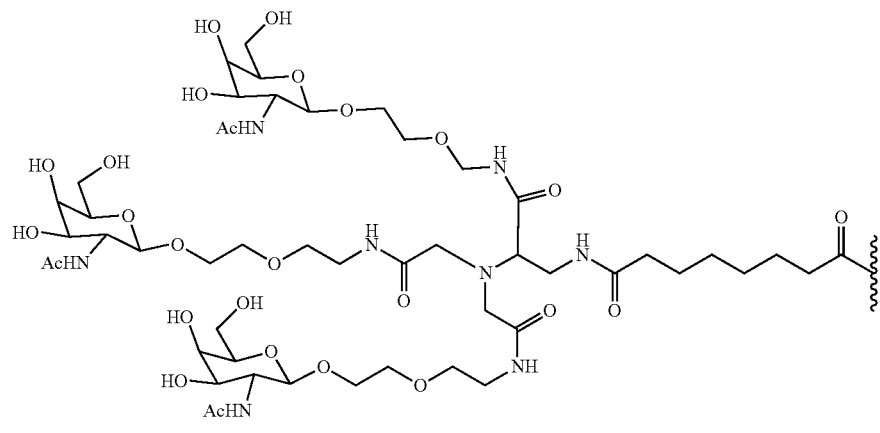
3'SANCa-02

-continued
| 7 | 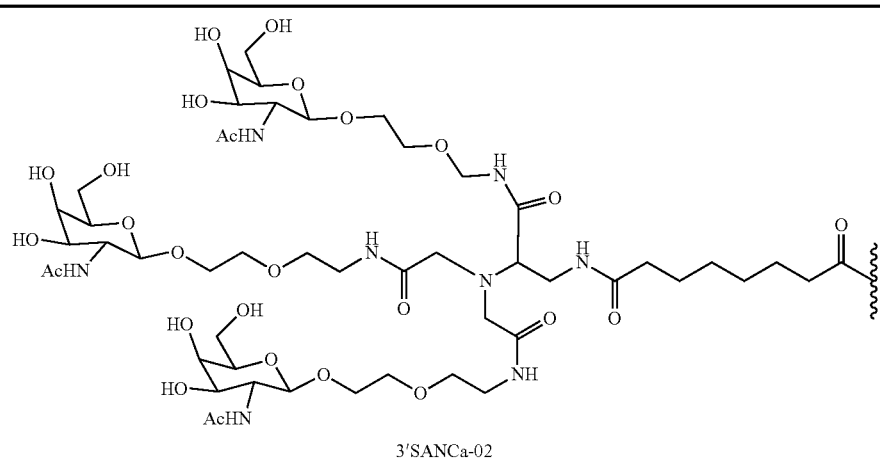
3'SANCa-02 |
| 8 | 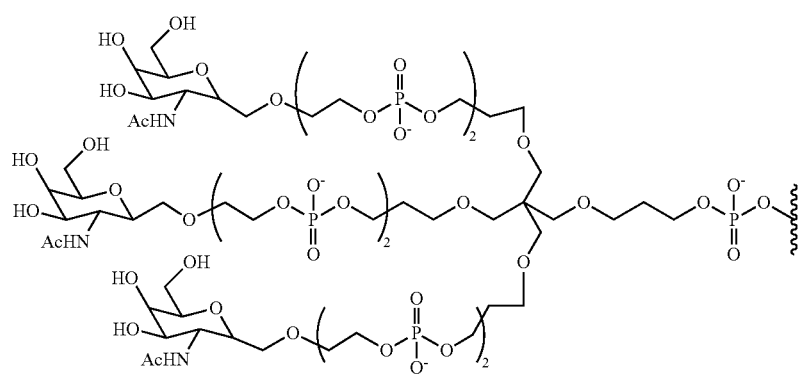
3'SANCr-03 |
| 9 | 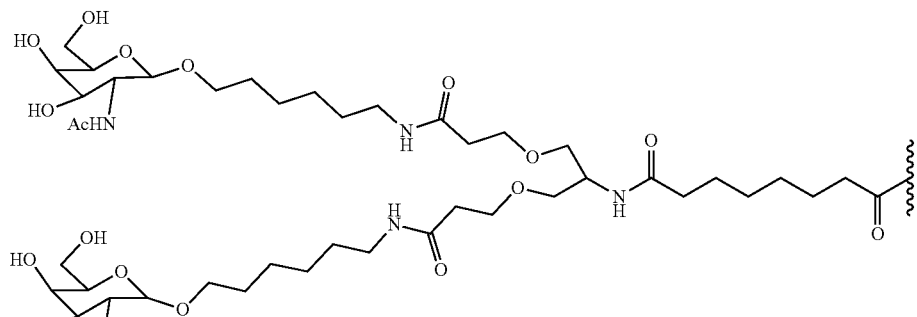
3'ERCd-01 |
| 10 | 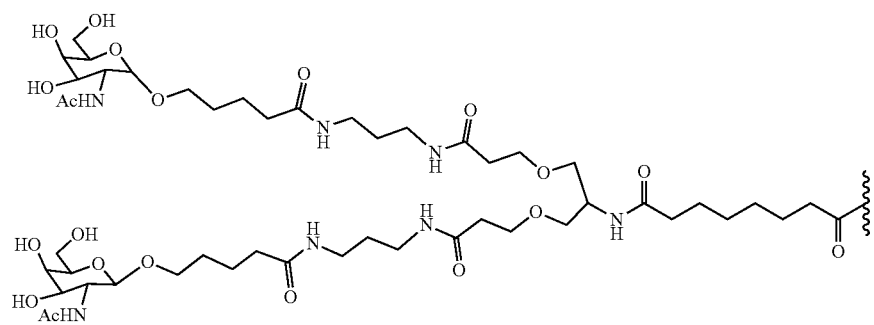
3'ERCc-01 |

11
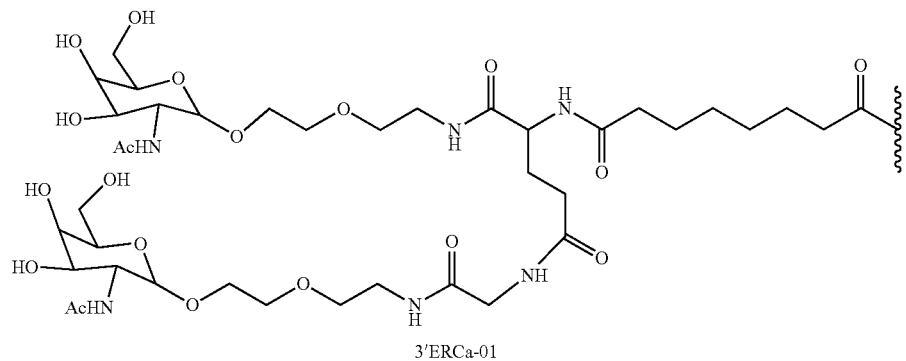 [SMILES: *C(=O)CCCCCCC(=O)NC(CCC(=O)NCC(=O)NCCOCCOC1OC(CO)C(O)C(O)C1NC(C)=O)C(=O)NCCOCCOC1OC(CO)C(O)C(O)C1NC(C)=O]
3'ERCa-01
12
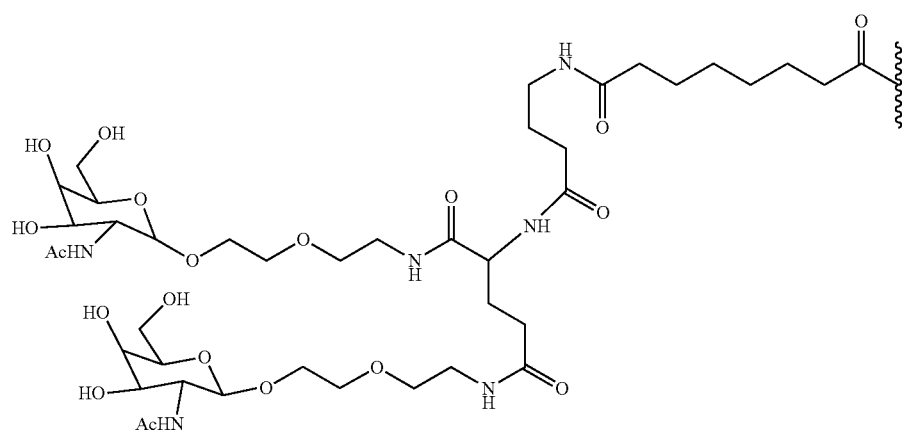
3'ERCa-02
13
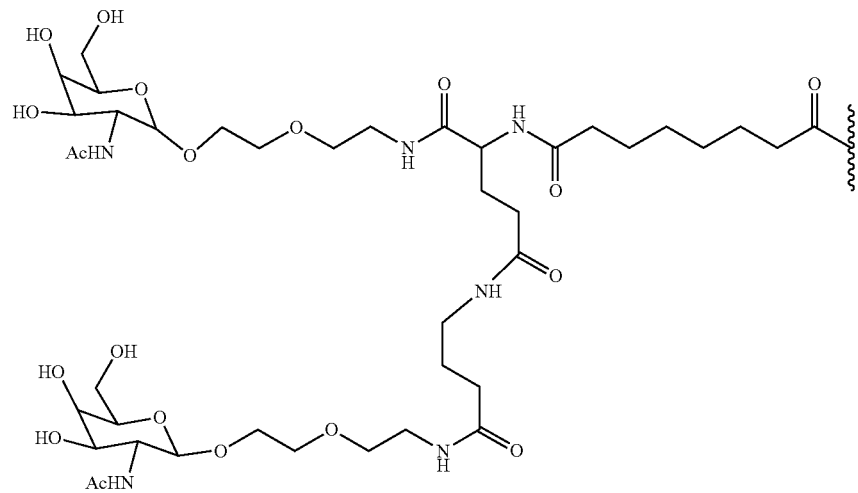
3'ERCa-03

| | |
|---|---|
| 14 | 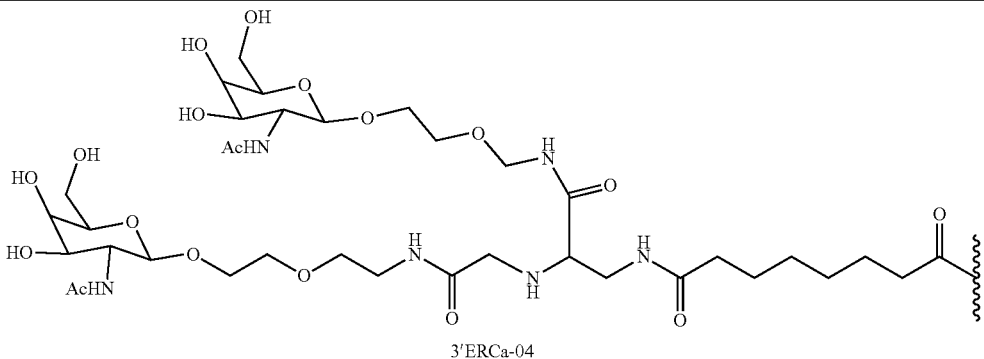<br>3'ERCa-04 |
| 15 | 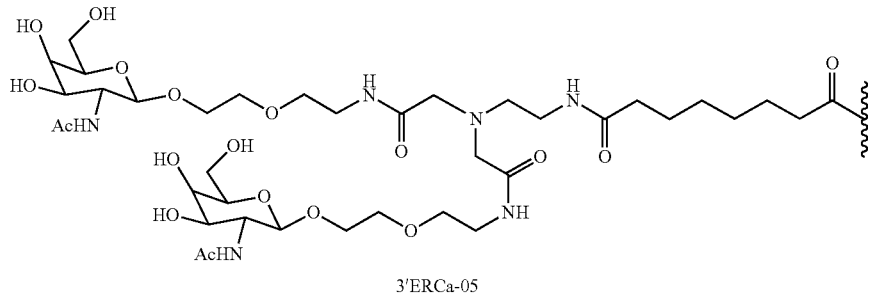 [SMILES: *C(=O)CCCCCCC(=O)NCCN(CC(=O)NCCOCCOC1OC(CO)C(O)C(O)C1NC(C)=O)CC(=O)NCCOCCOC1OC(CO)C(O)C(O)C1NC(C)=O]<br>3'ERCa-05 |
| 16 | 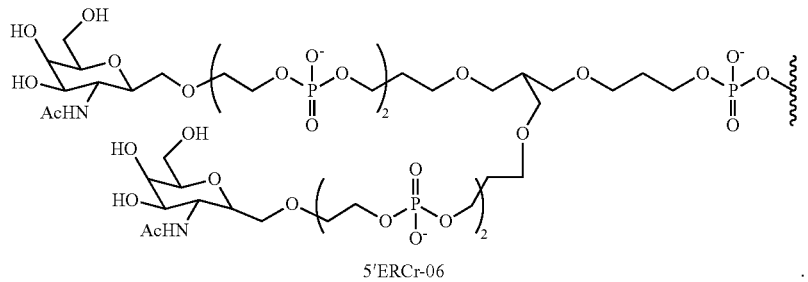<br>5'ERCr-06 |

In some preferable examples, the compound of the present invention comprises the sense strands with delivery chains linked at the 5' end and the antisense strands with delivery chains linked at the 3' end, as shown in the table below:

| Sense strand with a delivery chain 5'→3' | | Antisense strand with a delivery chain 5'→3' | | Code of siRNA with delivery | Code of the combination of delivery |
|---|---|---|---|---|---|
| Code | Sequence | Code | Sequence | chains | chains |
| Kys-01 | 5'YICd-01-R₁-<br>mGsmUsmUmUmUmUfC<br>mUfUfGfUmUmGmAmC<br>mAmAmAmAsmUsmU<br>(SEQ ID NO: 49) | Kyas-01 | mUsfUsmUmUmGfUmCfAfAfCm<br>AmAmGfAfAfAmAmAmCsmUsm<br>U-R₂-3'SANCd-01<br>(SEQ ID NO: 50) | Ky-0101 | GBL-01 |
| Kys-02 | 5'YICc-01-R₁-<br>mGsmGsmGmUmUmUfU<br>mUfCfUfUmGmUmUmG<br>mAmCmAmAsTsT<br>(SEQ ID NO: 43) | Kyas-02 | mUsfUsmGmUmCfAmAfCfAfAm<br>GmAmAfAfAfAmCmCmCsmUsm<br>U-R₂-3'SANCc-01<br>(SEQ ID NO: 44) | Ky-0202 | GBL-02 |
| Kys-03 | 5'ERCd-01-R₁-<br>mGsfAsmCfCmGmUmGm<br>UfGfCfAmCmUmUmCmG<br>mCmUmUsmAsmU<br>(SEQ ID NO: 51) | Kyas-03 | mAsfAsmGmCmGfAmAfGfUfGm<br>CmAmCfAfCfGmGmUmCsTsT-R₂<br>-3'ERCd-01<br>(SEQ ID NO: 52) | Ky-0303 | GBL-09 |

-continued

| Sense strand with a delivery chain 5'→3' | | Antisense strand with a delivery chain 5'→3' | | Code of siRNA with delivery chains | Code of the combination of delivery chains |
|---|---|---|---|---|---|
| Code | Sequence | Code | Sequence | | |
| Kys-04 | 5'ERCc-01-R₁-mAsmCsmCmGmUfGmUfGfCfAmCmUmUmCmGmCmUmUmCsTsT (SEQ ID NO: 53) | Kyas-04 | mGsfAsmAmGmCfGmAfAfGfUmGmCmAfCfAfCmGmGmUsmUsmU-R₂-3'ERCc-01 (SEQ ID NO: 54) | Ky-0404 | GBL-10 |
| Kys-05 | 5'YICa-01-R₁-mCsmGsmUmGmUmGfCmAfCfUfUmCmGmCmUmUmCmAmCsmUsmU (SEQ ID NO: 59) | Kyas-05 | mGsfUsmGmAmAfGmCfGfAfAmGmUGfCfAfCmAmCmGsmUsmU-R₂-3'SANCa-01 (SEQ ID NO: 60) | Ky-0505 | GBL-03 |
| Kys-06 | 5'ERCa-01-R₁-mUsmGsmUmGmCmAfCmUfUfCfGfCmUmUmCmAmCmUsmAsmU (SEQ ID NO: 63) | Kyas-06 | mAsfGsmUmGfAmAfGfCfGmAmAmGfUfGfCmAmCmAsmAsmU-R₂-3'ERCa-01 (SEQ ID NO: 64) | Ky-0606 | GBL-11 |
| Kys-07 | 5'YICr-01-R₁-mCsfGsmGfGmGfCmGfCmAfCmCfUmCfUmUfUmAsmUsmU (SEQ ID NO: 75) | Kyas-07 | mUsfAsmAmAmGfAmGfAfGfGfGmUmGmCfGfCfCmCmCmGsTsT-R₂-3'SANCr-01 (SEQ ID NO: 76) | Ky-0707 | GBL-08 |
| Kys-08 | 5'ERCr-01-R₁-mGsmGsmCmGmCmAfCmCfUfCfUfUmCmUmUmUmAmCmGsmAsmU (SEQ ID NO: 79) | Kyas-08 | mGsfCsmGmUmAfAmAfGfAfGmAmGfUfGfCmGmCmCsTsT-R₂-3'ERCr-01 (SEQ ID NO: 80) | Ky-0808 | GBL-16 |
| Kys-09 | 5'YICa-02-R₁-mGsmGsmCmGmCmAfCmCfUfCfUfUmCmUmUmUmAmCmGsmAsmU (SEQ ID NO: 79) | Kyas-09 | mGsfCsmGmUmAfAmAfGfAfGmAmGfUfGfCmGmCmCsTsT-R₂-3'SANCa-01 (SEQ ID NO: 80) | Ky-0909 | GBL-04 |
| Kys-10 | 5'YICa-03-R₁-mGsmGsmCmGmCmAfCmCfUfCfUfUmCmUmUmUmAmCmGsmAsmU (SEQ ID NO: 79) | Kyas-10 | mGsfCsmGmUmAfAmAfGfAfGmAmGfUfGfCmGmCmCsTsT-R₂-3'SANCa-01 (SEQ ID NO: 80) | Ky-1010 | GBL-05 |
| Kys-11 | 5'YICa-04-R₁-mGsmGsmCmGmCmAfCmCfUfCfUfUmCmUmUmUmAmCmGsmAsmU (SEQ ID NO: 79) | Kyas-11 | mGsfCsmGmUmAfAmAfGfAfGmAmGfUfGfCmGmCmCsTsT-R₂-3'SANCa-02 (SEQ ID NO: 80) | Ky-1111 | GBL-06 |
| Kys-12 | 5'YICa-05-R₁-mGsmGsmCmGmCmAfCmCfUfCfUfUmCmUmUmUmAmCmGsmAsmU (SEQ ID NO: 79) | Kyas-12 | mGsfCsmGmUmAfAmAfGfAfGmAmGfUfGfCmGmCmCsTsT-R₂-3'SANCa-02 (SEQ ID NO: 80) | Ky-1212 | GBL-07 |
| Kys-13 | 5'ERCa-02-R₁-mGsmGsmCmGmCmAfCmCfUfCfUfUmCmUmUmUmAmCmGsmAsmU (SEQ ID NO: 79) | Kyas-13 | mGsfCsmGmUmAfAmAfGfAfGmAmGfUfGfCmGmCmCsTsT-R₂-3'ERCa-02 (SEQ ID NO: 80) | Ky-1313 | GBL-12 |
| Kys-14 | 5'ERCa-03-R₁-mGsmGsmCmGmCmAfCmCfUfCfUfUmCmUmUmUmAmCmGsmAsmU (SEQ ID NO: 79) | Kyas-14 | mGsfCsmGmUmAfAmAfGfAfGmAmGfUfGfCmGmCmCsTsT-R₂-3'ERCa-03 (SEQ ID NO: 80) | Ky-1414 | GBL-13 |
| Kys-15 | 5'ERCa-04-R₁-mGsmGsmCmGmCmAfCmCfUfCfUfUmCmUmUmUmAmCmGsmAsmU (SEQ ID NO: 79) | Kyas-15 | mGsfCsmGmUmAfAmAfGfAfGmAmGfUfGfCmGmCmCsTsT-R₂-3'ERCa-04 (SEQ ID NO: 80) | Ky-1515 | GBL-14 |

-continued

| Sense strand with a delivery chain 5'→3' | | Antisense strand with a delivery chain 5'→3' | | Code of siRNA with delivery chains | Code of the combination of delivery chains |
|---|---|---|---|---|---|
| Code | Sequence | Code | Sequence | | |
| Kys-16 | 5'ERCa-05-R₁-mGsmGsmCmGmCmAfCmCfUfCfUmCmUmUmUmAmCmGmCsmAsmU (SEQ ID NO: 79) | Kyas-16 | mGsfCsmGmUmAfAmAfGfAfGmAmGmGfUfGfCmGmCmCsTsT-R₂-3'ERCa-05 (SEQ ID NO: 80) | Ky-1616 | GBL-15 |

In some preferable examples, the compound of the present invention has a structure shown in the table below:

| Code of siRNA with delivery chains | R₁ | R₂ | Code of compound |
|---|---|---|---|
| Ky-0101 | —NH(CH₂)₅CH₂— | 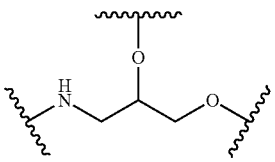 [SMILES: *NCC(CO*)O*] | GBL-0401 |
| Ky-0202 | —NH(CH₂)₅CH₂— | 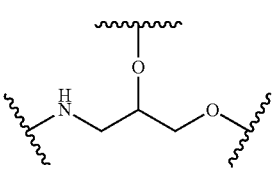 | GBL-0402 |
| Ky-0303 | —NH(CH₂)₅CH₂— | 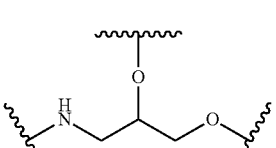 | GBL-0403 |
| Ky-0404 | —NH(CH₂)₅CH₂— | 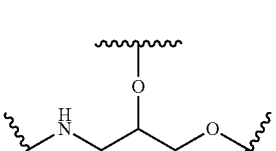 | GBL-0404 |
| Ky-0505 | —NH(CH₂)₅CH₂— | 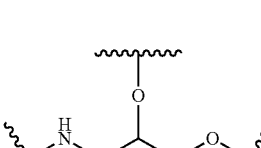 | GBL-0405 |
| Ky-0606 | —NH(CH₂)₅CH₂— | 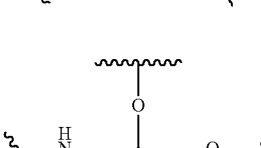 | GBL-0406 |

-continued

| Code of siRNA with delivery chains | R₁ | R₂ | Code of compound |
|---|---|---|---|
| Ky-0707 | —NH(CH₂)₅CH₂— | (structure: central CH with O-linker up, NH-linker left, O-linker right) | GBL-0407 |
| Ky-0808 | —NH(CH₂)₅CH₂— | (structure: central CH with O-linker up, NH-linker left, O-linker right) | GBL-0408 |
| Ky-0101 | —NH(CH₂)₅CH₂— | (pyrrolidine with O-linker at 4-position, CH₂OH at 2-position, N-linker) | GBL-0409 |
| Ky-0101 | —NH(CH₂)₅CH₂— | (piperidine with CH(CH₂OH)(CH₂O-linker) at 4-position, N-linker) | GBL-0410 |
| Ky-0909 | —NH(CH₂)₅CH₂— | (structure: central CH with O-linker up, NH-linker left, O-linker right) | GBL-0411 |
| Ky-1010 | —NH(CH₂)₅CH₂— | (structure: central CH with O-linker up, NH-linker left, O-linker right) | GBL-0412 |
| Ky-1111 | —NH(CH₂)₅CH₂— | (structure: central CH with O-linker up, NH-linker left, O-linker right) | GBL-0413 |
| Ky-1212 | —NH(CH₂)₅CH₂— | (structure: central CH with O-linker up, NH-linker left, O-linker right) | GBL-0414 |

| Code of siRNA with delivery chains | R₁ | R₂ | Code of compound |
|---|---|---|---|
| Ky-1313 | —NH(CH₂)₅CH₂— | 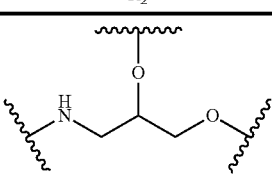 | GBL-0415 |
| Ky-1414 | —NH(CH₂)₅CH₂— | 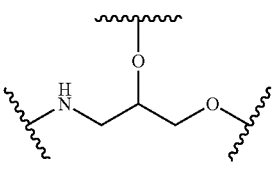 [SMILES: *NCC(CO*)O*] | GBL-0416 |
| Ky-1515 | —NH(CH₂)₅CH₂— | 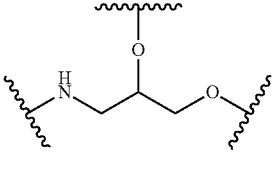 [SMILES: *NCC(CO*)O*] | GBL-0417 |
| Ky-1616 | —NH(CH₂)₅CH₂— | 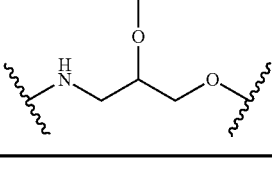 | GBL-0418. |

In another aspect, the present invention provides an application of the compound of the present invention in the preparation of a medicament for treating liver-related diseases, wherein, the liver-related diseases include acute and chronic hepatitis, liver cancer, hereditary liver-derived diseases, liver cirrhosis, fatty liver, diabetes.

In a further aspect, the present invention provides an application of the compound of the present invention in the preparation of a medicament for treating HBV infection-related diseases, wherein, the HBV infection includes chronic hepatitis B virus infection, acute hepatitis B virus infection.

Among others, the liver targeting specific ligand X is specific against asialoglycoprotein receptors (ASGPR) in liver, the HBV infection-related disease is chronic hepatitis B, and the compound can continuously inhibit the expression of HBsAg and HBeAg of HBV and HBV DNA.

In yet another aspect, the present invention provides a pharmaceutical composition, which comprises the compound of the present invention and pharmaceutically acceptable auxiliary materials, and its dosage form is preferably subcutaneous injection.

Compared to the prior art, the present invention has the following beneficial effects:
(1) Compared to liposome-mediated siRNA delivery: In liposome-mediated siRNA delivery, liposome mainly encapsulates siRNA within it to protect siRNA from nuclease degradation, thus improving the efficiency of siRNA passing the cell membrane barriers and promoting the uptake of cells. Liposome includes, e.g., anionic liposomes, pH-sensitive liposomes, immunoliposomes, fusogenic liposomes and cationic liposomes and the like. Although some progresses had been made, liposomes themselves are prone to triggering an inflammatory response, so before administration of a liposome, various antihistamine and hormone drugs, such as Cetirizine and dexamethasone, must be used so as to reduce acute inflammatory responses that may occur. Therefore, liposomes are not suitable for all therapeutic areas in practical clinical applications, especially diseases with long treatment cycles such as chronic hepatitis B, and the cumulative toxicity that may be generated from long-term use is a potential safety hazard.

(2) A completely new manner for introduction of N-acetylgalactosamine:

Comparison with siRNAs with three N-acetylgalactosamine moieties in terms of effect of HBsAg of HBV suppression: the siRNA drugs currently in phase I/II for the treatment of chronic hepatitis B include ARO-HBV and ALN-HBV02. In ARO-HBV, three N-acetylgalactosamine moieties are introduced through a linking chain at the 5' end of the sense strand of the siRNA, while in ALN-HBV02, three N-acetylgalactosamine moieties are introduced through a linking chain at the 3' end of the sense strand of the siRNA. In both of the above drugs, the sites for introducing galactosomines are on the sense strands, and three N-acetylgalactosamines are introduced. In the compound provided in the present invention, different or same numbers of N-acetylgalactosamines are introduced at the 5' end of the sense strand and the 3' end of the antisense strand of siRNA at the same time. So far, no report has been published about introduction at both of the 5' end of the sense strand and the 3' end of the antisense strand, especially introduction of three N-acetylgalactosamines at the 3' end of the antisense strand, which is a completely new introduction manner. It has been demonstrated through examples that, such an introduction manner allows siRNA to efficiently inhibit HBV gene.

BRIEF DESCRIPTION OF THE DRAWINGS

To make the objectives, technical solutions and beneficial effects of the present invention more clear, a brief description of the attached drawings is provided as below.

DETAILED DESCRIPTION

Figure 1:
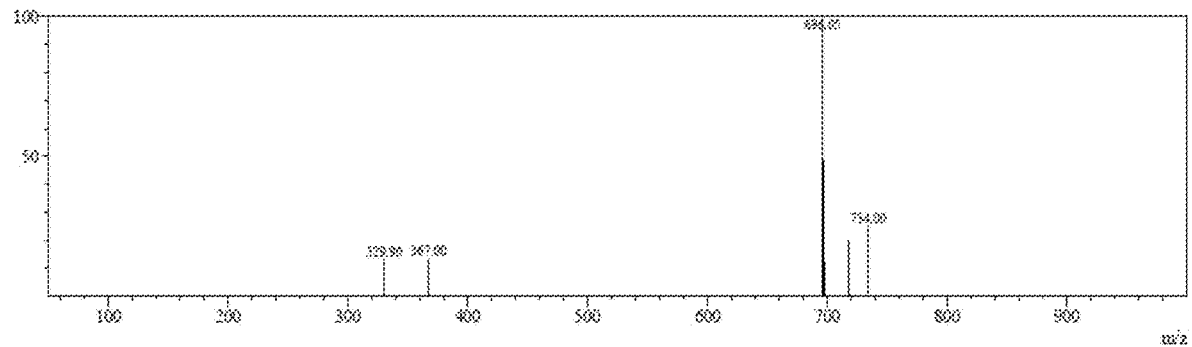
FIG. 1 is a high-resolution mass spectrum of 5'YICd-01-c4.

The following examples illustrate some embodiments disclosed in the present invention, but the present invention is not limited thereto. In addition, when providing specific embodiments, the inventors anticipated application of some specific embodiments, for example, compounds with specifically same or similar chemical structures for treatment of different liver-derived diseases.

Explanations

DMF refers to N,N-dimethylformamide;

HBTU refers to O-benzotriazole-tetramethylurea hexafluorophosphate;

DIPEA (DIEA) refers to N,N-diisopropylethylamine;

DCM refers to dichloromethane;

DMAP refers to 4-dimethylaminopyridine;

DMT-CL refers to 4,4'-dimethoxytriphenylchloromethane;

THF refers to tetrahydrofuran;

TBTU refers to O-benzotriazol-N,N,N',N'-tetramethylurea tetrafluoroborate;

DBU refers to 1,8-diazabicycloundec-7-ene;

HOBt refers to 1-hydroxybenzotrizole;

DCC refers to dicyclohexylcarbodiimide;

Pd—C refers to palladium-carbon catalyst;

⊙ refers to a solid phase carrier, such as a resin.

Example 1. Synthesis of GBL-0401

1. Synthesis of Kys-01

1.1. Compounds of 5'YICd-01: Synthesis of 5'YICd-01-PFP

1.1.1. Synthesis of 5'YICd-01-c1

Into 2-hydroxyethylamine (5.0 g, 81.9 mmol), were added 50 mL of dimethyl sulfoxide and 5 mL of a sodium hydroxide solution at a concentration of 1 g/mL, followed by dropwise addition of 12 mL of tert-butyl acrylate (81.9 mmol) within 1 hour. The mixture was reacted at room temperature for 24 h, and then 100 mL of petroleum ether was added, and the mixture was washed with saturated brine twice. The organic layer was dried and passed over a column to get 7.5 g of colorless oil.

1.1.2. Synthesis of 5'YICd-01-c2

Into 5'YICd-01-c1 (7.5 g, 39.7 mmol), were added 50 mL of DCM and 23 mL of a sodium carbonate solution (25%), followed by dropwise addition of benzyl chloroformate (7.7 g, 45.0 mmol) at room temperature. The mixture was reacted at room temperature overnight, washed with saturated brine twice, dried over anhydrous sodium sulfate, and evaporated off the solvent. The residue was passed over a chromatographic column (ethyl acetate:petroleum ether=15%-30%) to get 11.3 g of an oil.

1.1.3 Synthesis of 5'YICd-01-c3

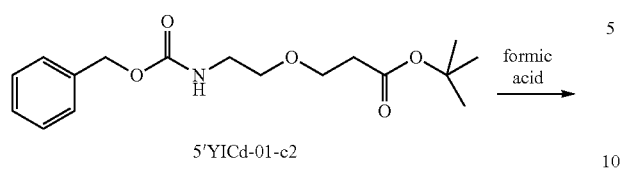

5'YICd-01-c2 formic acid

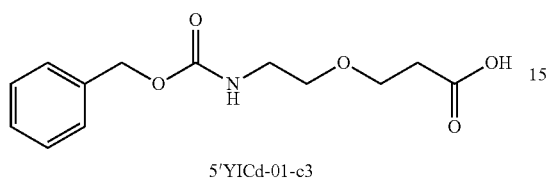

5'YICd-01-c3

5'YICd-01-c2 (11.3 g, 35.0 mmol) was added with 20 mL of formic acid, and reacted at room temperature overnight. The solvent was evaporated off at reduced pressure to get 9.2 g of 5'YICd-01-c3.

1.1.4. Synthesis of 5'YICd-01-c4

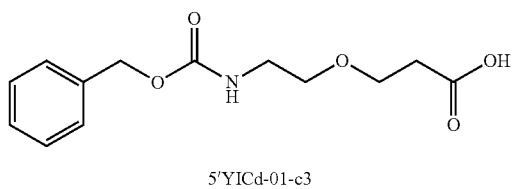

5'YICd-01-c3

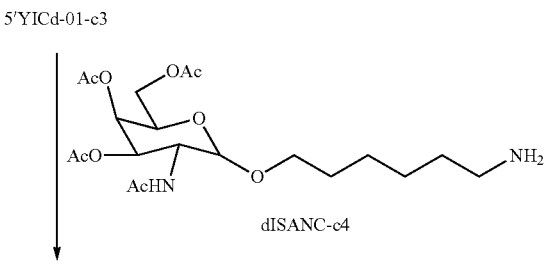

dISANC-c4

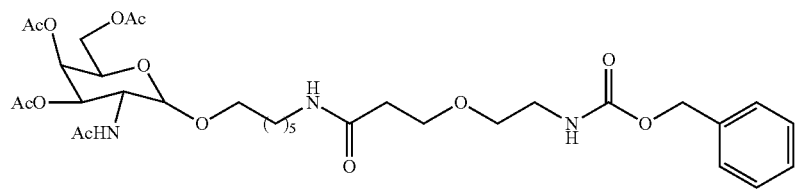

5'YICd-01-c4

1.0 g (3.73 mmol) of 5'YICd-01-c3 and 2.0 g (4.48 mmol) of dISANC-c4 were added into 30 mL of DMF, then added with 0.38 g of HOBt and 2.30 g of HBTU, followed by slow addition of 1.0 mL of DIEA. The mixture was added with 20 mL of water and extracted with 40 mL of DCM. The organic phase was washed with 100 mL of saturated brine, dried over anhydrous sodium sulfate, and evaporated at reduced pressure to dryness. The residue was purified by chromatography on a silica gel column (Eluent: 1-15% methanol in DCM) to get 2.2 g of a white foamy solid, of which the high-resolution mass spectrum is shown in FIG. 1.

1.1.5. Synthesis of 5'YICd-01-c5

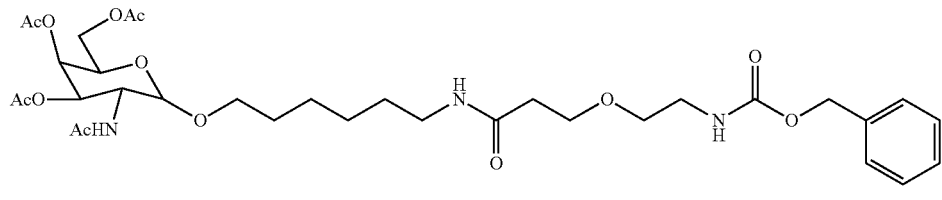

5'YICd-01-c4

↓

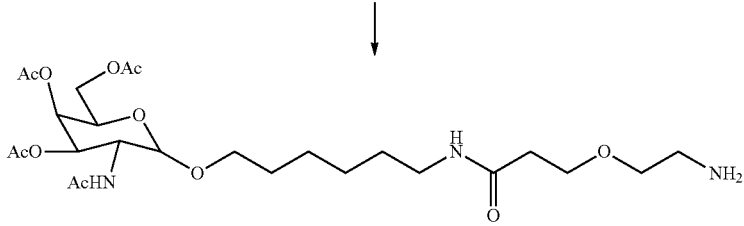

5'YICd-01-c5

2.2 g (3.2 mmol) of 5'YICd-01-c4 was dissolved in 30 mL of methanol, added with 1.0 g of 10% Pd—C (wet Degussa-type E101 NE/W), and hydrogenated at normal pressure overnight. The reaction mixture was filtered with diatomite, and the filtrate was evaporated at reduced pressure to dryness to get 1.70 g of white foam.

1.1.6. Synthesis of 5'YICd-01-c6

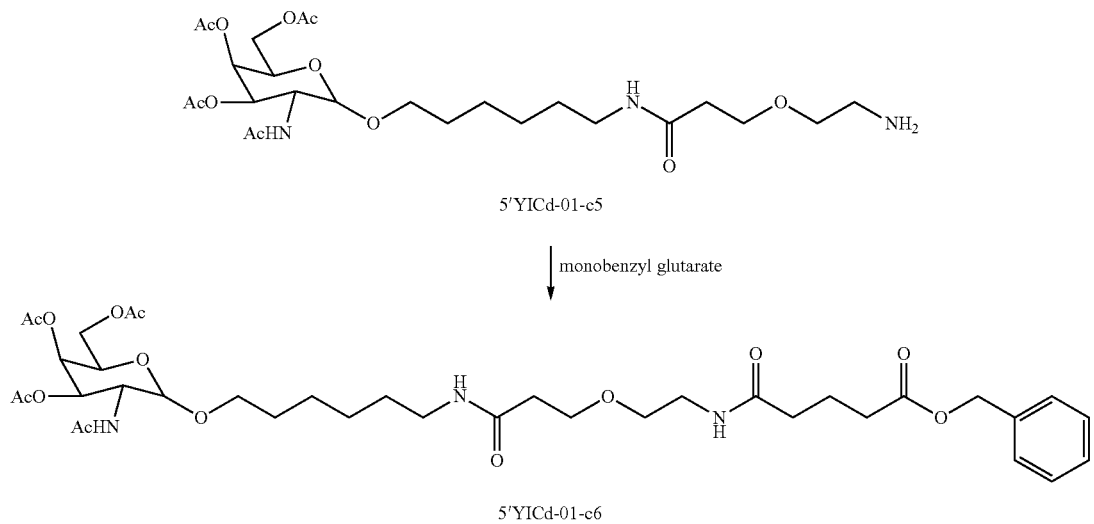

0.80 g (3.60 mmol) of monobenzyl glutarate was weighed and dissolved in 2 mL DMF, added with 1.28 g of TBTU and 2.0 mL of DIEA, reacted with stirring for 5 minutes, and then added with 1.70 g (3.0 mmol) of 5'YICd-01-c5, and reacted at room temperature with stirring overnight. The reaction solution was evaporated at reduced pressure, added with 50 mL of DCM and 50 mL of water and stirred for 5 minutes. The layers were separated, and the organic layer was dried over anhydrous sodium sulfate, passed over a chromatographic column (Eluent: DCM:methanol=1%-10%), and the solvent was evaporated at reduced pressure to get 2.1 g of a white product.

1.1.7. Synthesis of 5'YICd-01-c7

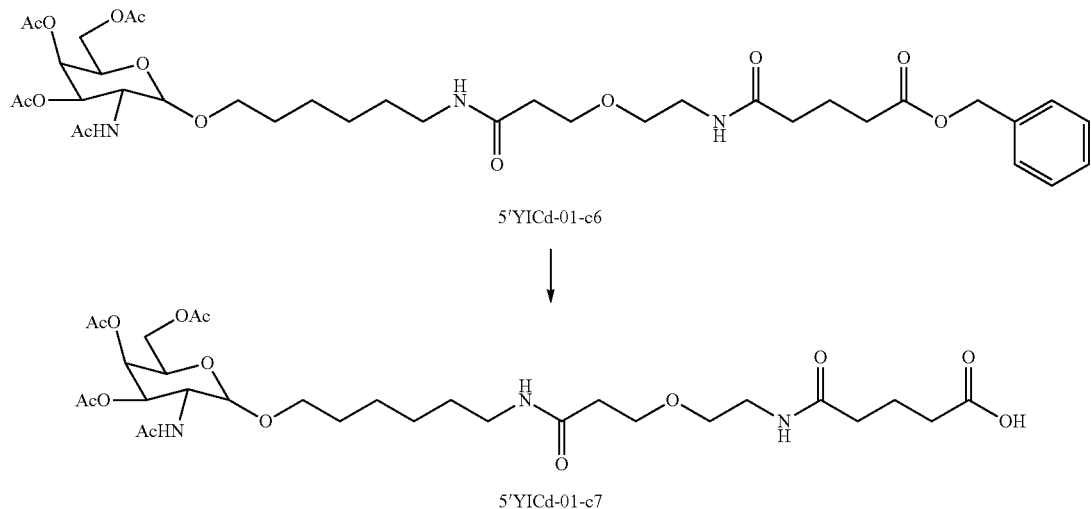

5'YICd-01-c6

5'YICd-01-c7

Into a 100 mL single-necked flask, were added 2.1 g (2.7 mmol) of 5'YICd-01-c6 and 0.2 g of palladium-carbon. The flask was evacuated by a water pump and supplemented with hydrogen in triplicate. The reaction was conducted under pressurized hydrogen overnight. On the next day, TLC showed that the reaction was completed. Palladium-carbon was filtered with diatomite, and the filtrate was evaporated at reduced pressure to get 1.8 g of a product.

1.1.8. Synthesis of 5'YICd-01-PFP

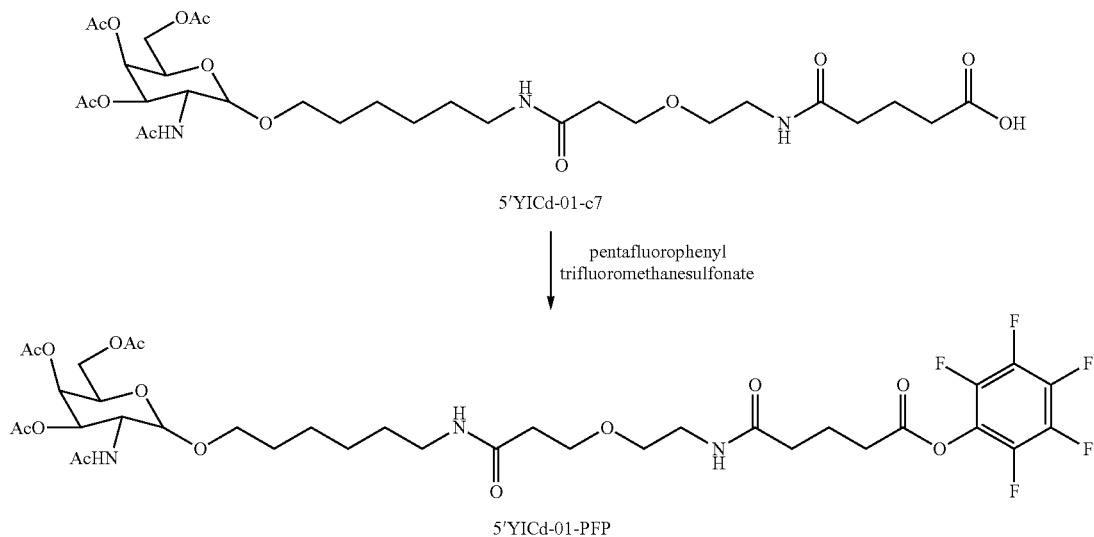

5'YICd-01-c7 pentafluorophenyl trifluoromethanesulfonate

5'YICd-01-PFP

Into a 100 mL single-necked flask, were added 1.8 g (2.66 mmol) of 5'YICd-01-c7 and 20 mL of DCM. 1.1 g (4.0 mmol) of pentafluorophenyl trifluoromethanesulfonate was dropwise added, and reacted at room temperature for 1 hour. The reaction mixture was washed with 40 mL of water and 10 mL of saturated sodium bisulfite. The organic layer was dried over anhydrous sodium sulfate and evaporated at reduced pressure to dryness to get 2.3 g of a product.

1.2. Solid-phase synthesis of C6NH-S-01 With mG as the initiation monomer and with C6NH phosphoramidite monomer as the end monomer, different phosphoramidite monomers were introduced by coupling through a solid-phase phosphoramidite method. The solid-phase phosphoramidite method includes the following basic steps: 1) deprotection: removing the protective group (DMT) on the oxygen atom of the solid phase carrier; 2) coupling: adding a first nucleotide monomer, coupling in the direction of 3' to 5'; 3) oxidation: oxidizing the resulting nucleoside phosphite into a more stable nucleoside phosphate (that is, oxidization of trivalent phosphorus to pentavalent phosphorus); 4) blocking: blocking 5'-OH of the nucleotide monomer unreacted in the previous step by capping to prevent it from reacting further; the above steps were repeated until the desired sequence was achieved. After being synthesized, the ester bond for linking the compound to the initial nucleoside on the solid phase carrier was cleaved with methylamine ethanol solution and aqueous ammonia, and protective groups on various bases and phosphoric acid on the oligonucleotide, including cyanoethyl (P), benzoyl (mA, fA), acetyl (mC, fC), isobutyryl (mG, fG) and 4-methoxy triphenylmethyl (C6NH), were removed. The product was purified by HPLC, filtered and sterilized, and freeze-dried.

1.3. Liquid-Phase Synthesis of Kys-01

1.3.1. Synthesis of Kys-01-c1

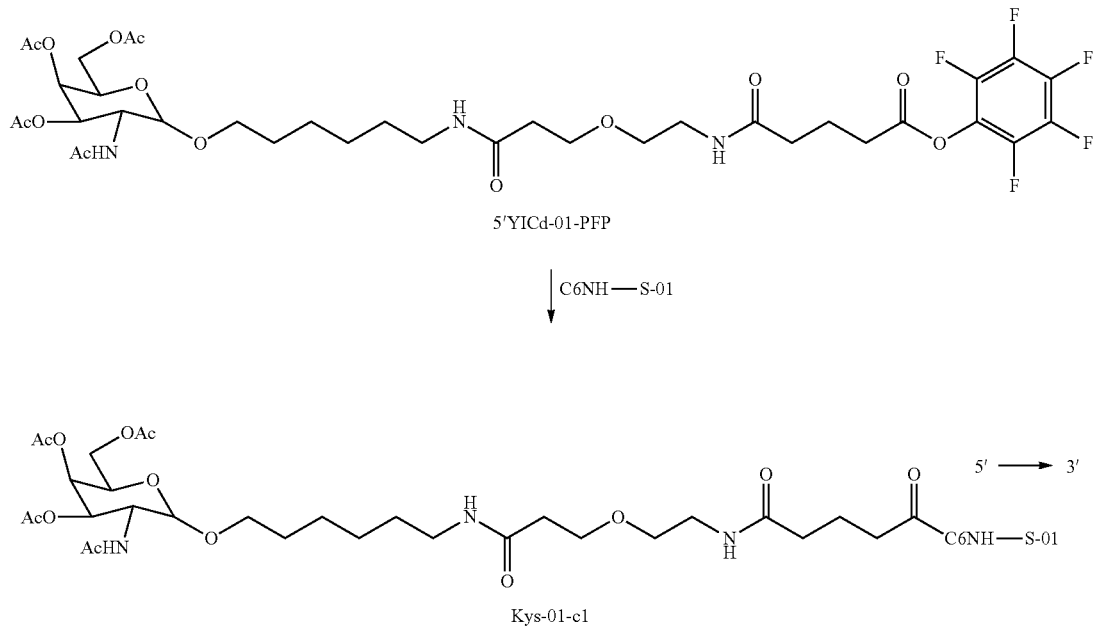

The purified and freeze-dried C6NH-S-01 (12.5 mg) was weighed and completely dissolved in a sodium borate buffer (650 μL, 0.06 mol/L). 5'YICd-01-PFP (10.3 mg) was weighed and dissolved in dimethyl sulfoxide (100 μL), and added into C6NH-S-01 and mixed uniformly, followed by addition of N-methylmorpholine (5 μL). The reaction mixture was ultrasonicated at room temperature for 3 h, and purified over a C18 column after HPLC detection showed the completion of the reaction.

1.3.2. Synthesis of Kys-01

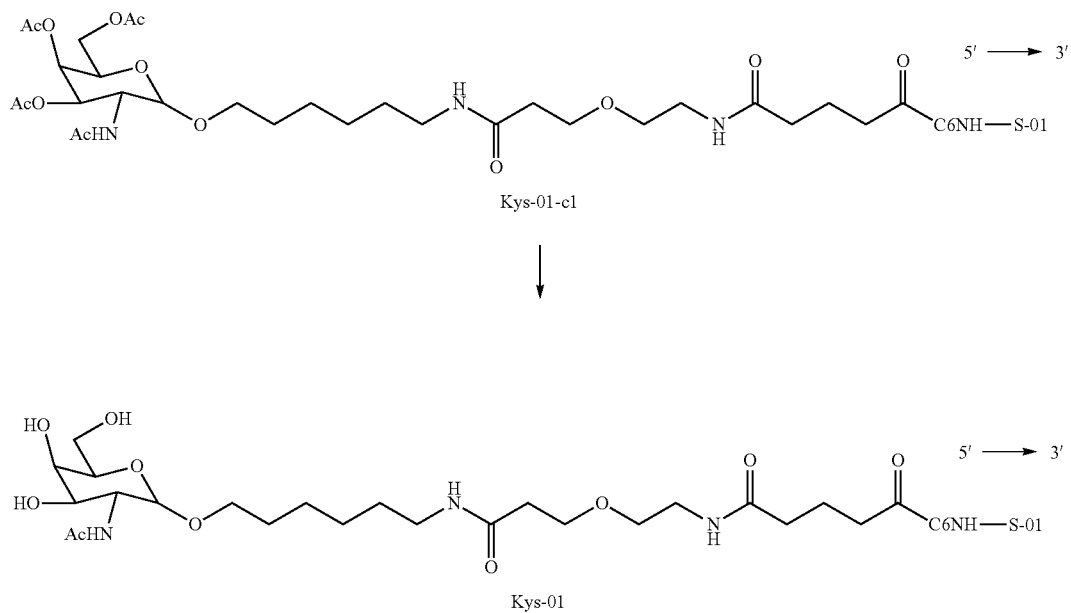

The purified Kys-01-c1 (32 mL, 5 mg) was taken into 25% hydrazine hydrate (16 mL), mixed uniformly, ultrasonicated at room temperature for 10 min, and purified through a C18 column after HPLC detection showed the completion of the reaction. The product was then freeze-dried to get Kys-01 (2 mg) as a white freeze-dried powder.

2. Synthesis of Kyas-01

2.1. Compounds of 3'SANCd-01: Synthesis of 3'SANCd-01 Resin 2.1.1. Synthesis of 3'SANCd-01-c1

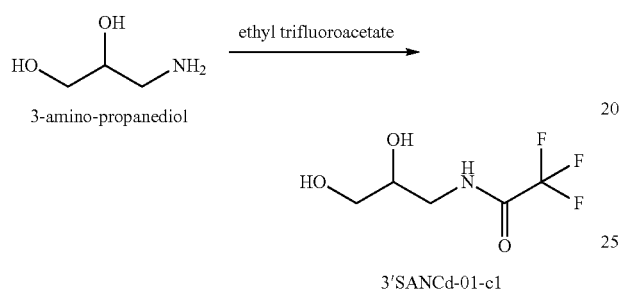

3-amino-propanediol (9.114 g, 0.100 mol) was weighed and dissolved in THF (50 mL), cooled, dropwise added with ethyl trifluoroacetate (15.62 g, 0.110 mol), and reacted at room temperature for 1 h. The reaction solution was rotary evaporated to get crude 3'SANCd-01-c1 (18.871 g).

2.1.2. Synthesis of 3'SANCd-01-c2

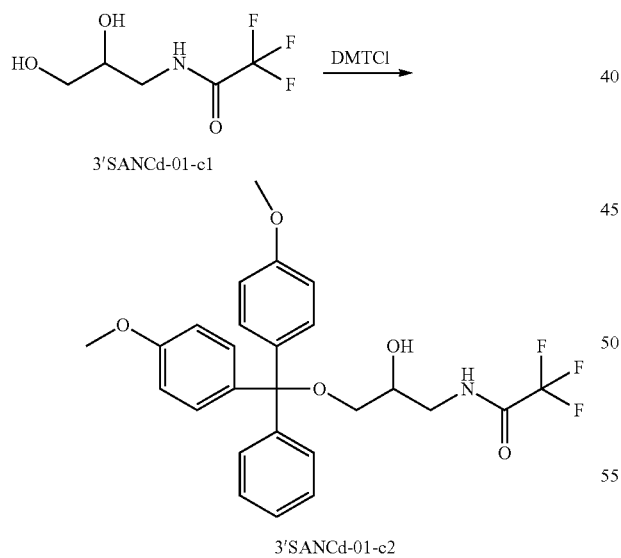

3'SANCd-01-c1 (5.480 g, 0.030 mol) was dissolved in pyridine (30 mL) and cooled, added with DMT-CL (10.423 g, 0.031 mol) batchwise, reacted in dark overnight, and then rotary evaporated to remove pyridine. The residue was dissolved in $CH_2Cl_2$ (50 mL), and washed with saturated brine (50 mL). The organic phase was dried over anhydrous sodium sulfate, filtered and rotary evaporated. The residue was passed over a column to get the product 3'SANCd-01-c2 (10.805 g).

2.1.3. Synthesis of 3'SANCd-01-c3

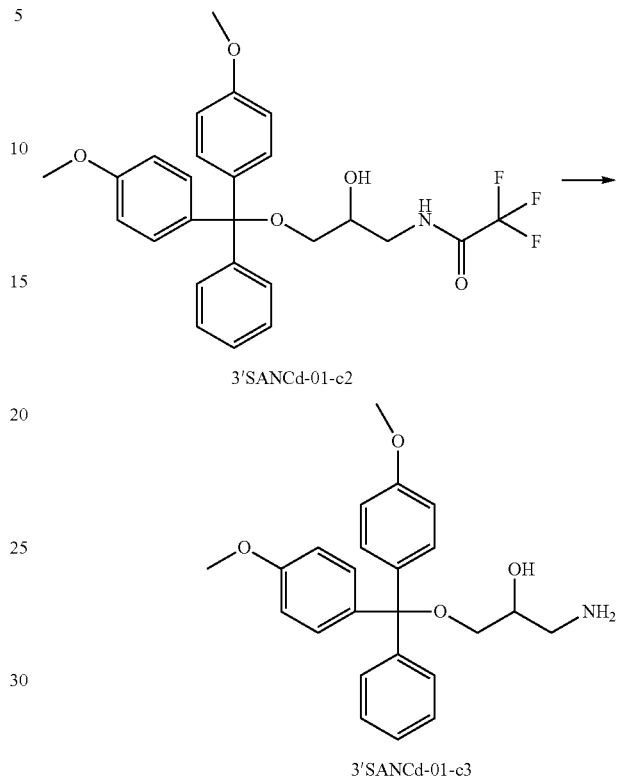

3'SANCd-01-c2 (10.805 g, 0.022 mol) was dissolved in methanol (60 mL) and THF (30 mL), cooled, dropwise added with a solution of KOH (5.69 g) in water (24 mL), reacted at room temperature for 2 h, and rotary evaporated to remove methanol and THF. The residue was added with water (50 mL) and extracted with EtOAc (30 mL*3). The organic phase was washed with saturated brine (50 mL), dried over anhydrous sodium sulfate, filtered, and rotary evaporated. The residue was passed over a column with an eluent containing 1% triethylamine to get the product 3'SANCd-01-c3 (8.286 g).

2.1.4. Synthesis of 3'SANCd-01-c4

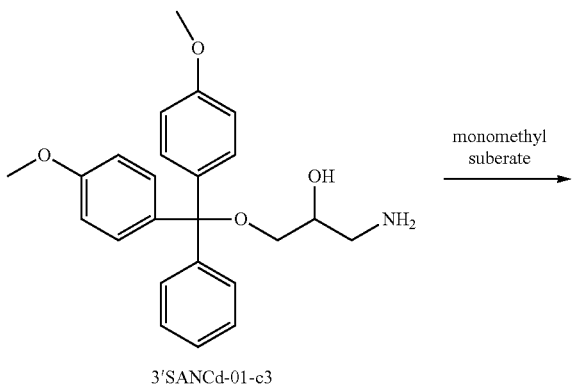

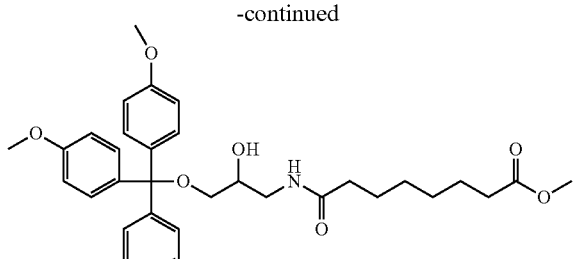

3'SANCd-01-c4

3'SANCd-01-c3(2.890 g, 0.007 mol) was dissolved in CH$_2$Cl$_2$ (20 mL) and cooled, dropwise added with a solution of DCC (1.680 g) in CH$_2$Cl$_2$ (10 mL), stirred for 20 minutes, added with a solution of monomethyl suberate (1.522 g) in CH$_2$Cl$_2$ (10 mL), and reacted at room temperature overnight. The reaction was quenched with 5% NaHCO$_3$(20 mL) and extracted with CH$_2$Cl$_2$ (20 mL*2). The organic phase was washed with saturated brine (10 mL), dried over anhydrous sodium sulfate, filtered, and rotary evaporated. The residue was passed over a column with an eluent containing 1% triethylamine to get the product 3'SANCd-01-c4 (3.193 g).

2.1.5. Synthesis of 3'SANCd-01-c5

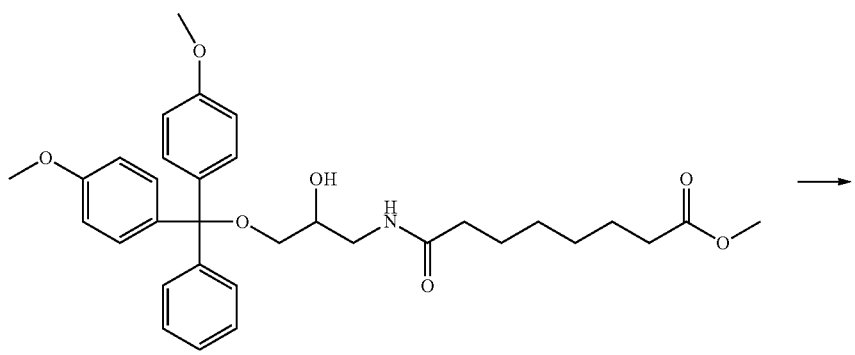

3'SANCd-01-c4

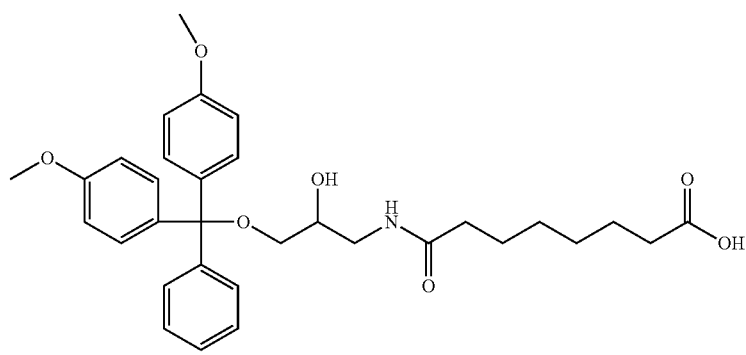

3'SANCd-01-c5

3'SANCd-01-c4 (2.193 g, 0.004 mol) was dissolved in THF (10 mL) and cooled, dropwise added with a solution of LiOH (0.645 g) in water (4.5 g) and reacted for 2 h. TLC indicated that there was no raw material. The reaction solution was rotary evaporated to remove the solvent. The residue was neutralized with saturated ammonium chloride, and extracted with $CH_2Cl_2$ (20 mL*2). The organic phase was washed with saturated brine (10 mL), dried over anhydrous sodium sulfate, filtered, and rotary evaporated. The residue was passed over a column with an eluent containing 1% triethylamine to get the product 3'SANCd-01-c5 (1.979 g).

2.1.6. Synthesis of 3'SANCd-01-c6

Figure 5:
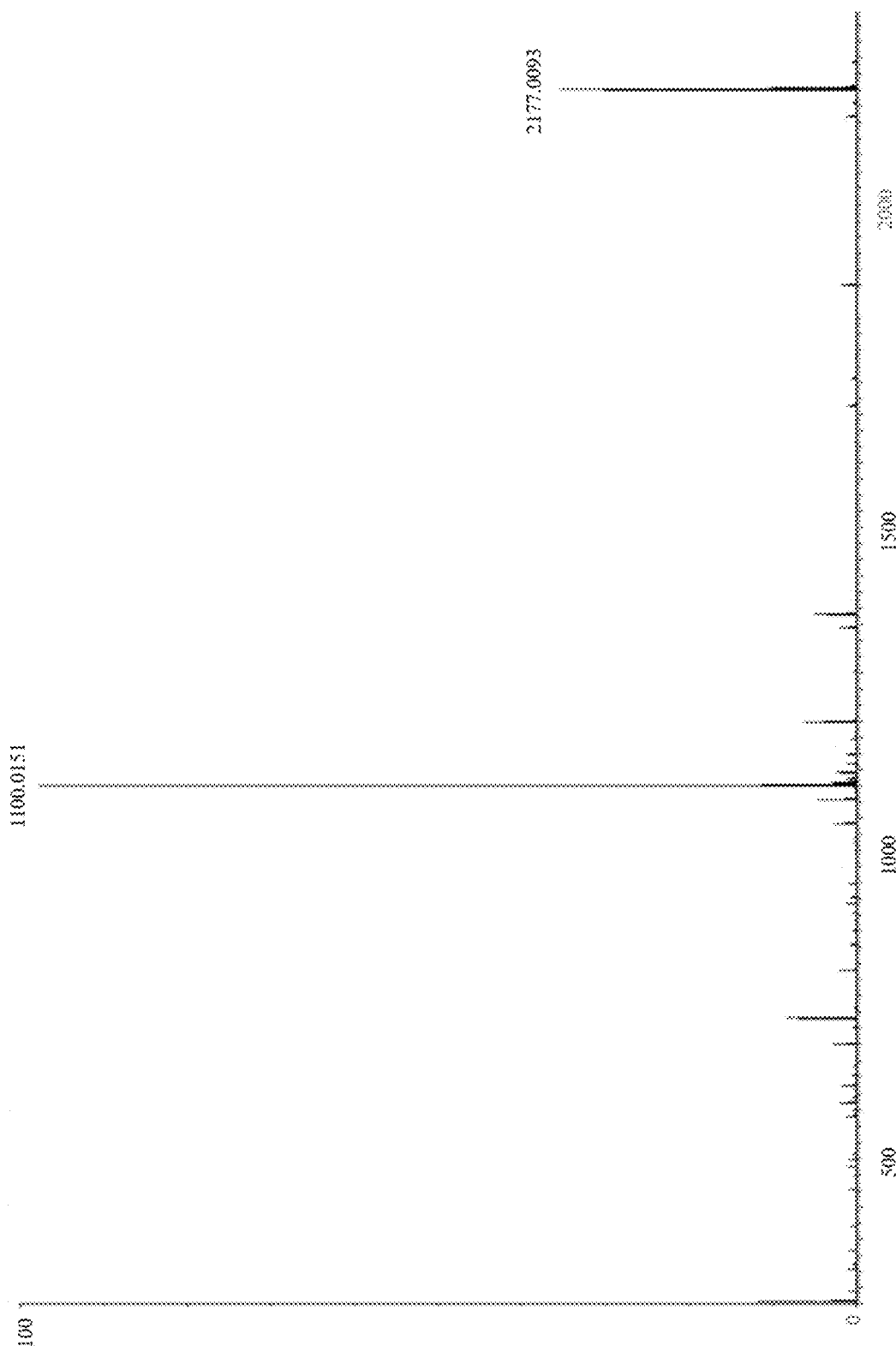
FIG. 5 is a high-resolution mass spectrum of 3'SANCd-01-c6.

3'SANCd-01-c5 (0.389 g, 0.004 mol) was dissolved in DMF (2 mL) and cooled, added with DIPEA (0.15 mL) and TBTU (0.183 g), stirred for 10 minutes, added with a solution of dISANC-c12 (0.756 g, 0.0005 mol) in DMF (2 mL), and reacted at room temperature overnight. The reaction was quenched with water (20 mL) and extracted with $CH_2Cl_2$ (20 mL*2). The organic phase was washed with saturated brine (10 mL), dried over anhydrous sodium sulfate, filtered, and rotary evaporated. The residue was passed over a column with an eluent containing 5% triethylamine to get the product 3'SANCd-01-c6 (0.803 g), of which the high-resolution mass spectrum is shown in FIG. 5.

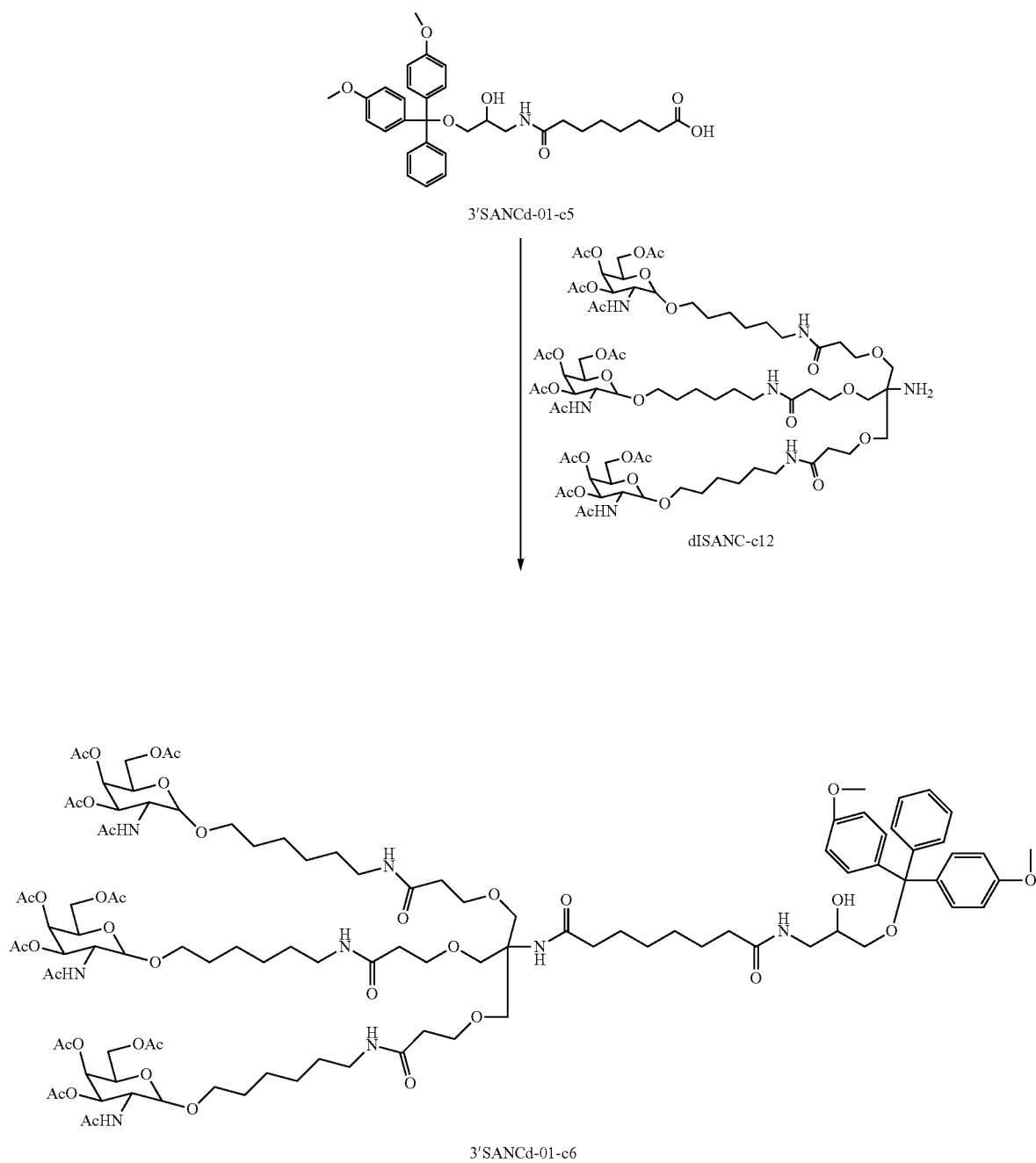

2.1.7. Synthesis of 3'SANCd-01-c7

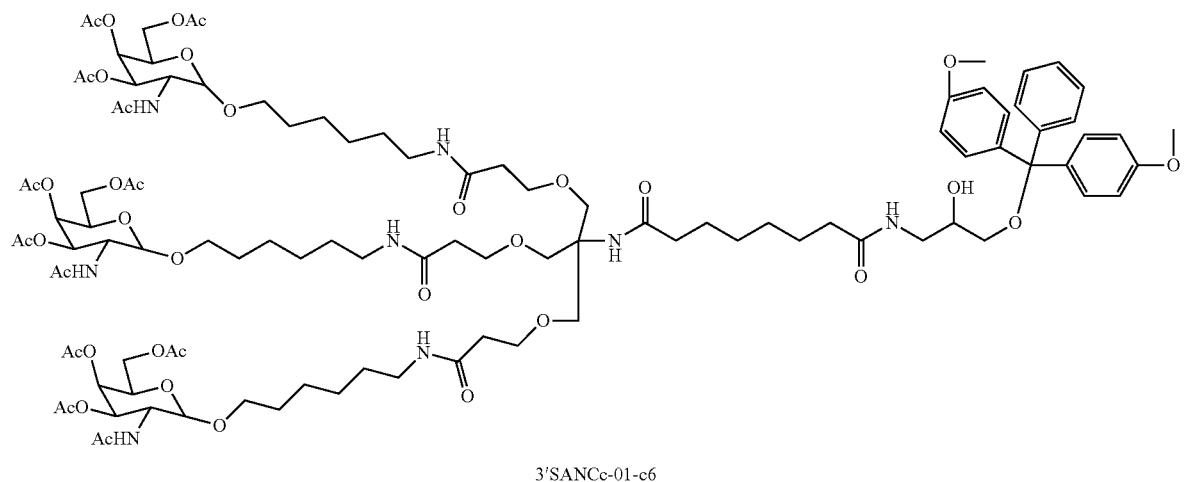

3'SANCc-01-c6

↓ succinic anhydride

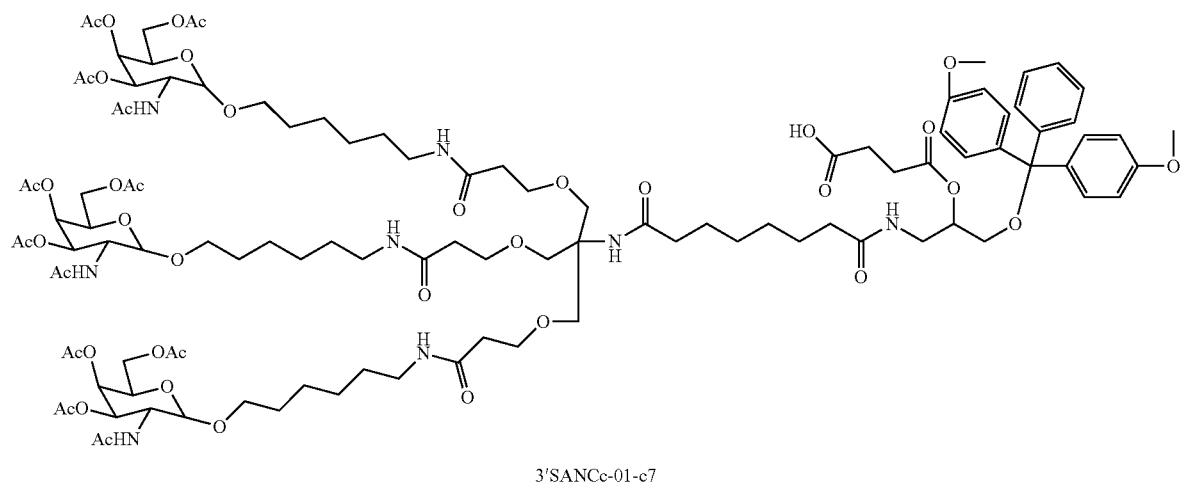

3'SANCc-01-c7

Into a reaction flask, 3'SANCd-01-c6 (2.15 g 0.001 mol) and 22 mL of DCM were added in order and dissolved with stirring at room temperature, and then added with DBU (0.156 g) and succinic anhydride (0.3 g, 0.003 mmol) in order, and reacted with stirring at room temperature. TLC analysis showed the reaction was completed. The reaction mixture was concentrated to remove DCM, and then added with water and extracted with DCM. The organic phase was further washed with saturated brine and dried over anhydrous sodium sulfate, filtered, and concentrated. Finally the residue was purified over a silica gel column to get 2.03 g of 3'SANCd-01-c7.

2.1.8. Synthesis of 3'SANCd-01 Resin

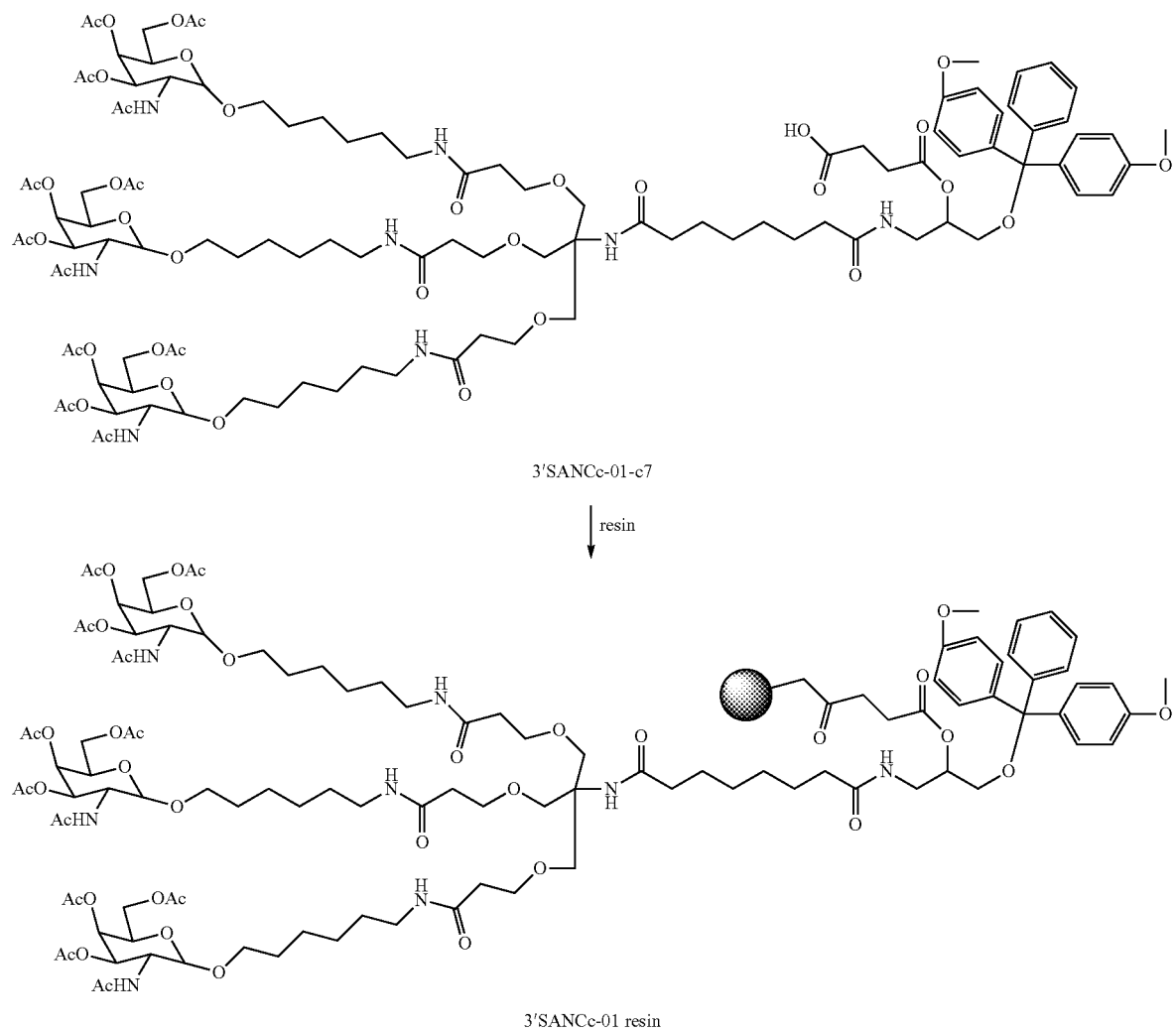

3'SANCc-01-c7

↓ resin

3'SANCc-01 resin

Into a reaction flask, 3'SANCd-01-c7 (1.13 g, 0.0005 mmol) and 12 mL of DMF were added in order and dissolved with stirring at room temperature, added with HBTU (0.11 g), DIPEA (0.104 g) and GE resin (1.80 g) in order, and shaken in a shaker at 35° C. for 24 h. The mixture was transferred into a synthesis tube and filtered. Under bubbled with nitrogen, the resin was rinsed with DMF for 4 times. Then CAP A+CAP B were added to conduct the end-capping reaction for half an hour under bubbling with nitrogen. A little amount of resin was taken for a kaiser test until the test solution appeared yellow. After completion of the end-capping, the filter cake was rinsed with methanol, DCM and methanol, respectively, and dried in vacuum to get 2.48 g of 3'SANCd-01 resin, of which the degree of substitution was 150 μmol/g.

2.2 Solid-Phase Synthesis of Kyas-01

With mU as the initiation monomer and with MU as the end monomer, different phosphoramidite monomers were introduced by coupling through a solid-phase phosphoramidite method. The solid-phase phosphoramidite method includes the following basic steps: 1) deprotection: removing the protective group (DMT) on the oxygen atom of 3'SANCd-01 resin; 2) coupling: adding a first nucleotide monomer, coupling in the direction of 3' to 5'; 3) oxidation: oxidizing the resulting nucleoside phosphite into a more stable nucleoside phosphate (that is, oxidization of trivalent phosphorus to pentavalent phosphorus); 4) blocking: blocking 5'-OH of the nucleotide monomer unreacted in the previous step by capping to prevent it from reacting further; the above steps were repeated until the desired sequence was achieved. After being synthesized, the ester bond for linking the compound to the initial nucleoside on the solid phase carrier was cleaved with methylamine ethanol solution and aqueous ammonia, and protective groups on various bases and phosphoric acid on the oligonucleotide, including cyanoethyl (P), benzoyl (mA, fA), acetyl (mC, fC) and isobutyryl (mG, fG), were removed. The product was purified by HPLC, filtered and sterilized, and freeze-dried to get Kyas-01.

3. Synthesis of GBL-0401

Kys-01 and Kyas-01 solutions were determined accurately for their concentration, mixed at equal molarity, added with 1 M PBS solution at 1/20 of the volume and mixed uniformly again. The mixed system was heated to 95° C. for 5 min, cooled naturally for 3 h to 40° C. or room temperature, and detected by HPLC. If the single-strand residue was <5%, the reaction is considered complete.

Example 2. Synthesis of GBL-0402

1. Synthesis of Kys-02

1.1. Compounds of 5'YICc-01: Synthesis of 5'YICc-01-PFP

1.1.1. Synthesis of 5'YICc-01-c1

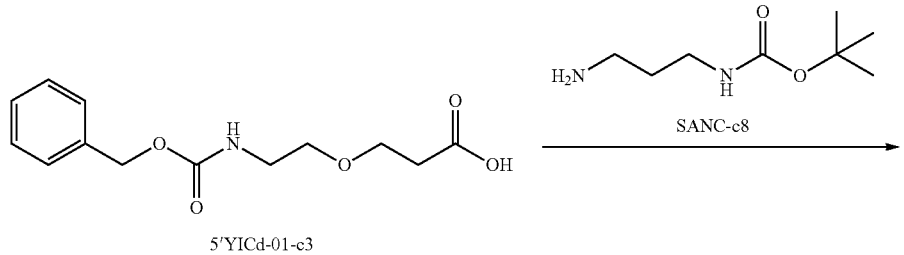

SANC-c8 (7.0 g, 40.0 mmol) and 5'YICd-01-c3 (9.2 g, 34.4 mmol) were dissolved in 25 mL of DMF, added with 9.0 g TBTU and cooled to 10° C., then added with 2 mL of DIEA and reacted at room temperature overnight. 30 mL of water and 50 mL of dichloromethane were added. The organic layer was washed with saturated brine for three times, dried, and evaporated at reduced pressure to dryness. The residue was passed over a chromatographic column (Eluent: dichloromethane:methanol=1%-10%) to get 10.0 g of a yellow sticky solid.

1.1.2. Synthesis of 5'YICc-01-c2

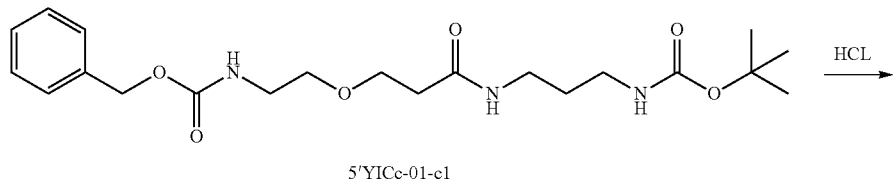

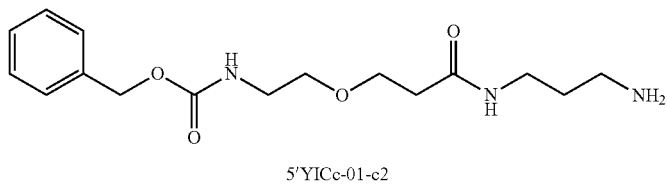

15 mL of concentrated hydrochloric acid was added into 10.0 g of 5'YICc-01-c1. The mixture was reacted at room temperature overnight, and then evaporated at reduced pressure to get 7.3 g of a product.

1.1.3. Synthesis of 5'YICc-01-c3

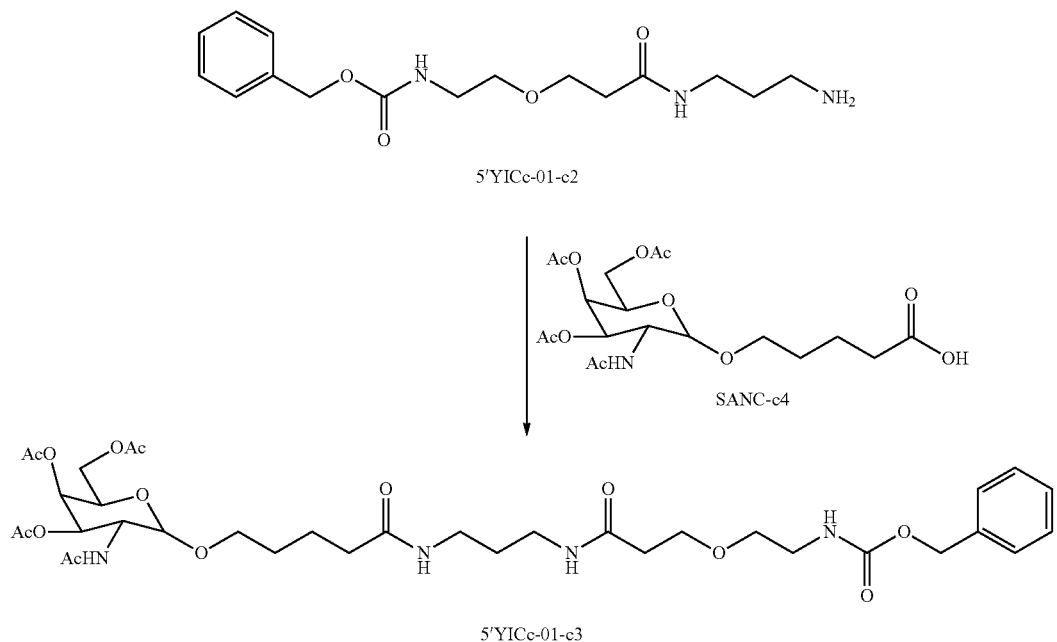

5'YICc-01-c2 (7.3 g, 22.6 mmol) and SANC-c4 (12.1 g, 27.1 mmol) were added into 60 mL of DMF, added with 3.8 g of HOBt and 12.4 g of HBTU, followed by slow addition of 5.0 ml of DIEA. The reaction solution was reacted at room temperature with stirring overnight. Then 50 mL of water was added, and the reaction solution was extracted with 100 mL of dichloromethane. The organic phase was washed with 100 mL of saturated brine, dried over anhydrous $Na_2SO_4$, and evaporated at reduced pressure to dryness. The residue was purified by chromatography on a silica gel column (Eluent:3-15% MeOH in DCM) to get 8.3 g of a white foamy solid.

1.1.4. Synthesis of 5'YICc-01-c7

Figure 2:
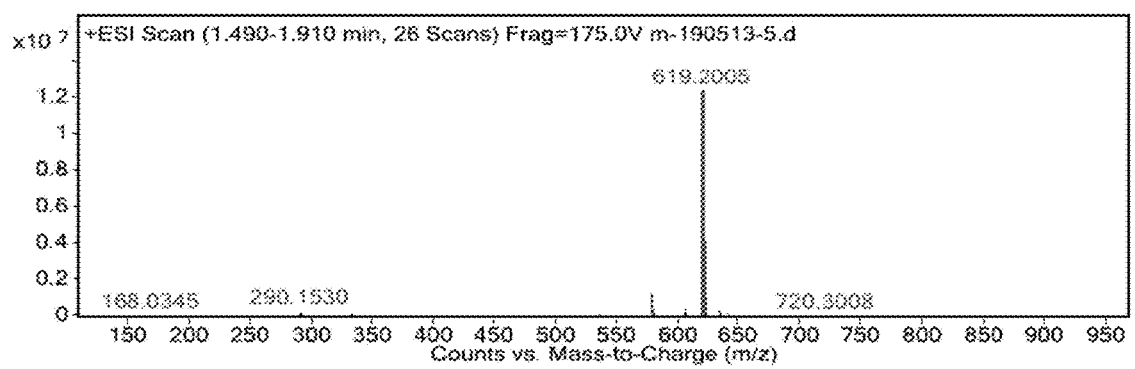
FIG. 2 is a high-resolution mass spectrum of 5'YICc-01-c7.

The synthetic steps were the same as those in 1.1.5 of Example 1, and the high-resolution mass spectrum is shown in FIG. 2.

1.1.5. Synthesis of 5'YICc-01-c8

The synthetic steps were the same as those in 1.1.6 of Example 1.

1.1.6. Synthesis of 5'YICc-01-c9

The synthetic steps were the same as those in 1.1.7 of Example 1.

1.1.7. Synthesis of 5'YICc-01-PFP

The synthetic steps were the same as those in 1.1.8 of Example 1.

1.2. Solid-Phase Synthesis of C6NH-S-02

With mG as the initiation monomer and with $C_6NH$ phosphoramidite monomer as the end monomer, different phosphoramidite monomers were introduced by coupling through a solid-phase phosphoramidite method. The synthetic steps were the same as those in 1.2 solid-phase synthesis of Example 1.

1.3. Liquid-Phase Synthesis of Kys-02

1.3.1. Synthesis of Kys-02-c1

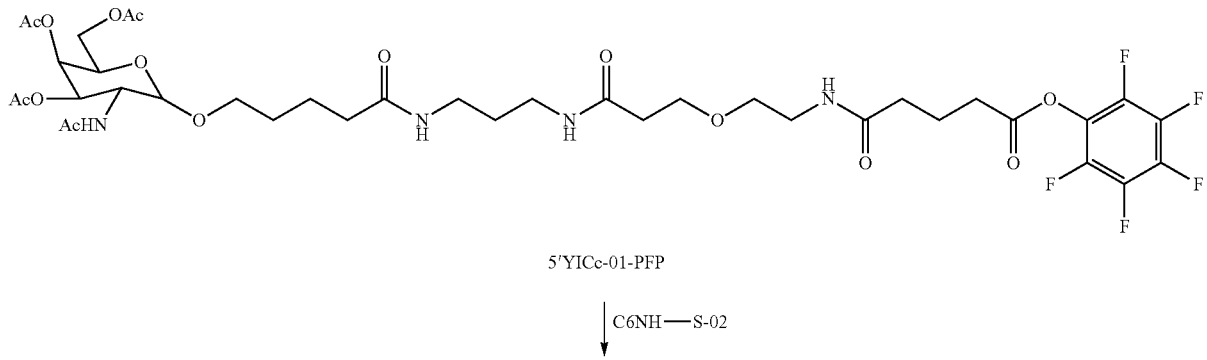

-continued
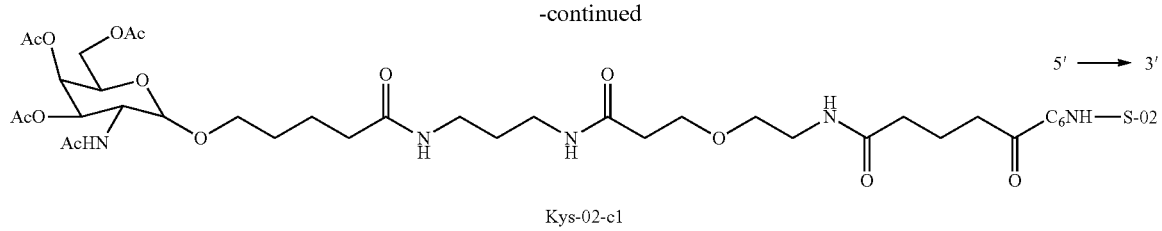
Kys-02-c1
The synthetic steps were the same as those in 1.3.1 of Example 1.
1.3.2. Synthesis of Kys-02
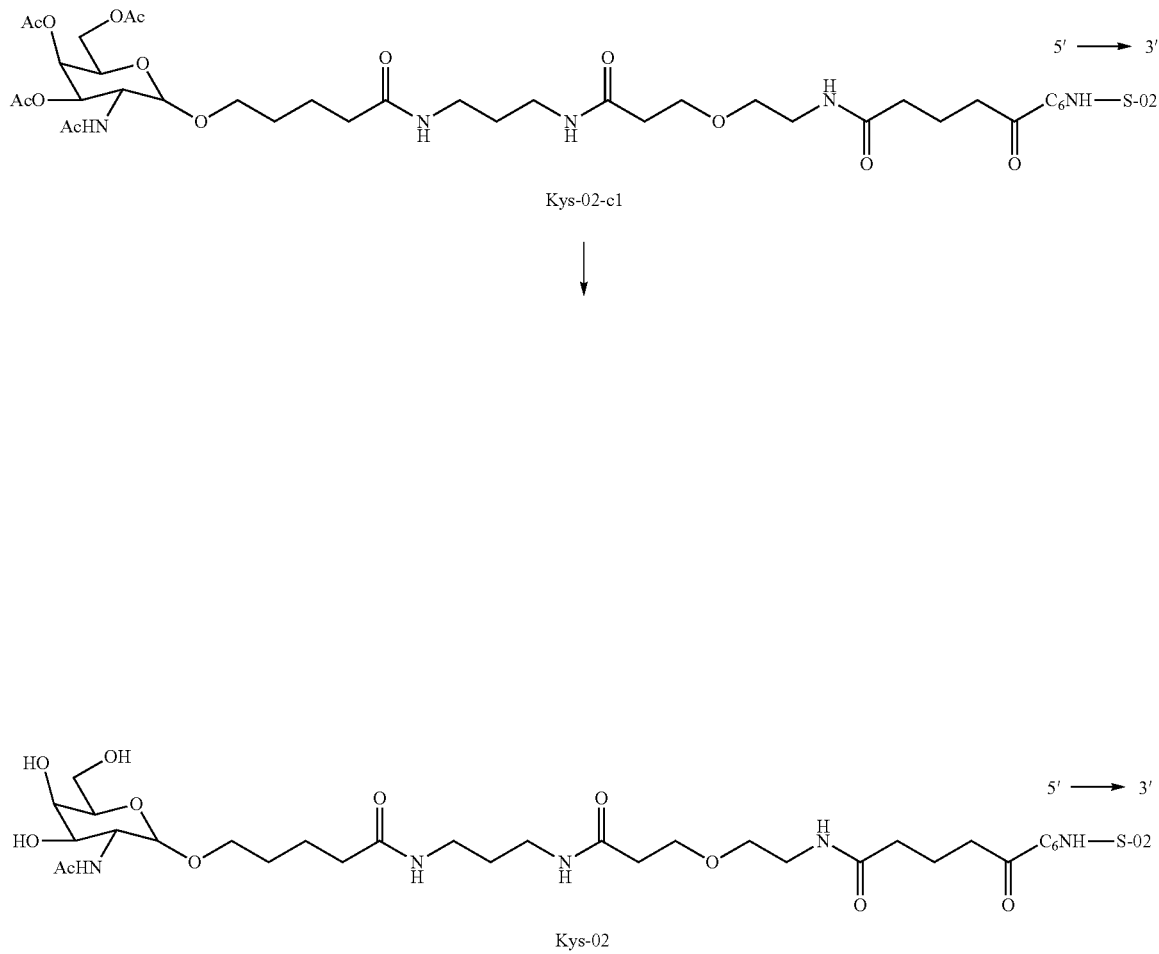
Kys-02-c1
Kys-02
The synthetic steps were the same as those in 1.3.2 of Example 1.
2. Synthesis of Kyas-02
2.1. Compounds of 3'SANCc-01: Synthesis of 3'SANCc-01 Resin
The synthetic route and process steps of 3'SANCc-01 resin were consistent with those of 3'SANCd-01 resin, except the synthesis of 3'SANCc-01-c6.

2.1.1. Synthesis of 3'SANCc-01-c1

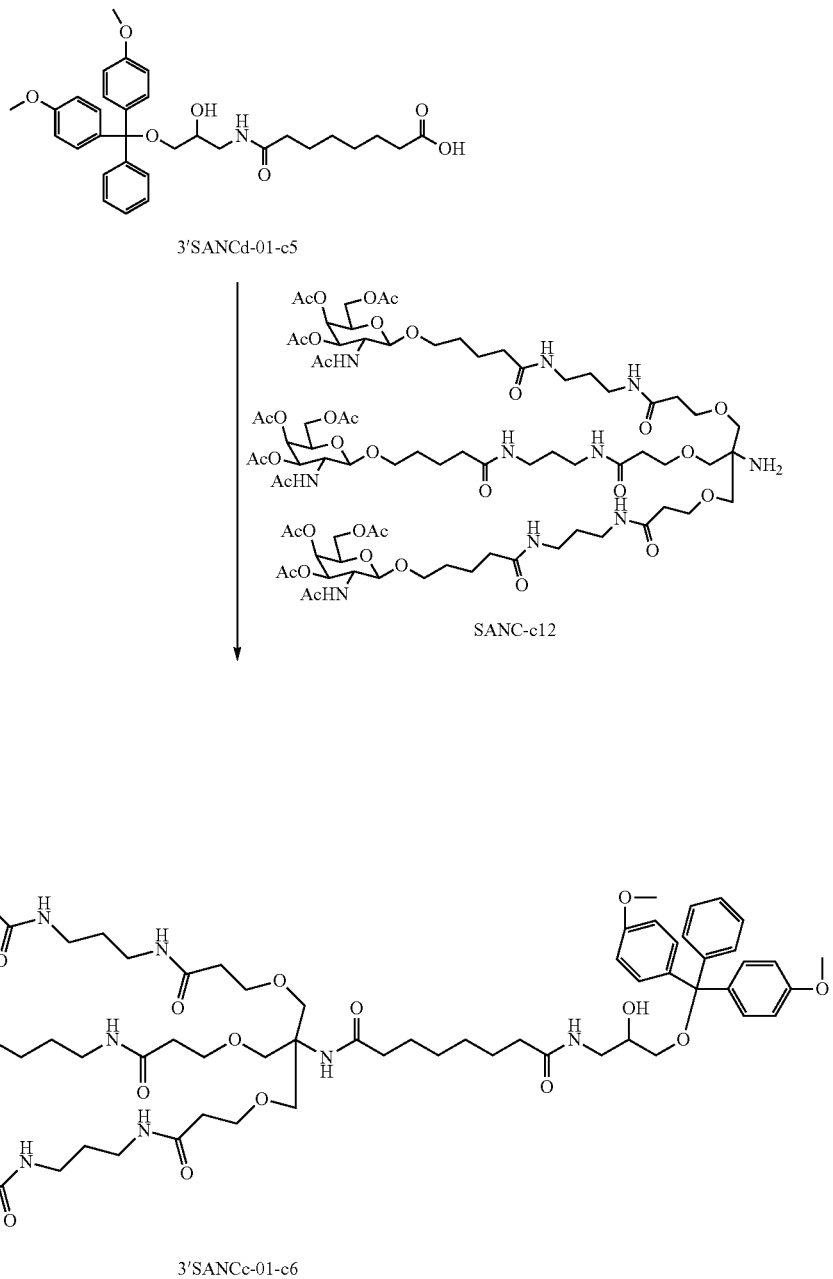

3'SANCd-01-c5 (0.295 g) was dissolved in DMF (2 mL) and cooled, added with DIPEA (0.14 mL) and TBTU (0.177 g) and stirred for 10 minutes, then added with a solution of SANC-c12 (0.756 g) in DMF (2 mL), and reacted at room temperature overnight. The system was quenched with water (50 mL) and extracted with $CH_2Cl_2$ (20 mL*2). The organic phase was washed with saturated brine (10 mL), dried over anhydrous sodium sulfate, filtered, and rotary evaporated. The residue was passed over a column with an eluent containing 5% triethylamine to get the product 3'SANCc-01-c6 (0.815 g).

2.2. Solid-Phase Synthesis of Kyas-02

With mU as the initiation monomer and with mU as the end monomer, different phosphoramidite monomers were introduced by coupling through a solid-phase phosphoramidite method. The synthetic steps were the same as those in 2.2 Solid-phase synthesis of Kyas-01 in Example 1.

3. Synthesis of GBL-0402

Kys-02 and Kyas-02 solutions were determined accurately for their concentration. The synthetic steps were the same as those in 3. Synthesis of GBL-0401 in Example 1.

Example 3. Synthesis of GBL-0403

1. Synthesis of Kys-03

1.1. Compounds of 5'ERCd-01: Synthesis of 5'ERCd-01-PFP

1.1.1. Synthesis of 5'ERCd-01-c1

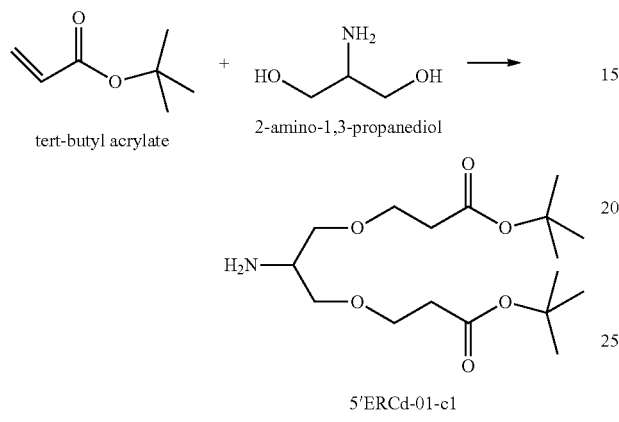

5'ERCd-01-c1

5.0 g (54.9 mmol) of 2-amino-1,3-propanediol was weighed, added with 50 mL of DMSO and 5 mL of a solution of sodium hydroxide at a concentration of 1 g/mL and cooled to 0° C., dropwise added with 20 mL (137.8 mol) of tert-butyl acrylate over 2 hours and reacted at room temperature for 48 h. The mixture was added with 100 mL petroleum ether. The organic phase was washed with saturated brine twice, dried and passed over a chromatographic column (Eluent: ethyl acetate:petroleum ether=25%-75% containing 0.05% triethylamine) to get 6.2 g of a colorless oil.

1.1.2. Synthesis of 5'ERCd-01-c2

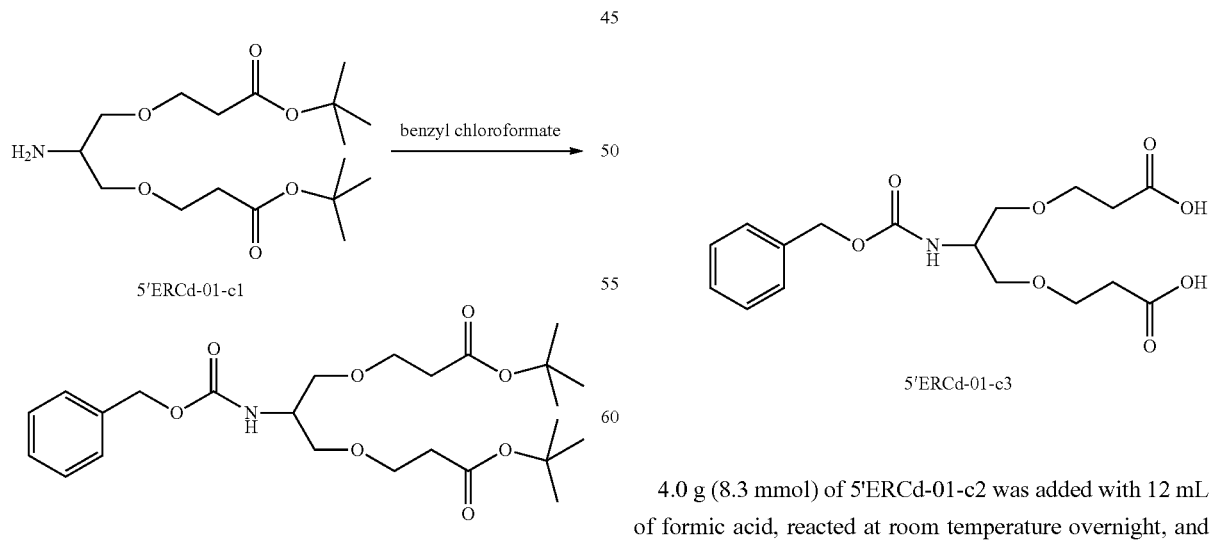

5'ERCd-01-c1

5'ERCd-01-c2

5'ERCd-01-c1 (6.2 g, 17.9 mmol) was weighed, added with 50 mL of dichloromethane and 23 mL of a sodium carbonate solution (25%), followed by dropwise addition of 8.2 mL (57.4 mmol) of benzyl chloroformate at room temperature over 2 hours. The mixture was reacted at room temperature overnight, washed with saturated brine for three times, dried over anhydrous sodium sulfate, and evaporated off the solvent. The residue was passed over a chromatographic column (ethyl acetate:petroleum ether=5%-30%) to get 4.0 g of an oil.

1.1.3. Synthesis of 5'ERCd-01-c3

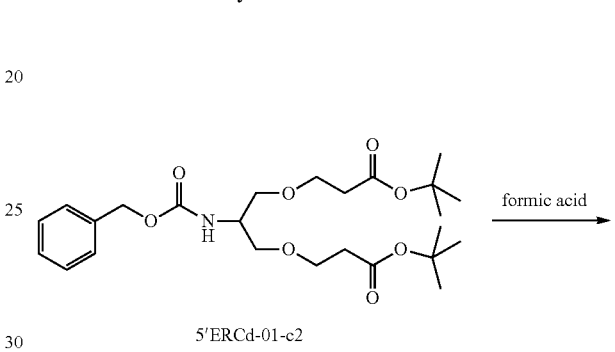

5'ERCd-01-c2

5'ERCd-01-c3

4.0 g (8.3 mmol) of 5'ERCd-01-c2 was added with 12 mL of formic acid, reacted at room temperature overnight, and evaporated off the solvent at reduced pressure to get 2.8 g of 5'ERCd-01-c3.

1.1.4. Synthesis of 5'ERCd-01-c4

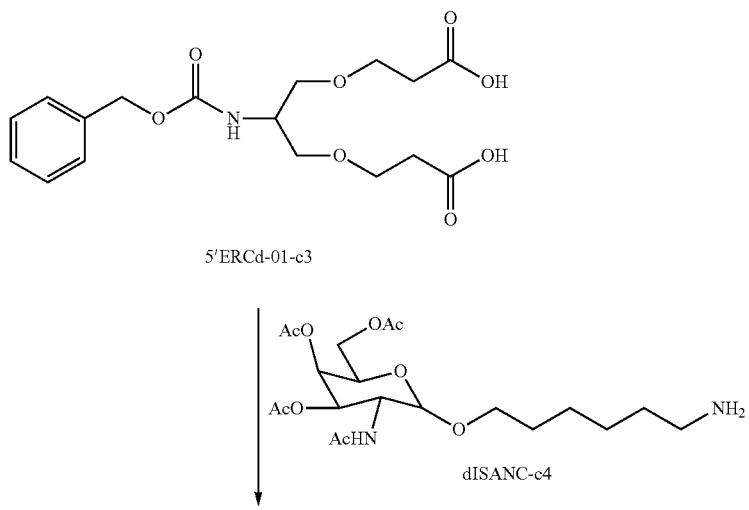

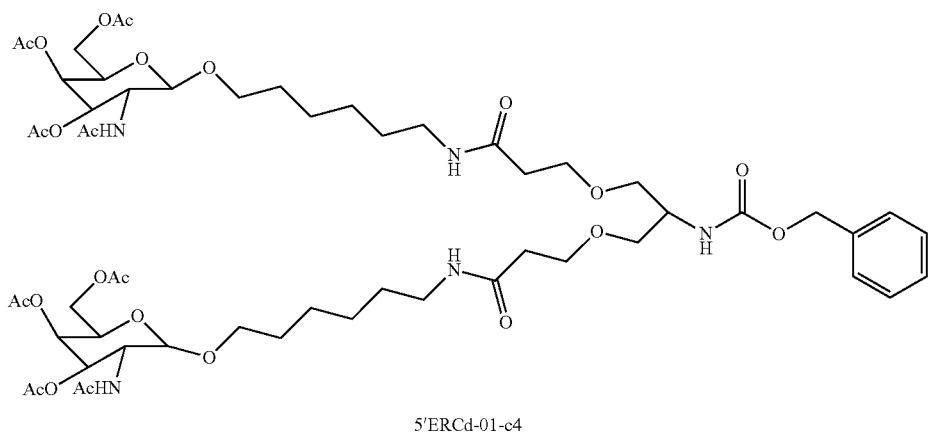

5'ERCd-01-c3 (1.11 g, 3.0 mmol) and dISANC-c4 (3.6 g, 8.04 mmol) were added into 60 mL of DMF, added with 2.24 g of HOBt and 3.36 g of HBTU, followed by slow addition of 4.16 mL of DIEA. The reaction solution was reacted with stirring at room temperature for 3 hours. Water was then added, and the aqueous layer was extracted with dichloromethane (2×10 mL). The organic layer was combined, and then washed with 80 mL of saturated NaHCO$_3$, water (2×60 mL), and saturated brine (60 mL) in order, dried over anhydrous Na$_2$SO$_4$, and evaporated at reduced pressure to dryness. The residue was purified by chromatography on a silica gel column (Eluent: 3-15% MeOH in DCM), to get 3.24 g of a light yellow solid.

1.1.5. Synthesis of 5'ERCd-01-c5
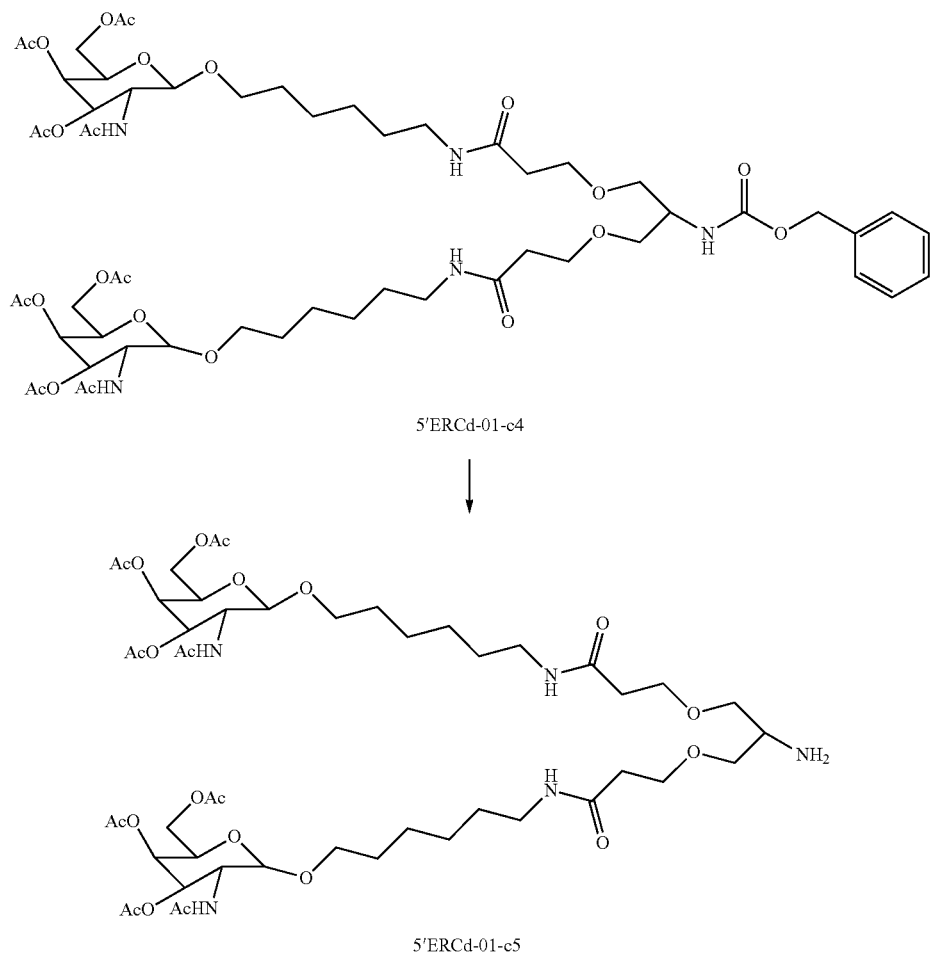
3.24 g (2.6 mmol) of 5'ERCd-01-c4 was dissolved in 60 mL of methanol, added with 0.3 g of 10% Pd—C(wet Degussa-type E101 NE/W) and 2.0 mL of acetic acid, and hydrogenated at normal pressure overnight. The reaction solution was filtered with diatomite, and the filtrate was evaporated at reduced pressure to get 2.9 g of an oil.
1.1.6. Synthesis of 5'ERCd-01-c6
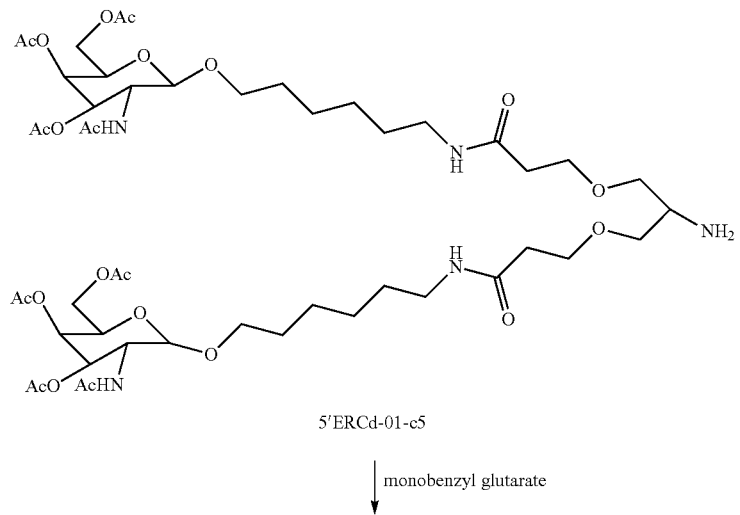

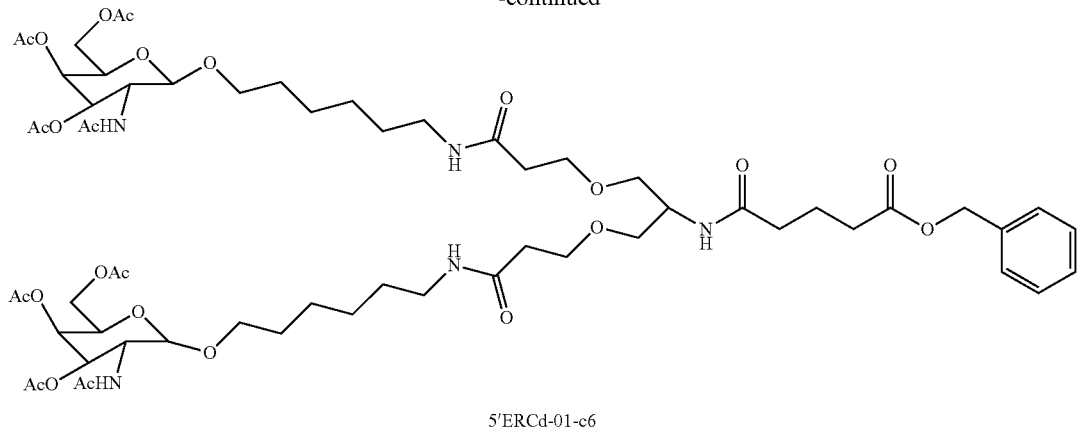

5'ERCd-01-c6

0.21 g (0.001 mol) of monobenzyl glutarate was weighed and dissolved in 2 mL of DMF, added with 0.36 g of TBTU and 0.4 mL of DIEA, reacted with stirring for 5 minutes, added with 0.50 g of 5'ERCd-01-c5 (dissolved in 10 ml DMF), and reacted at room temperature with stirring overnight. The reaction solution was evaporated at reduced pressure to dryness, and 40 mL of dichloromethane and 20 mL of water were added and stirred for 5 minutes. The layers were separated. The organic layer was dried over anhydrous sodium sulfate, and passed over a chromatographic column (Eluent: dichloromethane:methanol=1%-10%). The eluate was evaporated off the solvent at reduced pressure to get 0.51 g of a white product.

1.1.7. Synthesis of 5'ERCd-01-c7

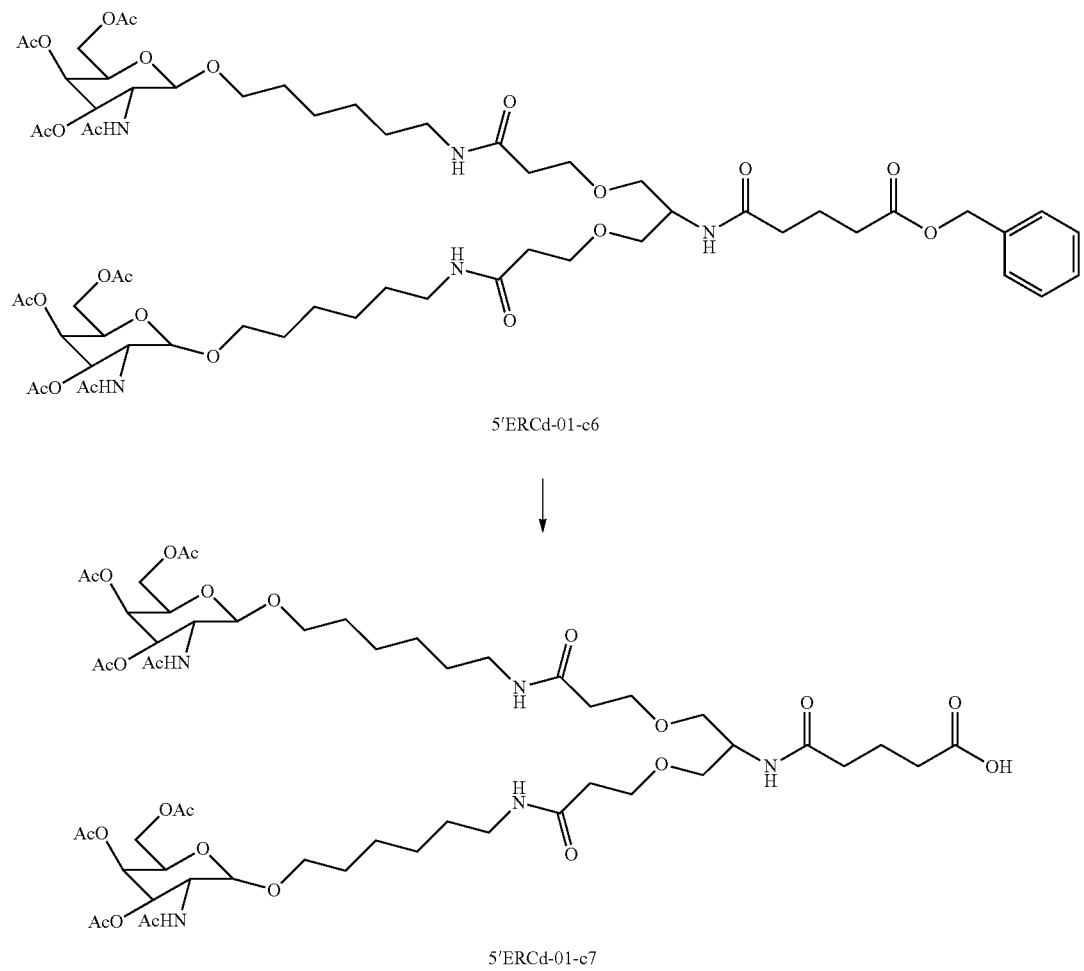

Figure 3:
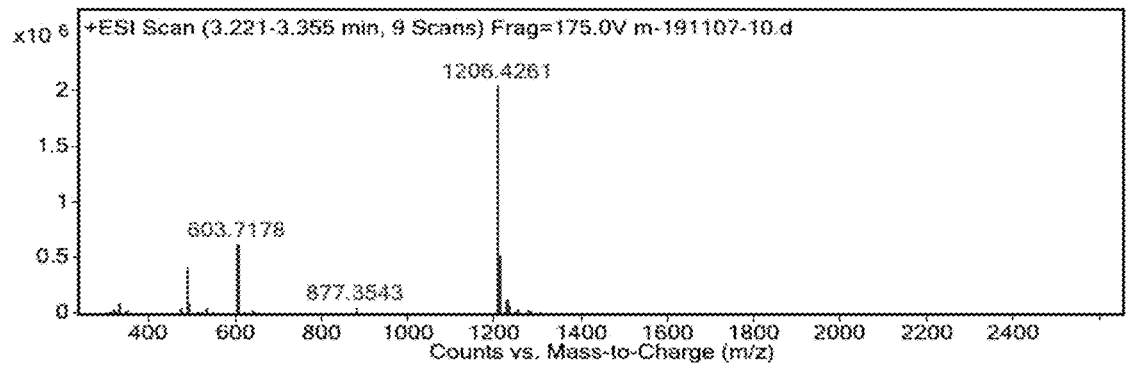
FIG. 3 is a high-resolution mass spectrum of 5'ERCd-01-c7.

Into a 100 mL single-necked flask, were added 0.51 g (0.42 mmol) of 5'ERCd-01-c6 and 127 mg of palladium-carbon. The flask was evacuated with a water pump and supplemented with hydrogen in triplicate. The mixture was reacted under pressurized hydrogen overnight. On the next day, TLC showed that the reaction was complete. Palladium-carbon was filtered with diatomite, and the filtrate was evaporated at reduced pressure to dryness to get 0.40 g of a product, of which the high-resolution mass spectrum is shown in FIG. 3.

1.1.8. Synthesis of 5'ERCd-01-PFP

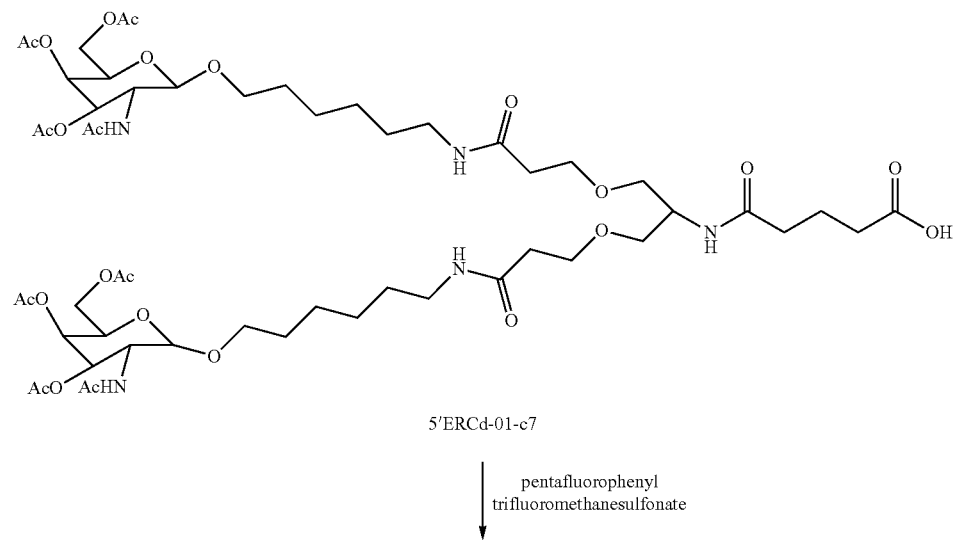

5'ERCd-01-c7

↓ pentafluorophenyl trifluoromethanesulfonate

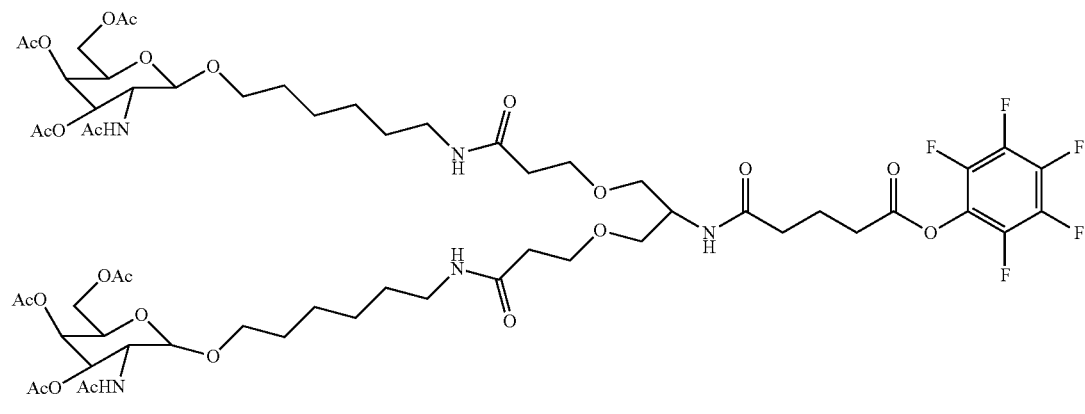

5'ERCd-01-PFP

Into a 50 mL single-necked flask, were added 0.40 g (0.33 mmol) of 5'ERCd-01-c7 and 10 mL of dichloromethane, and then dropwise added with 0.19 g (0.6 mmol) of pentafluorophenyl trifluoromethanesulfonate over 10 minutes and reacted at room temperature for 2 hours. The reaction solution was washed with 10 mL of water twice, and then with 5 mL of saturated sodium bisulfate once. The organic layer was dried over anhydrous sodium sulfate for 10 minutes and evaporated at reduced pressure to dryness to get 0.5 g of a product.

1.2. Solid-Phase Synthesis of C6NH-S-03

With mG as the initiation monomer and with $C_6NH$ phosphoramidite monomer as the end monomer, different phosphoramidite monomers were introduced by coupling through a solid-phase phosphoramidite method. The synthetic steps were the same as those in 1.2 Solid-phase synthesis in Example 1.

1.3. Liquid-Phase Synthesis of Kys-03

1.3.1. Synthesis of Kys-03-c1

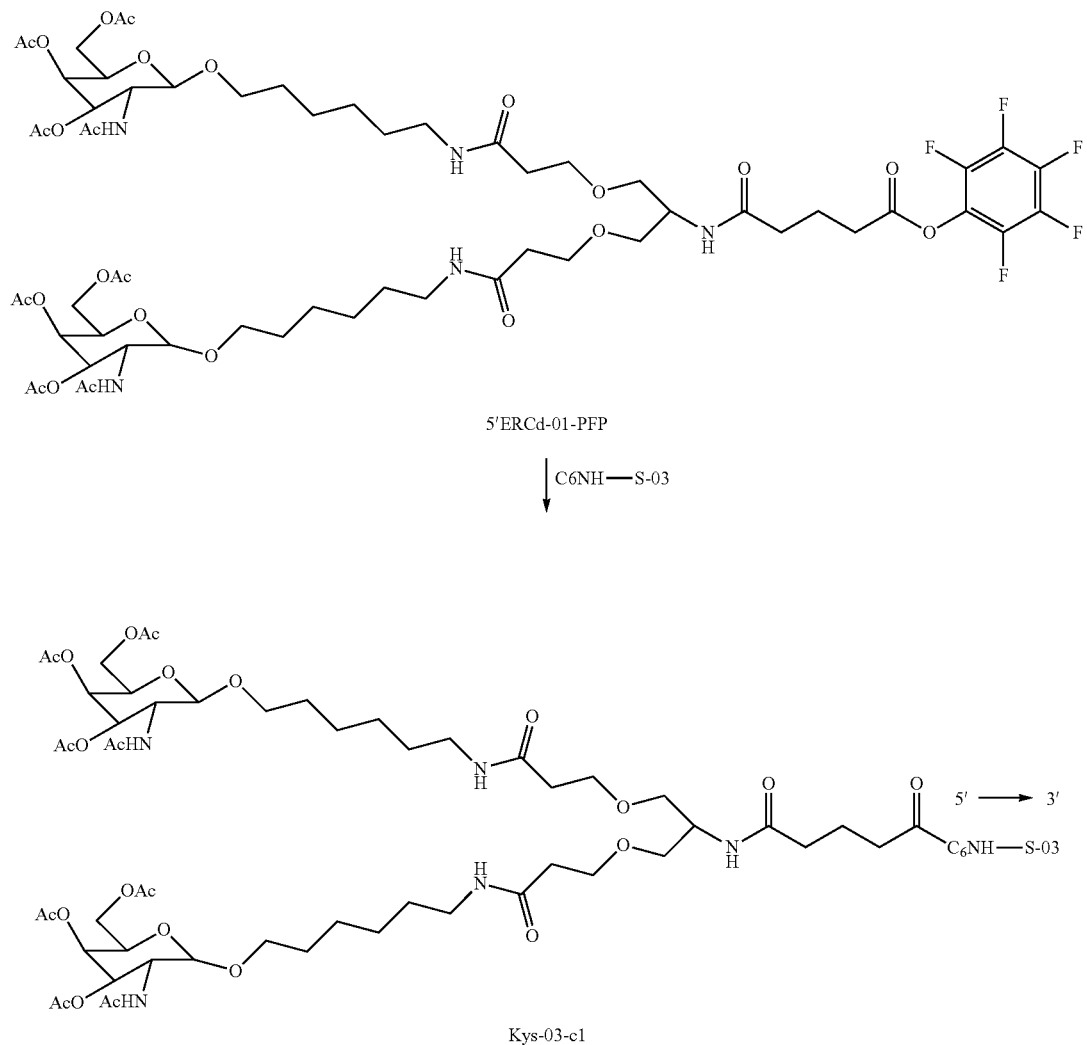

The synthetic steps were the same as those in 1.3.1 of Example 1.

1.3.2. Synthesis of Kys-03
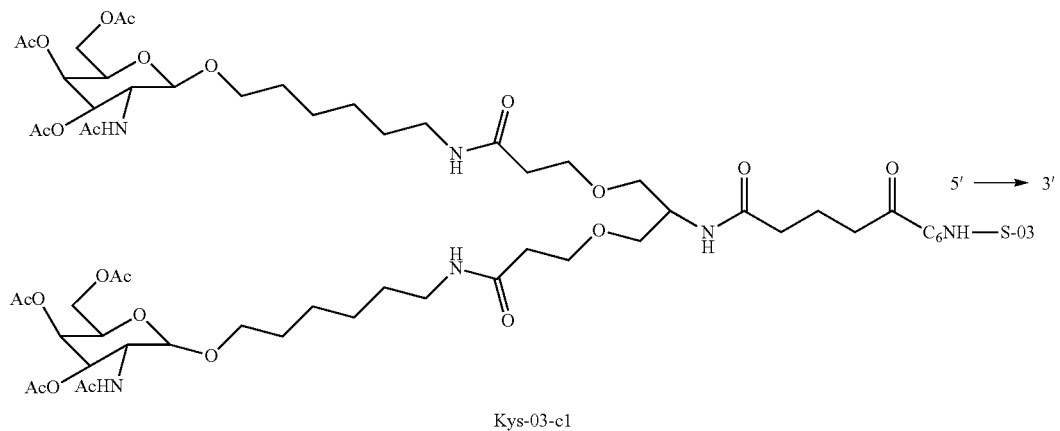
Kys-03-c1
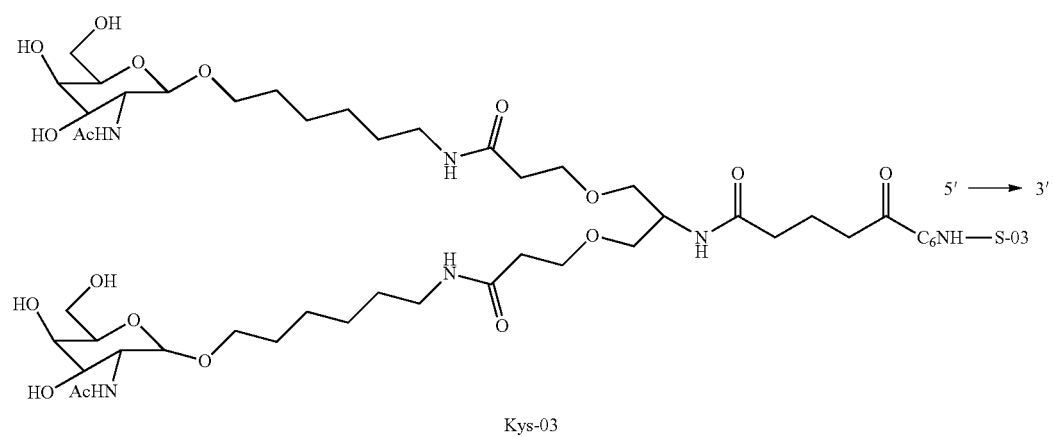
Kys-03
The synthetic steps were the same as those in 1.3.2 of Example 1.

2. Synthesis of Kyas-03

2.1. Compounds of 3'ERCd-01: Synthesis of 3'ERCd-01 Resin

2.1.1. Synthesis of 3'ERCd-01-c1

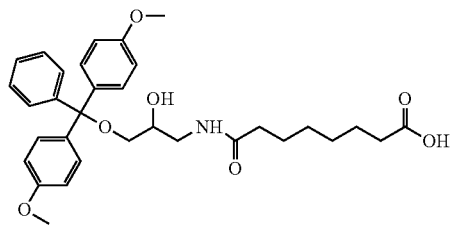

3'SANCd-01-c5

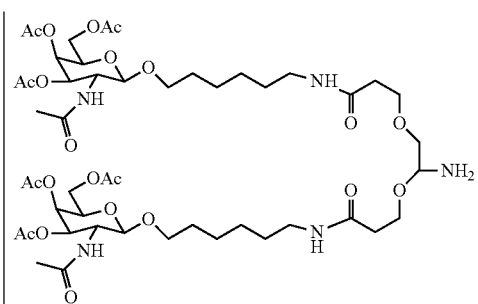

dIERC-c12

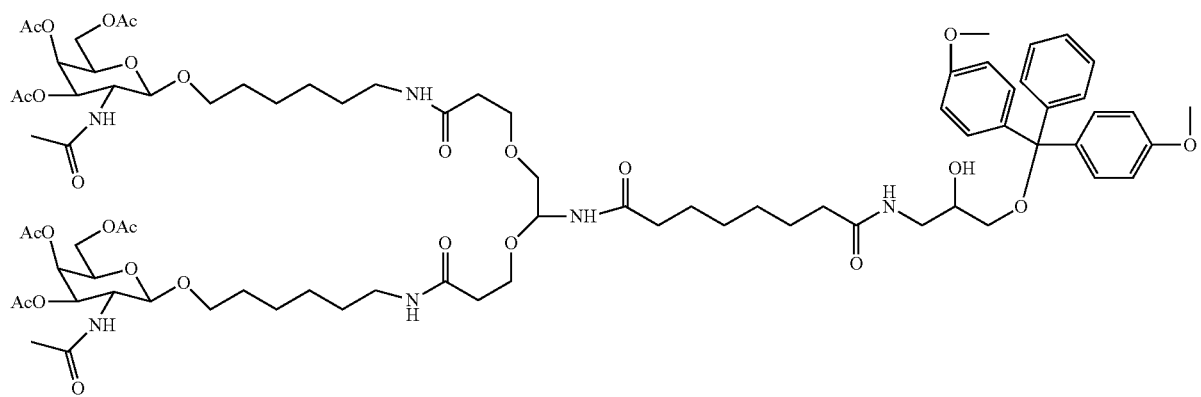

3'ERCd-01-c1

Into a reaction flask, 3'SANCd-01-c5 (0.824 g, 0.0015 mol) and 10 mL of DMF were added in order and dissolved with stirring at room temperature, and then added with TBTU (0.563 g) and DIPEA (0.517 g) in order and dissolved with stirring at room temperature, and finally added with dIERC-c12 (1.09 g, 0.001 mol) and reacted with stirring at room temperature overnight. TLC analysis showed the reaction was complete, the reaction mixture was concentrated to remove DMF, added with water and extracted with DCM. The organic phase was further washed with a saturated aqueous solution of sodium chloride, dried over anhydrous sodium sulfate, filtered, and concentrated. Finally the residue was purified over a silica gel column to get 1.3 g of an off-white foamy solid.

2.1.2. Synthesis of 3'ERCd-01-c2
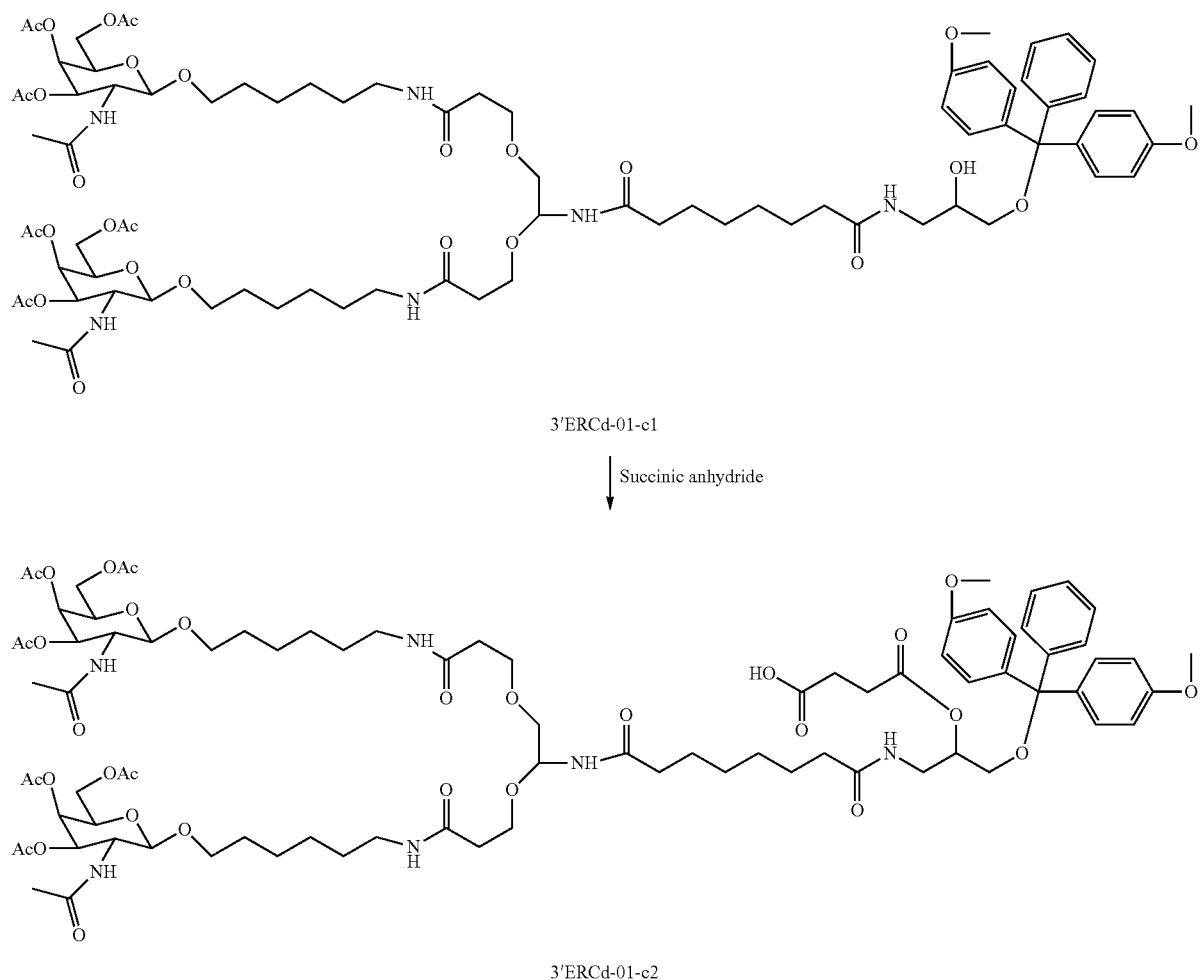
The synthetic steps were the same as those in 2.1.7 of Example 1.
2.1.3. Synthesis of 3'ERCd-01 Resin
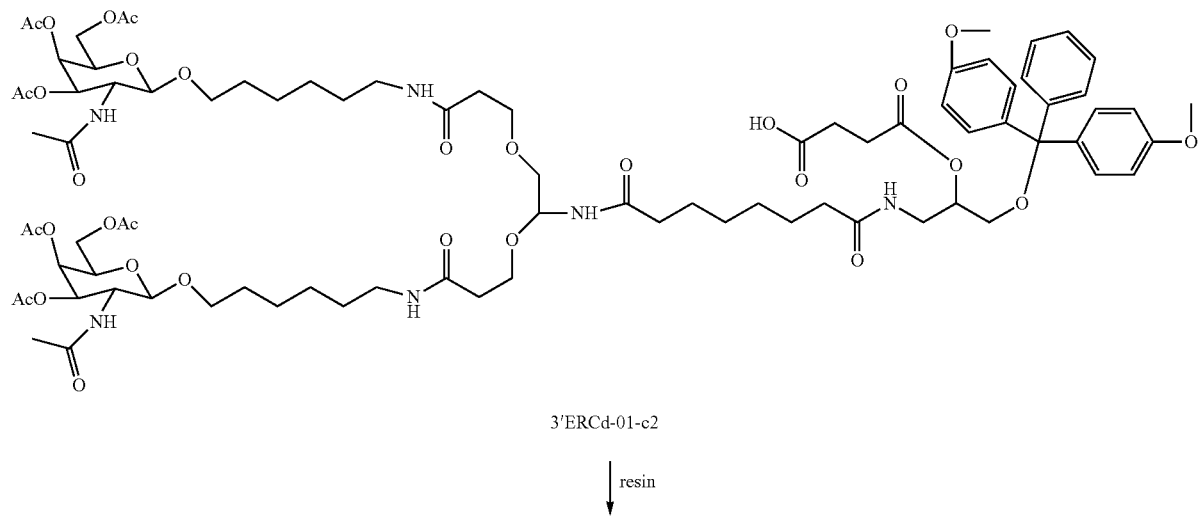

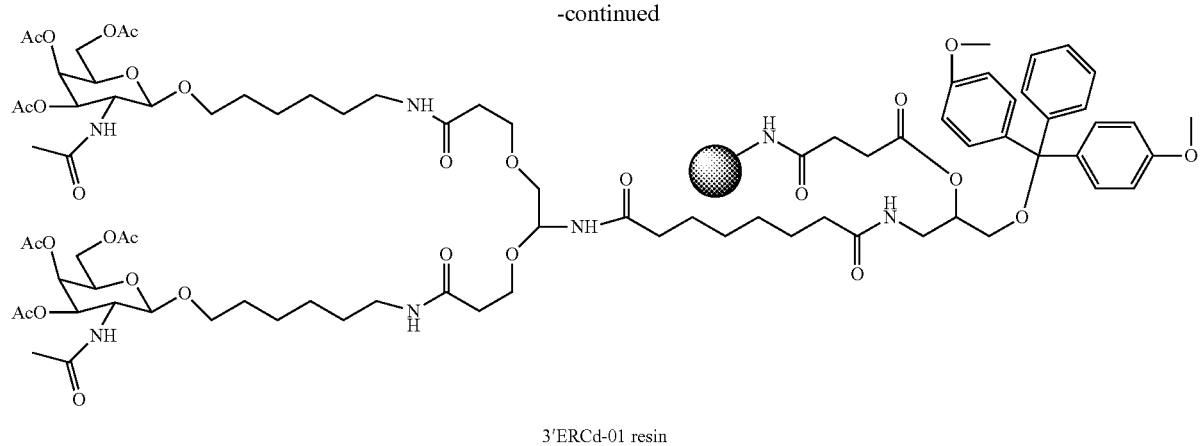

3'ERCd-01 resin

The synthetic steps were the same as those in 2.1.8 of Example 1.

2.2. Solid-Phase Synthesis of Kyas-03

With mA as the initiation monomer and with T as the end monomer, different phosphoramidite monomers were introduced by coupling through a solid-phase phosphoramidite method. The synthetic steps were the same as those in 2.2 Solid-phase synthesis of Kyas-01 in Example 1.

3. Synthesis of GBL-0403

Kys-03 and Kyas-03 solutions were determined accurately for their concentration. The synthetic steps were the same as those in 3. Synthesis of GBL-0401 in Example 1.

Example 4. Synthesis of GBL-0404

1. Synthesis of Kys-04

1.1. Compounds of 5'ERCc-01: Synthesis of 5'ERCc-01-PFP

1.1.1. Synthesis of 5'ERCc-01-c1

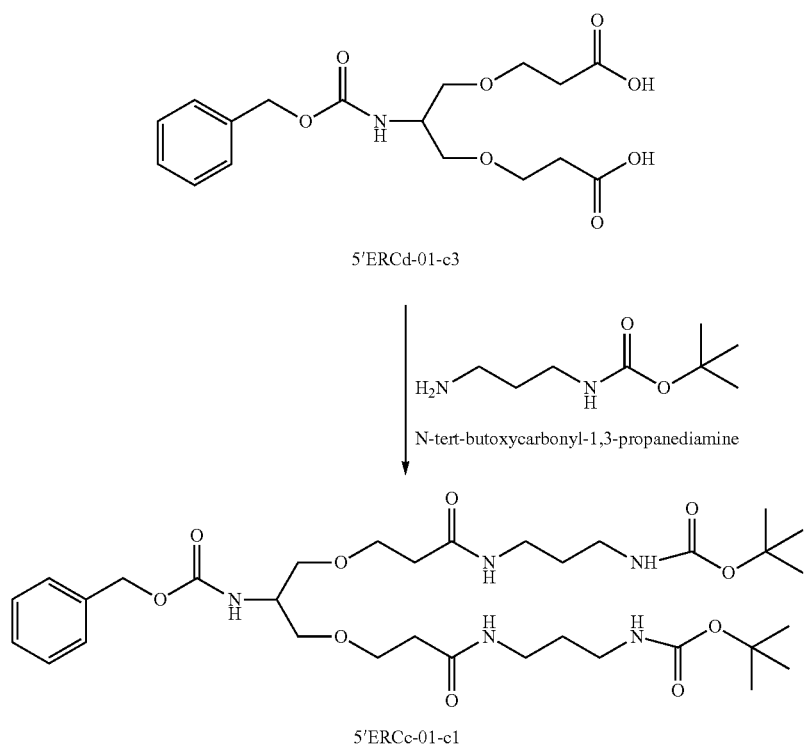

N-tert-butoxycarbonyl-1,3-propanediamine (5.0 g, 28.7 mmol) and 5'ERCd-01-c3 (2.8 g, 7.6 mmol) were dissolved in 25 mL of DMF, added with 9.0 g of TBTU and 2 mL of DIEA and reacted at room temperature overnight. 30 mL of water and 50 mL of DCM were added. The organic layer was washed with saturated brine and evaporated at reduced pressure to dryness. The residue was passed over a chromatographic column loaded with petroleum ether and rinsed with 1 L petroleum ether (Eluent: DCM:methanol=5%-10%) to get 2.9 g of a yellow sticky solid.

1.1.2. Synthesis of 5'ERCc-01-c2

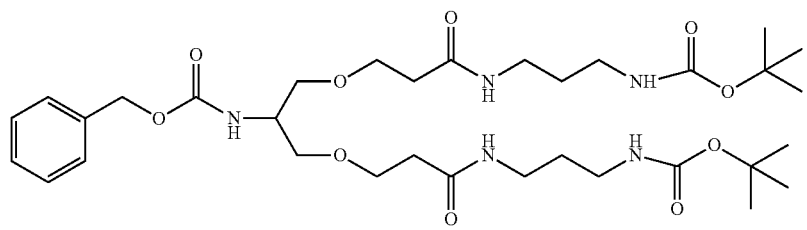

5'ERCc-01-c1

HCl

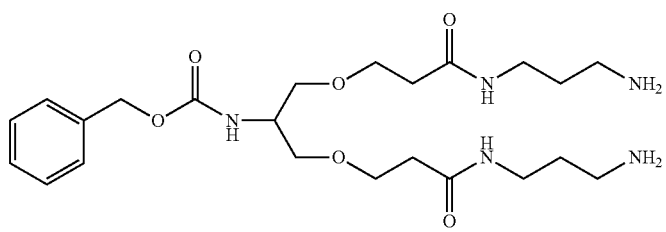

5'ERCc-01-c2

2.9 g of 5'ERCc-01-c1 was weighed, added with 9 mL of concentrated hydrochloric acid and reacted at room temperature overnight. The mixture was evaporated at reduced pressure to get 2.7 g of a product.

1.1.3. Synthesis of 5'ERCc-01-c3

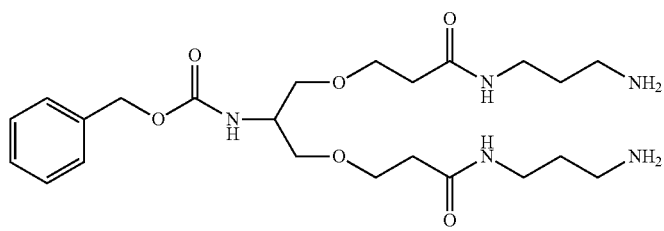

5'ERCc-01-c2

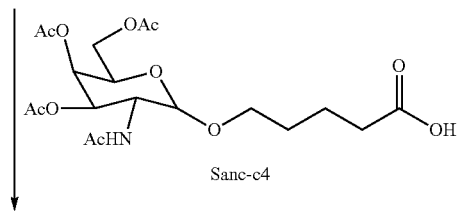

Sanc-c4

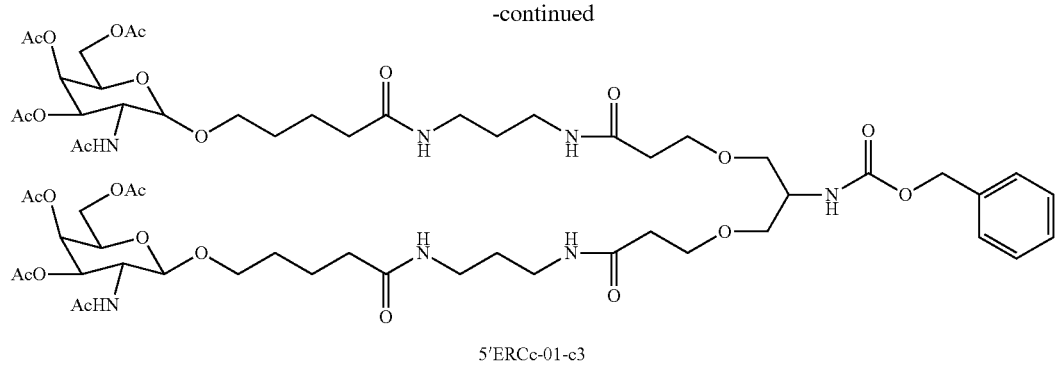

5'ERCc-01-c3

5'ERCc-01-c2 (1.56 g, 2.44 mmol) and Sanc-c4 (3.6 g, 8.04 mmol) were added into 60 mL of DMF, added with 2.24 g of HOBt and 3.36 g of HBTU, followed by slow addition of 4.16 mL of DIEA. The reaction solution was reacted at room temperature with stirring for 1 hour. Water was then added, and the aqueous layer was extracted with DCM (2×10 mL). The organic layer was combined, and then washed with 80 mL of saturated sodium bicarbonate, 40 mL of water, and 60 mL of saturated brine in order, dried over anhydrous sodium sulfate, and evaporated at reduced pressure to dryness. The residue was purified by chromatography on a silica gel column (Eluent: 3-15% methanol in DCM), to get 2.36 g of a light yellow solid.

1.1.4. Synthesis of 5'ERCc-01-c4

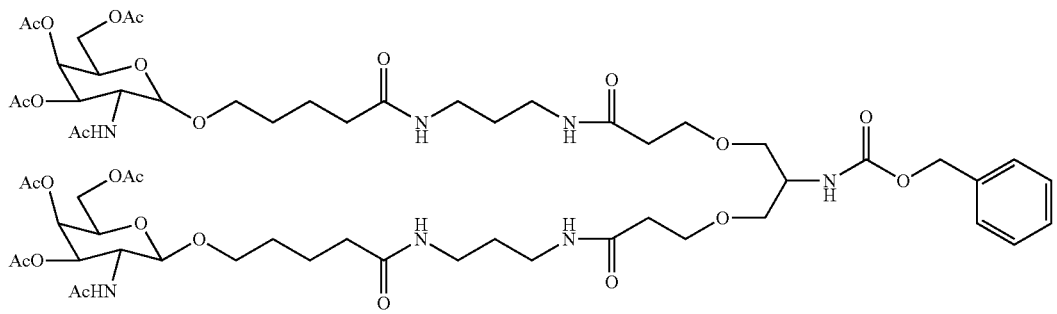

5'ERCc-01-c3

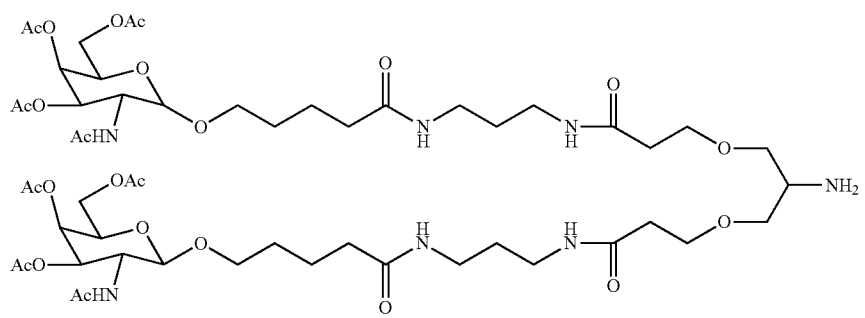

5'ERCc-01-c4

Figure 4:
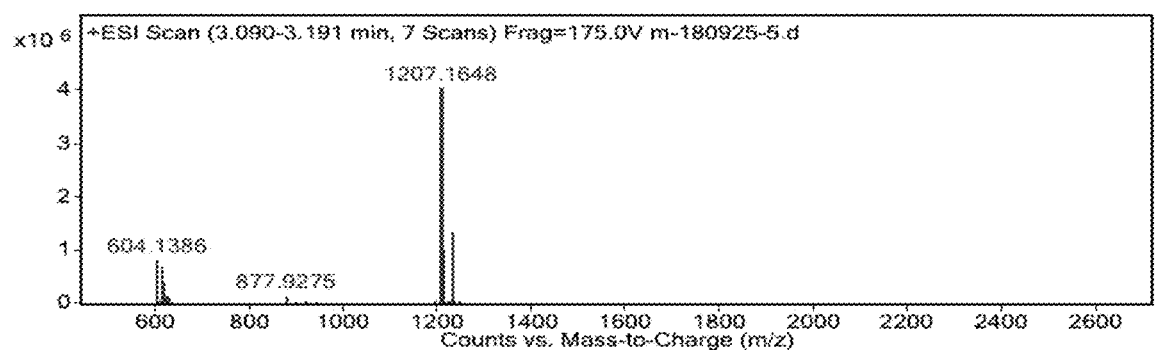
FIG. 4 is a high-resolution mass spectrum of 5'ERCc-01-c4.

2.36 g (1.2 mmol) of 5'ERCc-01-c3 was dissolved in 120 mL of methanol, added with 1.0 g of 10% Pd—C(wet Degussa-type E101 NE/W), and hydrogenated at normal pressure overnight. The reaction solution was filtered with diatomite, and the filtrate was evaporated at reduced pressure to dryness to get 1.8 g of oil, of which the high-resolution mass spectrum is shown in FIG. 4.

1.1.5. Synthesis of 5'ERCc-01-c5

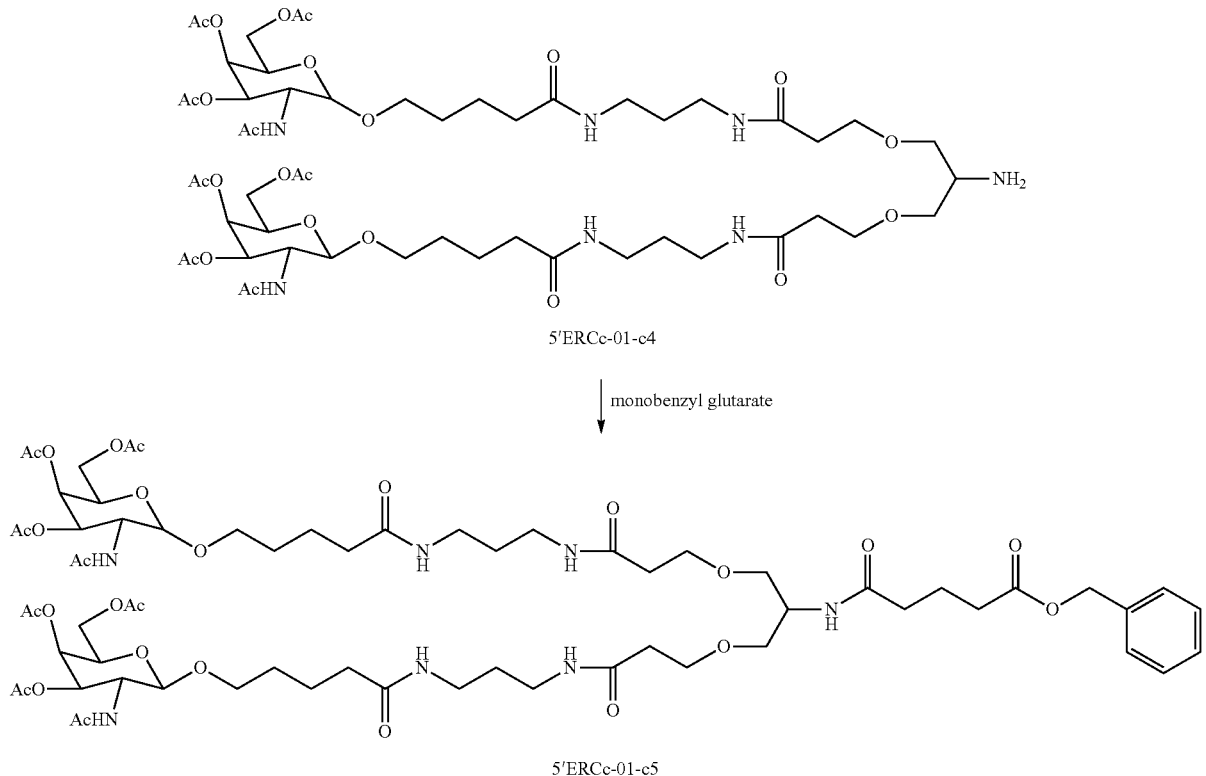

0.21 g (0.001 mol) of monobenzyl glutarate was dissolved in 2 mL of DMF, added with 0.36 g of TBTU and 0.4 mL of DIEA and reacted with stirring for 5 minutes, and added with 1.09 g of 5'ERCc-01-c4 and reacted at room temperature with stirring overnight. The reaction solution was evaporated at reduced pressure to dryness, added with 40 mL of DCM and 20 mL of water and stirred for 5 minutes. The layers were separated, and the organic layer was dried over anhydrous sodium sulfate and passed over a chromatographic column (Eluent: DCM:methanol=1%-10%), and the solvent was evaporated at reduced pressure to dryness to get 0.85 g of a white product.

1.1.6. Synthesis of 5'ERCc-01-c6

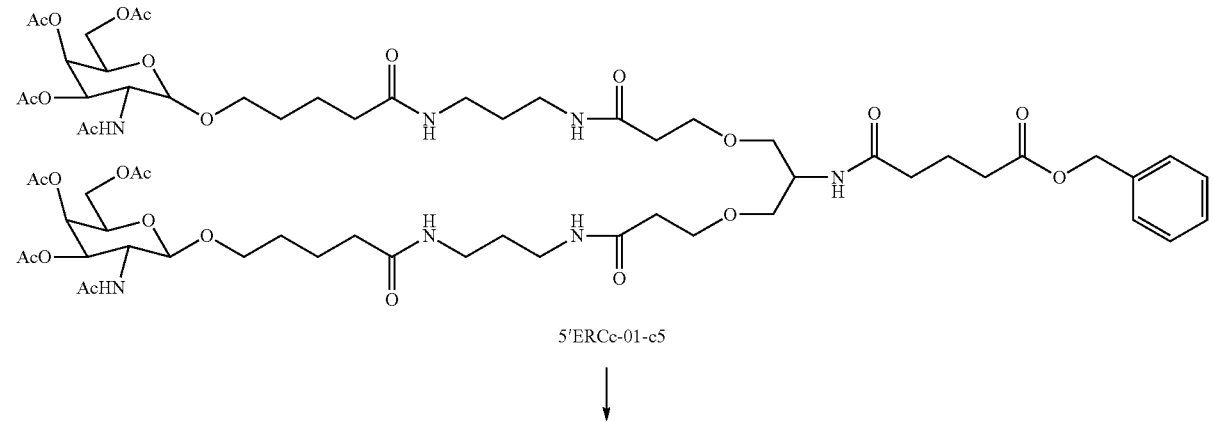

-continued

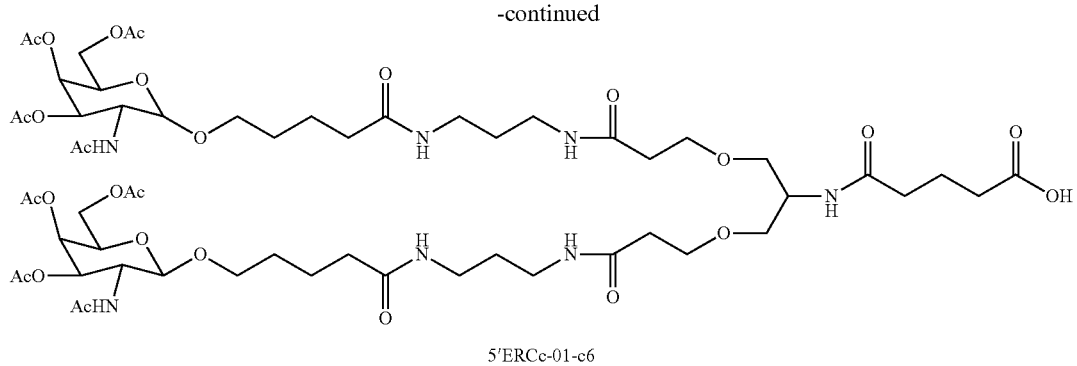

5'ERCc-01-c6

Into a 100 mL single-necked flask, were added 0.85 g (0.43 mmol) of 5'ERCc-01-c5 and 127 mg of palladium-carbon. The flask was evacuated by a water pump and supplemented with hydrogen in triplicate. The reaction was conducted under pressurized hydrogen overnight. On the next day, TLC showed the reaction was complete. Palladium-carbon was filtered with diatomite, and the filtrate was evaporated at reduced pressure to dryness to get 0.76 g of a product.

1.1.7. Synthesis of 5'ERCc-01-PFP

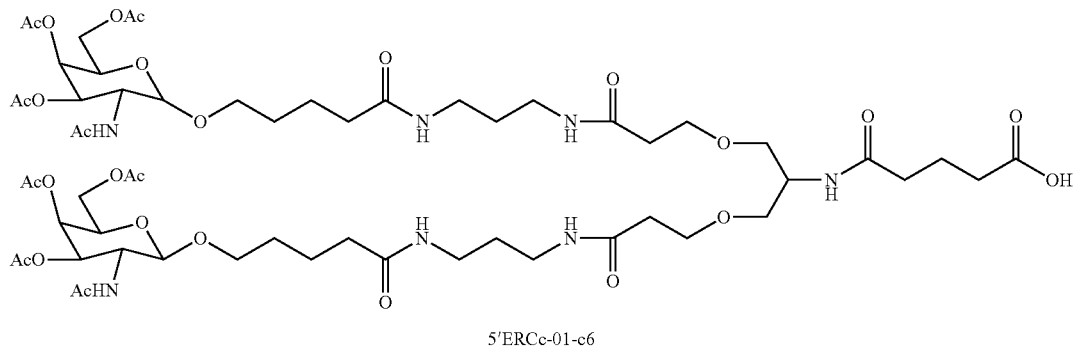

5'ERCc-01-c6

↓ pentafluorophenyl trifluoromethanesulfonate

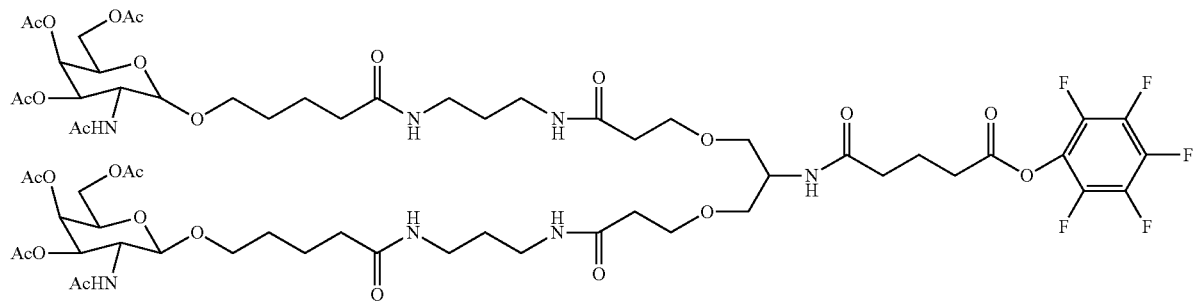

5'ERCc-01-PFP

Into a 50 mL single-necked flask, were added 0.76 g (0.40 mmol) of 5'ERCc-01-c6 and 10 mL of DCM, and dropwise added with 0.19 g (0.6 mmol) of pentafluorophenyl trifluoromethanesulfonate, reacted at room temperature for 1 hour, and washed with 10 mL of water and 5 mL of saturated sodium bisulfite in order. The organic layer was dried over anhydrous sodium sulfate for 10 minutes and evaporated at reduced pressure to dryness to get 0.8 g of a product.

1.2. Solid-Phase Synthesis of C6NH-S-04

With mA as the initiation monomer and with $C_6NH$ phosphoramidite monomer as the end monomer, different phosphoramidite monomers were introduced by coupling through a solid-phase phosphoramidite method. The synthetic steps were the same as those in 1.2 Solid-phase synthesis in Example 1.

1.3. Liquid-Phase Synthesis of Kys-04

1.3.1. Synthesis of Kys-04-c1

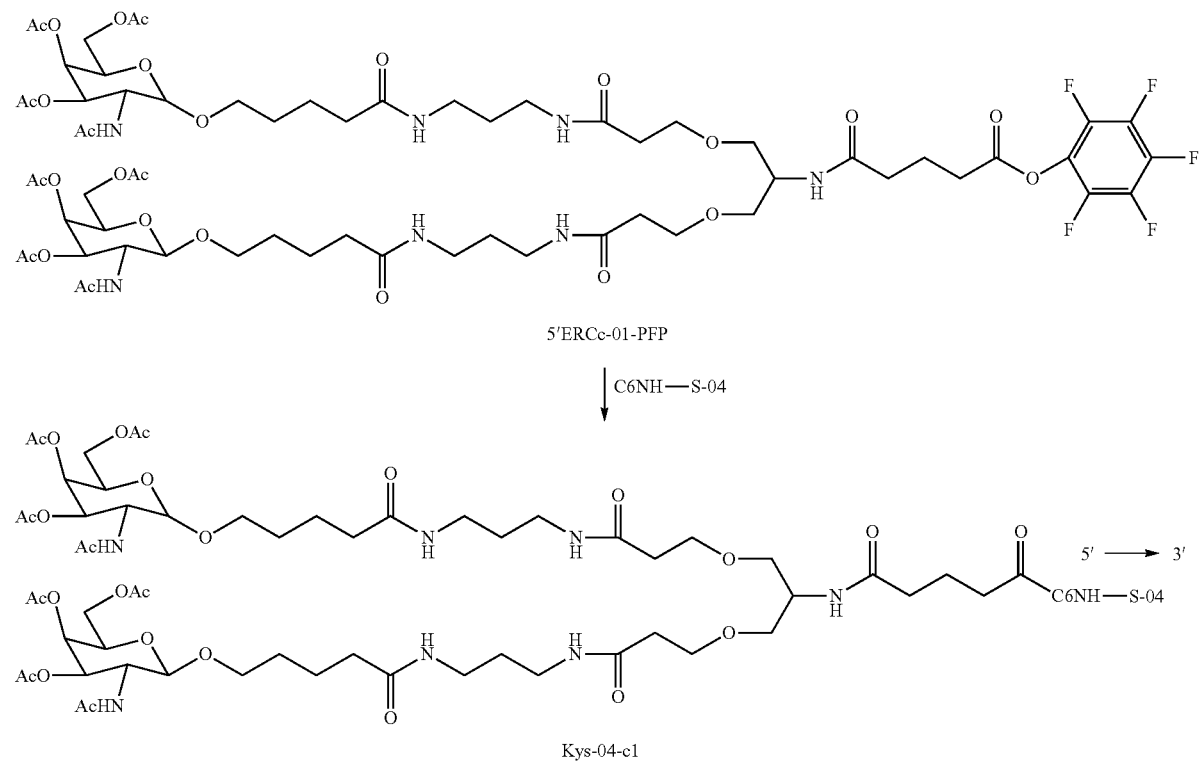

The synthetic steps were the same as those in 1.3.1 of Example 1.

1.3.2. Synthesis of Kys-04

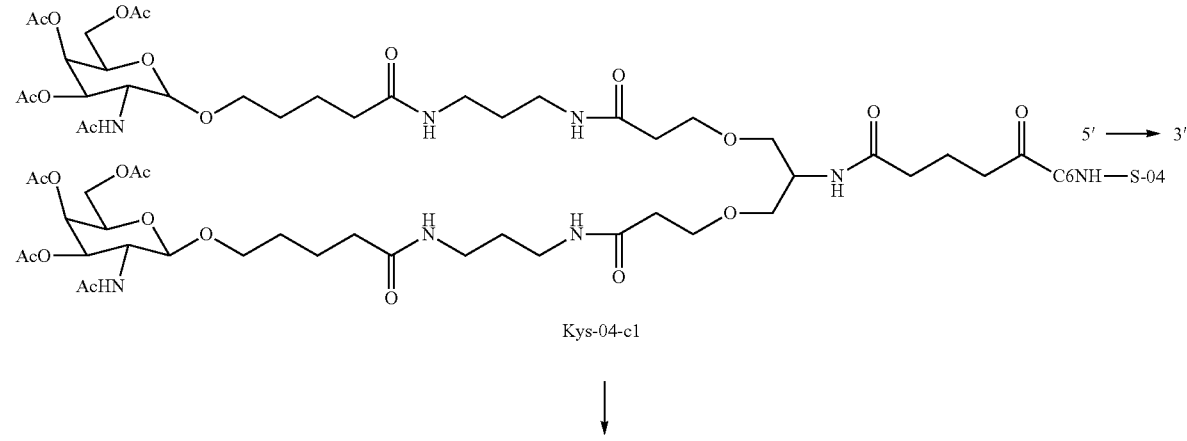

-continued
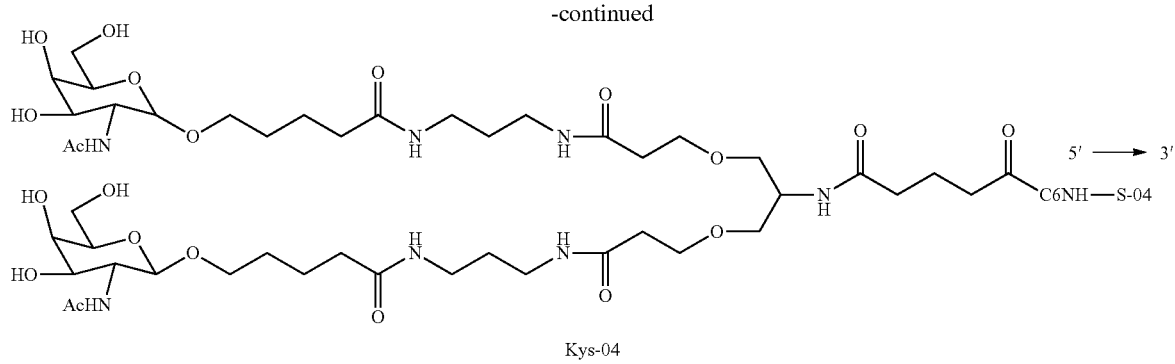
Kys-04
The synthetic steps were the same as those in 1.3.2 of Example 1.
2. Synthesis of Kyas-04
2.1. Compounds of 3'ERCc-01: Synthesis of 3'ERCc-01 Resin
2.1.1. Synthesis of 3'ERCc-01-c1
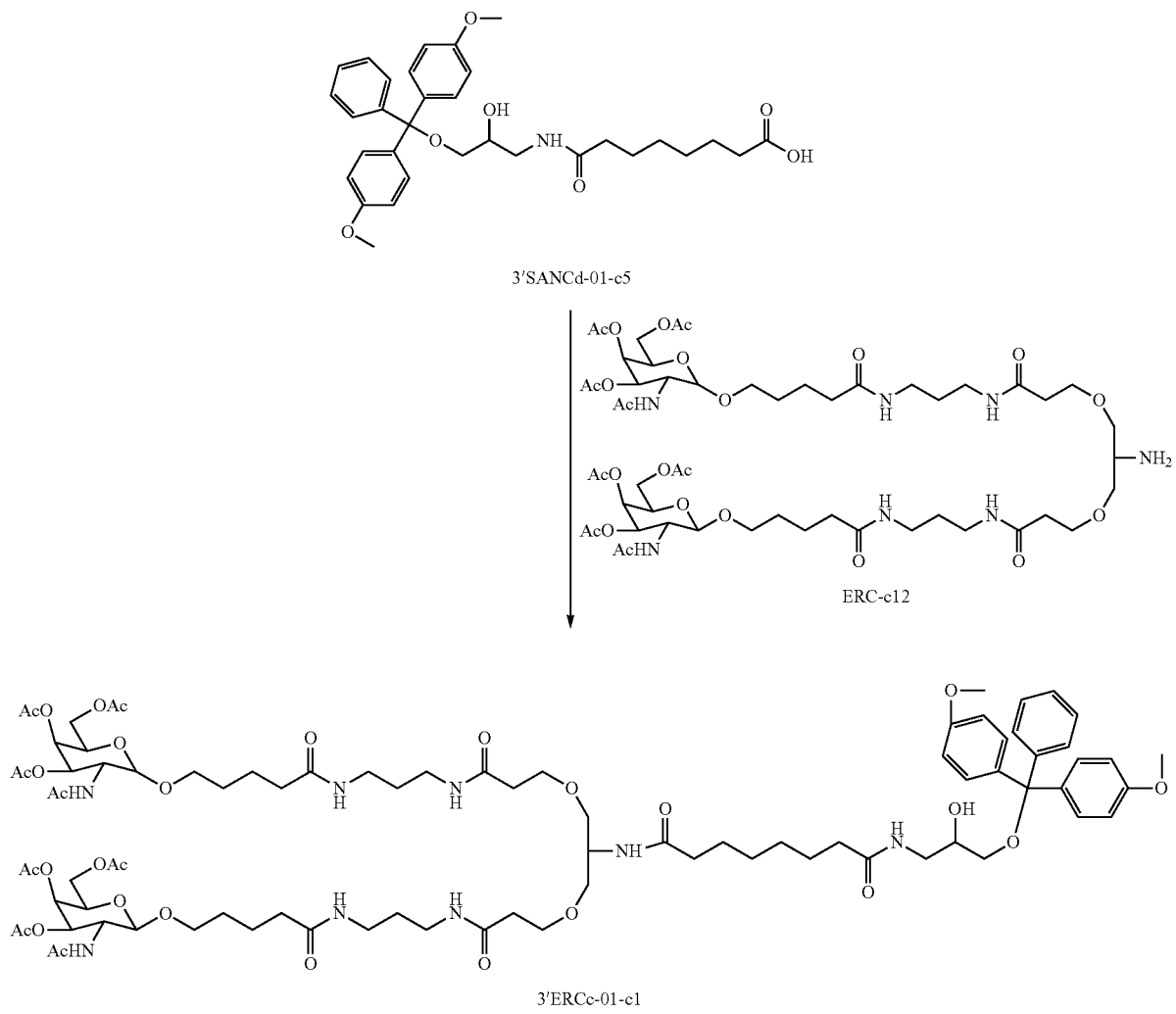

Into a reaction flask were added 3'SANCd-01-c5 (0.824 g, 0.0015 mol) and 10 mL of DMF in order and dissolved with stirring at room temperature, and then added with TBTU (0.563 g) and DIPEA (0.517 g) in order and dissolved with stirring at room temperature, and finally added with ERC-c12 (1.21 g, 0.001 mol) and reacted with stirring at room temperature overnight. TLC analysis showed that the reaction was complete, the reaction mixture was concentrated to remove DMF, added with water and extracted with DCM. The organic phase was further washed with a saturated aqueous solution of sodium chloride, dried over anhydrous sodium sulfate, filtered and concentrated. Finally the residue was purified over a silica gel column to get 1.4 g of a white foamy solid.

2.1.2. Synthesis of 3'ERCc-01-c2

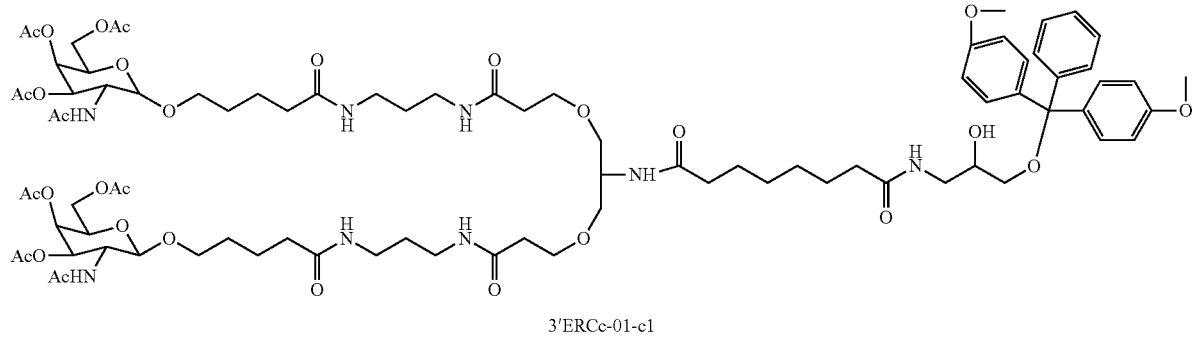

3'ERCc-01-c1

↓ Succinic anhydride

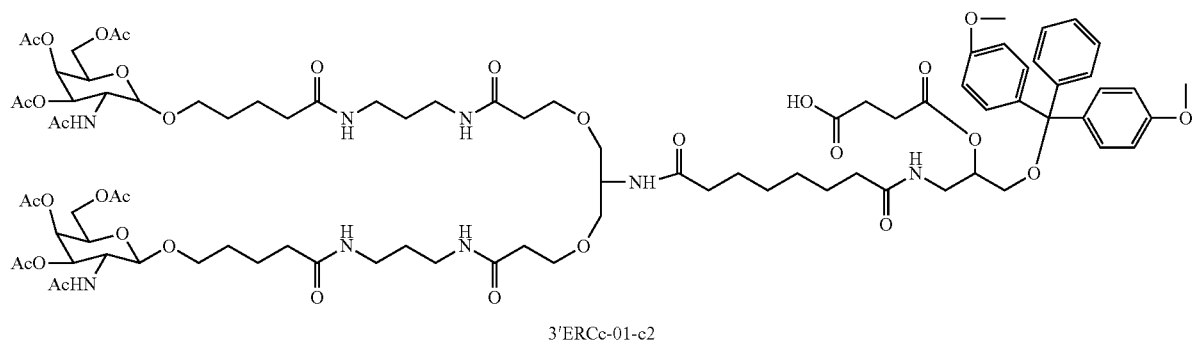

3'ERCc-01-c2

The synthetic steps were the same as those in 2.1.7 of Example 1.

2.1.3. Synthesis of 3'ERCc-01 Resin

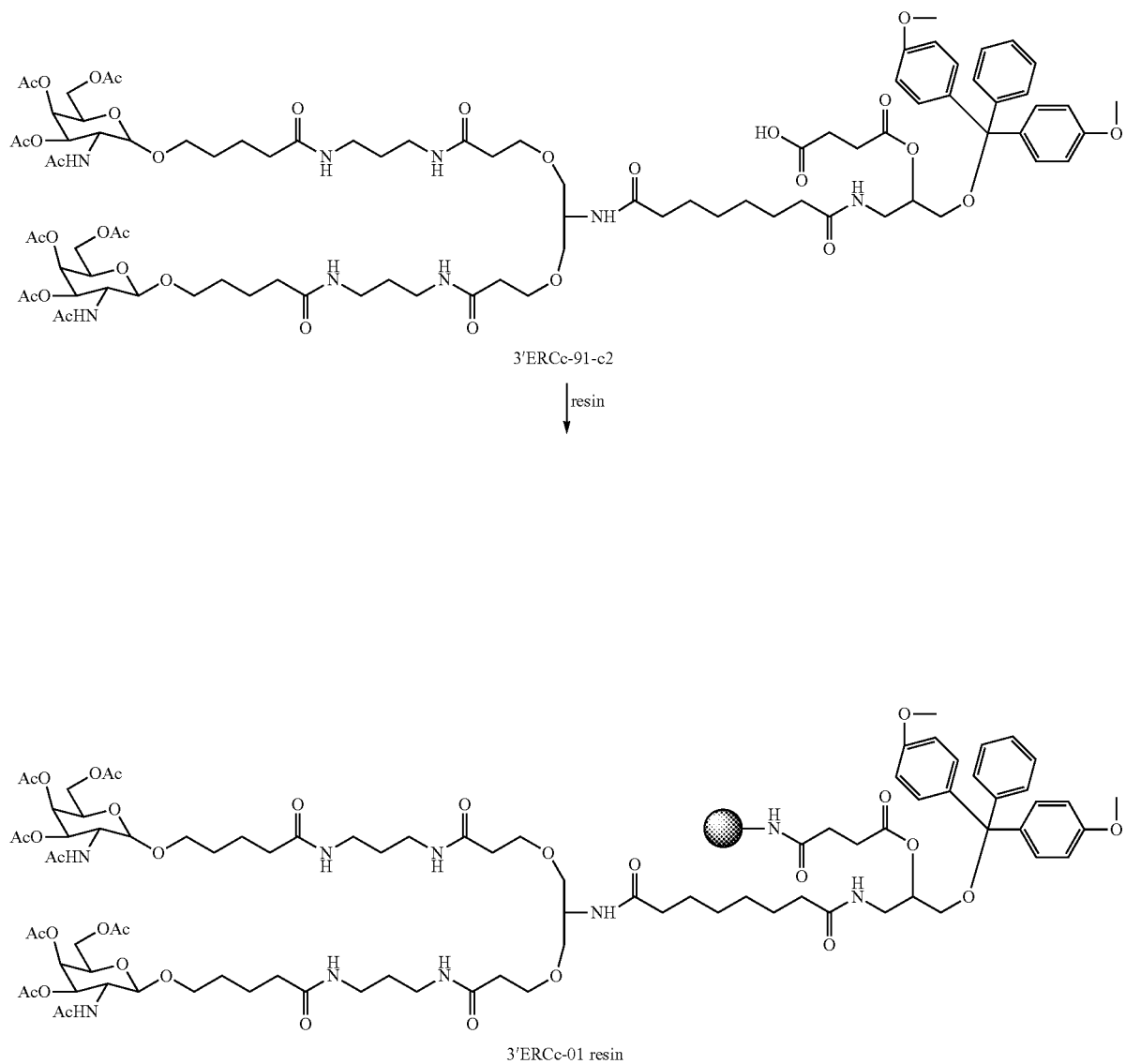

The synthetic steps were the same as those in 2.1.8 of Example 1.

2.2. Solid-Phase Synthesis of Kyas-04

With mG as the initiation monomer and with mU as the end monomer, different phosphoramidite monomers were introduced by coupling through a solid-phase phosphoramidite method. The synthetic steps were the same as those in 2.2 Solid-phase synthesis of Kyas-01 in Example 1.

3. Synthesis of GBL-0404

Kys-04 and Kyas-04 solutions were determined accurately for their concentration. The synthetic steps were the same as those in 3. Synthesis of GBL-0401 in Example 1.

Example 5. Synthesis of GBL-0409

1. Synthesis of Kyas-09

1.1. Compounds of 3'qfSANCd-01: Synthesis of 3'qfSANCd-01 Resin

1.1.1. Synthesis of 3'qfSANCd-01-c1

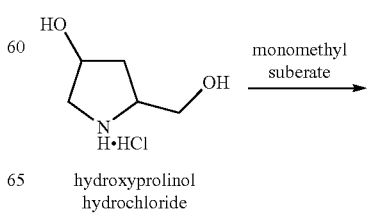

hydroxyprolinol hydrochloride

-continued

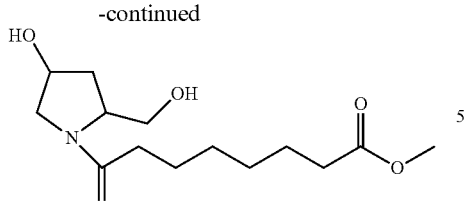

3'qfSANCd-01-c1

Into a reaction flask were added hydroxyprolinol hydrochloride (1.53 g, 0.01 mol) and 15 mL of DMF in order and dissolved with stirring at room temperature, and then added with monomethyl suberate (1.98 g, 0.0105 mol), HBTU (4.55 g) and DIPEA (3.88 g) in order, and reacted with stirring at room temperature overnight. TLC analysis showed that the reaction was complete, and the reaction mixture was concentrated to remove DMF, added with water and extracted with DCM. The organic phase was further washed with a saturated aqueous solution of sodium chloride, dried over anhydrous sodium sulfate, filtered, and concentrated. Finally the residue was purified over a silica gel column to get 2.38 g of a yellow sticky liquid.

1.1.2. Synthesis of 3'qfSANCd-01-c2

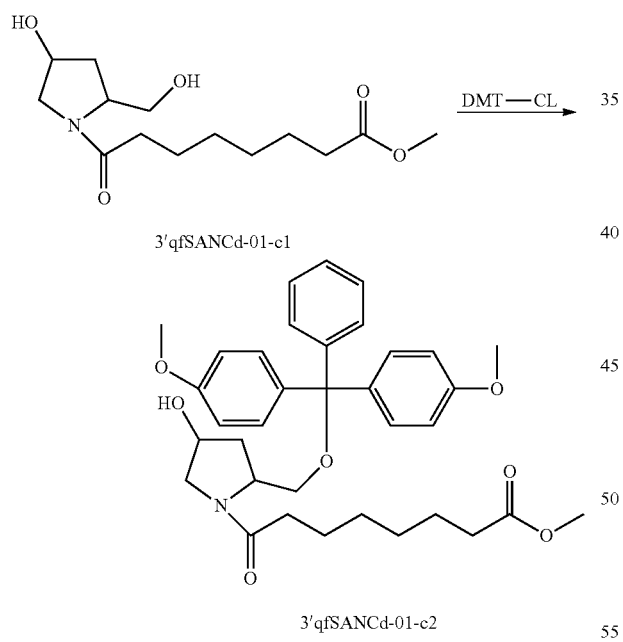

Into a reaction flask were added 3'qfSANCd-01-c1 (2.87 g 0.01 mol) and 30 ml of pyridine in order and dissolved with stirring at room temperature, and then added with DMAP (0.61 g) and DMT-CL (4.06 g, 0.012 mol) in order, and reacted with stirring at room temperature overnight. TLC analysis showed that the reaction was complete, and the reaction mixture was concentrated to remove pyridine, added with water and extracted with DCM. The organic phase was further washed with a saturated aqueous solution of sodium chloride, dried over anhydrous sodium sulfate, filtered, and concentrated. Finally the residue was purified over a silica gel column to get 4.13 g of a yellow sticky liquid (yield 70%).

1.1.3. Synthesis of 3'qfSANCd-01-c3

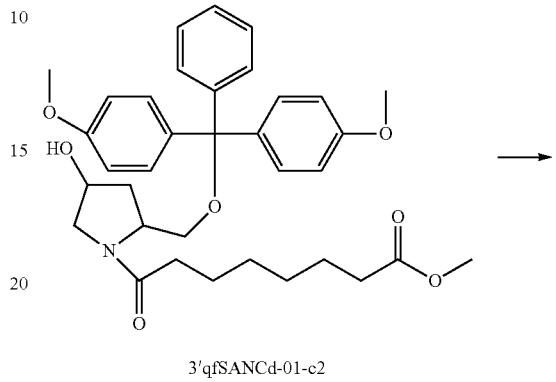

Into a reaction flask were added 3'qfSANCd-01-c2 (5.89 g 0.01 mol) and 60 mL of a solvent (THF/water/methanol=1:1:4) in order and dissolved with stirring at room temperature, and then added with LiOH (1.26 g) and reacted with stirring at room temperature for 2 h. TLC analysis showed that the reaction was complete, and the reaction mixture was concentrated to remove the solvent, added with water and extracted with DCM. The organic phase was further washed with a saturated aqueous solution of sodium chloride, dried over anhydrous sodium sulfate, filtered, and concentrated. Finally the residue was purified over a silica gel column to get 4.5 g of a yellow sticky liquid.

1.1.4. Synthesis of 3'qfSANCd-01-c4

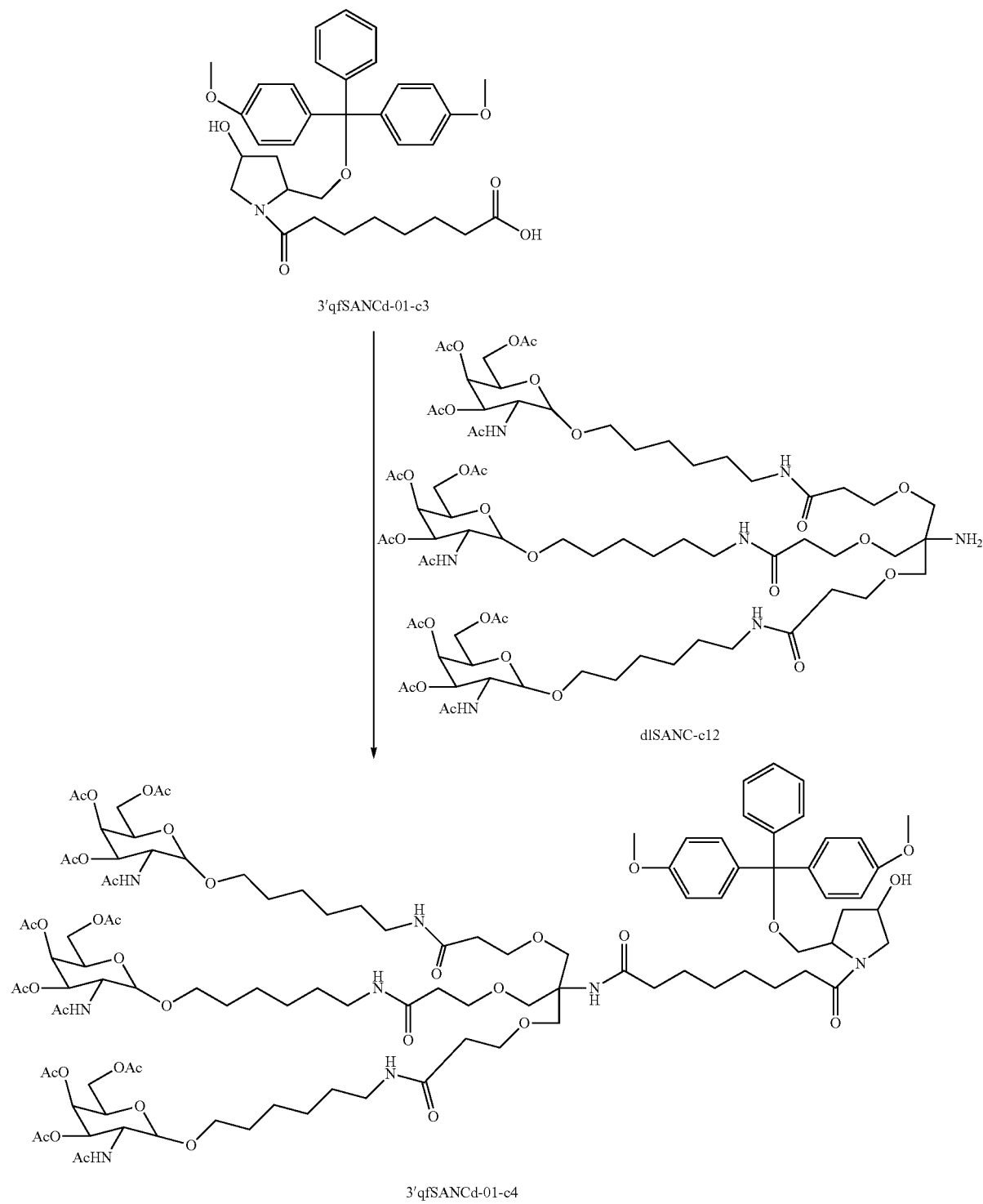

Into a reaction flask were added 3'qfSANCd-01-c3 (0.863 g, 1.5 mmol) and 10 mL of DMF in order and dissolved with stirring at room temperature, and then added with TBTU (0.963 g) and DIPEA (0.517 g) in order and dissolved with stirring at room temperature, and finally added with dlSANC-c12 (1.62 g 1 mmol) and reacted with stirring at room temperature overnight. TLC analysis showed that the reaction was complete, and the reaction mixture was concentrated to remove DMF, added with water and extracted with DCM. The organic phase was further washed with a saturated aqueous solution of sodium chloride, dried over anhydrous sodium sulfate, filtered, and concentrated. Finally the residue was purified over a silica gel column to get 1.743 g of a yellow sticky liquid.

1.1.5. Synthesis of 3'qfSANCd-01-c5

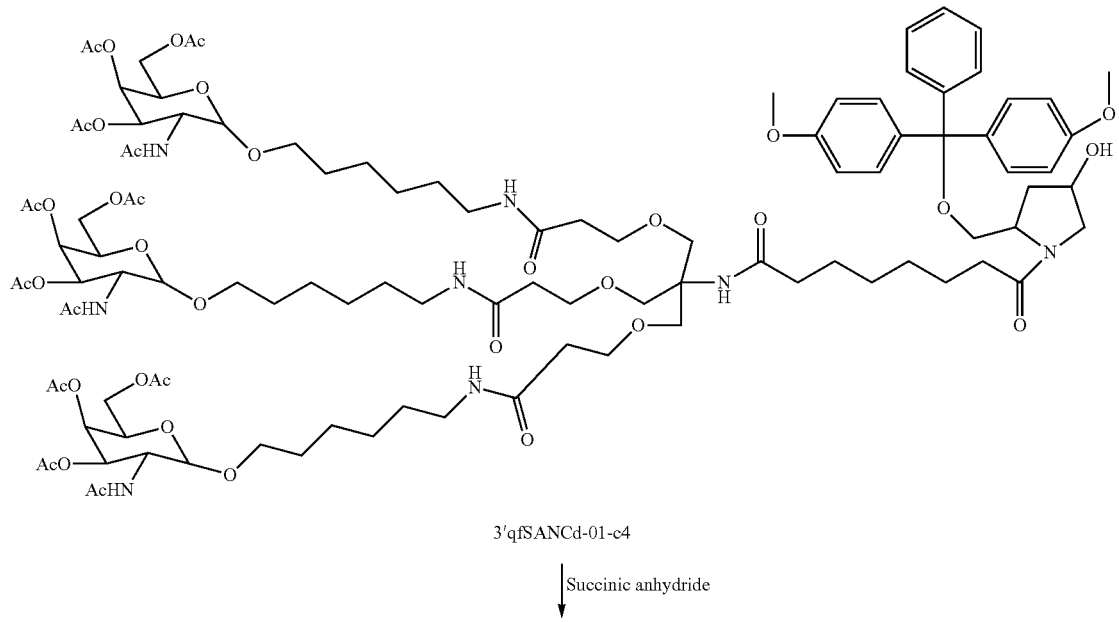

3'qfSANCd-01-c4

↓ Succinic anhydride

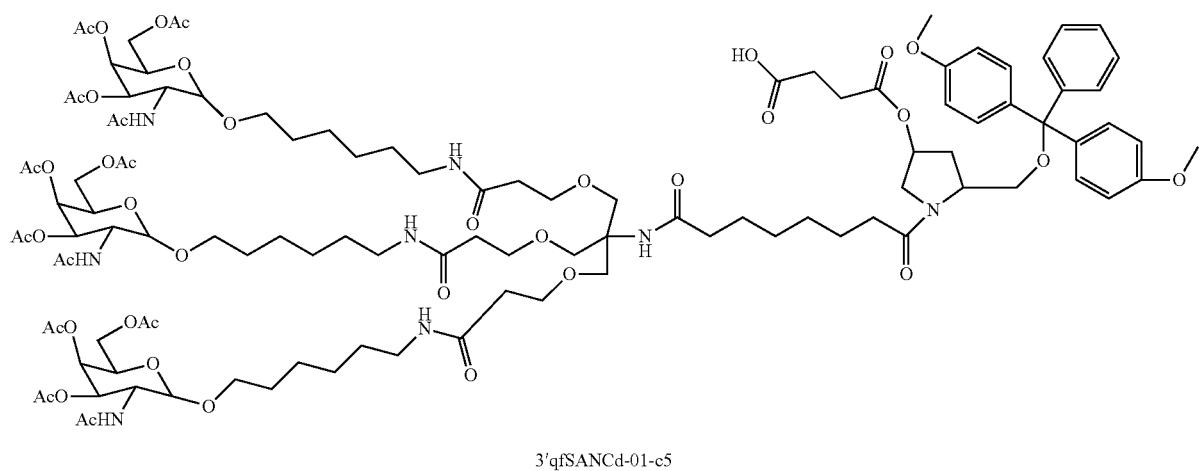

3'qfSANCd-01-c5

Into a reaction flask were added 3'qfSANCd-01-c4 (2.18 g, 0.001 mol) and 10 mL of DCM in order and dissolved with stirring at room temperature, and then added with DBU (0.256 g) and succinic anhydride (0.3 g, 0.003 mmol) in order and reacted with stirring at room temperature. TLC analysis showed that the reaction was complete, and the reaction mixture was concentrated to remove DCM, added with water and extracted with DCM. The organic phase was further washed with a saturated aqueous solution of sodium chloride, dried over anhydrous sodium sulfate, filtered, and concentrated. Finally the residue was purified over a silica gel column to get 2.05 g of 3'qfSANCd-01-c5.

1.1.6. Synthesis of 3'qfSANCd-01-c6

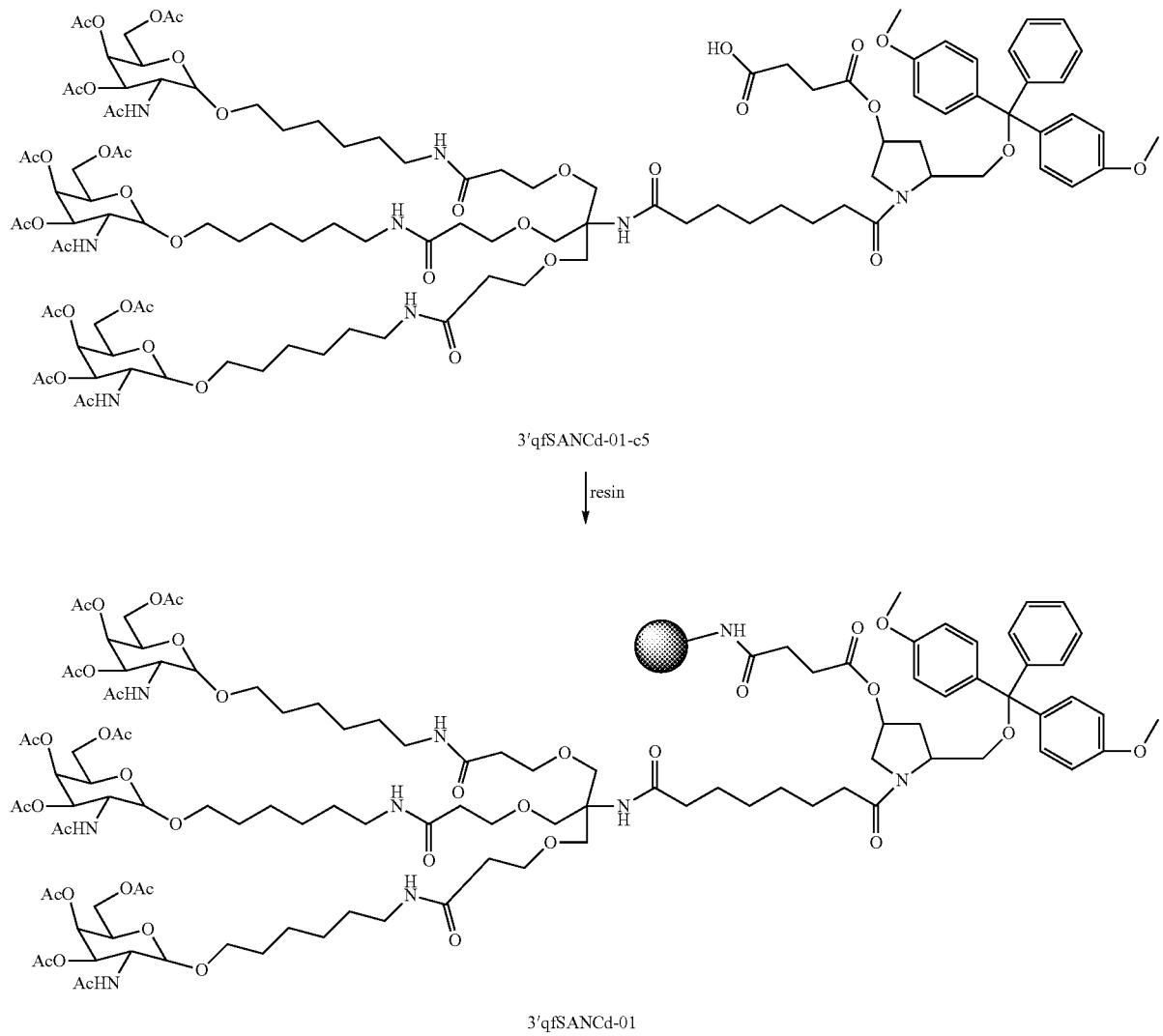

Into a reaction flask were added 3'qfSANCd-01-c5 (1.14 g, 0.0005 mmol) and 12 mL of DMF in order and dissolved with stirring at room temperature, and then added with HBTU (0.19 g), DIPEA (0.194 g) and GE resin (1.83 g) in order, and shaken in a shaker at 35° C. for 4 h. The mixture was transferred into a synthesis tube and filtered. Under bubbling with nitrogen, the resin was rinsed with DMF for 4 times, added with CAP A+CAP B to conduct the end-capping reaction for half an hour under bubbling with nitrogen. A little amount of the resin was taken for a kaiser test until the test solution appeared yellow. After completion of the end-capping, the filter cake was rinsed with methanol and DCM respectively, and dried in vacuum to get 2.5 g of 3'qfSANCd-01, of which the degree of substitution was 140 μmol/g.

1.2 Solid-Phase Synthesis of Kyas-09

With mU as the initiation monomer and with mU as the end monomer, different phosphoramidite monomers were introduced by coupling through a solid-phase phosphoramidite method. The synthetic steps were the same as those in 2.2 Solid-phase synthesis of Kyas-01 in Example 1.

2. Synthesis of GBL-0409

Kys-01 and Kyas-09 solutions were determined accurately for their concentration. The synthetic steps were the same as those in 3. Synthesis of GBL-0401 in Example 1.

Example 6. Synthesis of GBL-0410

1. Synthesis of Kys-10

1.1. Solid-Phase Synthesis of C9NH-S-01

With mU as the initiation monomer and with C9NH phosphoramidite monomer as the end monomer, different phosphoramidite monomers were introduced by coupling through a solid-phase phosphoramidite method. The synthetic steps were the same as those in 1.2 Solid-phase synthesis of C6NH-S-01 in Example 1.

1.2. Liquid-Phase Synthesis of Kys-10
1.2.1. Synthesis of Kys-10-c1
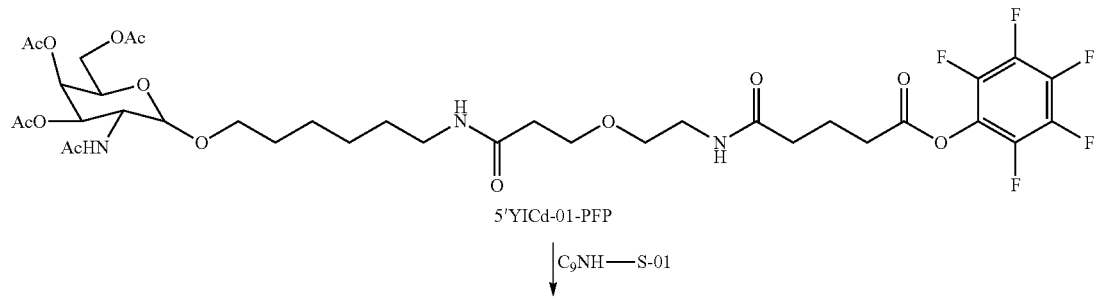
5′YICd-01-PFP
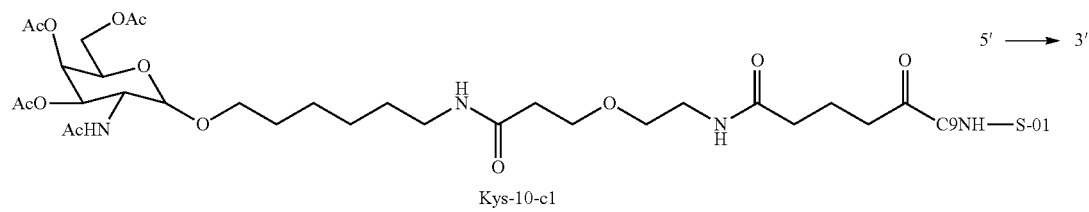
Kys-10-c1
The synthetic steps were the same as those in 1.3.3 of Example 1.
1.2.2. Synthesis of Kys-01
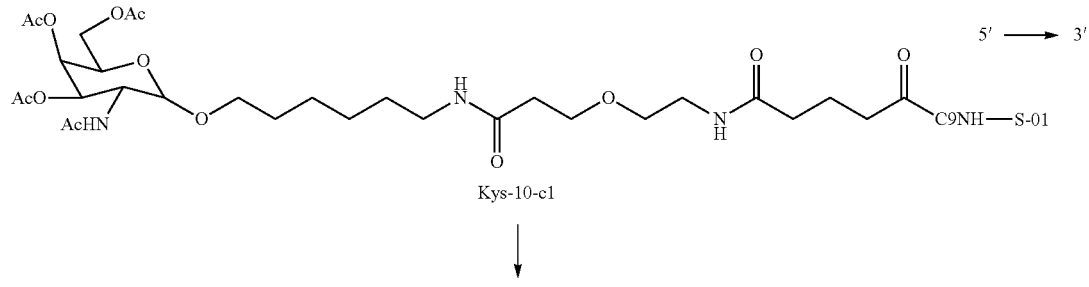
Kys-10-c1
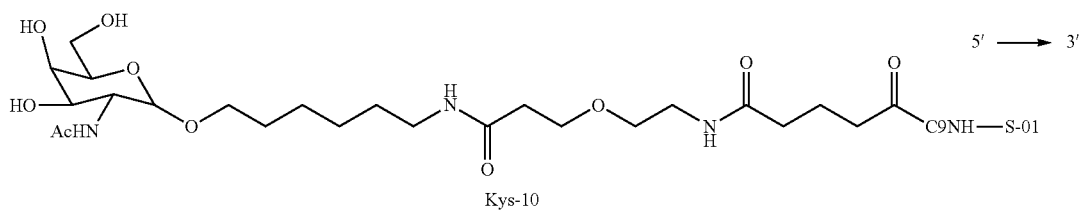
Kys-10
The synthetic steps were the same as those in 1.3.4 of Example 1.

2. Synthesis of Kyas-10

2.1. Compounds of 3'pdSANCd-01: Synthesis of 3'pdSANCd-01 Resin

2.1.1. Synthesis of 3'pdSANCd-01-c1

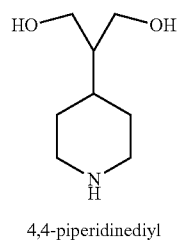

4,4-piperidinediyl dimethanol monomethyl suberate →

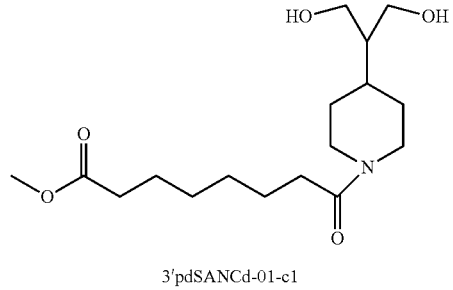

3'pdSANCd-01-c1

Into a reaction flask, 4,4-piperidinediyl dimethanol (1.59 g, 0.01 mol) and 20 mL of DMF were added in order and dissolved with stirring at room temperature, and then added with monomethyl suberate (1.98 g, 0.0105 mol), HBTU (4.55 g) and DIPEA (3.88 g) in order and reacted with stirring at room temperature overnight. TLC analysis showed that the reaction was complete, and the reaction mixture was concentrated to remove DMF, added with water and extracted with DCM. The organic phase was further washed with a saturated aqueous solution of sodium chloride and dried over anhydrous sodium sulfate, filtered, and concentrated. Finally the residue was purified over a silica gel column to get 2.65 g of a yellow sticky liquid.

2.1.2. Synthesis of 3'pdSANCd-01-c2

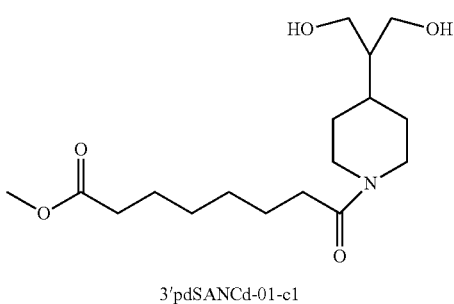

3'pdSANCd-01-c1

DMT—CL →

3'pdSANCd-01-c2

Into a reaction flask, 3'pdSANCd-01-c1 (3.29 g, 0.01 mol) and 33 mL pyridine were added in order and dissolved with stirring at room temperature, and then added with DMAP (0.61 g) and DMT-CL (4.06 g, 0.012 mol) in order and reacted with stirring at room temperature overnight. TLC analysis showed that the reaction was complete, and the reaction mixture was concentrated to remove pyridine, added with water and extracted with DCM. The organic phase was further washed with a saturated aqueous solution of sodium chloride, dried over anhydrous sodium sulfate, filtered, and concentrated. Finally the residue was purified over a silica gel column to get 4.74 g of a yellow sticky liquid.

2.1.3. Synthesis of 3'pdSANCd-01-c3

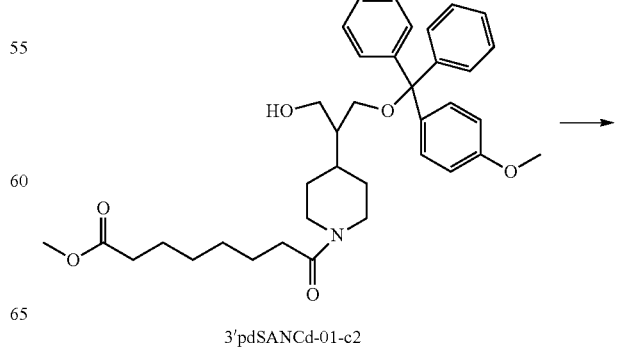

3'pdSANCd-01-c2

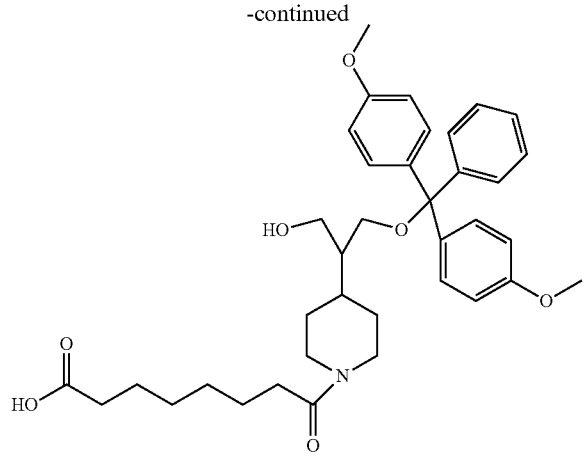

3'pdSANCd-01-c3

Into a reaction flask, 3'pdSANCd-01-c2 (3.16 g, 5 mmol) and 32 mL of a solvent (THF/water/methanol=1:1:4) were added in order and dissolved with stirring at room temperature, and then added with LiOH (0.63 g) and reacted with stirring at room temperature for 2 h. TLC analysis showed that the reaction was complete, and the reaction mixture was concentrated to remove the solvent, added with water and extracted with DCM. The organic phase was further washed with a saturated aqueous solution of sodium chloride and dried over anhydrous sodium sulfate, filtered, and concentrated. Finally the residue was purified over a silica gel column to get 2.78 g of a yellow sticky liquid.

2.1.4. Synthesis of 3'pdSANCd-01-c4

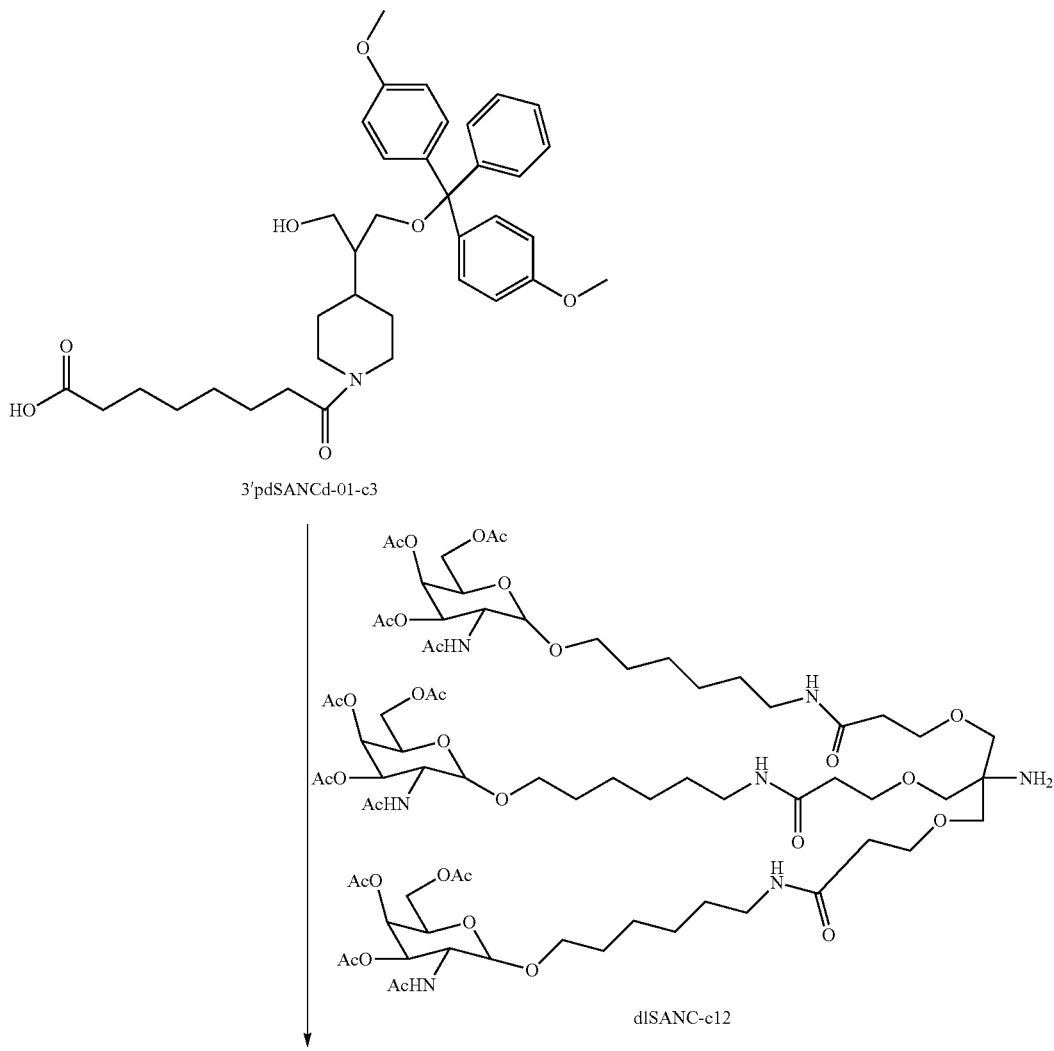

3'pdSANCd-01-c3 dlSANC-c12

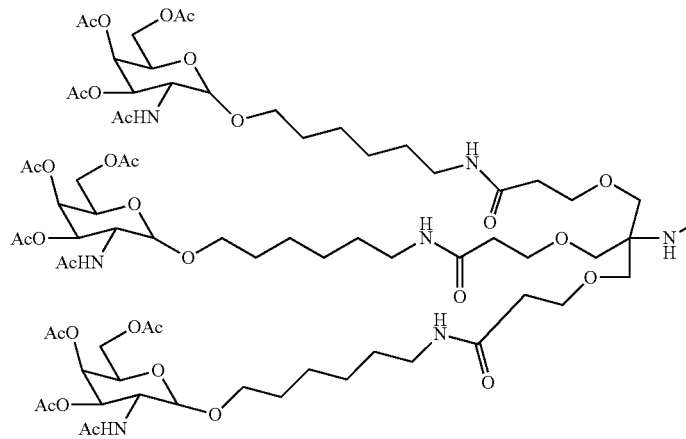

3'pdSANCd-01-c4

Into a reaction flask, 3'pdSANCd-01-c3 (0.93 g, 1.5 mmol) and 10 mL if DMF were added in order and dissolved with stirring at room temperature, and then added with TBTU (0.963 g) and DIPEA (0.517 g) in order and dissolved with stirring at room temperature, and finally added with dlSANC-c12 (0.562 g, 1 mmol) and reacted with stirring at room temperature overnight. TLC analysis showed that the reaction was complete, and the reaction mixture was concentrated to remove DMF, added with water and extracted with DCM. The organic phase was further washed with a saturated aqueous solution of sodium chloride, dried over anhydrous sodium sulfate, filtered, and concentrated. Finally the residue was purified over a silica gel column to get 1.688 g of a yellow sticky liquid.

2.1.5. Synthesis of 3'pdSANCd-01-c5

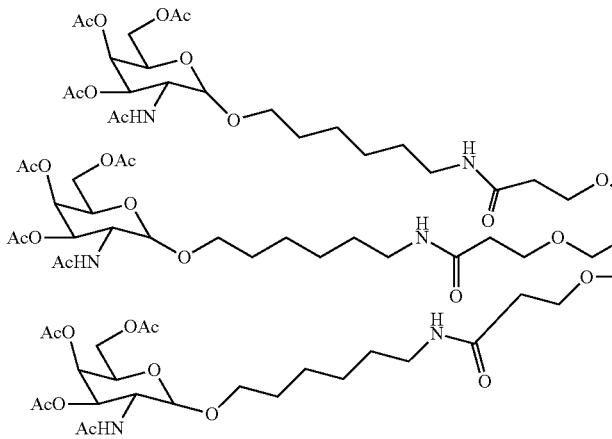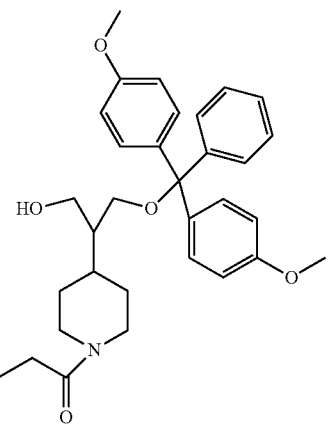

3'pdSANCd-01-c4

↓ succinic anhydride

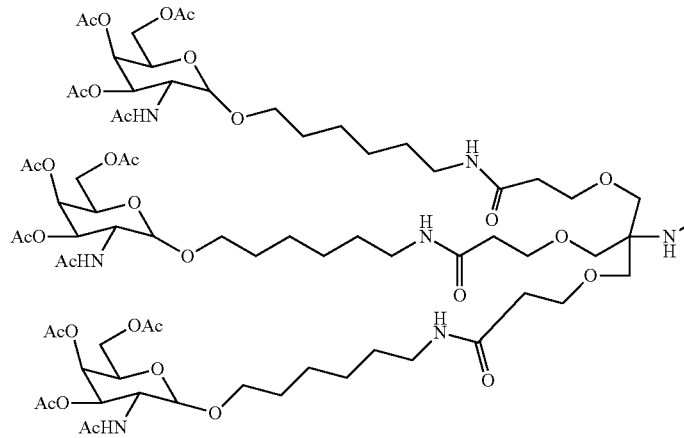
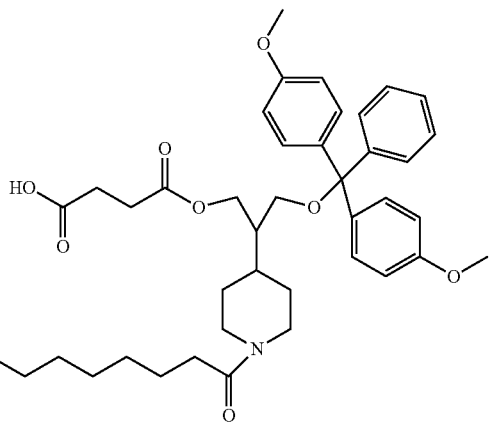

3'pdSANCd-01-c5

Into a reaction flask, 3'pdSANCd-01-c4 (2.22 g, 0.001 mol) and 22 mL of DCM were added in order and dissolved with stirring at room temperature, and then added with DBU (0.256 g) and succinic anhydride (0.3 g, 0.003 mmol) in order and reacted with stirring at room temperature. TLC analysis showed that the reaction was complete, and the reaction mixture was concentrated to remove DCM, added with water and extracted with DCM. The organic phase was further washed with a saturated aqueous solution of sodium chloride, dried over anhydrous sodium sulfate, filtered, and concentrated. Finally the residue was purified over a silica gel column to get 2.11 g of 3'pdSANCd-01-c5.

2.1.6. Synthesis of 3'pdSANCd-01

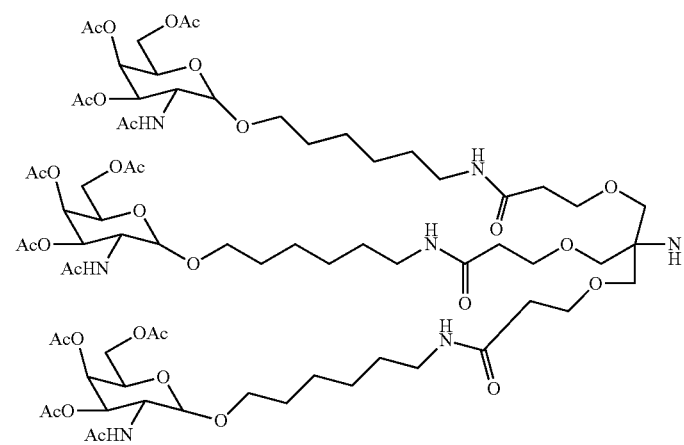
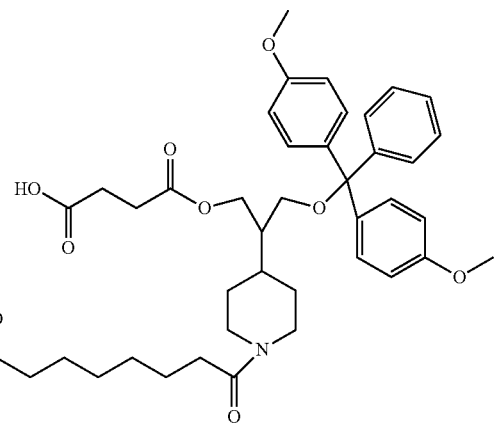

3'pdSANCd-01-c5

↓ resin

-continued

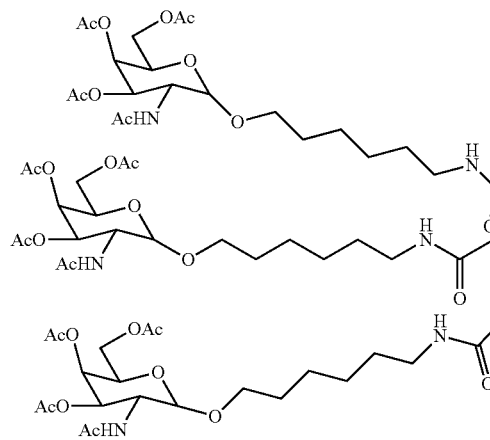
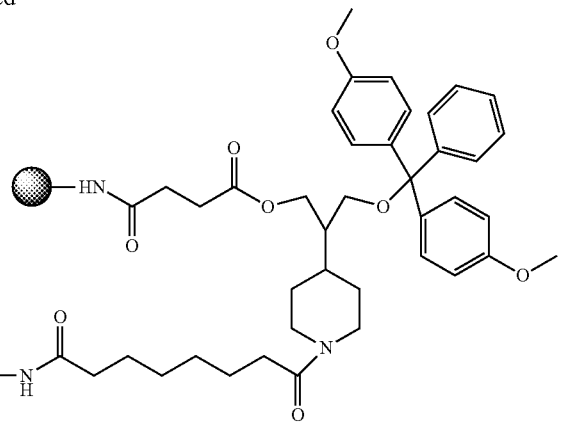

3'pdSANCd-01

Into a reaction flask, 3'pdSANCd-01-c5 (1.16 g, 0.0005 mmol) and 12 mL of DMF were added in order and dissolved with stirring at room temperature, and then added with HBTU (0.19 g), DIPEA (0.194 g) and GE resin (1.85 g) in order, and shaken in a shaker at 35° C. for 4 h. The mixture was transferred into a synthesis tube and filtered. Under bubbling with nitrogen, the resin was rinsed with DMF for 4 times, and then added with CAP A+CAP B to conduct the end-capping reaction for half an hour under bubbling with nitrogen. A little amount of the resin was taken for a kaiser test until the test solution appeared yellow After completion of the end-capping, the filter cake was rinsed with methanol and DCM respectively, and dried in vacuum to get 2.6 g of 3'pdSANCd-01, of which the degree of substitution was 145 μmol/g.

2. Solid-Phase Synthesis of Kyas-10

With mU as the initiation monomer and with mU as the end monomer, different phosphoramidite monomers were introduced by coupling through a solid-phase phosphoramidite method. The synthetic steps were the same as those in 2.2 Solid-phase synthesis of Kyas-01 in Example 1.

3. Synthesis of GBL-0410

Kys-10 and Kyas-10 solutions were determined accurately for their concentration. The synthetic steps were the same as those in of Example 1 3, Synthesis of GBL-0401.

Example 7. GBL0405 to GBL0408 and GBL0411 to GBL0418 were Synthesized Referring to GBL-0401 to GBL0404

Example 8. In Vitro Assay of the Inhibition Effects of the Compounds Against HBV Genes in HepG2.2.15 Cells 1. Experimental Grouping Blank control group: Adding a DMEM medium containing 2% FBS and incubating for 72 h.

Test sample groups: A test sample dilution at a concentration of 5 nM, 0.5 nM or 0.05 nM was added respectively. Each concentration was done in triplicate. The incubation was conducted in an incubator at 37° C. and 5% $CO_2$ for 72 h.

2. Experimental Materials

HepG2.2.15 cells

3. Experimental Reagents

| Name | Brand | Lot No. |
| --- | --- | --- |
| DMEM medium with high glucose | Gibco | 8119164 |
| Fetal bovine serum | Gibco | 20190907 |
| PBS | Solarbio | 20190624 |
| Trypsin-EDTA solution | Gibco | 2062475 |
| Dual antibiotic solution (Penicillin/Streptomycin solution) | Gibco | 2029632 |
| HBsAg, HBeAg kit | Shanghai Kehua | 201812381 |

4. Experimental Instruments

| Name | Brand | Model No. |
| --- | --- | --- |
| Biosafety cabinet | Haier | HR40-IIA2 |
| $CO_2$ Incubator | ASTEC | SCA-165DS |
| Ordinary optical microscope | Nikon | TS2-S-SM |
| Low-speed centrifuge | Flying pigeon | KA-1000 |
| Multi-door refrigerator | MeiLing | BCD-318WTPZM (E) |

5. Test Samples

| No. | Code of new compounds | Weight | Purity |
|---|---|---|---|
| 1 | GBL-0401 | 13.8 μg | 92.3% |
| 2 | GBL-0402 | 12.9 μg | 86.4% |
| 3 | GBL-0403 | 13.4 μg | 89.3% |
| 4 | GBL-0404 | 14.0 μg | 93.3% |
| 5 | GBL-0405 | 13.7 μg | 91.3% |
| 6 | GBL-0406 | 20.5 μg | 88.3% |
| 7 | GBL-0407 | 20.1 μg | 94.4% |
| 8 | GBL-0408 | 20.3 μg | 92.3% |
| 9 | GBL-0409 | 20.4 μg | 93.6% |
| 10 | GBL-0410 | 20.2 μg | 90.5% |
| 11 | GBL-0411 | 20.0 μg | 89.5% |
| 12 | GBL-0412 | 15.1 μg | 94.8% |
| 13 | GBL-0413 | 15.2 μg | 92.5% |
| 14 | GBL-0414 | 15.5 μg | 90.6% |
| 15 | GBL-0415 | 15.7 μg | 91.5% |
| 16 | GBL-0416 | 16.0 μg | 93.4% |
| 17 | GBL-0417 | 15.9 μg | 91.7% |
| 18 | GBL-0418 | 15.5 μg | 92.5% |

6. Test Process

HepG2.2.15 cells were incubated in a 96-well cell culture plate, and fresh medium was replaced every three days. Drug-containing culture media with different concentrations formulated above were added on Day 6, and the incubation continued until Day 9. The supernatants were collected and the contents of HBsAg, HbeAg and HBV DNA in the cell supernatant were detected with a detection kit. The results of OD values were compared with that of the control group without administration, and the effectiveness can be determined according to the ratio.

7. Experimental Results

Figure 6:
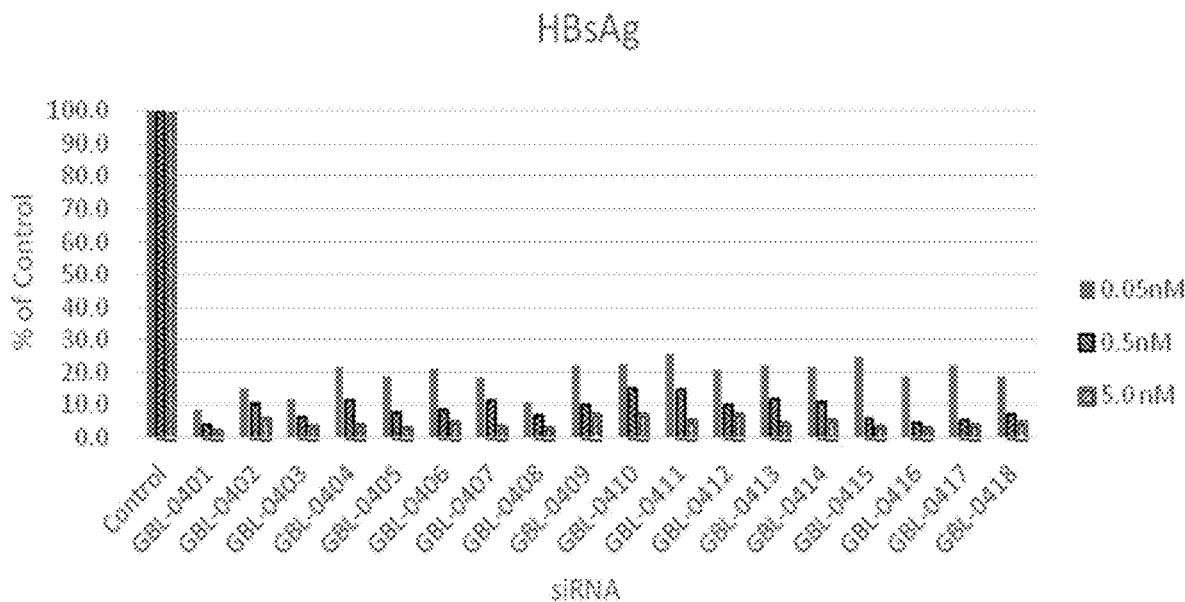
FIG. 6 is a histogram showing in vitro inhibition effect on HBsAg in HepG2.215 cells.

7.1 Inhibition Effects on HbsAg in HepG2.2.15 Cells: See FIG. 6

Figure 7:
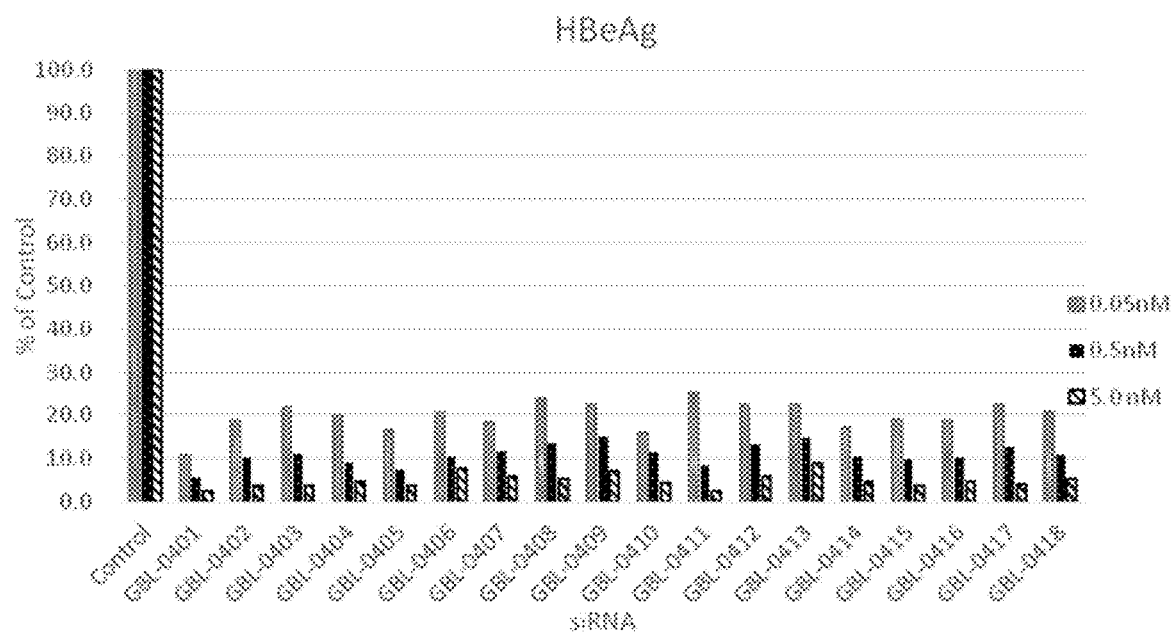
FIG. 7 is a histogram showing in vitro inhibition effect on HBeAg in HepG2.215 cells.

7.2 Inhibition Effects on HbeAg in the Supernatant of HepG2.2.15 Cells: See FIG. 7

Figure 8:
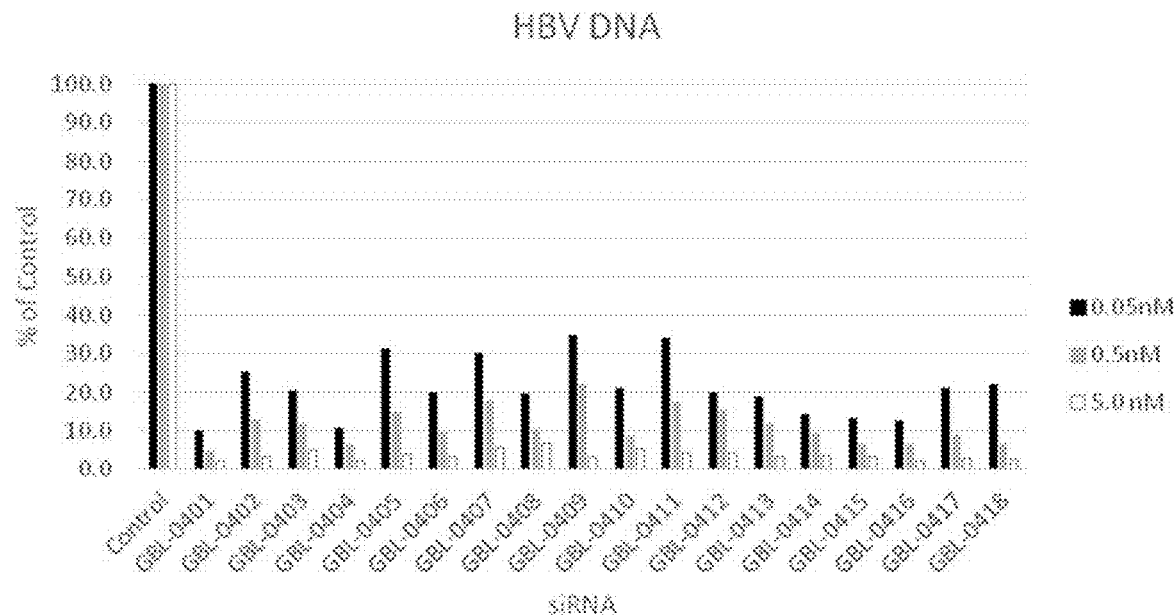
FIG. 8 is a histogram showing in vitro inhibition effect on HBV DNA in HepG2.215 cells.

7.3 Inhibition Effects on HBV DNA in the Supernatant of HepG2.2.15 Cells: See FIG. 8

Example 9. In Vivo Assay on Inhibitory Effects of the New Compounds Against HBV Genes in Transgenic Mice

1. Experimental Protocol

The experimental assay was performed on male HBV transgenic mice of proper age (requiring that HBsAg was significantly expressed). 90 mice weighing about 25 g were chosen and randomly divided into 18 groups, with 5 mice in each group. On Day 0, each mouse was administered by subcutaneous injection at 3 mg/kg with an administration volume of 100-200 μL. Before administration, HBsAg in the blood of mice was determined, and the average level of HBsAg in various groups was tried to be kept consistent.

2. Test Samples and Reagents

| No. | Code of new compounds | Specification | Purity/Content |
|---|---|---|---|
| 1 | GBL-0401 | 500 μg | 92.3% |
| 2 | GBL-0402 | 500 μg | 86.4% |
| 3 | GBL-0403 | 500 μg | 89.3% |
| 4 | GBL-0405 | 500 μg | 93.3% |
| 5 | GBL-0406 | 500 μg | 91.3% |
| 6 | GBL-0407 | 500 μg | 88.3% |
| 7 | GBL-0408 | 500 μg | 94.4% |
| 8 | GBL-0409 | 500 μg | 92.3% |
| 9 | GBL-0410 | 500 μg | 93.6% |
| 10 | GBL-0411 | 500 μg | 90.5% |
| 11 | GBL-0412 | 500 μg | 89.5% |
| 12 | GBL-0413 | 500 μg | 94.8% |
| 13 | GBL-0414 | 500 μg | 92.5% |
| 14 | GBL-0414 | 500 μg | 90.6% |
| 15 | GBL-0415 | 500 μg | 91.5% |
| 16 | GBL-0416 | 500 μg | 93.4% |
| 17 | GBL-0417 | 500 μg | 91.7% |
| 18 | GBL-0418 | 500 μg | 92.5% |
| 19 | Normal saline | 500 ml/flask | 0.9% |

4. Experimental Instruments

| Kit Name | Lot No. | Manufacturer |
|---|---|---|
| Kit for hepatitis B virus surface antigen (Electrochemiluminescence) | 39531900 | Roche Diagnostics (Shanghai) Ltd. Co. |

5. Experimental Results

| Name | Model No. | Manufacturer |
|---|---|---|
| Vortex blender | MIX-28 | DragonLAB |
| Centrifuge | S1010E | THERMO |
| Full-automatic chemiluminescent analyzer | 602 | Roche Diagnostics GmbH |

Figure 9:
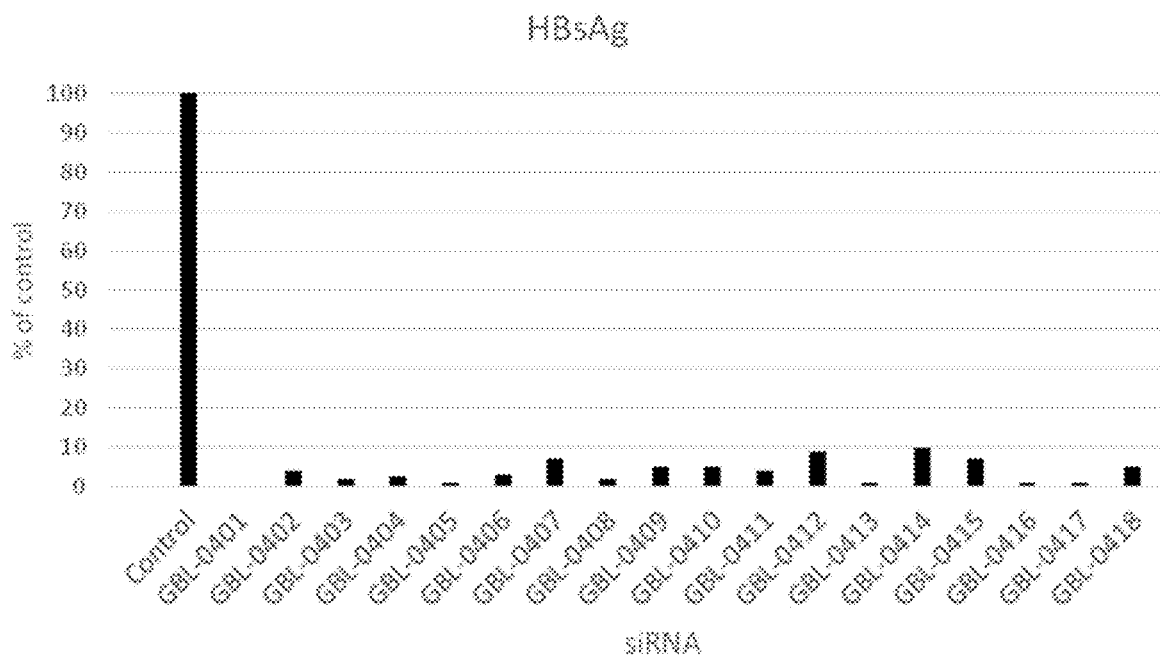
FIG. 9 is a histogram showing in vivo inhibition effect on HBV gene in Transgenic Mice.

The inhibition effects were shown in FIG. 9.

Example 10. In Vivo Assay on Inhibitory Effect of GBL-0401 on Expression of HBV HBsAg in Transgenic Mice

1. Experimental Protocol

The experimental assay was performed on male HBV transgenic mice of proper age (requiring that HBsAg was significantly expressed). 10 mice weighing about 25 g were chosen and randomly divided into 2 groups, a control group and an administration group respectively, with 5 mice in each group. On Day 0, each mouse was administered at 3 mg/kg by subcutaneous injection with an administration volume of 100-200 μL. Before administration, blood was taken to determine HBsAg, and the level of HBsAg in various groups was tried to be kept consistent. Whole blood was collected from orbital venous plexus of mice at the following time points: before administration (Day 0), after administration-Week 1, Week 2, Week 3, Week 4, Week 5 and Week 6, to detect HBsAg and investigate the persistence of GBL-0401 in inhibiting the expression of HBV gene.

The specific administration information was shown in the table below:

| No. | Test drug | Administration dosage | Number of mice/group | Solvent | Administration route |
|---|---|---|---|---|---|
| 1 | Blank solvent | — | 5 | Normal saline | Subcutaneous injection |
| 2 | GBL-0401 | 3 mg/kg | 5 | Normal saline | Subcutaneous injection |

2. Samples and Reagents

| No. | Name | Specification | Purity/Content |
|---|---|---|---|
| 1 | GBL-0401 | 500 μg/vial*1 vial | 92.3% |
| 2 | Normal saline | 500 ml/bottle | 0.9% |

3. Kit

| Kit Name | Lot No. | Manufacturer |
|---|---|---|
| Kit for hepatitis B virus surface antigen (Electrochemiluminescence) | 39531900 | Roche Diagnostics (Shanghai) Ltd. Co. |

4. Experimental instruments

| Name | Model No. | Manufacturer |
|---|---|---|
| Vortex blender | MIX-28 | DragonLAB |
| Centrifuge | S1010E | THERMO |
| Full-automatic chemiluminescent analyzer | 602 | Roche Diagnostics GmbH |

5. Test Results

Figure 10:
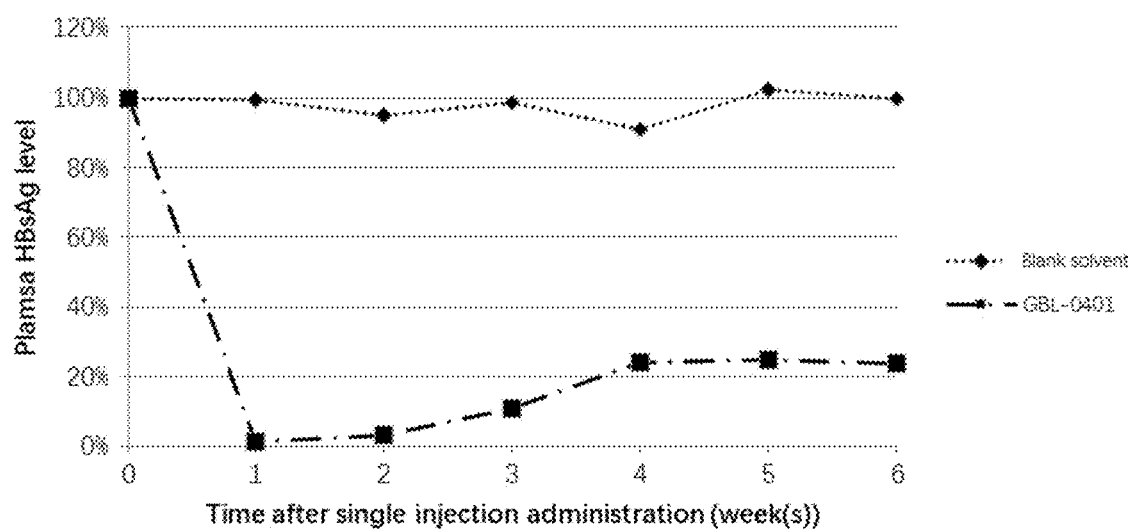
FIG. 10 is a diagram showing in vivo inhibition effect on HBV HBsAg by GBL-0401 in Transgenic Mice.

The results showed that, GBL-0401 reached the optimal inhibitory effect of 99.08% at Week 1, with a slightly decreasing trend from Week 2 to Week 3, but still presented a high inhibitory rate of about 90%, and a declining trend from Week 4 to Week 6, but still maintained an inhibitory effect of about 75%. GBL-0401 has a continuous inhibitory effect on the expression of HBV HBsAg, and can inhibit the expression stably for a period of about 6 weeks. The diagram showing the in vivo inhibitory effect of GBL-0401 on HBV HbsAg is shown in FIG. 10.

The invention claimed is:

1. A compound comprising an interfering nucleic acid having a sense strand and an antisense strand and delivery chains, wherein the compound has a structure of formula (I):

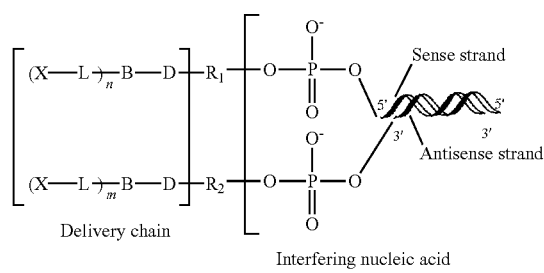

wherein:

R₁ has the structure of —NH(CH$_2$)$_x$CH$_2$—, wherein x is an integer of 3-10;

R₂ has the structure of —NHCH$_2$CH(OH)CH$_2$—;

the moiety

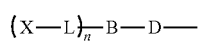

has the structure of

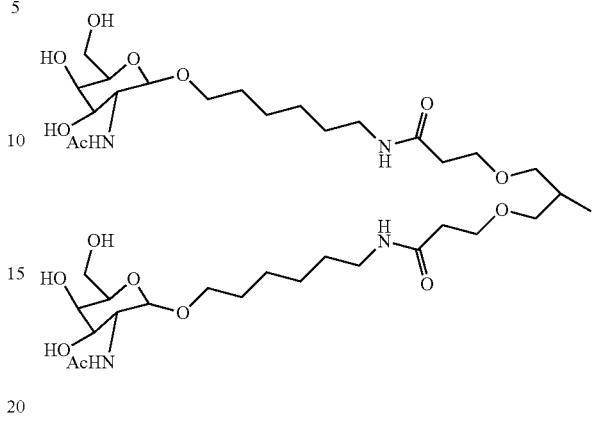

2. A compound comprising an interfering nucleic acid having a sense strand and an antisense strand and delivery chains, wherein the compound has a structure of formula (I):

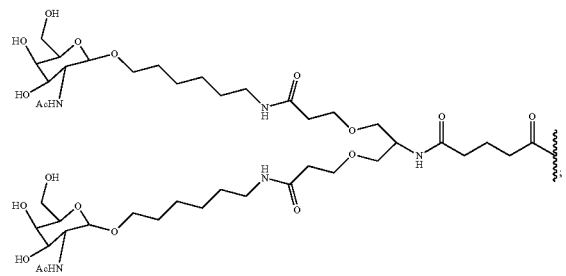

wherein:

R₁ has the structure of —NH(CH$_2$)$_5$CH$_2$—;

R₂ has the structure of —NHCH$_2$CH(OH)CH$_2$—;

the moiety

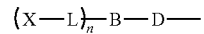

has the structure of

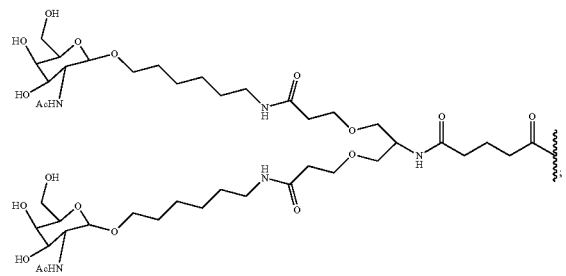

and the moiety

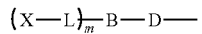

has the structure of

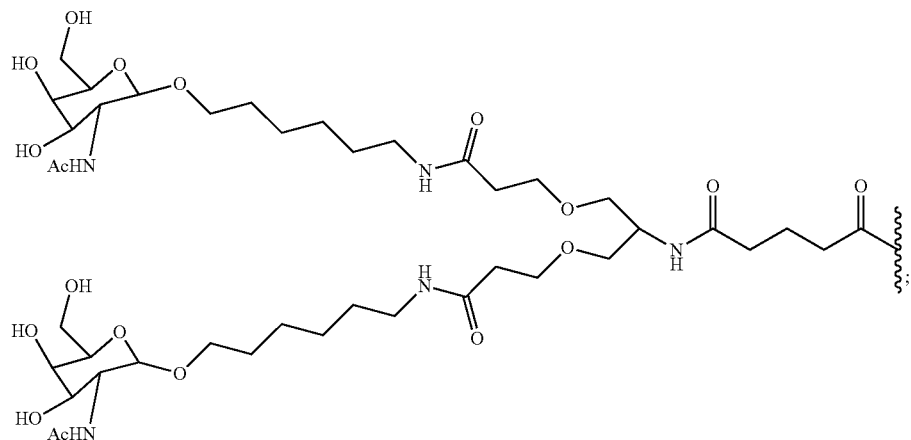 [SMILES: *C(=O)CCCC(=O)NC(COCCC(=O)NCCCCCCOC1OC(CO)C(O)C(O)C1NC(C)=O)COCCC(=O)NCCCCCCOC1OC(CO)C(O)C(O)C1NC(C)=O]

the moiety

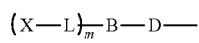

has the structure of

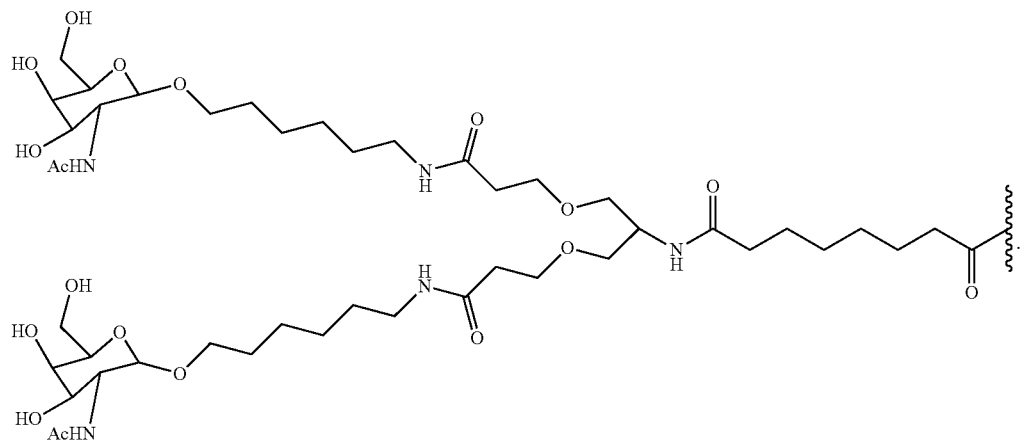 [SMILES: *C(=O)CCCCCCC(=O)NC(COCCC(=O)NCCCCCCOC1OC(CO)C(O)C(O)C1NC(C)=O)COCCC(=O)NCCCCCCOC1OC(CO)C(O)C(O)C1NC(C)=O]

3. The compound of claim 1, wherein said interfering nucleic acid is siRNA, miRNA or Agomir.

4. The compound of claim 1, wherein said interfering nucleic acid is siRNA.

5. A pharmaceutical composition comprising the compound of claim 1 and a pharmaceutically acceptable auxiliary material.

6. The compound of claim 1, wherein said interfering nucleic acid is miRNA.

7. The compound of claim 1, wherein said interfering nucleic acid is Agomir.

8. A pharmaceutical composition comprising the compound of claim 3 and a pharmaceutically acceptable auxiliary material.

9. A pharmaceutical composition comprising the compound of claim 4 and a pharmaceutically acceptable auxiliary material.

10. A pharmaceutical composition comprising the compound of claim 6 and a pharmaceutically acceptable auxiliary material.

11. A pharmaceutical composition comprising the compound of claim 7 and a pharmaceutically acceptable auxiliary material.

12. The compound of claim 2, wherein said interfering nucleic acid is siRNA, miRNA or Agomir.

13. The compound of claim 2, wherein said interfering nucleic acid is siRNA.

14. The compound of claim 2, wherein said interfering nucleic acid is miRNA.

15. The compound of claim 2, wherein said interfering nucleic acid is Agomir.

16. A pharmaceutical composition comprising the compound of claim 2 and a pharmaceutically acceptable auxiliary material.

17. A pharmaceutical composition comprising the compound of claim 12 and a pharmaceutically acceptable auxiliary material.

18. A pharmaceutical composition comprising the compound of claim 13 and a pharmaceutically acceptable auxiliary material.

19. A pharmaceutical composition comprising the compound of claim 14 and a pharmaceutically acceptable auxiliary material.

20. A pharmaceutical composition comprising the compound of claim 15 and a pharmaceutically acceptable auxiliary material.

* * * * *

```
                    SEQUENCE LISTING

<160> NUMBER OF SEQ ID NOS: 92

<210> SEQ ID NO 1
<211> LENGTH: 19
<212> TYPE: RNA
<213> ORGANISM: Artificial Sequence
<220> FEATURE:
<223> OTHER INFORMATION: Synthetic: Sense strand

<400> SEQUENCE: 1
ggguuuuucu uguugacaa                                                  19

<210> SEQ ID NO 2
<211> LENGTH: 19
<212> TYPE: RNA
<213> ORGANISM: Artificial Sequence
<220> FEATURE:
<223> OTHER INFORMATION: Synthetic: Antisense strand

<400> SEQUENCE: 2
uugucaacaa gaaaaccc                                                   19

<210> SEQ ID NO 3
<211> LENGTH: 19
<212> TYPE: RNA
<213> ORGANISM: Artificial Sequence
<220> FEATURE:
<223> OTHER INFORMATION: Synthetic: Sense strand

<400> SEQUENCE: 3
gguuuuucuu guugacaaa                                                  19
```

```
<210> SEQ ID NO 4
<211> LENGTH: 19
<212> TYPE: RNA
<213> ORGANISM: Artificial Sequence
<220> FEATURE:
<223> OTHER INFORMATION: Synthetic: Antisense strand

<400> SEQUENCE: 4
uuugucaaca agaaaaacc                                                  19

<210> SEQ ID NO 5
<211> LENGTH: 19
<212> TYPE: RNA
<213> ORGANISM: Artificial Sequence
<220> FEATURE:
<223> OTHER INFORMATION: Synthetic: Sense strand

<400> SEQUENCE: 5
guuuuucuug uugacaaaa                                                  19

<210> SEQ ID NO 6
<211> LENGTH: 19
<212> TYPE: RNA
<213> ORGANISM: Artificial Sequence
<220> FEATURE:
<223> OTHER INFORMATION: Synthetic: Antisense strand

<400> SEQUENCE: 6 uuugucaac aagaaaaac                                                   19

<210> SEQ ID NO 7
<211> LENGTH: 19
<212> TYPE: RNA
<213> ORGANISM: Artificial Sequence
<220> FEATURE:
<223> OTHER INFORMATION: Synthetic: Sense strand

<400> SEQUENCE: 7
gaccgugugc acuucgcuu                                                  19

<210> SEQ ID NO 8
<211> LENGTH: 19
<212> TYPE: RNA
<213> ORGANISM: Artificial Sequence
<220> FEATURE:
<223> OTHER INFORMATION: Synthetic: Antisense strand

<400> SEQUENCE: 8
aagcgaagug cacacgguc                                                  19

<210> SEQ ID NO 9
<211> LENGTH: 19
<212> TYPE: RNA
<213> ORGANISM: Artificial Sequence
<220> FEATURE:
<223> OTHER INFORMATION: Synthetic: Sense strand

<400> SEQUENCE: 9
accgugugca cuucgcuuc                                                  19

<210> SEQ ID NO 10
<211> LENGTH: 19
<212> TYPE: RNA
<213> ORGANISM: Artificial Sequence
<220> FEATURE:
<223> OTHER INFORMATION: Synthetic: Antisense strand
```

```
<400> SEQUENCE: 10
gaagcgaagu gcacacggu                                               19

<210> SEQ ID NO 11
<211> LENGTH: 19
<212> TYPE: RNA
<213> ORGANISM: Artificial Sequence
<220> FEATURE:
<223> OTHER INFORMATION: Synthetic: Sense strand

<400> SEQUENCE: 11
ccgugugcac uucgcuuca                                               19

<210> SEQ ID NO 12
<211> LENGTH: 19
<212> TYPE: RNA
<213> ORGANISM: Artificial Sequence
<220> FEATURE:
<223> OTHER INFORMATION: Synthetic: Antisense strand

<400> SEQUENCE: 12
ugaagcgaag ugcacacgg                                               19

<210> SEQ ID NO 13
<211> LENGTH: 19
<212> TYPE: RNA
<213> ORGANISM: Artificial Sequence
<220> FEATURE:
<223> OTHER INFORMATION: Synthetic: Sense strand

<400> SEQUENCE: 13
cgugugcacu ucgcuucac                                               19

<210> SEQ ID NO 14
<211> LENGTH: 19
<212> TYPE: RNA
<213> ORGANISM: Artificial Sequence
<220> FEATURE:
<223> OTHER INFORMATION: Synthetic: Antisense strand

<400> SEQUENCE: 14
gugaagcgaa gugcacacg                                               19

<210> SEQ ID NO 15
<211> LENGTH: 19
<212> TYPE: RNA
<213> ORGANISM: Artificial Sequence
<220> FEATURE:
<223> OTHER INFORMATION: Synthetic: Sense strand

<400> SEQUENCE: 15
gugugcacuu cgcuucacc                                               19

<210> SEQ ID NO 16
<211> LENGTH: 19
<212> TYPE: RNA
<213> ORGANISM: Artificial Sequence
<220> FEATURE:
<223> OTHER INFORMATION: Synthetic: Antisense strand

<400> SEQUENCE: 16
ggugaagcga agugcacac                                               19

<210> SEQ ID NO 17
<211> LENGTH: 19
```

```
<212> TYPE: RNA
<213> ORGANISM: Artificial Sequence
<220> FEATURE:
<223> OTHER INFORMATION: Synthetic: Sense strand

<400> SEQUENCE: 17
ugugcacuuc gcuucaccu                                                    19

<210> SEQ ID NO 18
<211> LENGTH: 19
<212> TYPE: RNA
<213> ORGANISM: Artificial Sequence
<220> FEATURE:
<223> OTHER INFORMATION: Synthetic: Antisense strand

<400> SEQUENCE: 18
aggugaagcg aagugcaca                                                    19

<210> SEQ ID NO 19
<211> LENGTH: 19
<212> TYPE: RNA
<213> ORGANISM: Artificial Sequence
<220> FEATURE:
<223> OTHER INFORMATION: Synthetic: Sense strand

<400> SEQUENCE: 19
cagcaauguc aacgaccga                                                    19

<210> SEQ ID NO 20
<211> LENGTH: 19
<212> TYPE: RNA
<213> ORGANISM: Artificial Sequence
<220> FEATURE:
<223> OTHER INFORMATION: Synthetic: Antisense strand

<400> SEQUENCE: 20
ggucguugac auugcugaa                                                    19

<210> SEQ ID NO 21
<211> LENGTH: 19
<212> TYPE: RNA
<213> ORGANISM: Artificial Sequence
<220> FEATURE:
<223> OTHER INFORMATION: Synthetic: Sense strand

<400> SEQUENCE: 21
ggaugugucu gcggcguuu                                                    19

<210> SEQ ID NO 22
<211> LENGTH: 19
<212> TYPE: RNA
<213> ORGANISM: Artificial Sequence
<220> FEATURE:
<223> OTHER INFORMATION: Synthetic: Antisense strand

<400> SEQUENCE: 22
aaacgccgca gacacaucc                                                    19

<210> SEQ ID NO 23
<211> LENGTH: 19
<212> TYPE: RNA
<213> ORGANISM: Artificial Sequence
<220> FEATURE:
<223> OTHER INFORMATION: Synthetic: Sense strand

<400> SEQUENCE: 23
```
uggauguguc ugcggcguu                                                19

<210> SEQ ID NO 24
<211> LENGTH: 19
<212> TYPE: RNA
<213> ORGANISM: Artificial Sequence
<220> FEATURE:
<223> OTHER INFORMATION: Synthetic: Antisense strand

<400> SEQUENCE: 24
aacgccgcag acacaucca                                                19

<210> SEQ ID NO 25
<211> LENGTH: 19
<212> TYPE: RNA
<213> ORGANISM: Artificial Sequence
<220> FEATURE:
<223> OTHER INFORMATION: Synthetic: Sense strand

<400> SEQUENCE: 25
cuggaugugu cugcggcgu                                                19

<210> SEQ ID NO 26
<211> LENGTH: 19
<212> TYPE: RNA
<213> ORGANISM: Artificial Sequence
<220> FEATURE:
<223> OTHER INFORMATION: Synthetic: Antisense strand

<400> SEQUENCE: 26
acgccgcaga cacauccag                                                19

<210> SEQ ID NO 27
<211> LENGTH: 19
<212> TYPE: RNA
<213> ORGANISM: Artificial Sequence
<220> FEATURE:
<223> OTHER INFORMATION: Synthetic: Sense strand

<400> SEQUENCE: 27
cggggcgcac cucucuuua                                                19

<210> SEQ ID NO 28
<211> LENGTH: 19
<212> TYPE: RNA
<213> ORGANISM: Artificial Sequence
<220> FEATURE:
<223> OTHER INFORMATION: Synthetic: Antisense strand

<400> SEQUENCE: 28
uaaagagagg ugcgccccg                                                19

<210> SEQ ID NO 29
<211> LENGTH: 19
<212> TYPE: RNA
<213> ORGANISM: Artificial Sequence
<220> FEATURE:
<223> OTHER INFORMATION: Synthetic: Sense strand

<400> SEQUENCE: 29
ggggcgcacc ucucuuuac                                                19

<210> SEQ ID NO 30
<211> LENGTH: 19
<212> TYPE: RNA
<213> ORGANISM: Artificial Sequence

```
<220> FEATURE:
<223> OTHER INFORMATION: Synthetic: Antisense strand

<400> SEQUENCE: 30
guaaagagag gugcgcccc                                                   19

<210> SEQ ID NO 31
<211> LENGTH: 19
<212> TYPE: RNA
<213> ORGANISM: Artificial Sequence
<220> FEATURE:
<223> OTHER INFORMATION: Synthetic: Sense Strand

<400> SEQUENCE: 31
ggcgcaccuc ucuuuacgc                                                   19

<210> SEQ ID NO 32
<211> LENGTH: 19
<212> TYPE: RNA
<213> ORGANISM: Artificial Sequence
<220> FEATURE:
<223> OTHER INFORMATION: Synthetic: Antisense strand

<400> SEQUENCE: 32
gcguaaagag aggugcgcc                                                   19

<210> SEQ ID NO 33
<211> LENGTH: 19
<212> TYPE: RNA
<213> ORGANISM: Artificial Sequence
<220> FEATURE:
<223> OTHER INFORMATION: Synthetic: Sense strand

<400> SEQUENCE: 33
gcgcaccucu cuuuacgcg                                                   19

<210> SEQ ID NO 34
<211> LENGTH: 19
<212> TYPE: RNA
<213> ORGANISM: Artificial Sequence
<220> FEATURE:
<223> OTHER INFORMATION: Synthetic: Antisense strand

<400> SEQUENCE: 34
cgcguaaaga gaggugcgc                                                   19

<210> SEQ ID NO 35
<211> LENGTH: 19
<212> TYPE: RNA
<213> ORGANISM: Artificial Sequence
<220> FEATURE:
<223> OTHER INFORMATION: Synthetic: Sense strand

<400> SEQUENCE: 35
ucuuguuggu ucuucugga                                                   19

<210> SEQ ID NO 36
<211> LENGTH: 19
<212> TYPE: RNA
<213> ORGANISM: Artificial Sequence
<220> FEATURE:
<223> OTHER INFORMATION: Synthetic: Antisense strand

<400> SEQUENCE: 36
uccagaagaa ccaacaaga                                                   19
```

```
<210> SEQ ID NO 37
<211> LENGTH: 19
<212> TYPE: RNA
<213> ORGANISM: Artificial Sequence
<220> FEATURE:
<223> OTHER INFORMATION: Synthetic: Sense strand

<400> SEQUENCE: 37
uucuuguugg uucuucugg                                                  19

<210> SEQ ID NO 38
<211> LENGTH: 19
<212> TYPE: RNA
<213> ORGANISM: Artificial Sequence
<220> FEATURE:
<223> OTHER INFORMATION: Synthetic: Antisense strand

<400> SEQUENCE: 38
ccagaagaac caacaagaa                                                  19

<210> SEQ ID NO 39
<211> LENGTH: 19
<212> TYPE: RNA
<213> ORGANISM: Artificial Sequence
<220> FEATURE:
<223> OTHER INFORMATION: Synthetic: Sense strand

<400> SEQUENCE: 39
cuuguugguu cuucuggac                                                  19

<210> SEQ ID NO 40
<211> LENGTH: 19
<212> TYPE: RNA
<213> ORGANISM: Artificial Sequence
<220> FEATURE:
<223> OTHER INFORMATION: Synthetic: Antisense strand

<400> SEQUENCE: 40
guccagaaga accaacaag                                                  19

<210> SEQ ID NO 41
<211> LENGTH: 19
<212> TYPE: RNA
<213> ORGANISM: Artificial Sequence
<220> FEATURE:
<223> OTHER INFORMATION: Synthetic: Sense strand

<400> SEQUENCE: 41
uuguugguuc uucuggacu                                                  19

<210> SEQ ID NO 42
<211> LENGTH: 19
<212> TYPE: RNA
<213> ORGANISM: Artificial Sequence
<220> FEATURE:
<223> OTHER INFORMATION: Synthetic: Antisense strand

<400> SEQUENCE: 42
aguccagaag aaccaacaa                                                  19

<210> SEQ ID NO 43
<211> LENGTH: 21
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 43
ggguuuuucu uguugacaat t                                            21

<210> SEQ ID NO 44
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 44
uugucaacaa gaaaaacccu u                                            21

<210> SEQ ID NO 45
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 45
ggguuuuucu uguugacaau u                                            21

<210> SEQ ID NO 46
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 46
uugucaacaa gaaaaaccca u                                            21

<210> SEQ ID NO 47
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 47
gguuuuucuu guugacaaaa u                                            21
```

-continued

```
<210> SEQ ID NO 48
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 48
uuugucaaca agaaaaaccu u                                               21

<210> SEQ ID NO 49
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 49
guuuuucuug uugacaaaau u                                               21

<210> SEQ ID NO 50
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 50
uuuugucaac aagaaaaacu u                                               21

<210> SEQ ID NO 51
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 51
gaccgugugc acuucgcuua u                                               21

<210> SEQ ID NO 52
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications
```

```
<400> SEQUENCE: 52
aagcgaagug cacacgguct t                                              21

<210> SEQ ID NO 53
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 53
accgugugca cuucgcuuct t                                              21

<210> SEQ ID NO 54
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 54
gaagcgaagu gcacacgguu u                                              21

<210> SEQ ID NO 55
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 55
accgugugca cuucgcuuca u                                              21

<210> SEQ ID NO 56
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 56
gaagcgaagu gcacacggut t                                              21

<210> SEQ ID NO 57
<211> LENGTH: 21
<212> TYPE: DNA
<213> ORGANISM: Artificial Sequence
<220> FEATURE:
```

<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 57
ccgugugcac uucgcuucat t                                            21

<210> SEQ ID NO 58
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 58
ugaagcgaag ugcacacggu u                                            21

<210> SEQ ID NO 59
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 59
cgugugcacu ucgcuucacu u                                            21

<210> SEQ ID NO 60
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 60
gugaagcgaa gugcacacgu u                                            21

<210> SEQ ID NO 61
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 61
gugugcacuu cgcuucacca u                                            21

<210> SEQ ID NO 62
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
    and inter-nucleoside phosphorothioate bonds; see specification as
    filed for detailed description of modifications

<400> SEQUENCE: 62
ggugaagcga agugcacaca u                                              21

<210> SEQ ID NO 63
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
    and inter-nucleoside phosphorothioate bonds; see specification as
    filed for detailed description of modifications

<400> SEQUENCE: 63
ugugcacuuc gcuucaccua u                                              21

<210> SEQ ID NO 64
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
    and inter-nucleoside phosphorothioate bonds; see specification as
    filed for detailed description of modifications

<400> SEQUENCE: 64
aggugaagcg aagugcacaa u                                              21

<210> SEQ ID NO 65
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
    and inter-nucleoside phosphorothioate bonds; see specification as
    filed for detailed description of modifications

<400> SEQUENCE: 65
cagcaauguc aacgaccgaa u                                              21

<210> SEQ ID NO 66
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
    and inter-nucleoside phosphorothioate bonds; see specification as

```
filed for detailed description of modifications

<400> SEQUENCE: 66
ggucguugac auugcugaaa u                                              21

<210> SEQ ID NO 67
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 67
ggaugugucu gcggcguuua u                                              21

<210> SEQ ID NO 68
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 68
aaacgccgca gacacaucct t                                              21

<210> SEQ ID NO 69
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 69
uggauguguc ugcggcguua u                                              21

<210> SEQ ID NO 70
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 70
aacgccgcag acacauccat t                                              21

<210> SEQ ID NO 71
<211> LENGTH: 21
<212> TYPE: RNA
<213> ORGANISM: Artificial Sequence
```

```
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 71
cuggaugugu cugcggcguu a                                              21

<210> SEQ ID NO 72
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 72
acgccgcaga cacauccagt t                                              21

<210> SEQ ID NO 73
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 73
cggggcgcac cucucuuuau a                                              21

<210> SEQ ID NO 74
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 74
uaaagagagg ugcgccccgu u                                              21

<210> SEQ ID NO 75
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 75
cggggcgcac cucucuuuau u                                              21
```

<210> SEQ ID NO 76
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
and inter-nucleoside phosphorothioate bonds; see specification as
filed for detailed description of modifications

<400> SEQUENCE: 76
uaaagagagg ugcgccccgt t                                              21

<210> SEQ ID NO 77
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
and inter-nucleoside phosphorothioate bonds; see specification as
filed for detailed description of modifications

<400> SEQUENCE: 77
ggggcgcacc ucucuuuacu a                                              21

<210> SEQ ID NO 78
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
and inter-nucleoside phosphorothioate bonds; see specification as
filed for detailed description of modifications

<400> SEQUENCE: 78
guaaagagag gugcgcccct t                                              21

<210> SEQ ID NO 79
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
and inter-nucleoside phosphorothioate bonds; see specification as
filed for detailed description of modifications

<400> SEQUENCE: 79
ggcgcaccuc ucuuuacgca u                                              21

<210> SEQ ID NO 80
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications and inter-nucleoside phosphorothioate bonds; see specification as
     filed for detailed description of modifications

<400> SEQUENCE: 80
gcguaaagag aggugcgcct t          21

<210> SEQ ID NO 81
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
     and inter-nucleoside phosphorothioate bonds; see specification as
     filed for detailed description of modifications

<400> SEQUENCE: 81
gcgcaccucu cuuuacgcgu a          21

<210> SEQ ID NO 82
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
     and inter-nucleoside phosphorothioate bonds; see specification as
     filed for detailed description of modifications

<400> SEQUENCE: 82
cgcguaaaga gaggugcgct t          21

<210> SEQ ID NO 83
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
     and inter-nucleoside phosphorothioate bonds; see specification as
     filed for detailed description of modifications

<400> SEQUENCE: 83
ucuuguuggu ucuucuggaa u          21

<210> SEQ ID NO 84
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
     and inter-nucleoside phosphorothioate bonds; see specification as
     filed for detailed description of modifications

<400> SEQUENCE: 84
uccagaagaa ccaacaagau a          21

<210> SEQ ID NO 85
<211> LENGTH: 21
<212> TYPE: RNA

<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 85
ucuuguuggu ucuucggau a                                                    21

<210> SEQ ID NO 86
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 86
uccagaagaa ccaacaagaa u                                                   21

<210> SEQ ID NO 87
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 87
uucuuguugg uucuucgga u                                                    21

<210> SEQ ID NO 88
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 88
ccagaagaac caacaagaaa u                                                   21

<210> SEQ ID NO 89
<211> LENGTH: 21
<212> TYPE: RNA
<213> ORGANISM: Artificial Sequence
<220> FEATURE:
<223> OTHER INFORMATION: Synthetic
<220> FEATURE:

```
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 89
cuuguugguu cuucuggaca u                                              21

<210> SEQ ID NO 90
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 90
guccagaaga accaacaagu a                                              21

<210> SEQ ID NO 91
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 91
uuguugguuc uucuggacua u                                              21

<210> SEQ ID NO 92
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: contains 2'-O-Me and 2'-fluoro modifications
      and inter-nucleoside phosphorothioate bonds; see specification as
      filed for detailed description of modifications

<400> SEQUENCE: 92
aguccagaag aaccaacaaa u                                              21
```